United States Patent
Pasternak et al.

(10) Patent No.: US 8,673,920 B2
(45) Date of Patent: Mar. 18, 2014

(54) INHIBITORS OF THE RENAL OUTER MEDULLARY POTASSIUM CHANNEL

(75) Inventors: Alexander Pasternak, Princeton, NJ (US); Aurash Shahripour, Iselin, NJ (US); Haifeng Tang, Metuchen, NJ (US); Nardos H. Teumelsan, Rahway, NJ (US); Lihu Yang, Edison, NJ (US); Yuping Zhu, Edison, NJ (US); Shawn P. Walsh, Bridgewater, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 286 days.

(21) Appl. No.: 12/768,209

(22) Filed: Apr. 27, 2010

(65) Prior Publication Data

US 2010/0286123 A1 Nov. 11, 2010

Related U.S. Application Data

(60) Provisional application No. 61/175,847, filed on May 6, 2009.

(51) Int. Cl.
- *A61K 31/496* (2006.01)
- *C07D 401/12* (2006.01)
- *C07D 405/12* (2006.01)
- *C07D 413/12* (2006.01)
- *A61K 31/407* (2006.01)
- *A61K 31/495* (2006.01)
- *A61K 31/551* (2006.01)
- *C07D 295/092* (2006.01)
- *C07D 487/08* (2006.01)

(52) U.S. Cl.
USPC ............ 514/253.11; 514/254.03; 514/254.11; 514/218; 514/252.12; 544/364; 544/368; 544/377; 544/349; 544/401; 546/122; 548/453; 540/575

(58) Field of Classification Search
None
See application file for complete search history.

(56) References Cited

U.S. PATENT DOCUMENTS

| | | | |
|---|---|---|---|
| 2,988,551 | A | 6/1961 | Morren |
| 3,435,002 | A | 3/1969 | Holub |
| 3,632,608 | A | 1/1972 | Holub |
| 3,749,722 | A | 7/1973 | Holub |
| 4,579,863 | A | 4/1986 | Horwell et al. |
| 4,806,536 | A | 2/1989 | Cross et al. |
| 4,992,547 | A | 2/1991 | Berner et al. |
| 5,145,885 | A | 9/1992 | Berner et al. |
| 5,215,989 | A | 6/1993 | Baldwin et al. |
| 5,614,526 | A | 3/1997 | Godel et al. |
| 5,736,546 | A | 4/1998 | Kawashima et al. |
| 6,258,813 | B1 | 7/2001 | Arlt et al. |
| 2004/0204404 | A1 | 10/2004 | Zelle et al. |
| 2005/0215526 | A1 | 9/2005 | Hulme et al. |
| 2005/0267121 | A1 | 12/2005 | Li et al. |
| 2006/0183739 | A1 | 8/2006 | Tsaklakidis et al. |
| 2006/0183742 | A1 | 8/2006 | Mederski et al. |
| 2006/0211692 | A1 | 9/2006 | Mederski et al. |
| 2007/0004750 | A1 | 1/2007 | Lorsbach et al. |
| 2007/0093472 | A1 | 4/2007 | Mederski et al. |
| 2008/0003214 | A1 | 1/2008 | Cezanne et al. |

FOREIGN PATENT DOCUMENTS

| | | |
|---|---|---|
| EP | 0099148 | 1/1984 |
| EP | 0175376 | 3/1986 |
| EP | 1094063 | 4/2001 |
| EP | 1939175 | 7/2008 |
| FR | 2673182 | 8/1992 |
| GB | 949088 | 2/1964 |
| GB | 1575310 | 9/1980 |
| GB | 2116967 | 10/1983 |
| JP | 10-203986 | 8/1998 |
| WO | 97/44329 | 11/1997 |
| WO | 00/51611 | 9/2000 |
| WO | 02/14314 | 2/2002 |
| WO | 02/14314 A2 | 2/2002 |
| WO | 02/32874 | 4/2002 |
| WO | 02/50061 | 6/2002 |
| WO | 2004/020422 | 3/2004 |
| WO | 2004/037817 | 5/2004 |
| WO | 2004/046110 | 6/2004 |
| WO | 2005/037843 | 4/2005 |
| WO | 2005/044797 | 5/2005 |
| WO | 2006/034341 | 3/2006 |
| WO | 2006/034769 | 4/2006 |

(Continued)

OTHER PUBLICATIONS

Felix et al. Assay and Drug Development Technologies,10(5),pp. 417-431 (2012).*

(Continued)

*Primary Examiner* — Emily Bernhardt
(74) *Attorney, Agent, or Firm* — Nicole M. Beeler; Catherine D. Fitch

(57) ABSTRACT

This invention relates to compounds having structural Formula I:

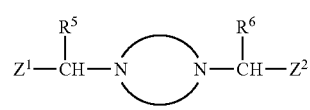

and pharmaceutically acceptable salts thereof which are inhibitors of the Renal Outer Medullary Potassium (ROMK) channel (Kir1.1). The compounds of Formula I are useful as diuretics and natriuretics and therefore are useful for the therapy and prophylaxis of disorders resulting from excessive salt and water retention, including cardiovascular diseases such as hypertension and chronic and acute heart failure.

54 Claims, No Drawings

(56) References Cited

FOREIGN PATENT DOCUMENTS

| | | |
|---|---|---|
| WO | 2006/098342 | 9/2006 |
| WO | 2006/129199 | 12/2006 |
| WO | 2007/075629 | 7/2007 |
| WO | 2008/147864 | 12/2008 |
| WO | 2009/149508 | 11/2009 |

OTHER PUBLICATIONS

Cerkvenik-Flajs, Anal. Chim. Acta (2007), vol. 586, pp. 374-382, "Determination of residues of azaperone in the kidneys . . . " (available on online Nov. 10, 2006).

Lutz et al., J. Org. Chem. (1947), vol. 12, pp. 771-775, "Antimalarials. Some Piperazine Derivatives".

Baltzly at al., J. Am. Chem. Soc. (1944), vol. 66, pp. 263-266, "The preparation of N-mono-substituted and unsymmetrically disubstituted piperazines".

Chemical Abstracts (2004), Abstract No. 697771-49-6, "1,3-Isobenzofurandione 5-[[4-[(5-chloro-2-methoxyphenyl) sulfonyl]-1- . . . ".

Kulkarni et al., Biol. Mem. (1987), vol. 13, pp. 141-144, "Possible antifertility agents, part III. Synthesis of 4-(substituted aminomethy)-5,6,7-trimethoxy phthalid . . . " (abstract).

Lewis, "High-throughput screening reveals a small molecular inhibitor . . . ", Mol. Pharmacol. (2009), vol. 76, pp. 1094-1103.

Int'l Search Report of PCT/US2010/032872, dated Aug. 3, 2010; 3 pages.

Int'l Preliminary Report on Patentability of PCT/US2010/032872, dated Nov. 9, 2011, 6 pages.

Fallen, "The Kir channel immunoglobulin domain is essential . . . ", Channels (2009), vol. 3, pp. 57-68.

Bhave, "Development of a selective small-molecule inhibitor Kir1.1 . . . ", Mol. Pharmacol. (2011), vol. 79, pp. 42-50.

Sica et al., "Diuretic use in renal disease", Nature (2012), vol. 8, pp. 100-109.

Felker et al., "Diuretic strategies in patients with acute decompensated heart failure", New Eng. J. Med. (2011), vol. 364, pp. 797-805.

Brater, "Diuretic Therapy", Drug Therapy (1998), vol. 339, pp. 387-395.

Frank, "Managing hypertension using combination therapy", Am. Fam. Physician (2008), vol. 77, pp. 1279-1286 and 1289.

ACCF/AHA Practice Guideline: Full text, "2009 Focused update incorporated into the ACC/AHA 2005 guidelines . . . " Circulation (2009), vol. 119, pp. e391-e436.

Singapore Search Report in Singapore Appln. 201108009-0, dated Aug. 17, 2012.

Georgia Search Report in Georgia Appln. AP 2010 012494, dated Aug. 30, 2012.

Japanese Search Report in Japanese Appl. No. 2012-509848, dated Jun. 25, 2012.

Brewster et al., "Antihypertensive 1,4-bis (2-indol-3-ylethyl)piperazines", Chimie Ther. (1973), vol. 2, pp. 169 -172 (English trans.).

Zejc et al., "Piperazine derivatives of dimethylxanthines", Polish J. Pharmacol. & Pharm. (1975), vol. 27, pp. 311-316 (English trans.).

Miyake et al., "Synthesis of 1-substituted isochroman . . . ", Takeda Res. Lab. (1982), vol. 41, pp. 24-40 (English trans.).

Lanyi et al., "Piperazine-Derivatives II", Res. Lab. of Chinoin-Fabrik Chemisch-Pharma. Prod. (1968), vol. 18, pp. 1431-1435 (English trans.).

Cheymol et al., "Increase in the effects of epinephrine and acetylcholine . . . ", Comptes Rendus des seances de la Societe de Biologie . . . (1951), vol. 145, pp. 496-499 (English trans.).

\* cited by examiner

INHIBITORS OF THE RENAL OUTER MEDULLARY POTASSIUM CHANNEL

CROSS REFERENCE TO RELATED APPLICATIONS

This application claims the benefit of U.S. Provisional Application No. 61/175,847, filed May 6, 2009. U.S. Provisional Application No. 61/175,847 is herein incorporated by reference in its entirety.

BACKGROUND OF THE INVENTION

The Renal Outer Medullary Potassium (ROMK) channel (Kir1.1) (see e.g., Ho, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the $Na^+/K^+/2Cl^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are predicted to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Banter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first small molecule selective inhibitors of ROMK were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76(5): p. 1094-1103.

SUMMARY OF THE INVENTION

One object of the present invention is to provide compounds of Formula I

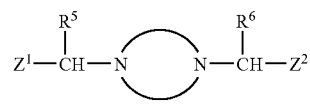

and the pharmaceutically acceptable salts thereof. The compounds of Formula I are inhibitors of the ROMK (Kir1.1) channel and can act as diuretics and natriuretics and are valuable pharmaceutically active compounds for the therapy and prophylaxis of diseases, including, but not limited to, cardiovascular diseases such as hypertension and conditions resulting from excessive salt and water retention. Therefore, an object of the invention is to provide methods of treatment comprising administering a therapeutically or prophylactically effective amount of a compound of Formula I to a patient in need of a diuretic and/or natriuretic agent. A further object is to provide the use of compounds of Formula I in combination with other therapeutically effective agents, including other drugs useful for the treatment of hypertension and conditions resulting from excessive salt and water retention. The invention furthermore relates to processes for preparing compounds of Formula I, and pharmaceutical compositions which comprise compounds of Formula I. These and other objects will be evident from the description contained herein.

DETAILED DESCRIPTION OF THE INVENTION

The present invention is directed to compounds having structural Formula I:

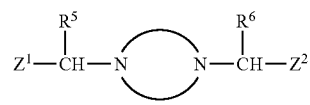

and the pharmaceutically acceptable salts thereof wherein:

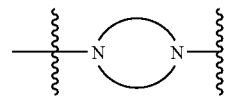

represents a heterocyclic ring selected from the group consisting of:

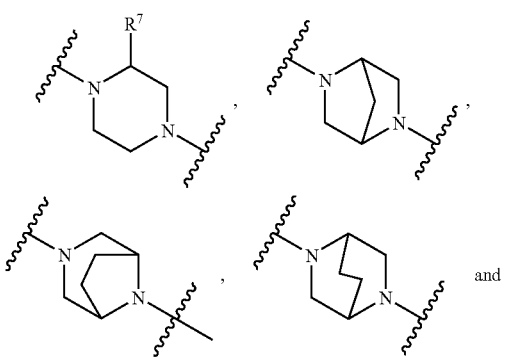

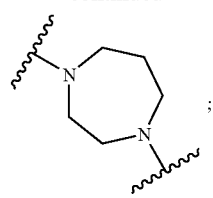
$Z^1$ is selected from the group consisting of:
z1-i
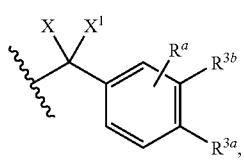
z1-ii
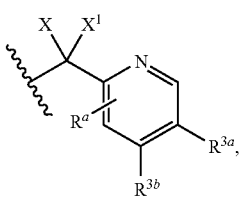
z1-iii
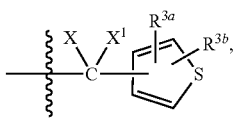
z1-iv
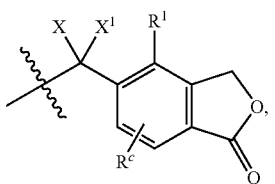
z1-v
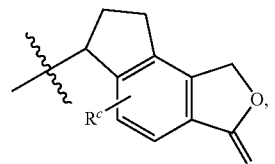
z1-vi
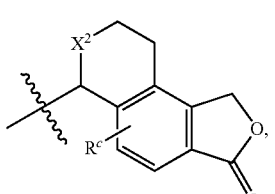
z1-vii
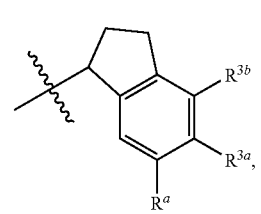
z1-viii
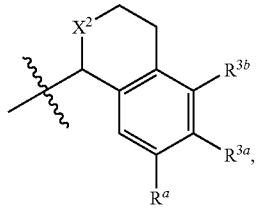
z1-ix
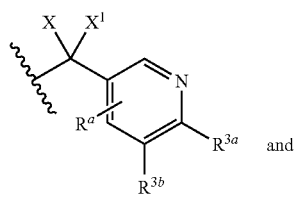
and
z1-x
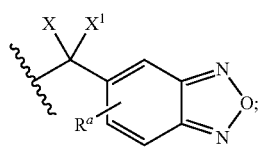
$Z^2$ is selected from the group consisting of:
z2-i
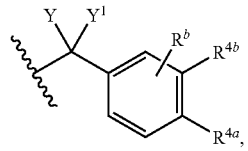
z2-ii
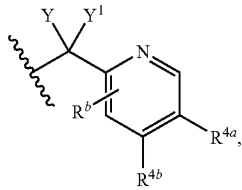
z2-iii
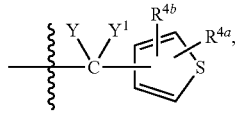
z2-iv
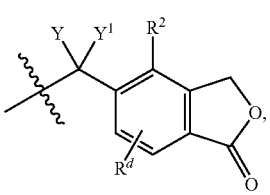
z2-v
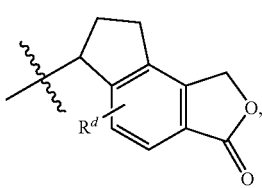

-continued

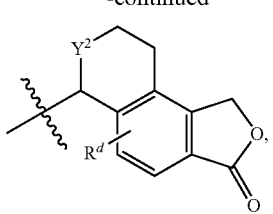
z2-vi

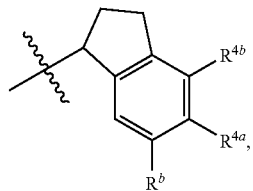
z2-vii

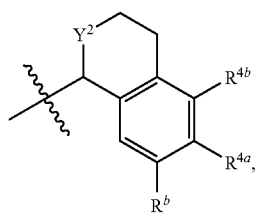
z2-viii

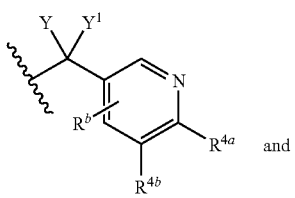
z2-ix

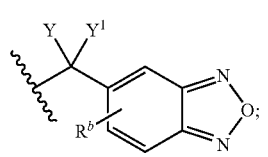
z2-x

X is selected from the group consisting of —H, —OH, —OC$_{1-3}$alkyl, —F, oxo (=O), NH$_2$, and —CH$_3$;
Y is selected from the group consisting of —H, —OH, —OC$_{1-3}$alkyl, —F, oxo (=O), NH$_2$, and —CH$_3$;
X$^1$ and Y$^1$ are each independently selected from the group consisting of —H and —CH$_3$;
X$^2$ and Y$^2$ are each —O—;
provided that when X is oxo then X$^1$ is absent and when Y is oxo then Y$^1$ is absent;
and further provided that when neither X$^2$ nor Y$^2$ is present, then at least one of X and Y is selected from the group consisting of —OH, —OC$_{1-3}$alkyl, —F and oxo;
R$^1$ and R$^2$ are each independently selected from the group consisting of —H, -halo, —C$_3$-C$_6$cycloalkyl, —OR$^8$, —SR$^8$, —SOR$^8$, —SO$_2$R$^8$, —(CH$_2$)$_n$OR$^8$ and C$_1$-C$_6$alkyl optionally substituted with 1-3 of —F;
one of R$^{3a}$ and R$^{3b}$ is selected from the group consisting of —CN and —NO$_2$ and the other is R$^e$;
one of R$^{4a}$ and R$^{4b}$ is selected from the group consisting of —CN and —NO$_2$ and the other is R$^f$;
R$^5$ and R$^6$ are each independently selected from the group consisting of —H, —C$_{1-6}$ alkyl, —C$_{3-6}$ cycloalkyl, —CF$_3$, —CHF$_2$, —CH$_2$F and —CH$_2$OH;
R$^7$ is selected from the group consisting of —H, —CH$_3$, —CF$_3$, —CHF$_2$, —CH$_2$F and —CH$_2$OH;
R$^a$ and R$^b$ are each independently selected from the group consisting of (a) —H, (b) halo, (c) —C$_{1-6}$ alkyl optionally substituted with 1-3 of —F, (d) —C$_{3-6}$ cycloalkyl, (e) —OC$_{1-3}$alkyl optionally substituted with 1-3 of —F, (f) —OR$^8$, (g) —CO$_2$C$_{1-6}$alkyl optionally substituted with 1-3 of —F, (h) —(CH$_2$)$_n$OR$^8$, (i) —SR$^8$, (j) —SOR$^8$, (k) —SO$_2$R$^8$, (l) —NHCOR$^8$ and (m) —NHSO$_2$R$^8$;

R$^c$ and R$^d$ are each independently selected from the group consisting of (a) —H, (b) halo, (c) —C$_{1-6}$ alkyl optionally substituted with 1-3 of —F, (d) —C$_{3-6}$ cycloalkyl, (e) —OC$_{1-3}$alkyl optionally substituted with 1-3 of —F, (f) —OR$^8$, (g) —CO$_2$C$_{1-6}$alkyl optionally substituted with 1-3 of —F, (h) —(CH$_2$)$_n$OR$^8$, (i) —SR$^8$, (j) —SOR$^8$, (k) —SO$_2$R$^8$, (l) —NHCOR$^8$ and (m) —NHSO$_2$R$^8$;

R$^e$ and R$^f$ are each independently selected from the group consisting of (a) —H, (b) halo, (c) —C$_{1-6}$ alkyl optionally substituted with 1-3 of —F, (d) —C$_{3-6}$ cycloalkyl, (e) —OC$_{1-3}$alkyl optionally substituted with 1-3 of —F, (f) —OR$^8$, (g) —CO$_2$C$_{1-6}$alkyl optionally substituted with 1-3 of —F, (h) —(CH$_2$)$_n$OR$^8$, (i) —SR$^8$, (j) —SOR$^8$, (k) —SO$_2$R$^8$, (l) —NHCOR$^8$ and (m) —NHSO$_2$R$^8$;

n is an integer selected from 1, 2 and 3; and

R$^8$ is independently selected at each occurrence from the group consisting of —H, —C$_{3-6}$cycloalkyl and —C$_{1-6}$ alkyl optionally substituted with 1-3 of —F.

In an embodiment of this invention are compounds of Formula I, referred to herein as compounds of Formula Ia and the pharmaceutically acceptable salts thereof, wherein: Z$^1$ is selected from the group consisting of:

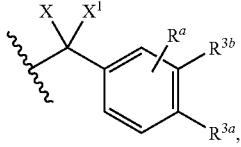
z1-i

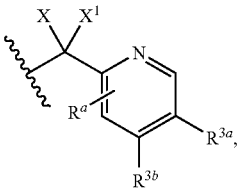
z1-ii

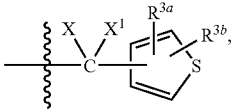
z1-iii

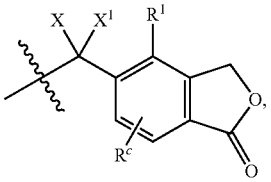
z1-iv

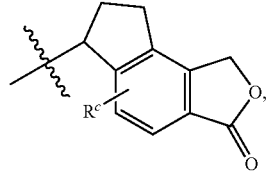
z1-v

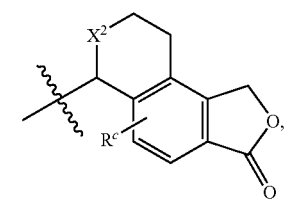
z1-vi

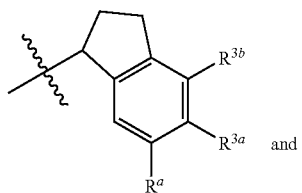
z1-vii  and

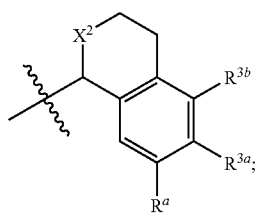
z1-viii $Z^2$ is selected from the group consisting of:

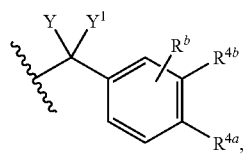
z2-i

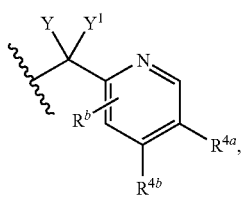
z2-ii

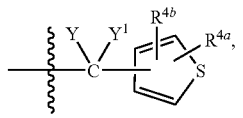
z2-iii

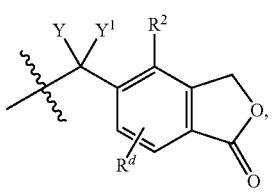
z2-iv

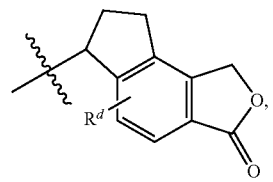
z2-v

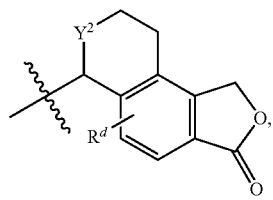
z2-vi

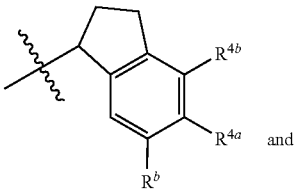
z2-vii  and

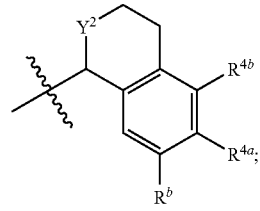
z2-viii

X is selected from the group consisting of —H, —OH, —OC$_{1-3}$alkyl, —F, oxo (=O), NH$_2$, and —CH$_3$;

Y is selected from the group consisting of —H, —OH, —OC$_{1-3}$alkyl, —F, oxo (=O), NH$_2$, and —CH$_3$;

$X^1$ and $Y^1$ are each independently selected from the group consisting of —H and —CH$_3$;

$X^2$ and $Y^2$ are each —O—;

provided that when X is oxo then $X^1$ is absent and when Y is oxo then $Y^1$ is absent;

and further provided that at least one of X and Y is selected from the group consisting of —OH, —OC$_{1-3}$alkyl, —F and oxo; and all other variables within Formula Ia (e.g., $R^1$, $R^2$, $R^{3a}$, $R^{3b}$, $R^{4a}$, $R^{4b}$, etc) are as defined in Formula I.

When neither $X^2$ nor $Y^2$ is present resulting in at least one of X and Y being selected from the group consisting of —OH, —OC$_{1-3}$alkyl, —F and oxo, it means that for a compound that does not contain an $X^2$-containing moiety (z1-vi, z1-viii) nor a $Y^2$-containing moiety (z2-vi, z2-viii) and which does contain at least one X-containing moiety (z1-i, z1-ii, z1-iii, z1-iv, z1-ix, z1-x) or Y-containing moiety (z2-i, z2-ii, z2-iii, z2-iv, z2-ix, z2-x), then at least one of X and Y is selected from the group consisting of —OH, —OC$_{1-3}$alkyl, —F and oxo.

Also encompassed within the scope of this invention are compounds of Formula I or Formula Ia as well as all other formulas, embodiments, classes and sub-classes described herein wherein at least one of X, Y, $X^2$ and $Y^2$ is present, and when neither $X^2$ nor $Y^2$ is present, then at least one of X and Y is selected from —OH, —OC$_{1-3}$alkyl, —F and oxo. When at least one of X, Y, $X^2$ and $Y^2$ is present, it means that the compound must contain at least one of an X-containing moiety (z1-i, z1-iii, z1-iv, z1-ix, z1-x), a Y-containing moiety (z2-i, z2-ii, z2-iii, z2-iv, z2-ix, z2-x), an $X^2$-containing moiety (z1-vi, z1-viii) or a $Y^2$-containing moiety (z2-vi, z2-viii).

In an embodiment of this invention are compounds of Formula I or Formula Ia wherein is selected from the group consisting of

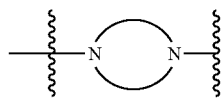

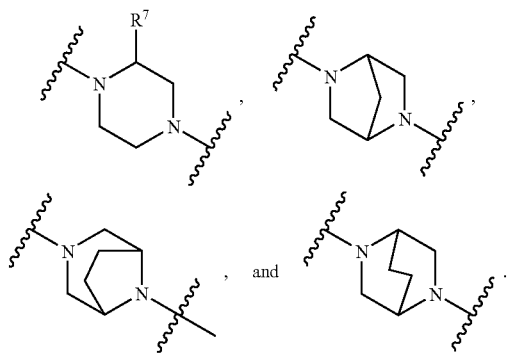

In an embodiment of this invention are compounds of Formula I or Ia having structural Formula II and the pharmaceutically acceptable salts thereof:

II

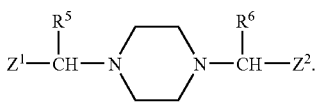

In another embodiment are compounds of Formula I or Ia having structural Formula III and the pharmaceutically acceptable salts thereof:

III

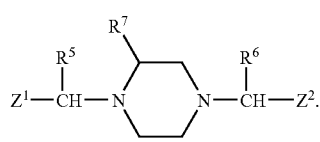

In another embodiment are compounds of Formula I or Ia having structural Formula IV and the pharmaceutically acceptable salts thereof:

IV

In another embodiment are compounds of Formula I or Ia having structural Formula V and the pharmaceutically acceptable salts thereof:

V

In another embodiment are compounds of Formula I or Ia having structural Formula VI and the pharmaceutically acceptable salts thereof:

VI

In another embodiment are compounds of Formula I or Ia having structural Formula VII and the pharmaceutically acceptable salts thereof:

VII

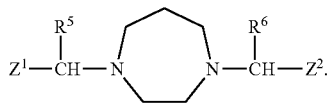

In another embodiment of this invention are compounds of Formula I, Ia or III having structural Formula VIII and the pharmaceutically acceptable salts thereof:

VIII

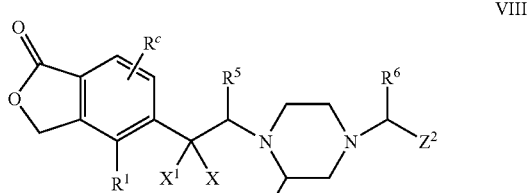

In another embodiment of this invention are compounds of Formula I, Ia, II or III having structural Formula VIIIa and the pharmaceutically acceptable salts thereof:

VIIIa

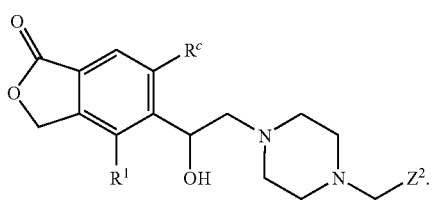

In another embodiment of this invention are compounds of Formula I, Ia or VII having structural Formula IX and the pharmaceutically acceptable salts thereof:

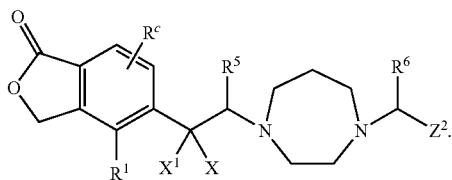

In another embodiment of this invention are compounds of Formula I, Ia, III or IV having structural Formula X and the pharmaceutically acceptable salts thereof:

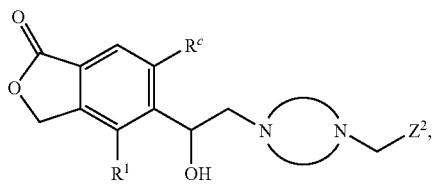

wherein

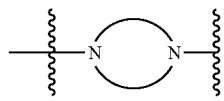

is selected from

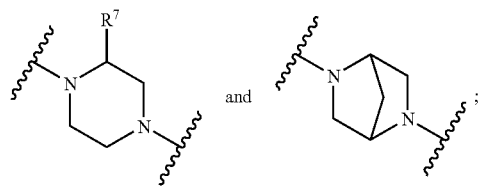

$R^1$ is selected from —H and —$CH_3$;
$R^c$ is selected from —H and —$CH_3$; and
$Z^2$ is selected from z2-ii, z2-iv, z2-v and z2-vi.

In Embodiment A are compounds of Formula I, Ia, II, III, IV, V, VI, or VII wherein $Z^1$ and $Z^2$ are selected from the group consisting of: (a) z1-i and z2-i; (b) z1-ii and z2-ii; (c) z1-iii and z2-iii; (d) z1-iv and z2-iv; (e) z1-vi and z2-vi; (f) z1-viii and z2-viii; (g) z1-ix and z2-ix; and (h) z1-x and z2-x.

In Embodiment B are compounds of Formula I, Ia, II, III, IV, V, VI, or VII wherein $Z^1$ and $Z^2$ are selected as follows: (a) when $Z^1$ is z1-i then $Z^2$ is not z2-i; (b) when $Z^1$ is z1-ii then $Z^2$ is not z2-ii; (c) when $Z^1$ is z1-iii then $Z^2$ is not z2-iii; (d) when $Z^1$ is z1-iv then $Z^2$ is not z2-iv; (e) when $Z^1$ is z1-v then $Z^2$ is not z2-v or z2-vii; (f) when $Z^1$ is z1-vi then $Z^2$ is not z2-vi; (g) when $Z^1$ is z1-vii then $Z^2$ is not z2-vii or z2-v; (h) when $Z^1$ is z1-viii then $Z^2$ is not z2-viii; (i) when $Z^1$ is z1-ix then $Z^2$ is not z2-ix; and (j) when $Z^1$ is z1-x then $Z^2$ is not z2-x.

In Embodiment C are compounds of Formula I, Ia, II, III, IV, V, VI, VII, VIII, VIIIa or IX or Embodiment A or B wherein $Z^2$ is z2-i. In a class of Embodiment C are compounds wherein one of $R^{4a}$ and $R^{4b}$ is —CN and the other is $R^e$. In a sub-class thereof $R^{4a}$ is —CN.

In Embodiment D are compounds of Formula I, Ia, II, III, IV, V, VI, VII, VIII, VIIIa or IX or Embodiment A or B wherein $Z^2$ is z2-ii or z2-ix. In a class of Embodiment D are compounds wherein one of $R^{4a}$ and $R^{4b}$ is —CN and the other is $R^e$. In a sub-class thereof $R^{4a}$ is —CN.

In Embodiment E are compounds of Formula I, Ia, II, III, IV, V, VI, VII, VIII, VIIIa or IX or Embodiment A or B wherein $Z^2$ is z2-iii.

In Embodiment F are compounds of Formula I, Ia, II, III, IV, V, VI, VII, VIII, VIIIa or IX or Embodiment A or B wherein $Z^2$ is z2-iv. In a class of Embodiment F are compounds wherein $R^2$ is selected from the group consisting of —$CH_3$, —$CH_2CH_3$, cyclopropyl, —F, —H, and —$OCH_3$; and $R^d$ is selected from selected from the group consisting of —$CH_3$, —$OCH_3$ and —H. In a sub-class thereof are compounds wherein Y is —OH, $Y^1$ is —H, $R^2$ is —$CH_3$ and $R^d$ is —H.

In Embodiment G are compounds of Formula I, Ia, II, III, IV, V, VI, VII, VIII, VIIIa or IX or Embodiment A or B wherein $Z^2$ is z2-v. In a class of this embodiment are compounds of Formula I, Ia, II, III, IV, V, VI or VII wherein $Z^1$ is selected from the group consisting of z1-i, z1-ii, z1-iii, z1-iv, z1-vi, z1-viii, z1-ix and z1-x. In a sub-class thereof, X is selected from —OH and —F and particularly it is —OH. In Embodiment H are compounds of Formula I, Ia, II, III, IV, V, VI, VII, VIII, VIIIa or IX or Embodiment A or B wherein $Z^2$ is z2-vi. In a class of this embodiment are compounds of Formula I, Ia, II, III, IV, V, VI or VII wherein $Z^1$ is selected from the group consisting of z1-v, z1-vi, z1-vii and z1-viii. In another class of this embodiment are compounds wherein $Z^1$ is selected from the group consisting of z1-i, z1-ii, z1-iii, z1-iv, z1-ix and z1-x, and X is selected from —H, —OH, —$OC_{1-3}$alkyl, —F, oxo, $NH_2$ and —$CH_3$ and particularly it is —H, —OH or —F.

In Embodiment I are compounds of Formula I, Ia, II, III, IV, V, VI, VII, VIII, VIIIa or IX or Embodiment A or B wherein $Z^2$ is z2-vii. In a class of this embodiment are compounds of Formula I, Ia, II, III, IV, V, VI and VII wherein $Z^1$ is selected from the group consisting of z1-i, z1-ii, z1-iii, z1-iv, z1-vi, z1-viii, z1-ix and z1-x. In a sub-class thereof, X is selected from —OH and —F and particularly it is —OH.

In Embodiment J are compounds of Formula I, Ia, II, III, IV, V, VI, VII, VIII, VIIIa or IX or Embodiment A or B wherein $Z^2$ is z2-viii. In a class of this embodiment are compounds of Formula I, Ia, II, III, IV, V, VI or VII wherein $Z^1$ is selected from the group consisting of z1-v, z1-vi, z1-vii and z1-viii. In another class of this embodiment are compounds wherein $Z^1$ is selected from the group consisting of z1-i, z1-ii, z1-iii, z1-iv, z1-ix and z1-x, and X is selected from —H, —OH, —$OC_{1-3}$alkyl, —F, oxo, $NH_2$ and —$CH_3$ and particularly it is —H, —OH or —F.

In Embodiment K are compounds of Formula I, Ia, II, III, IV, V, VI, VII, VIII, VIIIa or IX or Embodiment A or B wherein $Z^2$ is z2-x.

In Embodiment L are compounds of Formula I, Ia, II, III, IV, V, VI or VII, or Embodiment A, B, C, D, E, F, G, H, I or J and the classes and sub-classes thereof wherein $Z^1$, if otherwise undefined, is z1-iv. In a class of Embodiment L are compounds wherein $R^1$ is selected from the group consisting of —$CH_3$, —$CH_2CH_3$, cyclopropyl, —F, —H and —$OCH_3$; and $R^c$ is selected from selected from the group consisting of —$CH_3$, —$OCH_3$ and —H. In a sub-class thereof are compounds wherein X is —OH, $X^1$ is —H, $R^1$ is —$CH_3$ and $R^c$ is —H.

In another embodiment of this invention are compounds of Formula I, Ia, II, III, IV, V, VI, VII, VIII, VIIIa, IX or X or Embodiment A, B, C, D, E, F, G, H, I, J, K or L and the classes and sub-classes thereof wherein X and Y, when either or both are present, are each independently selected from —H, —OH, —F and —CH$_3$, and provided that when none of z1-vi, z1-viii, z2-vi and z2-viii are present (that is, when neither X$^2$ nor Y$^2$ is present) in the compound, then at least one of X and Y is selected from —OH and —F. In a class thereof, at least one of X and Y is —OH and the other is selected from —H, —OH, —F and —CH$_3$. In a sub-class thereof X and Y, when either or both are present, are —OH.

In another embodiment of this invention are compounds of Formula I, II, III, IV, V, VI, VII, VIII or IX or Embodiment B, C, D, E, F, G, H, I, J, or K or L and the classes and sub-classes thereof wherein when only one of z1-vi, z1-viii, z2-vi and z2-viii is present in the compound, then X, when present, and Y, when present, are each independently selected from the group consisting of —H, —OH, —OC$_{1-3}$alkyl, —F, oxo, NH$_2$ and —CH$_3$; provided that when X is oxo then X$^1$ is absent and when Y is oxo then Y$^1$ is absent. In a class thereof, X, when present, and Y, when present, are each independently selected from —H, —OH, —F and —CH$_3$. It is noted that X or Y is present in compounds of this embodiment when one of z1-i, z1-ii, z1-iii, z1-iv, z1-ix, z1-x, z2-i, z2-ii, z2-iii, z2-iv, z2-ix or z2-x is present along with one of z1-vi, z1-viii, z2-vi or z2-viii. It is further noted that compounds wherein one of z1-v, zi-vii, z2-v or z2-vii is present along with one one of z1-vi, z1-viii, z2-vi or z2-viii are also encompassed by this embodiment.

In another embodiment of this invention are compounds of Formula I, Ia, II, III, IV, V, VI, VII, VIII or IX or Embodiment B, C, D, E, F, G, H, I, J, K or L and the classes and sub-classes thereof wherein when only one of z1-v, z1-vii, z2-v or z2-vii is present in the compound, then at least one of X, when present, or Y, when present, is independently selected from the group consisting of —OH, —OC$_{1-3}$alkyl, —F and oxo; provided that when X is oxo then X$^1$ is absent and when Y is oxo then Y$^1$ is absent. In a class thereof, one of X when present, or Y when present, is selected from —OH and —F, and more particularly it is —OH. It is noted that X or Y is present in compounds of this embodiment when one of z1-i, z1-ii, z1-iii, z1-iv, z1-ix, z1-x, z2-i, z2-ii, z2-iii, z2-iv, z2-ix or z2-x is present along with one of z1-v, z1-vii, z2-v or z2-vii. It is further noted that compounds wherein one of z1-vi, z1-viii, z2-vi or z2-viii is present along with one one of z1-v, z1-vii, z2-v or z2-vii are also encompassed by this embodiment.

In another embodiment of this invention are compounds of Formula I, Ia, II, III, IV, V, VI, VII, VIII, VIIIa, IX or X or Embodiment A, B, C, D, E, F, G, H, I, J, K or L and the classes and sub-classes thereof wherein X$^1$ and Y$^1$, when either or both are present, are each independently selected from the group consisting of —H and —CH$_3$. In a class thereof X$^1$ and Y$^1$ are both —H.

In another embodiment of this invention are compounds of Formula I, Ia, II, III, IV, V, VI, VII, VIII, VIIIa, IX or X Embodiment A, B, C, D, E, F, G, H, I, J, K or L and the classes and sub-classes thereof wherein R$^1$ and R$^2$, when either or both are present, are each independently selected from the group consisting of (a) —H, (b) —F, (c) —Cl, (d) —Br, (e) —C$_{1-3}$alkyl optionally substituted with 1-3 of —F, (f) cyclopropyl, (g) —OC$_{1-3}$alkyl optionally substituted with 1-3 of —F, and (h) —(CH$_2$)$_{1-3}$ alkyl-OH. In a sub-class thereof R$^1$ and R$^2$ are each independently selected from the group consisting of —H, —CH$_3$, —CH$_2$CH$_3$, cyclopropyl, —F and —OCH$_3$. In another sub-class, at least one of R$^1$ and R$^2$ is —CH$_3$ and the other is selected from —H and —CH$_3$. In another sub-class, R$^1$ and R$^2$ are both —CH$_3$.

In another embodiment of this invention are compounds of Formula I, Ia, II, III, IV, V, VI, VII, VIII, VIIIa, IX or X or Embodiment A, B, C, D, E, F, G, H, I, J, K or L and the classes and sub-classes thereof wherein R$^c$ and R$^d$, when either or both are present, are each independently selected from the group consisting of —H, —CH$_3$ and —OCH$_3$, and more particularly R$^c$ and R$^d$ are both —H.

In another embodiment of this invention are compounds of Formula I, Ia, II, III, IV, V, VI or VII or Embodiment A, B, C, D, E, F, G, H, I, J, K or L and the classes and sub-classes thereof wherein one of R$^{3a}$ and R$^{3b}$, when present, is —CN and the other is R$^e$. In one class thereof, R$^{3a}$ is —CN and R$^{3b}$ is R$^e$, and particularly R$^e$ is selected from the group consisting of —H, —CH$_3$—OCH$_3$ and —F and more particularly it is —H, —CH$_3$, and —OCH$_3$. In another class thereof, R$^{3b}$ is —CN and R$^{3a}$ is R$^e$, and particularly, R$^e$ is selected from the group consisting of —H, —CH$_3$, —OCH$_3$ and —F and more particularly it is —H, —CH$_3$, and —OCH$_3$.

In another embodiment of this invention are compounds of Formula I, Ia, II, III, IV, V, VI or VII or Embodiment A, B, C, D, E, F, G, H, I, J, K or L and the classes and sub-classes thereof wherein R$^a$, when present, is selected from the group consisting of —H, —CH$_3$ and —F. In a class thereof, R$^a$ is —H.

In another embodiment of this invention are compounds of Formula I, Ia, II, III, IV, V, VI, VII, VIII, VIIIa, IX or X or Embodiment A, B, C, D, E, F, G, H, I, J, K or L and the classes and sub-classes thereof wherein R$^b$, when present, is selected from the group consisting of —H, —CH$_3$ and —F. In a class thereof, R$^b$ is —H or —CH$_3$.

In another embodiment of this invention are compounds of Formula I, Ia, II, III, IV, V, VI, VII, VIII, VIIIa, IX or X or Embodiment A, B, C, D, E, F, G, H, I, J, K or L and the classes and sub-classes thereof wherein one of R$^{4a}$ and R$^{4b}$, when present, is —CN and the other is R$^f$. In one class thereof, R$^{4a}$ is —CN and R$^{4b}$ is R$^f$, and particularly R$^f$ is selected from the group consisting of —H, —CH$_3$, —OCH$_3$ and —F, and more particularly it is —H, —CH$_3$, and —OCH$_3$. In another class thereof, R$^{4b}$ is —CN and R$^{4a}$ is R$^f$, and particularly R$^f$ is selected from the group consisting of —H, —CH$_3$, —OCH$_3$ and —F, and more particularly it is —H, —CH$_3$, and —OCH$_3$.

In another embodiment of this invention are compounds of Formula I, Ia, II, III, IV, V, VI, VII, VIII or IX or Embodiment A, B, C, D, E, F, G, H, I, J, K or L and the classes and sub-classes thereof wherein R$^5$ and R$^6$ are each independently selected from the group consisting of —H and —CH$_3$. In a class thereof, R$^5$ and R$^6$ are both —H.

In another embodiment of this invention are compounds of Formula I, Ia, III or VIII, or Embodiment A, B, C, D, E, F, G, H, I, J, K or L and the classes and sub-classes thereof wherein R$^7$ is —H.

In another embodiment of this invention are compounds of Formula I, Ia, II, III, IV, V, VI, VII, VIII, VIIIa or IX or Embodiment A, B, C, D, E, F, G, H, I, J, K or L and the classes and sub-classes thereof wherein R$^8$ is independently selected at each occurrence from the group consisting of —H, —C$_{3-6}$ cycloalkyl and —C$_{1-3}$alkyl optionally substituted with 1-3 of —F. More particularly R$^8$ is selected from —H, —CH$_3$, —CF$_3$, —CHF$_2$, —CH$_2$CF$_3$ and cyclopropyl.

In another embodiment of this invention are compounds of Formula I, Ia, II, III, IV, V, VI or VII, and the classes and sub-classes thereof wherein Z$^2$ is selected from the group consisting of z2-i, z2-ii, z2-iv, z2-v and z2-vi. In a class thereof are compounds wherein Z$^2$ is selected from the group consisting of:

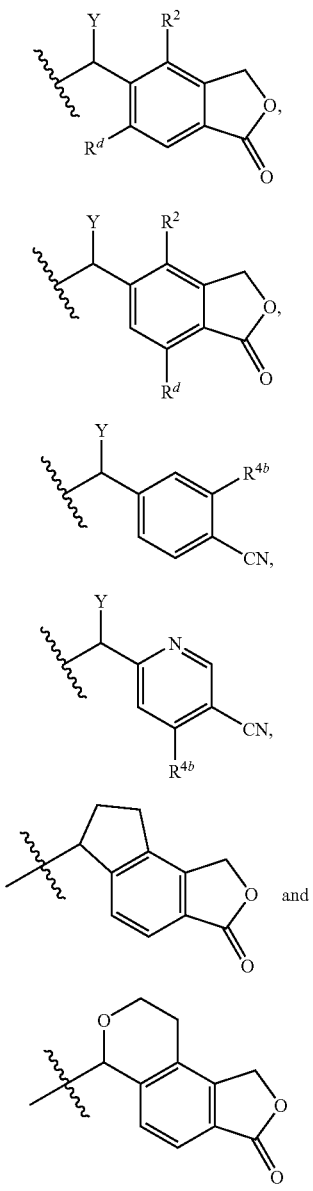

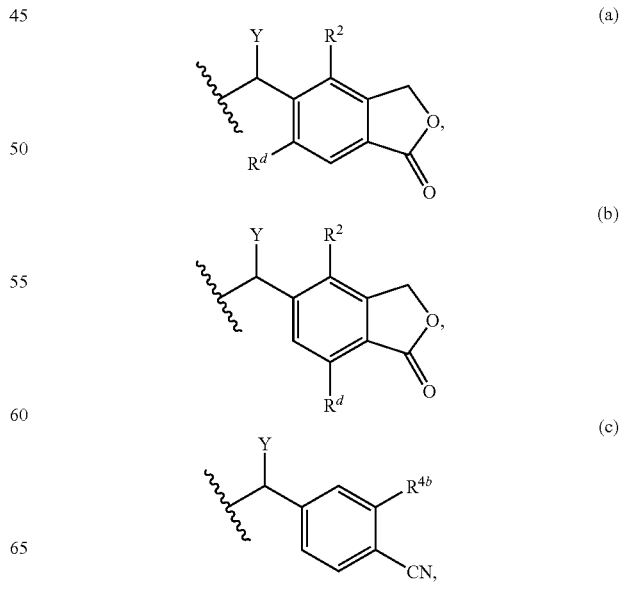

and particularly Z² is selected from (a), (b), (c) and (d), and more particularly it is (a) or (d).

In another embodiment of this invention are compounds of Formula I, Ia, II, III, IV, V, VI, VII, VIII, VIIIa or IX or Embodiment A, B, C, D, E, F, G, H, I, J, K or L and the classes and sub-classes thereof wherein the variables (e.g., X, Y, R¹ through R⁸, R$^a$ etc.), when present in each of the Formulas or Embodiments, are defined as follows:

X and Y are each independently selected from —H, —OH, —F and —CH₃ provided that at least one of X and Y is selected from —OH and —F, particularly wherein at least one of X and Y is —OH and the other is selected from —H, —OH, —F and —CH₃, and more particularly wherein X and Y are both —OH;

X¹ and Y¹ are each independently selected from the group consisting of —H and —CH₃ and particularly wherein X¹ and Y¹ are both —H;

R¹ and R² are each independently selected from the group consisting of (a) —H, (b) —F, (c) —Cl, (d) —Br, (e) —C$_{1-}$ ₃alkyl optionally substituted with 1-3 of —F, (f) cyclopropyl, (g) —OC$_{1-3}$alkyl optionally substituted with 1-3 of —F, and (h) —(CH₂)$_{1-3}$ alkyl-OH; and particularly wherein R¹ and R² are each independently selected from the group consisting of —H, —CH₃—CH₂CH₃, cyclopropyl, —F and —OCH₃, more particularly wherein R¹ and R² are each independently selected from the group consisting of —H and —CH₃, and even more particularly wherein at least one of R¹ and R² is —CH₃ and the other is selected from —H and —CH₃, and most particularly wherein R¹ and R² are both —CH₃;

one of R$^{3a}$ and R$^{3b}$ is —CN and the other is R$^e$, and particularly wherein R$^{3a}$ is —CN and R$^{3b}$ is R$^e$;

one of R$^{4a}$ and R$^{4b}$ is —CN and the other is R$^f$, and particularly wherein R$^{4a}$ is —CN and R$^{4b}$ is R$^f$;

R⁵ and R⁶ are each independently selected from the group consisting of —H and —CH₃, and particularly wherein R⁵ and R⁶ are both —H;

R⁷ is —H;

R$^a$ is selected from the group consisting of —H, —CH₃ and —F, and particularly wherein R$^a$ is —H;

R$^b$ is selected from the group consisting of —H, —CH₃ and —F, and particularly wherein R$^b$ is —H;

R$^c$ and R$^d$ are each independently selected from the group consisting of —H, —CH₃ and —OCH₃, and more particularly wherein R$^c$ and R$^d$ are both —H;

R$^e$ is selected from the group consisting of —H, —CH₃, —OCH₃ and —F and more particularly it is —H, —CH₃, and —OCH₃;

R$^f$ is selected from the group consisting of —H, —CH₃, —OCH₃ and —F and more particularly it is —H, —CH₃, and —OCH₃; and R⁸ is independently selected at each occurrence from the group consisting of —H, —C$_{3-6}$ cycloalkyl and —C$_{1-3}$alkyl optionally substituted with 1-3 of —F, and particularly wherein R⁸ is selected from —H, —CH₃, —CF₃, —CHF₂, —CH₂CF₃ and cyclopropyl.

In another embodiment of this invention are compounds of Formula VIII, VIIIa or IX wherein Z² is selected from the group consisting of z2-i, z2-ii, z2-iv, z2-v and z2-vi. In a class thereof are compounds wherein Z² is selected from the group consisting of:

-continued (d)
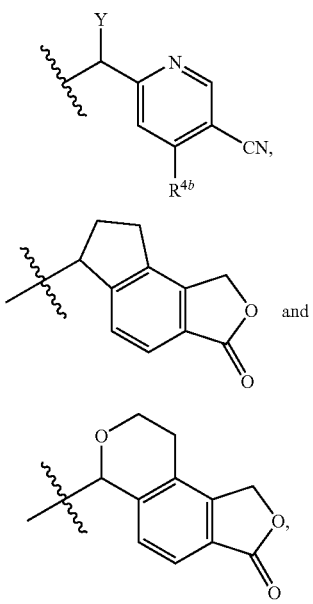
(e)

(f)

and particularly $Z^2$ is selected from (a), (b), (c) and (d) and more particularly it is (a) or (d).

In another class of Formula VIII, VIIIa or IX are compounds wherein $R^1$ is selected from the group consisting of —H, —CH$_3$, —CH$_2$CH$_3$, cyclopropyl, —F and —OCH$_3$ and more particularly it is —H or —CH$_3$. In another class of Formula VIII, VIIIa or IX are compounds wherein $R^c$ is selected from the group consisting of —H and —CH$_3$.

In another class of Formula VIII, VIIIa or IX are compounds wherein Y is selected from the group consisting of —H, —OH, —F and —CH$_3$ provided that Y is —OH or —F when X is not —OH, —OC$_{1-3}$alkyl, —F or oxo; in a sub-class thereof Y is —OH and in a different sub-class Y is —H, —F or —CH$_3$. In another class of Formula VIII, VIIIa or IX are compounds wherein $R^2$ is selected from the group consisting of —H, —CH$_3$, —CH$_2$CH$_3$, cyclopropyl, —F and —OCH$_3$, and more particularly it is —H or —CH$_3$ and even more particularly it is —CH$_3$. In another class of Formula VIII, VIIIa or IX are compounds wherein $R^d$ is selected from the group consisting of —H and —CH$_3$ and more particularly $R^d$ is —H. In another class of Formula VIII, VIIIa or IX are compounds wherein $R^{4b}$ is selected from the group consisting of —H, —CH$_3$, —OCH$_3$ and —F and more particularly it is selected from —H, —CH$_3$ and —OCH$_3$.

In a further sub-class of Formula VIII, VIIIa or IX are compounds wherein $R^1$ is selected from the group consisting of —H, —CH$_3$, —CH$_2$CH$_3$, cyclopropyl, —F and —OCH$_3$ and more particularly it is —H or —CH$_3$; $R^c$ is selected from the group consisting of —H and —CH$_3$; $Z^2$ is selected from the group consisting of (a)
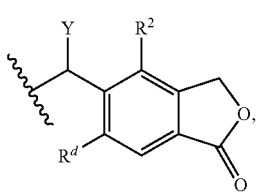

(b)
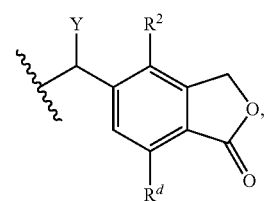

(c)
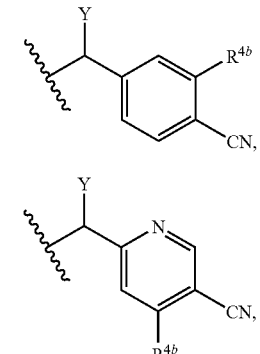

(d)

(e)
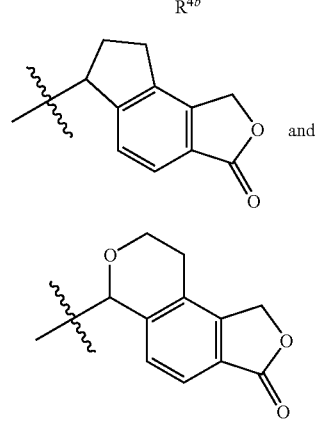

and (f)

and particularly $Z^2$ is selected from (a), (b), (c) or (d), and more particularly it is (a) or (d); Y is selected from the group consisting of —H, —OH, —F and —CH$_3$ provided that Y is —OH or —F when X is not —OH, —OC$_{1-3}$alkyl, —F or oxo; $R^2$ is selected from the group consisting of —H, —CH$_3$, —CH$_2$CH$_3$, cyclopropyl, —F and —OCH$_3$, and more particularly it is —H or —CH$_3$ and even more particularly it is —CH$_3$; $R^d$ is selected from the group consisting of —H and —CH$_3$ and more particularly $R^d$ is —H; and $R^{4b}$ is selected from the group consisting of —H, —CH$_3$, —OCH$_3$ and —F and more particularly it is selected from —H, CH$_3$ and —OCH$_3$.

As used herein except if noted otherwise, "alkyl" is intended to include both branched- and straight-chain saturated aliphatic hydrocarbon groups having the specified number of carbon atoms. Commonly used abbreviations for alkyl groups are used throughout the specification. For example the term "$C_{1-6}$ alkyl" (or "$C_1$-$C_6$ alkyl"), means linear or branched chain alkyl groups, including all isomers, having the specified number of carbon atoms and includes all of the hexyl and pentyl isomers as well as n-, iso-, sec- and tert-butyl (butyl, s-butyl, i-butyl, t-butyl; Bu=butyl), n- and i-propyl (Pr=propyl), ethyl (Et) and methyl (Me).

"Cycloalkyl" is a cyclized alkyl ring having the indicated number of carbon atoms. Examples of cycloalkyl include cyclopropyl, cyclobutyl, cyclopentyl and cyclohexyl. The cycloalkyl ring may be substituted on any available carbon which results in the creation of a stable structure, including the ring carbon which serves as the point of attachment to the rest of the molecule.

In some instances the number of substituents which may be optionally present on a moiety is specified, for example but not limited to, 1 to 3 of —F (fluoro). For example, an alkyl group that can be optionally substituted with 1-3 of —F includes, but is not limited to, —$CH_3$, —$CH_2F$, —$CHF_2$, —$CF_3$, —$CH_2CH_3$, —$CH_2$—$CH_2F$, —$CH_2$—$CHF_2$, —CHF—$CH_2F$, —$CH_2CF_3$, —CHF—$CHF_2$, —$(CH_2)_2CH_3$, —$CH(CF_3)$—$CH_3$, —$(CH_2)_3$—$CF_3$, —$(CH_2)_2CH(CF_3)$$CH_3$, and —$(CH_2)_5$—$CF_3$, as appropriate for the defined number of carbon atoms for the given alkyl group.

Halo or halogen refers to —F (fluoro), —Cl (chloro), —Br (bromo) and —I (iodo). Preferred halogens are —F and —Cl.

Unless expressly depicted or described otherwise, variables depicted in a structural formula with a "floating" bond, such as each of substituents $R^a$, $R^b$, $R^c$ and $R^d$ in structural Formula I, are permitted on any available carbon atom in the ring to which each is attached.

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

Reference to the compounds of this invention as those of a specific formula or embodiment, e.g., Formula I (which includes the compounds of Formulas II-X and all embodiments thereof) or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

When the compounds of Formula I contain one or more acidic or basic groups the invention also includes the corresponding physiologically or toxicologically acceptable salts, in particular the pharmaceutically utilizable salts. Thus, the compounds of Formula I which contain acidic groups can be used according to the invention, for example, as alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically (i.e., pharmaceutically) acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO$^-$ depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention are inhibitors of ROMK, and are therefore useful as diuretic and/or natriuretic agents. ROMK inhibitors help to increase urination and increase urine volume and also to prevent or reduce reabsorption of sodium in the kidneys leading to increased excretion of sodium and water. Therefore, the compounds are useful for treatment or prophylaxis of disorders that benefit from increased excretion of water and sodium from the body. Accordingly, an object of the instant invention is to provide a method for inhibiting ROMK comprising administering a compound of Formula I in a ROMK-inhibitory effective amount to a patient in need thereof. The inhibition of ROMK by the compounds of Formula I can be examined, for example, in any of the activity assays described below. Another object is to provide a method for causing diuresis, natriuresis or both, comprising administering a compound of Formula I in a therapeutically effective amount to a patient in need thereof.

Due to their activity as diuretics and natriuretic agents, this invention further provides the use of compounds of Formula I in methods for treatment of, prevention of or reduction of risk for developing medical conditions that benefit from increased excretion of water and sodium, such as but not limited to one or more of hypertension, heart failure (both acute and chronic, also known as congestive heart failure) and/or other conditions resulting from excessive salt and water retention. It further includes the use of the compounds of Formula I in methods for treatment of, prevention of or reduction of risk for developing one or more disorders such as pulmonary arterial hypertension (PAH), cardiovascular disease, diabetes, endothelial dysfunction, diastolic dysfunction, stable and unstable angina pectoris, thromboses, restenosis, myocardial infarction, stroke, cardiac insufficiency, pulmonary hypertonia, atherosclerosis, hepatic cirrhosis, ascites, pre-eclampsia, cerebral edema, nephropathy, nephrotic syndrome, acute and chronic kidney insufficiency, hypercalcemia, Dent's disease, Meniere's disease, edetamous states, and other conditions for which a diuretic would have therapeutic or prophylactic benefit. The compounds of the invention can be administered to a patient having, or at risk of having, one or more conditions for which a diuretic would have therapeutic or prophylactic benefit such as those described herein.

In general, compounds that are ROMK inhibitors can be identified as those compounds which, when tested, have an $IC_{50}$ of 5 µM or less, preferably 1 µM or less, and more preferably 0.25 µM or less, in at least one of the following assays: 1) the $^{86}Rb^+$ Efflux Assay, 2) the Thallium Flux Assay, 3) the Electrophysiology Assay. These assays are described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, preferably 0.001 to 30 mg/kg, in particular 0.001 to 10 mg/kg (in each case mg per kg of bodyweight) is appropriate for administration to an adult weighing approximately 75 kg in order to obtain the desired results. The daily dose is preferably administered in a single dose or, in particular when larger amounts are administered, can be divided into several, for example two, three or four individual doses, and may be, for example but not limited to, 0.1 mg, 0.25 mg, 0.5 mg, 0.75 mg, 1 mg, 1.25 mg, 2.5 mg, 5 mg, 10 mg, 20 mg, 40 mg, 50 mg, 75 mg, 100 mg, etc., on a daily basis. In some cases, depending on the individual response, it may be necessary to deviate upwards or downwards from the given daily dose. Furthermore, the compound may be formulated for immediate or modified release such as extended or controlled release.

The term "patient" includes animals, preferably mammals and especially humans, who use the instant active agents for the prohhylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment of hypertension, and a prophylactically effective amount, e.g., for prevention or reduction of risk of myocardial infarction or prevention and reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. Oral formulations are preferred, particularly solid oral dosage units such as pills, tablets or capsules.

Accordingly, this invention also provides pharmaceutical compositions comprised of a compound of Formula I and a pharmaceutically acceptable carrier. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. The carrier is comprised of one or more pharmaceutically acceptable excipients. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I and/or its pharmaceutically acceptable salts in the pharmaceutical composition may be, for example but not limited to, from 0.1 to 200 mg, preferably from 0.1 to 50 mg, per dose on a free acid/free base weight basis, but depending on the type of the pharmaceutical composition and potency of the active ingredient it could also be lower or higher. Pharmaceutical compositions usually comprise 0.5 to 90 percent by weight of the active compound on a free acid/free base weight basis.

The compounds of Formula I inhibit ROMK. On account of this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. An additional active agent (or agents) is intended to mean a pharmaceutically active agent (or agents) different from the compound of Formula I. Generally, any suitable additional active agent or agents, including but not limited to anti-hypertensive agents, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists also known as angiotensin receptor blockers or ARBs (e.g., losartan i.e., COZAAR®, valsartan, candesartan, olmesartan, telmisartan and any of these drugs used in combination with hydrochlorothiazide such as HYZ-AAR®), neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, vasodilators (e.g. nitroprusside), calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., HMG-CoA reductase inhibitors such as simvastatin, lovastatin, pravastatin, atorvastatin and rosuvastatin, and cholesterol absorption inhibitors such as ezetimibe); niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors (e.g., sitagliptin, saxagliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide.

Several methods for preparing the compounds of this invention are described in the following Schemes and Examples. Starting materials and intermediates are purchased, made from known procedures, or as otherwise illustrated. The Ar group shown in the below schemes can represent any of the substituted aromatic or substituted heterocyclic groups found in $Z^1$ or $Z^2$ as defined previously.

The preparation of the compounds I1, I2, and I3 is detailed in Scheme 1. Treatment of the electrophile 1-2 (such as bromide, iodide, mesylate, or tosylate) with 1-Boc Piperazine 1-1 under basic conditions (such as in the presence of triethylamine) affords the alkylation adduct 1-3. The Boc protecting group (Greene, T.; Wuts, P. G. M. *protective Groups in Organic Synthesis*, John Wiley and Sons, Inc., New York, N.Y. 1991) of 1-3 can be removed under acidic conditions, such as with TFA or HCl. Alternatively, the piperazine may be protected with another protecting group such as Cbz, and subsequently removed by hydrogenolysis. Subsequent alkylation of 1-4 with bromo-ketone 1-5 (the Ar—CO group represents an example of $Z^1$) in the presence of a base such as triethylamine gives rise to compounds H. The benzylic carbonyl of I1 can be reduced to the corresponding alcohol with standard reducing agents such as sodium borohydride to yield I2 (the Ar—CHOH— group represents an example of $Z^1$). Compound I2 can be converted to I3 (the Ar—CHF— group represents an example of $Z^1$) by treating with fluorination agents such as DAST (Hudlicky, M. Organic Reactions, 1988, 35).

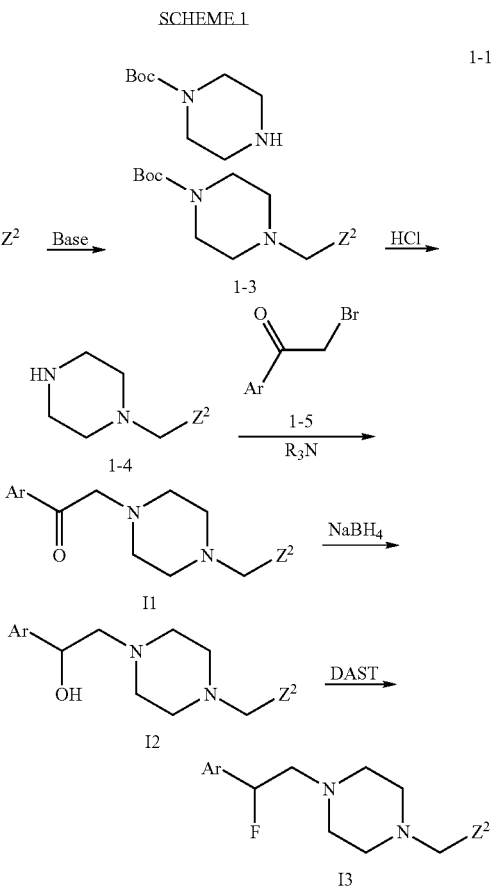

More generally, compounds of formula I2 can also be prepared by the sequence detailed in Scheme 2. Treating epoxides 2-1 with commercial 1-Boc Piperazine at elevated temperatures gives rise to alcohol 2-2 (Nomura, Y. et al. Chemical & Pharmaceutical Bulletin, 1995, 43(2), 241-6). Alternatively, the piperazine may be protected with another protecting group such as Cbz. The Ar—CHOH— group in 2-2 represents an example of $Z^1$. The Boc group can be removed under acidic conditions such as with TFA or HCl to afford piperazine 2-3 (if the piperazine is protected with a Cbz protecting group, then that group is removed using hydrogen and a catalyst such as Pd/C). The coupling of 2-3 and 2-4 can be achieved either by alkylation under basic conditions where 2-4 is an electrophile where A is bromide, iodide, mesylate, or tosylate, or by standard reductive amination conditions where 2-4 is an aldehyde with A being a carbonyl oxygen (for example using sodium borohydride or sodium triacetoxy borohydride).

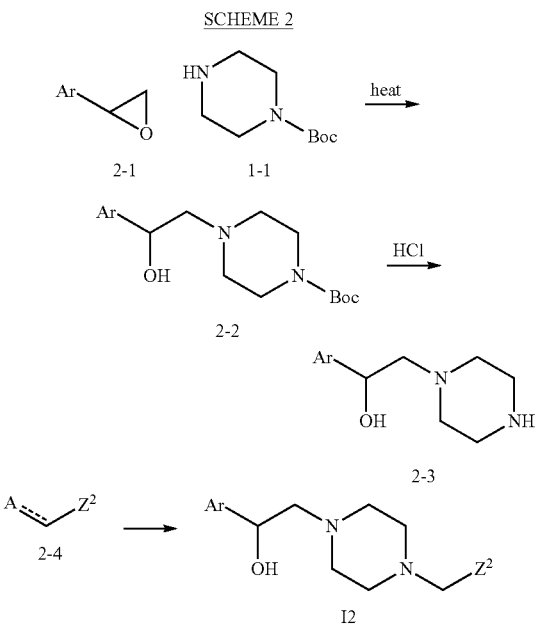

Compounds of formula I3 can also be prepared from alcohol 2-2 previously described in Scheme 2 (Scheme 3). Treatment of alcohol 2-2 with a fluorinating reagent such as DAST gives rise to fluoride 3-1 (Hudlicky, M. Organic Reactions, 1988, 35). The Ar—CHF— group in 3-1 represents an example of $Z^1$. The Boc group can be removed under acidic conditions to afford piperazine 3-2, which can then be coupled to 2-4 via either alkylation or reductive amination reaction conditions described above in Scheme 2.

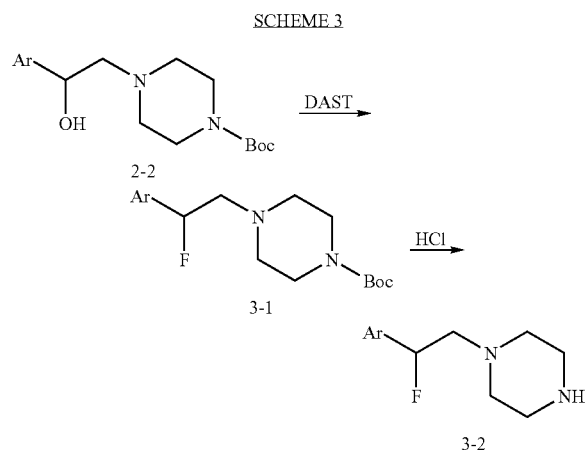

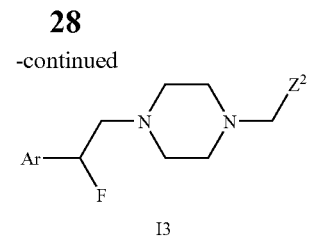

The epoxides 2-1 can be prepared following the method detailed in Scheme 4A. Treatment of 4-1 (where $A^2$ is bromide, iodide, or trifluoromethane sulfonate) with commercially available potassium vinyl trifluoroborate 4-2 (Molander, G.; Luciana, A. Journal of Organic Chemistry, 2005, 70(10), 3950-3956) under palladium catalyzed coupling conditions with an appropriate phosphine ligand gives rise to styrene 4-3 (Molander, G.; Brown, A. Journal of Organic Chemistry, 2006, 71(26), 9681-9686). The olefins can be converted to the corresponding epoxides 2-1 under standard epoxidation conditions with, for example, m-CPBA (Fringuelli, F. et al. Organic Preparations and Procedures International, 1989, 21(6), 757-761). If the Ar group contains a heterocyle that is not compatible with use of m-CPBA, then a two step sequence involving formation of a bromohydrin intermediate with, for example, $Br_2$/water, followed by epoxide formation with base (for example $Na_2CO_3$) can be substituted. The racemic epoxide can be resolved under chiral HPLC chromatography conditions to afford its enantiomers, which can be used in place of 2-1 according to Scheme 2.

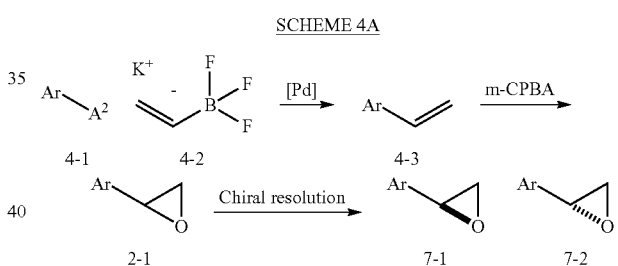

Alternatively, enantiopure epoxides 7-1 or 7-2 can be prepared as shown in Scheme 4B. Treatment of 4-1 (where $A^2$ is bromide, iodide, or trifluoromethane sulfonate) with commercial available vinyl butylether 4-2b under palladium catalyzed conditions with a suitable ligand (for example $Pd(OAc)_2$, DPPP) can provide the enol ethers 4-3b. Treatment with NBS or other similar reagents affords the corresponding bromomethyl ketones 4-4b. These can be subjected to a variety of asymmetric ketone reduction conditions, for example with an enzyme that can affect such a transformation with high enantioselectivity. Subsequent treatment with a base such as triethylamine leads to cyclization, affording the enantioenriched epoxides 7-2 (or depending upon the asymmetric reducing agent 7-1).

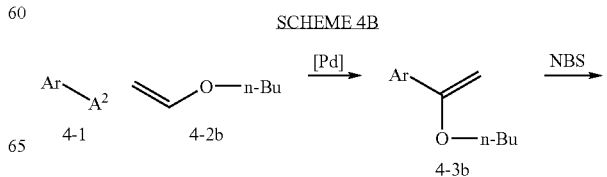

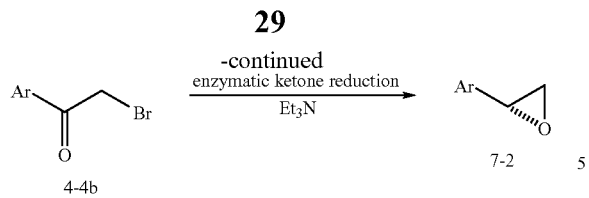
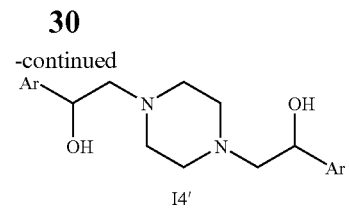

Compound I4, which is substituted at both benzylic positions with an OH group, can be prepared following the sequence detailed in Scheme 5. Coupling of epoxide 2-1 to commercial 1-Boc piperazine 1-1 at elevated temperatures leads to the formation of alcohol 2-2. Alternatively, 1-Cbz piperazine may be used in place of the 1-Boc piperazine 1-1. The Ar—CHOH— group in 2-2 represents an example of $Z^1$. Removal of the Boc group of 2-2 under acidic conditions, such as with HCl or TFA, gives 2-3 (if the protecting group on the piperazine was Cbz, then it can be removed using, for example, hydrogen and a catalyst such as Pd/C). It is often helpful for the success of the subsequent epoxide opening reaction to convert 2-3 to its free base form by washing with an aqueous base solution. The free base form of 2-3 can then be coupled to the right hand epoxide, which is prepared in similar manners as described in Scheme 4, to afford compound I4. The Ar'—CHOH— group in 2-2 represents an example of $Z^2$.

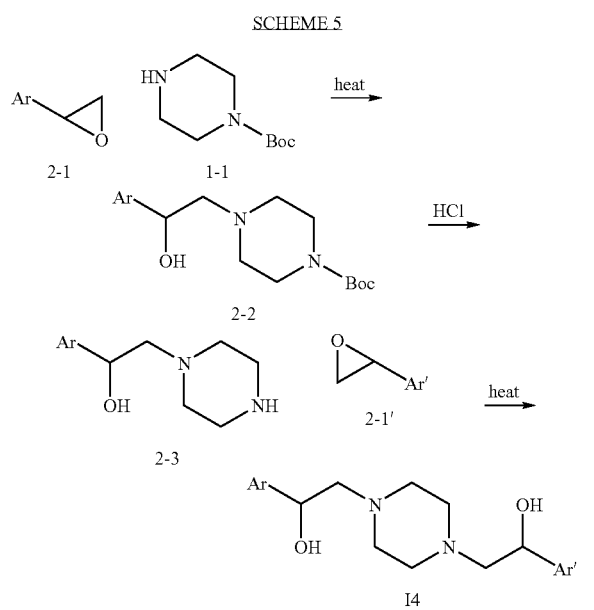

Compounds of this class bearing the same aromatic substitution patterns ($Z^1$ is the same as $Z^2$) can be prepared in one step by treating the epoxide 2-1 with piperazine at elevated temperatures in solvents such as ethanol or DMSO (Scheme 6). The Ar—CHOH— groups in I4' represent examples of either $Z^1$ or $Z^2$.

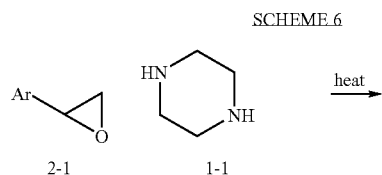

The stereochemistry of the epoxide is conserved during the ring-opening reaction. Thus, reacting enantio-pure epoxide with piperazine at elevated temperatures gives rise to (R,R) or (S,S) isomer of I4' (Scheme 7). The (R,S)-meso isomer of I4' can be prepared in a step-wise epoxide-opening sequence with the two enantiomers of the epoxide (Scheme 7). The Ar—CHOH— groups in I4' represent examples of either $Z^1$ or $Z^2$.

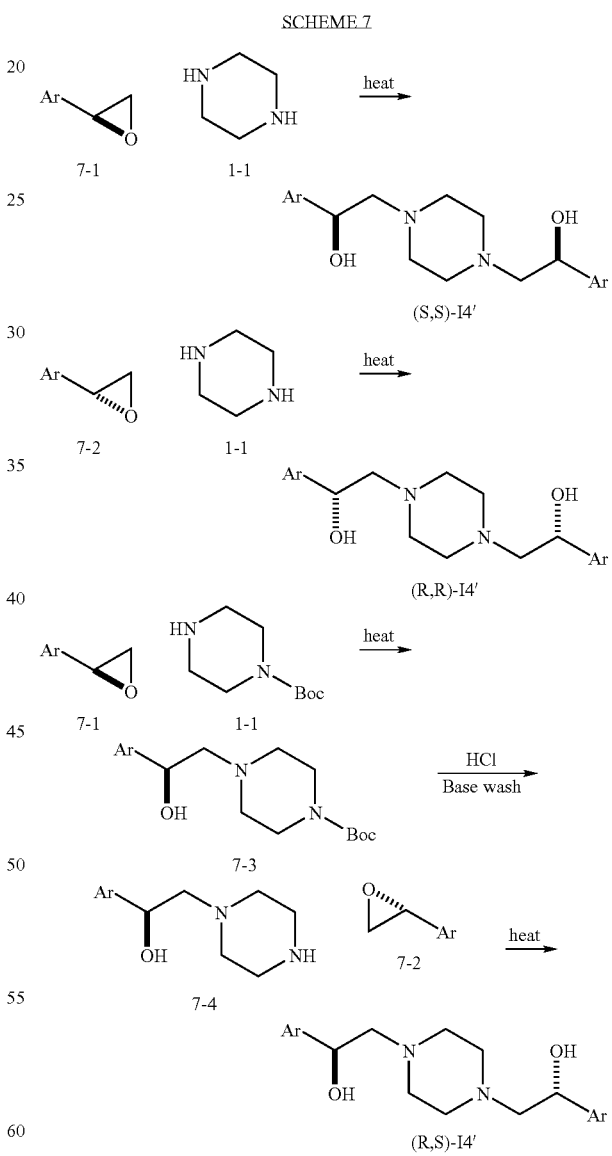

Compound I5, which is substituted at both benzylic positions with a fluorine atom, can be prepared by treating compound I4 with fluorinating reagents such as DAST in one step (Scheme 8). The Ar—CHF— groups in I4' represent examples of either $Z^1$ or $Z^2$.

SCHEME 8

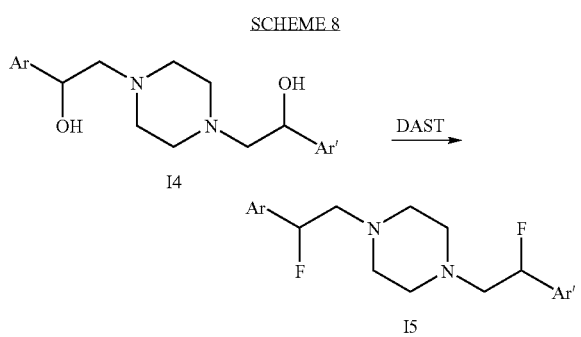

The preparation of compounds I6 can be achieved following the sequence detailed in Scheme 9. Treating epoxide 2-1 with commercially available 1-Boc piperazine at elevated temperatures gives rise to alcohol 2-2 (Nomura, Y. et al. Chemical & Pharmaceutical Bulletin, 1995, 43(2), 241-6). The hydroxyl group of 2-2 can be converted to the fluoride by treatment of such fluorinating reagent as DAST (Hudlicky, M. Organic Reactions, 1988, 35). Removal of the Boc group of 3-1 under acidic conditions such as TFA gives rise to piperazine 3-2. Piperazine 3-2 can be washed with an aqueous base solution followed by extraction with organic solvents to generate the free base form. The free base of 3-2 can be coupled to epoxide 5-1 at elevated temperatures to afford compound I6. The Ar—CHF— and Ar'—CHOH— groups in I6 represent examples of either $Z^1$ or $Z^2$.

SCHEME 9

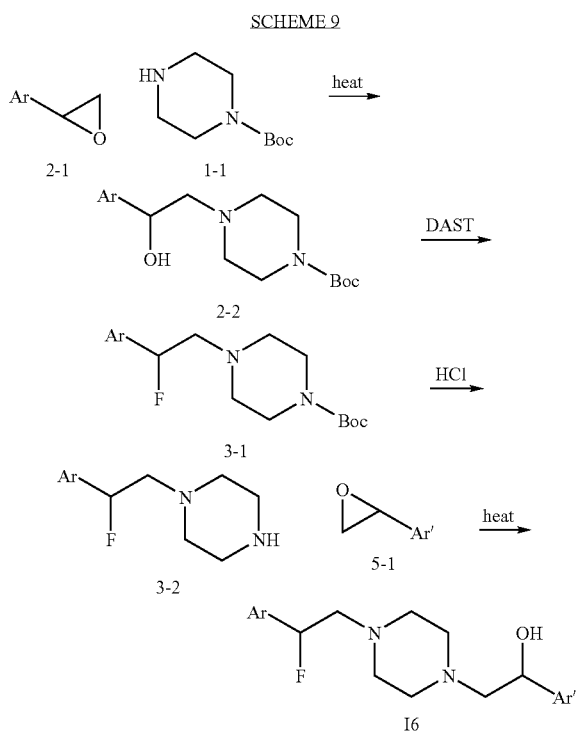

General Procedures.

Reactions sensitive to moisture or air were performed under nitrogen or argon using anhydrous solvents and reagents. The progress of reactions was determined by either analytical thin layer chromatography (TLC) usually performed with E. Merck precoated TLC plates, silica gel 60F-254, layer thickness 0.25 mm or liquid chromatography-mass spectrometry (LC-MS). Typically the analytical LC-MS system used consisted of a Waters ZQ platform with electrospray ionization in positive ion detection mode with an Agilent 1100 series HPLC with autosampler. The column was usually a Water Xterra MS C18, 3.0×50 mm, 5 µm. The flow rate was 1 mL/min, and the injection volume was 10 µL. UV detection was in the range 210-400 nm. The mobile phase consisted of solvent A (water plus 0.06% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min. Preparative HPLC purifications were usually performed using a mass spectrometry directed system. Usually they were performed on a Waters Chromatography Workstation configured with LC-MS System Consisting of: Waters ZQ single quad MS system with Electrospray Ionization, Waters 2525 Gradient Pump, Waters 2767 Injector/Collector, Waters 996 PDA Detector, the MS Conditions of: 150-750 amu, Positive Electrospray, Collection Triggered by MS, and a Waters Sunfire C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 µL, and the UV detection range was 210-400 nm. Mobile phase gradients were optimized for the individual compounds.

Reactions performed using microwave irradiation were normally carried out using an Emrys Optimizer manufactured by Personal Chemistry, or an Initiator manufactured by Biotage. Concentration of solutions was carried out on a rotary evaporator under reduced pressure. Flash chromatography was usually performed using a Biotage Flash Chromatography apparatus (Dyax Corp.) on silica gel (32-63 mM, 60 Å pore size) in pre-packed cartridges of the size noted. $^1$H NMR spectra were acquired at 500 MHz spectrometers in CDCl$_3$ solutions unless otherwise noted. Chemical shifts were reported in parts per million (ppm). Tetramethylsilane (TMS) was used as internal reference in CD$_3$Cl solutions, and residual CH$_3$OH peak or TMS was used as internal reference in CD$_3$OD solutions. Coupling constants (J) were reported in hertz (Hz). Chiral analytical chromatography was usually performed on one of Chiralpak AS, Chiralpak AD, Chiralcel OD, Chiralcel IA, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was usually conducted on one of Chiralpak AS, Chiralpak AD, Chiralcel OD, Chiralcel IA, or Chiralcel OJ columns (20×250 mm) (Daicel Chemical Industries, Ltd.) with desired isocratic solvent systems identified on chiral analytical chromatography or by supercritical fluid (SFC) conditions. Where retention times are provided, they are not intended to be a definitive characteristic of a particular compound, since retention times will vary depending on the chromatographic conditions and equipment used.

Aside from where crystal product is noted in Example 3B (Method 2), terminology referencing the process of crystallization, crystals or the like in the Intermediates and Examples section is used to describe the process and product resulting from precipitating a solid product from solution and does not necessarily mean that the precipitated solid was determined to be in a crystalline physical form.

Abbreviations used herein include: —C(O)CH$_3$ (Ac); acetic acid (AcOH); —OC(O)CH$_3$ (OAc); aqueous (aq); Cbz (benzyloxycarbonyl); N;N-diisopropylethylamine (DIEA); diethylamine (DEA); N;N-dimethylformamide (DMF); ethyl acetate (EtOAc); diethyl ether (ether or Et$_2$O); petroleum ether (PE); gram(s) (g); hour(s) (h or hr); 2-propanol (IPA); iso-butyl alcohol (IBA); mass spectrum (ms or MS); microliter(s) (μL); milligram(s) (mg); milliliter(s) (mL); millimole (mmol); minute(s) (min); methyl t-butylether (MTBE); (benzotriazol-1-yloxy)tripyrrolidino-phosphonium hexafluorophosphate (PyBOP); retention time ($t_R$); room temperature (rt or RT); saturated aq sodium chloride solution (brine); trifluoroacetic acid (TFA); tetrahydrofuran (THF); flash chromatography (FC); liquid chromatography (LC); liquid chromatography-mass spectrometry (LCMS or LC-MS); supercritical fluid chromatography (SFC); t-butyloxycarbonyl (Boc or BOC); Diethylaminosulfur trifluoride (DAST); dichloromethane (DCM); dimethylacetamide (DMA; DMAC); dimethylsulfoxide (DMSO); 1,3-Bis(diphenylphosphino)propane (DPPP); acetic acid (HOAc); 3-chloroperoxybenzoic acid (m-CPBA); methyl (Me); methanol (MeOH); N-bromosuccinamide (NBS); thin layer chromatography (TLC); diisobutylaluminum hydride (DIBAL-H); Tmax (maximum temperature); nicotinamide adenine dinucleotide phosphate (NADP).

The following are representative procedures for the preparation of the compounds used in the following Examples, or which can be substituted for the compounds used in the following Examples which may not be commercially available.

INTERMEDIATE 1

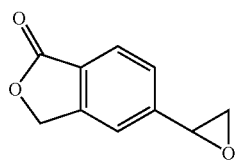

5-Oxirane-2-yl-2-benzofuran-1(3H)-one

Step A: 5-allyl-2-benzofuran-1(3H)-one

A 4-neck, 22-L, round bottom flask equipped with a mechanical stirrer, thermocouple, nitrogen bubbler, and condenser was charged with 5-bromophthalide (650 g, 3.0 mol), allyltri-n-butyltin (1200 g, 3.6 mol), palladium tetrakis triphenylphosphine (100 g, 0.089 mol), lithium chloride (250 g, 5.9 mol) and toluene (8.8 L). The mixture was evacuated and flushed with nitrogen 3 times and then was stirred at 100° C. for 4 hours. After slowly cooling to ambient temperature, the mixture was filtered and concentrated. The resulting solid was purified by silica gel column chromatography (heptane: ethyl acetate, 0→40%) to provide 5-allyl-2-benzofuran-1 (3H)-one. $^1$H NMR (500 MHz, CD$_3$OD) δ 7.83 (d, J=8.0 Hz, 1H), 7.38 (d, J=8.0 Hz, 1H), 7.33 (s, 1H), 5.98 (m, 1H), 5.29 (s, 2H), 5.11-5.18 (m, 2H), 3.52 (d, J=8.2 Hz, 2H); LC/MS: [(M+1)]$^+$=175.1; $t_R$=2.9 min.

Step B: 5-(2-hydroxyethyl)-2-benzofuran-1(3H)-one 5-allyl-2-benzofuran-1(3H)-one (1.53 g, 8.78 mmol) was dissolved in methanol (30 mL). THF was added to solubilize the starting material. The resulting mixture was cooled in a dry ice acetone bath (−78° C.) and ozone was bubbled into the reaction until the color of the mixture changed to orange. Nitrogen was bubbled into the reaction for one minute to remove the excess ozone. Sodium borohydride (0.65 g, 2.9 mmol) was added at −78° C., and the reaction mixture was allowed to warm to ambient temperature. The reaction mixture was concentrated part way and then taken up in ethyl acetate and water. The layers were separated and the organic layer was washed with brine, dried over magnesium sulfate, filtered, and concentrated to provide 5-(2-hydroxyethyl)-2-benzofuran-1(3H)-one.

$^1$H NMR (500 MHz, CD$_3$OD) δ 7.77 (m, 1H), 7.37-7.41 (m, 2H), 5.23 (s, 2H), 3.92 (m, 2H), 2.99 (m, 2H); LC/MS: [(M+1)]$^+$=179.1; $t_R$=1.4 min.

Step C: 5-Oxirane-2-yl-2-benzofuran-1(3H)-one

To a solution of 5-(2-hydroxyethyl)-2-benzofuran-1(3H)-one (0.50 g, 2.8 mmol) and Et$_3$N (0.65 ml, 4.7 mmol) in dichloromethane (5 ml) was added methanesulfonyl chloride (0.24 mL, 3.1 mmol) at 0° C. After 15 min. the reaction mixture was poured into saturated ammonium chloride and extracted with dichloromethane. The combined organics were washed with 1 N HCl, saturated sodium bicarbonate solution, and brine, then dried (MgSO$_4$) and concentrated in vacuo. The residue (LC/MS: [(M+1)]$^+$=257.2; $t_R$=0.45 min) was redissolved in dichloromethane (5 ml) and treated with DBU (0.80 ml, 5.3 mmol) and stirred 2 h. TLC monitoring showed conversion to the olefin. The reaction mixture was diluted with water and extracted with dichloromethane. The combined organics were washed with 1 N HCl, saturated sodium bicarbonate solution, and brine, then dried (MgSO$_4$) and concentrated in vacuo. The resulting olefin (LC/MS: [(M+1)]$^+$=161.2; $t_R$=0.86 min) was dissolved in dichloromethane (5 ml) and treated with meta-chloro perbenzoic acid (0.90 g, 3.7 mmol) at 0° C. After 3 h, the mixture was diluted with saturated sodium bicarbonate solution and extracted twice with dichloromethane. The combined organic extracts were washed with brine, dried (MgSO$_4$), filtered and concentrated in vacuo. The crude epoxide was purified by silica gel column chromatography (5→80% EtOAc:hexane) to provide the 5-oxirane-2-yl-2-benzofuran-1 (3H)-one.

$^1$H NMR (500 MHz, CD$_3$OD) δ 7.84 (d, J=8.0 Hz, 1H), 7.55 (s, 1H), 7.52 (d, J=8.0 Hz, 1H), 5.38 (s, 2H), 4.05 (dd, J=2.6, 3.9 Hz, 1H), 3.21 (dd, J=4.3, 5.4 Hz, 1H), 2.82 (dd, J=2.4, 5.5 Hz, 1H); LC/MS: [(M+1)]$^+$=177.1; $t_R$=0.32 min.

INTERMEDIATE 2

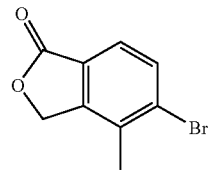

5-bromo-4-methyl-2-benzofuran-1(3H)-one

Step A: (3-bromo-2-methylphenyl)methanol

To a solution of 3-bromo-2-methyl benzoic acid (35 g, 163 mmol) in THF (200 mL) was added Borane THF Complex (1.0 M, 212 mL, 212 mmol). The mixture was allowed to stir for 24 h. TLC showed one single product spot. The reaction was quenched with water. The solvent THF was removed under reduced pressure. The resulting solid was dissolved in ethyl acetate (500 mL), washed with 1N HCl, sodium carbonate, and brine. The organic layer was dried over sodium sulfate and concentrated to afford (3-bromo-2-methylphenyl) methanol.

$^1$H NMR (500 MHz, CDCl$_3$) δ 7.76 (d, J=8.0 Hz, 1H), 7.63 (d, J=8.0 Hz, 1H), 5.30 (s, 2H), 2.42 (s, 3H).

Step B: 5-bromo-4-methyl-2-benzofuran-1(3H)-one

To a flask charged with (3-bromo-2-methylphenyl)methanol (6.0 g, 30 mmol) was added a 1M TFA solution of Thallium Trifluoroacetate (16.2 g, 29.8 mmol). The mixture was stirred at RT overnight. Analysis by TLC showed no starting material remaining. The solvent was removed under vacuum, and the residue was pumped under high vacuum for 30 min to ensure complete removal of TFA. To the residue was then added Palladium(II) Chloride (529 mg, 2.98 mmol), Lithium Chloride (2.53 g, 59.7 mmol), Magnesium Oxide (2.41 g, 59.7 mmol), and MeOH (150 mL). The reaction was flushed with CO twice, and kept under CO at room temperature. Analysis by LC showed a big product spot within 2 hours. To this solution was added ethyl acetate to precipitate the salts. The black solution was filtered through a celite pad, washed with EtOAc, adsorbed onto silica and purified by silica gel chromatography to afford 5-bromo-4-methyl-2-benzofuran-1(3H)-one.

$^1$H-NMR (500 MHz, CDCl$_3$) δ ppm 7.71 (d, J=8.0 Hz, 1H), 7.58 (d, J=8.0 Hz, 1H), 5.25 (s, 2H), 2.37 (s, 3H).

INTERMEDIATE 3

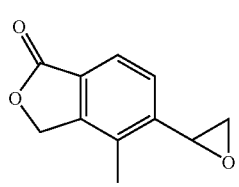

4-methyl-5-oxiran-2-yl-2-benzofuran-1(3H)-one

Step A: 5-ethenyl-4-methyl-2-benzofuran-1(3H)-one

5-Bromo-4-methyl-2-benzofuran-1(3H)-one (598 mg, 4.47 mmol), potassium vinyl trifluoroborate (507 mg, 2.23 mmmol), PdCl$_2$(dppf)-CH$_2$Cl$_2$Adduct (182 mg, 0.223 mmmol), and TEA (0.622 mL, 4.47 mmol) were added to 10 mL ethanol in a 20 mL microwave tube. The tube was sealed and degassed, then heated to 140° C. for 20 min. Analysis by LC-MS showed product peak. The reaction mixture was diluted with ethyl acetate, washed with brine twice, dried and evaporated to dryness. The crude product was purified by MPLC chromatography using a 120 g Redi-sep column and 0-80% ETOAC/Hexane solvent system to yield 5-ethenyl-4-methyl-2-benzofuran-1(3H)-one. $^1$H-NMR (500 MHz, CDCl$_3$): δ ppm 7.76 (d, J=8 Hz, 1H), 7.03 (dd, J=11, 17 Hz, 1H), 5.84 (d, J=17 Hz, 1H), 5.55 (d, J=11 Hz, 1H), 5.29 (s, 2H), 2.34 (s, 3H). LC-MS: M+1=175; t$_R$=2.42 min

Step B: 4-methyl-5-oxiran-2-yl-2-benzofuran-1(3H)-one 5-ethenyl-4-methyl-2-benzofuran-1(3H)-one (1.46 g, 8.38 mmol) was added to DCM (25 mL) at 0° C. then mCPBA (2.89 g, 16.8 mmol) was added and the mixture was stirred at RT overnight. The reaction mixture was washed once each with saturated aqueous Na$_2$S$_2$O$_3$, NaHCO$_3$, and brine. The organic layer was dried over Na$_2$SO$_4$, filtered, and evaporated to dryness. The crude material was purified by MPLC chromatography through 120 g Redi-sep column eluting with 0-80% EtOAc/hexane solvent system to yield target 4-methyl-5-oxiran-2-yl-2-benzofuran-1(3H)-one. $^1$H-NMR (500 MHz, CDCl$_3$): δ ppm 7.77 (d, J=8 Hz, 1H), 7.43 (d, J=8 Hz, 1H), 5.30 (s, 2H), 4.12 (s, 1H), 3.27 (t, J=4 Hz, 1H), 2.735 (dd, J=2.2, 5.5 Hz, 1H), 2.43 (s, 3H).

LC-MS: M+1=191; t$_R$=2.2 min.

(Method 1)

INTERMEDIATES 3A AND 3B

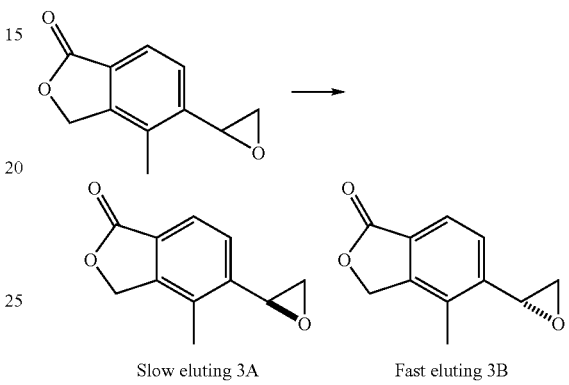

Slow eluting 3A    Fast eluting 3B

3A: 4-methyl-5-[(2S)-oxiran-2-yl]-2-benzofuran-1(3H)-one

3B: 4-methyl-5-[(2R)-oxiran-2-yl]-2-benzofuran-1(3H)-one

Racemic 4-methyl-5-oxiran-2-yl-2-benzofuran-1(3H)-one was resolved on a ChiralPak® AD-H column (5×25 cm) under supercritical fluid chromatography (SFC) conditions on a Berger MGIII preparative SFC instrument. The racemate was diluted to 50 mg/ml in 1:1 DCM:MeOH. The separation was accomplished using 10% EtOH/CO2, flow rate 200 ml/min, 100 bar, 25° C. 500 ul Injections were spaced every 2.12 mins. The fast epoxide (4-methyl-5-[(2R)-oxiran-2-yl]-2-benzofuran-1(3H)-one, 3B) eluted at 5.2 min, and the slow epoxide (4-methyl-5-[(2S)-oxiran-2-yl]-2-benzofuran-1(3H)-one, 3A) eluted at 5.6 min.

Alternatively, the resolution could also be achieved using a mobile phase of 8% MeOH/98% CO$_2$ with a flow rate of 100 ml/min. In that case the sample was prepared by dissolving in methanol, 20 mg/ml, and using a 1 mL volume per injection. After separation, the fractions were dried off via rotary evaporator at bath temperature 40° C.

The absolute stereochemistry of each enantiomer was inferred based on the X-ray crystal structure determination of a final compound made with 3B (EXAMPLE 2A), and by Mosher ester and Trost ester HNMR analysis of esters made starting from 3B (used tert-butyl-4-[(2R-2-hydroxy-2-(4-methyl-1-oxo-1,3-dihydro-2-benzofuran-5-yl) ethyl}piperazine-1-carboxylate, prepared as described in the synthesis of INTERMEDIATE (R)-8). Both epoxide isomers find utility in the present invention.

INTERMEDIATE 3B

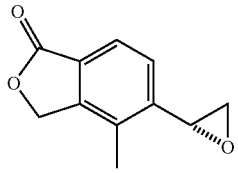

4-methyl-5-[(2R)-oxiran-2-yl]-2-benzofuran-1(3H)-one

Step A: 3-hydroxymethyl-2-methyl phenol

To a 5 L 3 neck RB equipped with overhead stirrer was charged NaBH4 (87.0 g, 2.30 mol) and THF (3.0 L) and the resulting slurry was cooled to 10° C. To the slurry was then added 3-hydroxy-2-methyl benzoic acid (175 g, 1.15 mol) portionwise over 20 min (Tmax 17° C.). A stirrable slurry formed, and was aged for an additional 45 min at 10-15° C. after which $BF_3$—$OEt_2$ (321 mL, 2.53 mol) was added slowly over 1.5 hours. The slurry was aged at 10° C.-15° C. for 2 h then assayed for reaction completion (98.5% conversion). The slurry was cooled to <10° C. and quenched with 931 mL MeOH slowly over 1.5 h (gas evolution). The resulting slurry was aged overnight at RT. The batch was cooled to <10° C. then quenched with 1 N HCl (1.5 L) to get a homogeneous solution (pH solution ~1), which was aged for 30 min and then the organic solvents were removed by rotary evaporation to approximately 1.8 L of total reaction volume (bath temperature was set to 50° C.; internal temp of concentrate after rotary evaporation was ~40° C.). The slurry was held at 45° C. for 30 min then cooled slowly to 15° C. The solids were filtered and washed with cold (15° C.) water (2×300 mL), providing 3-hydroxymethyl-2-methyl phenol.

$^1$H-NMR (400 MHz, DMSO-$d_6$): δ 9.11 (s, 1H), 6.95 (t, J=7.8 Hz, 1H), 6.82 (d, J=7.4 Hz, 1H), 6.71 (d, J=7.8 Hz, 1H), 4.93 (t, J=5.5 Hz, 1H), 4.44 (d, J=5.5 Hz, 2H), 2.06 (s, 3H).

Step B: 4-Bromo-3-hydroxymethyl-2-methyl phenol

3-Hydroxymethyl-2-methyl phenol (113.9 g, 824.0 mmol) was dissolved in a mixture of acetonitrile (850 mL) and trifluoroacetic acid (750.0 mL, 9,735 mmol) in a 3-neck 5-L flask under nitrogen. The reaction mixture was cooled to –33° C. N-bromosuccinimide (141 g, 791 mmol) was added over 15 minutes, with the temperature during addition in the range of –35 to –33° C. The reaction mixture was allowed to stir for an additional 15 min during which time the temperature decreased to –40° C. The cooling bath was removed, and potassium carbonate (741.0 g, 5,358 mmol) diluted with water to a total of 1.0 L was added. Off-gassing was observed, and the temperature increased to 25° C. MTBE (1.5 L) was added, and the reaction mixture was transferred to a separatory funnel. The layers were separated. The aqueous layer was diluted with water (500 mL) and extracted with MTBE (1 L)+EtOAc (500 mL), and then MTBE (500 mL)+EtOAc (250 mL). The combined organic layers were washed with water (240 mL) and dried over sodium sulfate. The sodium sulfate was removed by filtration, washed with additional MTBE and concentrated under reduced pressure. MTBE (684 mL, 2 volumes) was added, and the suspension was heated to 40° C. to produce a homogeneous solution. The solution was allowed to cool to room temperature. Six volumes of heptane were added, and the suspension was stirred overnight. The suspension was filtered, and the crystals were washed with 4:1 heptane:MTBE (500 mL), followed by heptane (500 mL). The solid was dried under vacuum, providing 4-bromo-3-hydroxymethyl-2-methyl phenol.

$^1$H NMR (400 MHz, DMSO-$d_6$): δ 9.52 (s, 1H), 7.21 (d, J=8.6 Hz, 1H), 6.71 (d, J=8.6 Hz, 1H), 4.88 (t, J=5.1 Hz, 1H), 4.59 (d, J=5.1 Hz, 2H), 2.23 (s, 3H)

Step C:
5-Hydroxy-4-methyl-3H-isobenzofuran-1-one

To a 2 L 3 neck flask equipped with overhead stirrer, $N_2$ inlet, and condenser were charged 4-bromo-3-hydroxymethyl-2-methyl phenol (100 g, 461 mmol), CuCN (83.0 g, 921 mmol), and DMF (500 mL). The solution was sparged with $N_2$ for 15 min then heated to 145° C. to obtain a homogeneous solution. The solution was aged at 145° C. for 2 h, then the reaction mixture was cooled to 95° C. 41.5 mL water was added (sparged with $N_2$), and the reaction aged for 20 h. The reaction was cooled to RT then the solids filtered through solka flok and the cake washed with 50 mL DMF. To a 3 L flask containing 1 L EtOAc was added the DMF filtrate. A precipitate coating formed in bottom of flask. The DMF/EtOAc suspension was filtered through solka flok and the cake was washed with 250 mL EtOAc. The resulting filtrate was washed with 5% brine solution (3×500 mL). The aqueous layers were extracted with 500 mL EtOAc and the combined organics were dried over MgSO4, filtered and evaporated. The solids were slurried in 250 mL MTBE at RT then filtered and washed with 100 mL MTBE. The solids were dried under vacuum at RT, providing 5-hydroxy-4-methyl-3H-isobenzofuran-1-one.

$^1$H NMR (400 MHz, DMSO-$d_6$): δ 10.52 (s, 1H), 7.51 (d, J=8.3 Hz, 1H), 6.99 (d, J=8.3 Hz, 1H), 5.28 (s, 2H), 2.07 (s, 3H).

Step D: Trifluoromethanesulfonic acid
4-methyl-1-oxo-1,3-dihydro-isobenzofuran-5-yl
ester 5-Hydroxy-4-methyl-3H-isobenzofuran-1-one (46.8 g, 285 mmol) was suspended in dichloromethane (935 mL) in 2-L roundbottom flask equipped with overhead stirrer under nitrogen. Triethylamine (59.5 mL, 427 mmol) was added, and the reaction mixture was cooled in an ice bath to 3.8° C. Trifluoromethanesulfonic anhydride (67.4 mL, 399 mmol) was added via addition funnel over 50 min, keeping the temperature <10° C. After stirring the reaction mixture for an additional 15 min, the reaction mixture was quenched with water (200 mL), then stirred with DARCO® KB (activated carbon, 25 g) for 15 min. The biphasic mixture was filtered over Solka floc, washing with additional dichloromethane, and transferred to a separatory funnel, whereupon it was diluted with additional water (300 mL). The layers were separated, and the organic layer was washed with water (500 mL) and 10% brine (200 mL). The dichloromethane solution was dried over sodium sulfate, filtered and evaporated. The orange-red solid was adsorbed onto silica gel (27.5 g) and eluted through a pad of silica gel (271 g) with 25% ethyl acetate/hexanes. The resulting solution was concentrated under vacuum with the product crystallizing during concentration. The suspension was filtered, the solid washed with heptane and dried under vacuum and nitrogen, providing trifluoromethanesulfonic acid 4-methyl-1-oxo-1,3-dihydroisobenzofuran-5-yl ester. $^1$H NMR (400 MHz, CDCl$_3$): δ 7.87 (d, J=8.4 Hz, 1H), 7.47 (d, J=8.4 Hz, 1H), 5.32 (s, 2H), 2.41 (s, 3H)

Step E: 5-(1-Butoxy-vinyl)-4-methyl-3H-isobenzofuran-1-one

To a 1 L 3-neck was charged trifluoromethanesulfonic acid 4-methyl-1-oxo-1,3-dihydro-isobenzofuran-5-yl ester (63.0 g, 213 mmol), DMF (315 mL), butyl vinyl ether (138 mL, 1063 mmol)) then Et$_3$N (35.6 mL, 255 mmol). The solution was sparged with N$_2$ for 20 min. To the solution was added Pd(OAc)$_2$ (1.19 g., 5.32 mmol) and DPPP (2.41 g., 5.85 mmol) and sparged for an additional 10 min then heated to 80° C. After a 1 hr age, the solution was cooled to <10° C. then quenched with 630 mL EtOAc and washed with 5% NH$_4$Cl (2×315 mL), 10% brine (2×315 mL), dried over MgSO$_4$, filtered, concentrated by rotary evaporation and flushed with EtOAc (3×100 mL) to remove excess butyl vinyl ether, providing crude 5-(1-butoxy-vinyl)-4-methyl-3H-isobenzofuran-1-one.

$^1$H NMR (400 MHz, DMSO-d$_6$): δ 7.67 (d, J=7.7 Hz, 1H), 7.48 (d, J=7.7 Hz, 1H), 5.42 (s, 2H), 4.54 (d, J=2.3 Hz, 1H), 4.27 (d, J=2.3 Hz, 1H), 3.85 (t, J=6.4 Hz, 2H), 2.27 (s, 3H), 1.71-1.64 (m, 2H), 1.46-1.37 (m, 2H), 0.92 (t, J=7.4 Hz, 3H)

Step F: 5-(2-Bromo-acetyl)-4-methyl-3H-isobenzofuran-1-one

To a 1 L 3-neck flask equipped with overhead stirrer was added crude 5-(1-butoxy-vinyl)-4-methyl-3H-isobenzofuran-1-one (55.8 g) and THF (315 mL). The solution was cooled to <5° C. after which water (79 mL) was added and the solution was maintained at <5° C. NBS (41.6 g) was then added portionwise while maintaining Tmax=19° C. The solution was then warmed to RT for 30 minutes. HBr (48%, 0.241 mL) was added and the reaction was aged at RT for approximately 1 h after which 236 mL water was then added to the batch. A water bath is used to maintain temp at 20° C. Another 315 mL of water was added (solvent composition 1:2 THF: water) and the slurry was cooled to 15° C. The resulting solids were filtered and washed with cold 1:2 THF:water (15° C.): 150 mL displacement wash followed by 100 mL slurry wash. The solids were dried under vacuum at RT to provide 5-(2-bromo-acetyl)-4-methyl-3H-isobenzofuran-1-one. $^1$H NMR (400 MHz, DMSO-d$_6$): δ 7.99 (d, J=7.8 Hz, 1H), 7.82 (d, J=7.8 Hz, 1H), 5.49 (s, 2H), 4.92 (s, 2H), 2.33 (s, 3H)

Step G: 4-methyl-5-[(2R)-oxiran-2-yl]-2-benzofuran-1(3H)-one 5-(2-Bromo-acetyl)-4-methyl-3H-isobenzofuran-1-one (48.8 g., 181 mmol) was charged to a 5 L 3 neck round bottom equipped with overhead stirrer, thermocouple, and heating mantle. 2-Propanol (1.22 L) was added, followed by 610 mL of pH 7 0.1M potassium phosphate buffer. Buffer solution (610 mL) was charged to a 1.0 L erlenmeyer, and 2.44 g of NADP was added to the erlenmeyer and swirled to dissolve. A reducing enzyme, KRED MIF-20 (2.44 g) (available from Codexis, Inc., 200 Penobscot Drive, Redwood City, Calif. 94063, www.codexis.com, tel. 1-650-421-8100) was added to the erlenmeyer flask and the mixture was swirled to dissolve the solids. The resulting solution was added to the 5 L round bottom, which was then heated to 28° C. and aged for 6 hours, at which point the reaction was cooled to RT and triethylamine (50.2 mL, 360 mmol) was added. The resulting solution was aged at 40° C. for 1 h. The light slurry solution was cooled to RT, after which 122 g NaCl was added. The solution was aged at RT then extracted with 1.22 L isopropyl acetate (IPAc). The aqueous layer was re-extracted with 400 mL IPAc and the combined organics were washed with 400 mL 20% brine solution, dried over MgSO$_4$, filtered and concentrated by rotary evaporation. The resulting solids were taken up in 100 mL IPAc (thick slurry). Hexanes were added (400 mL) and the suspension aged at RT then filtered and washed w/5:1 Hexanes:IPAc solution (150 mL). The crystalline solids were dried under vacuum at RT to provide 4-methyl-5-[(2R)-oxiran-2-yl]-2-benzofuran-1(3H)-one. $^1$H NMR (400 MHz, CDCl$_3$): δ 7.75 (d, J=8.1 Hz, 1H), 7.42 (d, J=8.1 Hz, 1H), 5.28 (s, 2H), 4.10 (dd, J=4.0, 2.8, 1H), 3.26 (dd, J=5.6, 4.0, 1H), 2.72 (dd, J=5.6, 2.8, 1H), 2.42 (s, 3H)

INTERMEDIATE 4

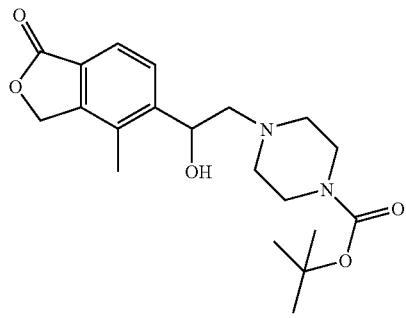

1,1-dimethylethyl-4-[2-hydroxy-2-(4-methyl-1-oxo-1,3-dihydro-2-benzofuran-5-yl)ethyl]piperazine-1-carboxylate To a 25 mL microwave tube was added 4-methyl-5-oxiran-2-yl-2-benzofuran-1(3H)-one (1.2 g, 6.0 mmol, 1.0 eq) and tert-butyl piperazine-1-carboxylate (1.7 g, 9.0 mmol, 1.5 eq). To the mixture was added EtOH (15 mL). The reaction was heated in a microwave apparatus at 150° C. for 30 min. The reaction mixture was concentrated to dryness. The crude product was purified by flash column chromatography yielding 1,1-dimethylethyl-4-[2-hydroxy-2-(4-methyl-1-oxo-1,3-dihydro-2-benzofuran-5-yl)ethyl]piperazine-1-carboxylate.

$^1$H NMR (500 MHz, CDCl$_3$, δ in ppm): 7.80 (1H, s), 7.26 (1H, s), 5.25 (2H, s), 5.10 (1H, dxd, J=3.0 Hz, J=10.8 Hz), 3.50 (4H, m), 2.73 (2H, m), 2.53-2.40 (4H, m), 2.28 (3H, s, Me), 1.47 (9H, s). LC-MS (IE, m/z): 377.1 [M+1]$^+$; t$_R$=2.1 min.

INTERMEDIATE 5

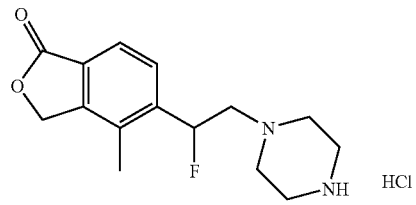

5-(1-fluoro-2-piperazin-1-ylethyl)-4-methyl-2-benzofuran-1(3H)-one hydrochloride Step A: 1,1-dimethylethyl-4-[2-fluoro-2-(4-methyl-1-oxo-1,3-dihydro-2-benzofuran-5-yl)ethyl]piperazine-1-carboxylate 1,1-Dimethylethyl-4-[2-hydroxy-2-(4-methyl-1-oxo-1,3-dihydro-2-benzofuran-5-yl)ethyl]piperazine-1-carboxylate (0.500 g, 1.46 mmol) was added to a 25 ml flask containing a stir bar and dissolved in THF (4 mL). To the solution was added DAST (0.232 mL, 1.76 mmol) and triethylamine (0.175 mL, 1.33 mmol) and subsequently stirred for 45 min; LC as well as TLC (hexanes/EtOAc=1/0.3) indicated that reaction had gone to completion. Reaction mixture was concentrated to dryness, absorbed into silica gel and loaded into silica column. Compound 1,1-dimethylethyl-4-[2-fluoro-2-(4-methyl-1-oxo-1,3-dihydro-2-benzofuran-5-yl)ethyl]piperazine-1-carboxylate was obtained.

Step B: 5-(1-fluoro-2-piperazin-1-ylethyl)-4-methyl-2-benzofuran-1(3H)-one hydrochloride 1,1-Dimethylethyl-4-[2-fluoro-2-(4-methyl-1-oxo-1,3-dihydro-2-benzofuran-5-yl)ethyl]piperazine-1-carboxylate (0.18 g) was treated with 4M HCl in dioxane (4 mL) and stirred at room temperature for 1 h. The mixture was then concentrated to dryness. Analysis by LC indicated complete removal of the Boc group and formation of compound 5-(1-fluoro-2-piperazin-1-ylethyl)-4-methyl-2-benzofuran-1(3H)-one hydrochloride. $^1$H-NMR (DMSO, 500 MHz), δ 7.744 (d, J=7.5 Hz, 1H), 7.612 (d, J=7.5 Hz, 1H), 6.264-6.167 (m, 1H), 5.382 (s, 2H), 3.362-3.309 (m, 2H), 3.255-3.125 (m, 8H), 3.078-3.049 (m, 1H), 2.499 (s, 3H)

INTERMEDIATE 6

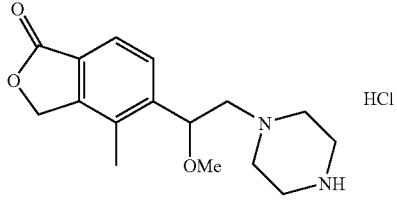

4-methyl-5-[1-(methyloxy)-2-piperazin-1-ylethyl]-2-benzofuran-1(3H)-one hydrochloride Step A: 1,1-dimethylethyl-4-[2-(4-methyl-1-oxo-1,3-dihydro-2-benzofuran-5-yl)-2-(methyloxy)ethyl]-piperazine-1-carboxylate 1,1-Dimethylethyl-4-[2-hydroxy-2-(4-methyl-1-oxo-1,3-dihydro-2-benzofuran-5-yl)ethyl]piperazine-1-carboxylate (0.10 g, 0.27 mmol) was combined in a 50 mL flask with DMF (2 mL) and DCM (1 mL) and the flask was placed in a cooling bath at −20° C. The mixture was then treated with NaH (0.021 g, 0.53 mmol) and stirred for 30 minute, followed by addition of iodomethane (0.0414 mL, 0.664 mmol) at −20° C. The resulting mixture was stirred for another 1 h after which analysis by LC as well as TLC (5% MeOH in DCM) indicated that reaction had gone to completion. The reaction mixture was quenched by addition of MeOH and stirred for 10 min at room temperature. The reaction mixture was concentrated to dryness, dissolved in EtOAc and absorbed into silica gel where it was separated on silica column; to obtain 1,1-dimethylethyl-4-[2-(4-methyl-1-oxo-1,3-dihydro-2-benzofuran-5-yl)-2-(methyloxy)ethyl]-piperazine-1-carboxylate was isolated.

Step B: 4-methyl-5-[1-(methyloxy)-2-piperazin-1-ylethyl]-2-benzofuran-1(3H)-one hydrochloride 1,1-Dimethylethyl-4-[2-(4-methyl-1-oxo-1,3-dihydro-2-benzofuran-5-yl)-2-(methyloxy)ethyl]-piperazine-1-carboxylate was treated with 4M HCl in dioxane (4 mL) and stirred at room temperature for 1 h. The reaction mixture was concentrated to dryness. Analysis by LC indicated complete removal of the Boc group and formation of compound 4-methyl-5-[1-(methyloxy)-2-piperazin-1-ylethyl]-2-benzofuran-1(3H)-one hydrochloride. $^1$H-NMR (DMSO, 500 MHz), δ 7.747 (d, J=7.5 Hz, 1H), 7.577 (d, J=7.5 Hz, 1H), 5.402-5.388 (m, 2H), 5.113 (d, J=9 Hz, 1H), 3.850 (s, 3H), 3.496-3.327 (m, 8H), 3.228-3.140 (m, 3H), 2.500 (s, 3H).

INTERMEDIATE 7

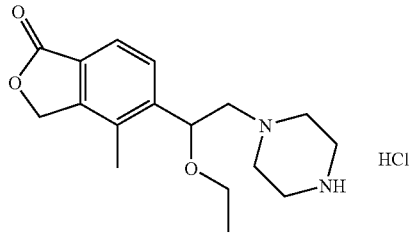

5-[1-(ethyloxy)-2-piperazin-1-ylethyl]-4-methyl-2-benzofuran-1(3H)-one hydrochloride Step A: 1,1-dimethylethyl-4-[2-(ethyloxy)-2-(4-methyl-1-oxo-1,3-dihydro-2-benzofuran-5-yl)ethyl] piperazine-1-carboxylate 1,1-Dimethylethyl-4-[2-hydroxy-2-(4-methyl-1-oxo-1,3-dihydro-2-benzofuran-5-yl)ethyl]piperazine-1-carboxylate (0.15 g, 0.40 mmol) in a 50 mL flask was dissolved in DMF (1.5 mL) and DCM (1.5 mL) and the flask was placed in a cooling bath at −30° C. The mixture was then treated with NaH (0.023 g, 0.99 mmol) and the resulting mixture was stirred for 30 minutes, followed by treatment with iodoethane (0.080 mL, 0.99 mmol) at −30° C. The resulting mixture was stirred for another 1 h after which LC as well as TLC (5% MeOH in DCM) indicated that reaction had gone to completion. The reaction mixture was quenched with MeOH and stirred for 10 min at room temperature. The reaction mixture was then concentrated to dryness, dissolved in EtOAc, and absorbed into silica gel where it was separated on silica column to afford of 1,1-dimethylethyl-4-[2-(ethyloxy)-2-(4-methyl-1-oxo-1,3-dihydro-2-benzofuran-5-yl)ethyl]piperazine-1-carboxylate.

$^1$H-NMR (CDCl3, 500 MHz), δ 7.683 (d, J=8 Hz, 1H), 7.554 (d, J=8 Hz, 1H), 5.200 (s, 2H), 3.356 (s, 1H), 2.899-2.810 (m, 5H), 2.703-2.660 (m, 8H), 2.253 (m, 2H), 1.405 (s, 3H), 1.386 (s, 9H).

Step B: 5-[1-(ethyloxy)-2-piperazin-1-ylethyl]-4-methyl-2-benzofuran-1(3H)-one hydrochloride 1,1-Dimethylethyl-4-[2-(ethyloxy)-2-(4-methyl-1-oxo-1,3-dihydro-2-benzofuran-5-yl)ethyl]piperazine-1-carboxylate was treated with 4M HCl in dioxane (4 mL) and stirred at room temperature for 1 h. The reaction mixture was concentrated to dryness. Analysis by LC indicated complete removal of the Boc group and formation of 5-[1-(ethyloxy)-2-piperazin-1-ylethyl]-4-methyl-2-benzofuran-1(3H)-one hydrochloride.

LC-MS (IE, m/z): 305 [M+1]$^+$; $t_R$=0.69 min

INTERMEDIATE 8

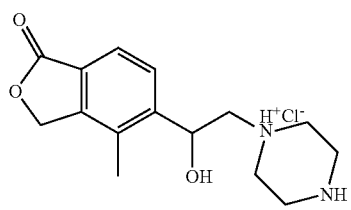

1-[2-hydroxy-2-4-methyl-1-oxo-1,3-dihydro-2-benzofuran-5-yl)ethyl]piperazin-1-ium chloride tert-Butyl-4-[2-hydroxy-2-(4-methyl-1-oxo-1,3-dihydro-2-benzofuran-5-yl)ethyl]piperazine-1-carboxylate (800 mg, 2.1 mmol, 1.0 eq) was treated with 4 NHCl in dioxane (4 mL). The reaction was stirred at r.t. for 3 h and then concentrated. The product was dried under high vacuum pump for 6 hr. The intermediate is often converted to the corresponding free base prior to use by partitioning between saturated Na2CO3 solution and CHCl$_3$-IPA (3:1).

LC-MS (IE, m/z): 277.1 [M+1]$^+$; $t_R$=0.4 min.

INTERMEDIATE (R)-8

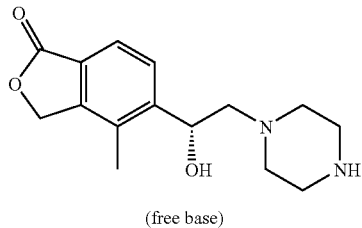

(free base)

5-[(1R)-1-hydroxy-2-piperazin-1-ylethyl]-4-methyl-2-benzofuran-1(3H)-one

To a 20 mL microwave tube charged with 4-methyl-5-[(2R)-oxiran-2-yl]-2-benzofuran-1(3H)-one (1020 mg, 5.40 mmol) and a stir bar was added 1-Boc Piperazine (800 mg, 4.3 mmol) and EtOH (15 mL). The tube was sealed and heated in a microwave apparatus to 150° C. for 1 hour. The crude product was adsorbed onto silica gel, and purified by flash chromatography (Hexanes-EtOAc with 10% EtOH: 0~100% gradient), and solvent removed to afford tert-butyl-4-[(2R-2-hydroxy-2-(4-methyl-1-oxo-1,3-dihydro-2-benzofuran-5-yl)ethyl]piperazine-1-carboxylate. LCMS M+1 (calc. 377.20, found 377.13). This product was treated with neat TFA for 15 minutes to remove the Boc group. After removal of TFA under reduced pressure, the residue was taken into aq NaHCO$_3$, and back-extracted with CHCl$_3$-IPA (3:1). The organic layers were combined, dried over sodium sulfate, and concentrated to afford 5-[(1R)-1-hydroxy-2-piperazin-1-ylethyl]-4-methyl-2-benzofuran-1(3H)-one.

$^1$H NMR (DMSO-d$_6$, 500 MHz) δ 7.68 (d, J=8.0 Hz, 1H), 7.65 (d, J=8.0 Hz, 1H), 5.38, 5.35 (AB system, J=15.4, J=16.7, 2H), 5.06 (dd, J=3.9 Hz, J=3.7 Hz, 1H), 3.76 (m, 1H), 2.72 (m, 4H), 2.42 (m, 4H), 2.34 (d, J=3.8 Hz, 1H), 2.32 (d, J=3.8 Hz, 1H), 2.24 (s, 3H); LC/MS: (IE, m/z) [M+1]$^+$=277.03.

INTERMEDIATE 9

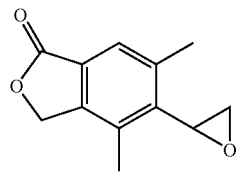

4,6-dimethyl-5-oxiran-2-yl-2-benzofuran-1(3H)-one

Step A: 3-bromo-2,4-dimethylbenzoic acid 2,4-Dimethylbenzoic acid (7.00 g, 46.6 mmol) and NBS (12.4 g, 69.9 mmol) were dissolved in TFA (150 mL). The mixture was then heated at 50° C. for overnight. Analysis by LC as well as TLC (hexanes/EtOAc=1/1) indicated that reaction had gone to completion. The solvent was removed in vacuo and the resulting residue was dissolved in DCM, absorbed onto silica gel, and loaded onto a silica MPLC column for separation. The desired product was separated using the solvent system of hexanes/EtOAc (1/1) to yield 3-bromo-2,4-dimethylbenzoic acid. The undesired isomeric 5-bromo-2,4-dimethylbenzoic acid was also isolated. $^1$H-NMR (CDCl$_3$, 500 MHz), δ 7.868 (d, J=7.5 Hz, 1H), 7.2 (d, J=7.5 Hz, 1H), 2.793 (s, 3H), 2.526 (s, 3H).

Step B: (3-bromo-2,4-dimethylphenyl)methanol

3-Bromo-2,4-dimethylbenzoic acid (6.50 g, 28.4 mmol), in THF (50 mL) was treated with borane tetrahydrofuran complex (42.6 mL, 42.6 mmol) and stirred for 12 h. Analysis by LC indicated that reaction had gone to completion. The solution was concentrated to dryness, redissolved in DCM, and washed with brine. The organic layer was dried over Na2SO4, filtered, and concentrated. The resulting (3-bromo-2,4-dimethylphenyl)methanol was used for the next step without further purification. $^1$H-NMR (CDCl3, 500 MHz), δ 7.227 (d, J=7.5 Hz, 1H), 7.122 (d, J=7.5 Hz, 1H), 4.730 (m, 2H), 2.492 (s, 3H), 2.456 (s, 3H).

Step C: 5-bromo-4,6-dimethyl-2-benzofuran-1(3H)-one (3-bromo-2,4-dimethylphenyl)methanol (2.0 g, 9.3 mmol), and thallium(III) trifluoroacetate (7.50 g, 14.0 mmol) were added to a 250 mL flask containing a stir bar. The flask was then placed in a cooling bath at 0° C. To the flask was added TFA (150 mL) slowly. The resulting mixture was then stirred at room temperature overnight. The TFA was removed under reduced pressure at 30° C. and the resulting residue was redissolved in dichloroethane and concentrated twice (2×100 mL). The residue was then pumped under high vacuum for 45 min. To the dried residue was then added palladium dichloride (165 mg, 0.930 mmol), lithium chloride (788 mg, 18.6 mmol), and magnesium chloride (750 mg, 18.6 mmol). The resulting mixture was dissolved in MeOH (160 mL). The mixture was then degassed and purged with CO (3 times). The flask under CO was stirred at room temp for 4 hours; the color of the reaction mixture changed from white to cream then to brownish. The color of the reaction then finally changed from brownish to black up on which time the reaction had gone to completion as evidenced by LC as well as TLC (hexanes/ EtOAc=1/0.3) analysis. The reaction mixture was then poured into a 1 L Erlenmeyer flask containing DCM (400 mL) and EtOAc (400 mL). The solution was then passed through a celite plug, and rinsed several times with DCM until all the organic material had passed through. The solution was then concentrated to dryness, re-dissolved in DCM, absorbed into silica gel, and separated over silica column to give 5-bromo-4,6-dimethyl-2-benzofuran-1(3H)-one. LC-MS: M+1=242

Step D: 5-ethenyl-4,6-dimethyl-2-benzofuran-1(3H)-one

5-Bromo-4,6-dimethyl-2-benzofuran-1(3H)-one (375 mg, 1.56 mmol), potassium vinyl trifluoroborate (417 mg, 3.11 mmol), Pd(dppf)Cl$_2$ (127 mg, 0.156 mmol), and triethylamine (409 μL, 3.11 mmol) were combined together in EtOH (10 mL) and heated at 140° C. for 30 min. Analysis by LC as well as TLC (hexanes/EtOAc=1/0.3) indicated that reaction had gone to completion. The reaction mixture was then diluted with EtOAc, washed with NaCl, dried over Na$_2$SO$_4$, filtered, and concentrated to dryness. The resulting residue was then re-dissolved in dichloromethane, absorbed to silica gel, concentrated, and loaded onto a silica MPLC column for separation to afford of 5-ethenyl-4,6-dimethyl-2-benzofuran-1(3H)-one.
$^1$H-NMR (CDCl3, 500 MHz), δ 7.626 (s, 1H), 6.771-6.712 (m, 1H), 5.746-5.723 (m, 1H), 5.383-5.346 (m, 1H), 5.254 (s, 2H), 2.415 (s, 3H), 2.349 (s, 3H).

Step E: 4,6-dimethyl-5-oxiran-2-yl-2-benzofuran-1 (3H)-one

5-Ethenyl-4,6-dimethyl-2-benzofuran-1(3H)-one (150 mg, 0.797 mmol), mCPBA (275 mg, 1.59 mmol), were combined together in DCM (20 mL) and stirred at room temperature for 12 h. The reaction mixture was then diluted with DCM and washed with Na$_2$S$_2$O$_3$ solution, NaHCO$_3$ solution, and brine. The organic layer was dried over Na$_2$SO$_4$, filtered, and concentrated to dryness. The resulting residue was then re-dissolved DCM, absorbed onto silica gel, concentrated, and loaded into silica column for separation giving 4,6-dimethyl-5-oxiran-2-yl-2-benzofuran-1(3H)-one.
$^1$H-NMR (CDCl3, 500 MHz), δ 7.591 (s, 1H), 7.296 (s, 1H), 5.252 (s, 2H) 4.028 (s, 1H), 3762-3.749 (m, 1H), 3.299 (s, 1H), 2.524 (s, 3H), 2.423 (s, 3H)

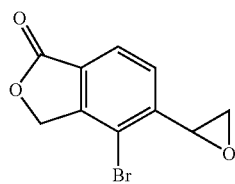

INTERMEDIATE 10

4-bromo-5-oxiran-2-yl-2-benzofuran-1(3H)-one

Step A: 4,5-dibromo-2-benzofuran-1(3H)-one

To a flask containing a stir bar was added 5-bromo-2-benzofuran-1(3H)-one (12.0 g, 56.3 mmol) and NBS (15 g, 84 mmol). Triflic acid (50 mL) was then added at 0° C. and the resulting mixture was allowed to warm to rt and stir for 2 days. TLC analysis of the reaction mixture showed complete reaction. The reaction mixture was poured into ice and the organic layer was separated, washed with brine, water, dried over Na$_2$SO$_4$, filtered, and concentrated to dryness. The residue was then absorbed into silica gel and subjected for purification over a silica MPLC column to give 4,5-dibromo-2-benzofuran-1(3H)-one. LC-MS: M+1=291

Step B: 4-bromo-5-ethenyl-2-benzofuran-1(3H)-one 4,5-Dibromo-2-benzofuran-1(3H)-one (3.00 g, 10.3 mmol), potassium vinyltrifluoroborate (12.7 g, 20.6 mmol) and Pd (dppf)Cl$_2$ (839 mg, 1.03 mmol) in TEA (2.7 mL) and EtOH (15 mL) were heated at 60° C. for 2 h. Analysis by TLC showed clean and complete reaction. The reaction mixture was diluted with EtOAc (500 mL), washed with brine, dried over sodium sulfate, filtered, and concentrated. The resulting residue was subjected to purification over silica gel to give 4-bromo-5-ethenyl-2-benzofuran-1(3H)-one.
$^1$H-NMR (CDCl3, 500 MHz), δ 7.867 (d, J=8 Hz, 1H), 7.768 (d, J=7.5 Hz, 1H), 7.184-7.127 (m, 1H), 5.957 (d, J=17.5 Hz, 1H), 5.643 (d, J=11 Hz, 1H), 5.251 (m, 2H)

Step C: 4-bromo-5-oxiran-2-yl-2-benzofuran-1(3H)-one

To a solution 4-bromo-5-ethenyl-2-benzofuran-1(3H)-one (2.00 g, 8.37 mmol) in DCM (20 mL) was slowly added mCPBA (2.60 g, 8.37 mmol) at 0° C. The flask was warmed to room temperature and the mixture was then stirred for 12 hours. Analysis by TLC as well as LC indicated that reaction had gone to completion. The reaction mixture was washed with aqueous Na$_2$S$_2$O$_3$, NaHCO$_3$, and water. The organic layer was washed with brine and then concentrated to dryness. The residue was purified over silica gel to give 4-bromo-5-oxiran-2-yl-2-benzofuran-1(3H)-one.
$^1$H-NMR (CDCl3, 500 MHz), δ 7.896 (d, J=8 Hz, 1H), 7.547 (d, J=7.5 Hz, 1H), 5.274 (m, 2H), 4.273 (s, 1H), 3.314 (s, 1H), 2.733 (s, 1H).

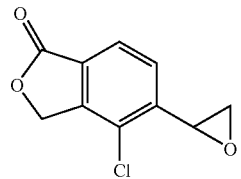

INTERMEDIATE 11

4-chloro-5-oxiran-2-yl-2-benzofuran-1(3H)-one

Step A: 2-chloro-3-(hydroxymethyl)phenol

To a solution of 2-chloro-3-hydroxybenzaldehyde (8.10 g, 51.7 mmol) in MeOH was added NaBH$_4$ (1.96 g, 51.7 mmol) at 0° C. The reaction was allowed to stir for 30 minutes. TLC showed clean conversion to a more polar spot. The reaction was diluted with EtOAc (400 mL), washed with water and brine, dried over sodium sulfate, and concentrated. The crude 2-chloro-3-(hydroxymethyl)phenol was used in Step B without further purification.

Step B: 4-bromo-2-chloro-3-(hydroxymethyl)phenol

To the flask charged with 2-chloro-3-(hydroxymethyl)phenol from Step A and a stir bar was added NBS (10.8 g, 60.5 mmol) and TFA (50 mL). The reaction was allowed to stir for 16 hours at RT. TLC showed complete reaction at that point. The solvent was removed under vacuum. The residue was re-dissolved in EtOAc, washed with water, and purified by silica gel flash chromatography. A pair of regio-isomers was collected from the separation. The less polar spot was the desired 4-bromo-2-chloro-3-(hydroxymethyl)phenol according to noe NMR analysis. $^1$H-NMR (500 MHz, CDCl$_3$) δ ppm 7.42 (d, J=8.5 Hz, 1H), 6.92 (d, J=8.5 Hz, 1H), 4.96 (s, 2H).

Step C: 4-chloro-5-hydroxy-2-benzofuran-1(3H)-one

To a flask charged with 4-bromo-2-chloro-3-(hydroxymethyl)phenol (2.44 g, 10.3 mmol) and a stir bar was added CuCN (2.76 g, 30.8 mmol) and DMF (25 mL). The flask was fitted with a condenser and purged three times with Nitrogen. The solution was then heated to 145° C. for 2 hours. At that point, water (0.555 mL, 30.8 mmol) was added to the reaction via a syringe, and the reaction was kept at 100° C. for another 24 hours. The reaction was cooled to RT, diluted with DCM (100 mL), and filtered through a pad of celite to remove the solids. The filtrate was washed with saturated NH$_4$OAc, dried over sodium sulfate, concentrated and purified by silica gel flash chromatography. 4-Chloro-5-hydroxy-2-benzofuran-1 (3H)-one was collected after removal of solvents. $^1$H-NMR (500 MHz, CDCl$_3$) δ ppm 9.13 (broad, 1H), 7.68 (d, J=8.5 Hz, 1H), 7.19 (d, J=8.5 Hz, 1H), 5.23 (s, 2H).

Step D: 4-chloro-5-ethenyl-2-benzofuran-1(3H)-one

To a cold solution of 4-chloro-5-hydroxy-2-benzofuran-1 (3H)-one (1.39 g, 7.53 mmol) in DCM (25 mL) was added Hunig's Base (3.29 mL, 18.8 mmol) and trifluoromethanesulfonic anhydride (2.54 mL, 15.1 mmol). The mixture was allowed to stir for 16 hours. Analysis by TLC showed complete consumption of all SM. The reaction was diluted with Hexane and washed with water. The solution was dried with sodium sulfate, concentrated, and purified by flash chromatography on a silica column. The solvent was removed under reduced pressure to give intermediate triflate. LC-MS (M+1=317).

To the triflate was added a stir bar, potassium vinyltrifluoroborate (1.33 g, 9.90 mmol), PdCl$_2$(dppf) (0.243 g, 0.332 mmol), triethylamine (1.89 mL, 13.3 mmol), and iso-propanol (50 mL). The mixture was purged three times with nitrogen, and heated to 60° C. for 2 hours. TLC showed complete reaction at that point. Most of the solvent was removed under vacuum. The crude residue was diluted with EtOAc (200 mL), washed with brine, dried over sodium sulfate, adsorbed onto silica gel, and purified by flash chromatography to give 4-chloro-5-ethenyl-2-benzofuran-1(3H)-one.
$^1$H-NMR (500 MHz, CDCl$_3$) δ ppm 7.82 (d, J=8.0 Hz, 1H), 7.70 (d, J=8.0 Hz, 1H), 7.18 (dd, J=11, 17.5 Hz, 1H), 5.97 (d, J=17.5 Hz, 1H), 5.65 (d, J=11 Hz, 1H), 5.31 (s, 2H).

Step E: 4-chloro-5-oxiran-2-yl-2-benzofuran-1(3H)-one

To a solution of 4-chloro-5-ethenyl-2-benzofuran-1(3H)-one (1.1 g, 5.7 mmol) in DCM (40 mL) was added m-CPBA (1.9 g, 8.5 mmol). The solution was allowed to stir at RT for 16 hours. Analysis by TLC and LC showed formation of the desired product, along with some untouched starting material. The reaction was diluted with DCM (200 mL), washed with aqueous Na$_2$S$_2$O$_3$ and Na$_2$CO$_3$, dried over sodium sulfate, concentrated, and purified by silica gel flash chromatography to afford 4-chloro-5-oxiran-2-yl-2-benzofuran-1(3H)-one.
$^1$H-NMR (500 MHz, CDCl$_3$) δ ppm 7.86 (d, J=8.0 Hz, 1H), 7.48 (d, J=8.0 Hz, 1H), 5.34 (s, 2H), 4.33 (m, 1H), 3.33 (m, 1H), 2.75 (m, 1H).

INTERMEDIATE 12

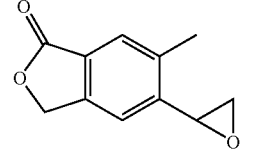

(racemate and individual enantiomers)

6-methyl-5-oxiran-2-yl-2-benzofuran-1(3H)-one

Step A: 5-prop-2-en-1-yl-2-benzofuran-1(3H)-one

A mixture of 5-bromo-2-benzofuran-1(3H)-one (15.0 g, 70.4 mmol), allyl-tributyl-stannane (25.6 g, 77.5 mmol), LiCl (11.8 g, 282 mmol) and Pd(PPh$_3$)$_4$ (1.2 g, 1.0 mmol) in 100 mL toluene was heated under N$_2$ at 90~100° C. overnight. After cooling to r.t., the mixture was diluted with 250 mL EtOAc and filtered. The filtrate was washed with water and brine, dried over anhydrous Na$_2$SO$_4$ and concentrated to dryness. The residue was purified via column (DCM/Petrol Ether=1:5) to give 5-prop-2-en-1-yl-2-benzofuran-1(3H)-one.

Step B: 5-(2-hydroxyethyl)-2-benzofuran-1(3H)-one

To a solution of 5-prop-2-en-1-yl-2-benzofuran-1(3H)-one (13.5 g, 45.2 mmol) in 200 mL DCM/MeOH (V/V=1:1) was bubbled O$_3$ at −78° C. for 30 min, and N$_2$ was bubbled for another 15 min at −78° C. Then 20 mL of Me$_2$S were added, and the mixture was stirred at r.t. overnight before concentrating to dryness. The residue was dissolved in MeOH (100 mL) and then cooled to 0° C. NaBH$_4$ (5.90 g, 155 mmol) was added in portions. The resulting mixture was stirred at 0° C. for 1 h, then quenched with citric acid (aq.) and extracted three times with EtOAc. The combined organic layers were washed with NaHCO$_3$ (aq.) and brine, dried over anhydrous Na$_2$SO$_4$ and concentrated to dryness. The residue was purified via column chromatography (EtOAc/Petrol Ether=1:5) to give 5-(2-hydroxyethyl)-2-benzofuran-1(3H)-one.
$^1$H-NMR (400 MHz, CDCl$_3$) δ ppm 7.86 (d, J=7.8 Hz, 1H), 7.41 (d, J=7.8 Hz, 1H), 7.38 (s, 1H), 5.29 (s, 2H), 3.92~3.98 (m, 2H), 3.01 (t, J=6.4 Hz, 2H).

Step C: 5-(2-hydroxyethyl)-6-iodo-2-benzofuran-1(3H)-one

To a cooled (0° C.) solution of 5-(2-hydroxyethyl)-2-benzofuran-1(3H)-one (9.00 g, 50.6 mmol) in 100 mL of TfOH was added NIS (12.5 g, 55.6 mmol), then the mixture was stirred at 0° C. for 2 hrs and then poured into ice-water (500 mL). The solution was extracted three times with 500 mL of EtOAc and the combined organic layers were washed with saturated NaHCO$_3$ and brine, dried over anhydrous sodium sulfate, filtered and concentrated. The residue was purified by column chromatography (EtOAc/Petrol Ether=1:5) to give the desired 5-(2-hydroxyethyl)-6-iodo-2-benzofuran-1(3H)- one (6 g) and isomeric by-product 5-(2-hydroxyethyl)-4-iodo-2-benzofuran-1(3H)-one.

$^1$H-NMR (400 MHz, CDCl$_3$) δ ppm 7.84 (d, J=7.8 Hz, 1H), 7.46 (d, J=7.8 Hz, 1H), 5.09 (s, 2H), 3.93 (q, J=6.3 Hz, 2H), 3.16 (t, J=6.3 Hz, 2H), 1.45 (t, J=5.5 Hz, 1H).

Step D: 5-(2-hydroxyethyl)-6-methyl-2-benzofuran-1(3H)-one

To a flask charged with 5-(2-hydroxyethyl)-6-iodo-2-benzofuran-1(3H)-one (6.00 g, 19.7 mmol) and a stir bar was added Pd$_2$(dba)$_3$ (452 mg, 0.493 mmol), PPh$_3$ (1 g, 4 mmol) and NMP (50 mL). The mixture was purged with N$_2$ and heated to 50° C. for 10 min, followed by addition of CuI (375 mg, 1.97 mmol). After the mixture was heated for another 10 min, Sn(CH$_3$)$_4$ (5.30 g, 29.6 mmol) was added into the reaction, and it was heated to 120° C. for 2 h. After cooled to room temperature, the mixture was diluted with saturated NH$_4$Cl (200 mL) and extracted with EtOAc (3*200 mL). The combined organic layers were washed with water and brine, dried over anhydrous sodium sulfate, filtered and concentrated. The residue was purified by prep-HPLC to give 5-(2-hydroxyethyl)-6-methyl-2-benzofuran-1(3H)-one.

$^1$H-NMR (400 MHz, CDCl$_3$) δ ppm 7.72 (s, 1H), 7.33 (s, 1H), 5.27 (s, 2H), 3.93 (t, J=6.3 Hz, 2H), 3.01 (t, J=6.3 Hz, 2H), 2.44 (s, 3H).

Step E: 2-(6-methyl-1-oxo-1,3-dihydro-2-benzofuran-5-yl)ethyl methanesulfonate

To a solution of 5-(2-hydroxyethyl)-6-methyl-2-benzofuran-1(3H)-one (1.20 g, 6.25 mmol) and TEA (2.5 g, 25 mmol) in DCM (100 mL) was added MsCl (1.40 g, 12.5 mmol) at 0° C. The mixture was stirred at ambient temperature overnight, then was washed with water and brine. The organic layer was dried and concentrated to dryness. The collected 2-(6-methyl-1-oxo-1,3-dihydro-2-benzofuran-5-yl)ethyl methanesulfonate was used for the next step without any purification.

Step F: 5-ethenyl-6-methyl-2-benzofuran-1(3H)-one

To a mixture of 2-(6-methyl-1-oxo-1,3-dihydro-2-benzofuran-5-yl)ethyl methanesulfonate (2.00 g, 7.41 mmol) and TEA (5 mL) in DCM (50 mL) was added DBU (5 mL) slowly at 0° C. The mixture was stirred at r.t. overnight, and then was diluted with 50 mL of DCM, washed with 2 N HCl in three times and brine. The organic layer was dried and concentrated to dryness. The residue was purified by prep-TLC to give 5-ethenyl-6-methyl-2-benzofuran-1(3H)-one.

Step G: 6-methyl-5-oxiran-2-yl-2-benzofuran-1(3H)-one

To a solution of 5-ethenyl-6-methyl-2-benzofuran-1(3H)-one (1.00 g, 5.75 mmol) in 50 mL of DCM was slowly added mCPBA (3.50 g, 17.4 mmol) in 50 mL of DCM at 0° C. The mixture was warmed to room temperature, and stirred for 2 days. The mixture was washed with aqueous Na$_2$SO$_3$ until KI indicator paper didn't change color. The organic layer was washed with brine and then concentrated. The residue was purified via silica column to give product 6-methyl-5-oxiran-2-yl-2-benzofuran-1(3H)-one.

LC-MS M+1 (calc. 191, found 191).

The enantiomers of the product were resolved via chiral HPLC (Column: Chiralpak AD-H 250*4.6 mm I.D., 5 um; Mobile phase: methanol 15% in MeCN).
Isomer A: LC-[MS M+1] 191.
Isomer B: LC-[MS M+1] 191.

INTERMEDIATE 13

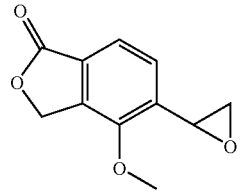

4-(methyloxy)-5-oxiran-2-yl-2-benzofuran-1(3H)-one

Step A: (3-Bromo-2-methoxyphenyl)methanol

In a 250 ml round bottom flask, 3-bromo-2-methoxybenzoic acid (4.0 g, 17 mmol, 1.0 eq) was dissolved in THF (100 mL). The solution was cooled to 0° C. To above solution was added dropwise borane/THF complex (1 N, 17.3 mL, 17.3 mmol). The solution was warmed to r.t. and let stirred at r.t for 15 hr. The reaction was quenched with addition of aqueous ammonium chloride and concentrated. The mixture was diluted with EtOAc, washed with 1 N HCl followed by aqueous sodium bicarbonate solution, brine and water. The organic phase was dried over MgSO4, filtered and concentrated. The crude product was used without purification.

LC-MS (IE, m/z): 200.95 [M+1-OH]$^+$; t$_R$=2.27 min.

Step B: 5-Bromo-4-methoxy-2-benzofuran-1(3H)-one

To a flask charged with (3-bromo-2-methoxyphenyl)methanol (3.0 g, 14 mmol, 1.0 eq) was added thallic trifluoroacetate (10.0 g, 18.4 mmol, 1.3 eq). To above mixture was added trifluoroacetic acid (25 mL). The reaction was stirred at r.t. for 16 hr, then concentrated. The excess TFA was removed using high vacuum pump. To the residue was added palladium chloride (245 mg, 1.38 mmol, 0.1 eq), magnesium oxide (1.10 g, 27.6 mmol, 2.0 eq) and methanol (35 mL). The reaction was flushed with carbon monoxide three times and stirred under CO at r.t. for 2 hr. To this solution was added ethyl acetate. The mixture was filtered through a pad of celite and washed with EtOAc. The filtrate was concentrated and loaded on silica gel column. The fractions containing 5-bromo-4-methoxy-2-benzofuran-1(3H)-one were concentrated. $^1$H NMR (500 MHz, CDCl$_3$, δ in ppm): 7.72 (1H, aromatic, d, J=8.0 Hz), 7.49 (1H, aromatic, d, J=8.0 Hz), 5.44 (2H, s, CH$_2$ lactone), 4.00 (3H, s, Me). LC-MS (IE, m/z): 244.88 [M+1]$^+$; t$_R$=2.67 min.

Step C: 4-Methoxy-5-vinyl-2-benzofuran-1(3H)-one

To a 100 mL round bottom flask was added 5-Bromo-4-methoxy-2-benzofuran-1(3H)-one (430 mg, 1.8 mmol, 1.0 eq), potassium trifluoro(vinyl)borate (474 g, 3.5 mmol, 2.0 eq), [1,1'-bis(diphenylposphino)-ferrocene]dichloropalladium(II) complex with dichloromethane(1:1) (144 mg, 0.2 mmol, 0.1 eq) and triethylamine (493 μL, 3.5 mmol, 2.0 eq). To above mixture was added ethanol (12 mL). The flask was degassed and filled with nitrogen. The reaction was heated to reflux for 12 hr. The mixture was then diluted with EtOAc, filtered through a pad of celite and washed with brine. The organic phase was dried over Na$_2$SO$_4$, filtered and purified by flash column chromatography using biotage and the solvent systems (0-50% EtOAc/Hexane). The fractions containing desired product were collected and concentrated to 4-methoxy-5-vinyl-2-benzofuran-1(3H)-one.

$^1$H NMR (500 MHz, CDCl$_3$) δ in ppm: 7.62 (1H, aromatic, d, J=7.9 Hz), 7.55 (1H, aromatic, d, J=7.9 Hz), 7.02 (1H, —CH=CH$_2$, d×d, J=11.3 Hz, J=17.8 Hz), 5.79 (1H, —CH=CH$_2$, d, J=17.7 Hz), 5.24 (1H, —CH=CH$_2$, d, J=11.3 Hz), 5.39 (2H, CH$_2$—O—, s), 3.88 (3H, Me, s).

Step D: 4-Methoxy-5-oxiran-2-yl-2-benzofuran-1(3H)-one

4-Methoxy-5-vinyl-2-benzofuran-1(3H)-one (120 mg, 0.63 mmol, 1.0 eq) was added into a 100 mL round bottom flask and dissolved in dichloromethane (5 mL). The solution was cooled to 0° C., and 3-chloroperoxybenzoic acid (327 mg, 1.89 mmol, 2.0 eq) was added portion wise. The mixture was then purged with N$_2$ and stirred at r.t. for 18 hr. To above solution was added water (5 mL). The crude product was extracted with dichloromethane. The organic phase was washed with brine (5 mL), dried over anhydrous Na$_2$SO$_4$, filtered, concentrated and purified by flash column chromatography (hexane/EtOAc 0-50%). The desired product was obtained. $^1$H NMR (500 MHz, CDCl$_3$, δ in ppm): 7.56 (1H, aromatic, d, J=7.6 Hz), 7.31 (1H, aromatic, d, J=7.6 Hz), 5.50 (2H, m, CH$_2$ lactone), 4.23 (1H, m), 4.02 (3H, s, Me), 3.22 (1H, m), 2.72 (1H, m).

INTERMEDIATE 14

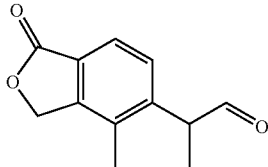

2-(4-Methyl-1-oxo-1,3-dihydro-2-benzofuran-5-yl)propanal

Step A: 4-methyl-5-prop-2-en-1-yl-2-benzofuran-1(3H)-one

A mixture of 5-bromo-4-methyl-2-benzofuran-1(3H)-one (980 mg, 4.3 mmol), allyl-tributyl-stannane (1.7 g, 5.2 mmol), LiCl (550 mg, 12.9 mmol) and Pd(PPh$_3$)$_4$ (0.1 g) in anhydrous toluene was stirred at reflux under N$_2$ overnight. The solvent was removed under reduced pressure, and the residue was purified with silica gel column chromatography to give the product 4-methyl-5-prop-2-en-1-yl-2-benzofuran-1(3H)-one.

Step B: (4-methyl-1-oxo-1,3-dihydro-2-benzofuran-5-yl)acetic acid

To a stirred solution of 4-methyl-5-prop-2-en-1-yl-2-benzofuran-1(3H)-one (2.10 g, 11.2 mmol) in CCl$_4$ (50 mL), acetonitrile (50 mL) and water (75 mL) was added sodium periodate (12 g, 55.8 mmol) and ruthenium oxide hydrate (210 mg) and the resulting mixture was stirred at ambient temperature overnight. The mixture was diluted with 100 mL DCM and 100 mL of water. The organic layer was dried over anhydrous sodium sulfate and concentrated. The residue was purified with silica gel column chromatography to afford (4-methyl-1-oxo-1,3-dihydro-2-benzofuran-5-yl)acetic acid.

Step C: 1,1-dimethylethyl(4-methyl-1-oxo-1,3-dihydro-2-benzofuran-5-yl)acetate

To a solution of (4-methyl-1-oxo-1,3-dihydro-2-benzofuran-5-yl)acetic acid (100 mg, 0.48 mmol) in anhydrous DCM (10 mL) was added 1,1-dimethylethyl-N,N-bis(1-methylethyl)imidocarbamate (485 mg, 2.50 mmol) dropwise at 0° C. under N$_2$. Then the mixture was stirred at r.t. over night. The mixture was filtered and the filtrate was washed with 2N HCl and brine, dried over anhydrous sodium sulfate and concentrated. The residue was purified by preparative TLC to give 1,1-dimethylethyl(4-methyl-1-oxo-1,3-dihydro-2-benzofuran-5-yl)acetate. $^1$H-NMR (400 MHz, CDCl$_3$) δ ppm 7.70 (d, J=7.8 Hz, 1H), 7.38 (d, J=7.0 Hz, 1H), 5.25 (s, 2H), 3.67 (s, 3H), 2.27 (s, 3H), 1.44 (s, 9H).

Step D: 1,1-dimethylethyl-2-(4-methyl-1-oxo-1,3-dihydro-2-benzofuran-5-yl)propanoate A solution of 1,1-dimethylethyl(4-methyl-1-oxo-1,3-dihydro-2-benzofuran-5-yl)acetate (770 mg, 3.1 mmol) in 30 mL of anhydrous THF was cooled to −78° C. NaHMDS (4.0 mmol) was added to the reaction dropwise at −78° C. After the addition, the mixture was stirred at −78° C. for 1 h and then CH$_3$I (462 mg, 3.20 mmol) was added dropwise at −78° C. The reaction was warmed to room temperature slowly and stirred at ambient temperature over night. The reaction was quenched with NH$_4$Cl solution, and extracted with EtOAc. The organic layer was washed with brine, dried over anhydrous sodium sulfate and concentrated. The residue was purified via preparative TLC to afford 1,1-dimethylethyl-2-(4-methyl-1-oxo-1,3-dihydro-2-benzofuran-5-yl)propanoate.

$^1$H-NMR (400 MHz, CDCl$_3$) δ ppm 7.67 (d, J=7.8 Hz, 1H), 7.37 (d, J=7.8 Hz, 1H), 5.19 (s, 2H), 3.80 (dd, J=7.0 Hz, 1H), 2.24 (s, 3H), 1.40 (d, J=7.0 Hz, 1H), 1.32 (s, 9H).

Step E: 2-(4-methyl-1-oxo-1,3-dihydro-2-benzofuran-5-yl)propanoic acid

To a solution of 1,1-dimethylethyl-2-(4-methyl-1-oxo-1,3-dihydro-2-benzofuran-5-yl)propanoate (400 mg, 1.4 mmol) in 10 mL of anhydrous DCM was added TFA (2.5 mL) dropwise at r.t. Then the mixture was stirred for 1 hour. The solvent was removed under vacuum to give the crude 2-(4-methyl-1-oxo-1,3-dihydro-2-benzofuran-5-yl)propanoic acid, which was used for next step without purification.

Step F: 5-(2-hydroxy-1-methylethyl)-4-methyl-2-benzofuran-1(3H)-one

To a solution of 2-(4-methyl-1-oxo-1,3-dihydro-2-benzofuran-5-yl)propanoic acid (300 mg, 1.4 mmol) in 18 mL of anhydrous THF was added BH$_3$. THF (2 mL, 2 mmol) dropwise at 0° C. Then the mixture was warmed to room temperature slowly and then stirred for 3 hours. Then the mixture was quenched with MeOH and the solvent was removed under vacuum. The residue was the purified via prep-TLC to give 5-(2-hydroxy-1-methylethyl)-4-methyl-2-benzofuran-1(3H)-one.

$^1$H-NMR (400 MHz, CDCl$_3$) δ ppm 7.73 (d, J=7.8 Hz, 1H), 7.40 (d, J=7.8 Hz, 1H), 5.23 (s, 2H), 3.77 (d, J=7.0 Hz, 2H), 3.36-3.42 (m, 1H), 2.30 (s, 3H), 1.27 (d, J=7.0 Hz, 3H).

Step G: 2-(4-Methyl-1-oxo-1,3-dihydro-2-benzofuran-5-yl)propanal 5-(2-Hydroxy-1-methylethyl)-4-methyl-2-benzofuran-1 (3H)-one (161 mg, 0.781 mmol, 1.0 eq) was dissolved in DCM (6 ml). To above solution was added Dess-MartinPeriodinane (397 mg, 0.937 mmol, 1.2 eq). The reaction was stirred at rt for 2 hr. To the reaction was added DCM (10 Ml), $Na_2S_2O_3$ (6 mL) and $H_2O$ (6 mL). The mixture was stirred at r.t. for 30 minutes and formed two layers. The bottom layer was separated and washed with aqueous $NaHCO_3$, brine and water, dried over $Na_2SO_4$, filtered, and concentrated to dryness. The crude product was used to next step without purification.

$^1$H NMR (500 MHz, $CDCl_3$, δ in ppm): 9.70 (1H, s, CHO), 7.79 (1H, d, J=7.8 Hz), 7.28 (1H, d, J=7.8 Hz), 5.28 (2H, s), 3.27 (1H, m), 2.32 (3H, s), 1.50 (3H, d, J=7.2 Hz).

INTERMEDIATE 15

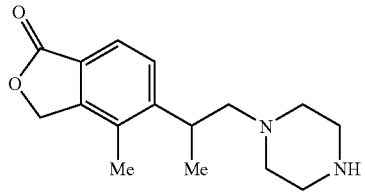

4-methyl-5-(1-methyl-2-piperazin-1-ylethyl)-2-benzofuran-1(3H)-one

Step A: tert-Butyl-4-[2-(4-methyl-1-oxo-1,3-dihydro-2-benzofuran-5-yl)propyl]piperazine-1-carboxylate In a 100 mL round bottom flask, 2-(4-methyl-1-oxo-1,3-dihydro-2-benzofuran-5-yl)propanal (100 mg, 0.49 mmol, 1.0 eq) and Boc-piperazine (91 mg, 0.49 mmol, 1.0 eq) was dissolved in DCM (10 mL). To above solution was added sodium triacetoxyborohydride (208 mg, 0.98 mmol, 2.0 eq). The reaction was stirred at r.t. for 16 hr. The reaction was then diluted with DCM (10 mL), washed with aqueous bicarbonate, water and brine. The organic phase was dried over $MgSO_4$, filtered and concentrated. The product was obtained after purification by flash column chromatography (5% MeOH/DCM). LC-MS (IE, m/z): 375.41 [M+1]$^+$; $t_R$=2.47 min.

Step B: 4-Methyl-5-(1-methyl-2-piperazin-1-ylethyl)-2-benzofuran-1(3H)-one tert-Butyl-4-[2-(4-methyl-1-oxo-1,3-dihydro-2-benzofuran-5-yl)propyl]piperazine-1-carboxylate (160 mg, 0.43 mmol) was stirred in TFA (3 mL) at r.t for 3 hr. The reaction was concentrated and pump over high vacuum pump overnight to give the desired product, which could be converted to it's freebase by partitioning between an organic solvent and saturated NaHCO3 solution. LC-MS (IE, m/z): 275.38 [M+1]$^-$; $t_R$=0.38 min.

INTERMEDIATE 16

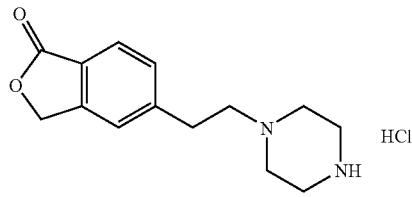

5-(2-piperazin-1-ylethyl)-2-benzofuran-1(3H)-one hydrochloride

Step A: 5-(1,3-dioxolan-2-ylmethyl)-2-benzofuran-1(3H)-one

A three-neck 5 L round bottomed flask equipped with a stir bar, firestone valve, thermocouple, condenser and heating mantle was charged with tri-t-butyl phosphonium tetrafluoroborate (500 mg, 1.72 mmol), palladium (II) acetate (250 mg, 1.1 mmol) and 5-bromo-2-benzofuran-1(3H)-one (100 g, 469 mmol). DMF (1.88 L) was added to the flask, and the mixture was degassed three times by alternating vacuum and nitrogen purge. Commercially available bromo(1,3-dioxolan-2-ylmethyl)zinc solution (1.033 L, 516 mmol) was added via canula and the mixture was again degassed three times. The mixture was then heated at 85° C. for 5 h. Analysis by HPLC-MS indicated the reaction was not complete. The mixture was stirred at 85° C. for 5 more h. The mixture was then allowed to return to room temperature for overnight. 2-methylTHF (2 L) and brine were added, and the mixture was stirred for 5 min. The layers were separated and the aqueous layer was extracted again with 2-methylTHF. The organic layers were combined, washed three times with brine (4 L each), dried over MgSO4, filtered, and concentrated. The crude product was purified by flash chromatography (1.5 kg silica cartridge), eluting with 0-20% ethyl acetate in dichloromethane to afford 5-(1,3-dioxolan-2-ylmethyl)-2-benzofuran-1(3H)-one. MS: m/z 221 (M+1)$^+$.

Step B: (1-oxo-1,3-dihydro-2-benzofuran-5-yl)acetaldehyde 5-(1,3-Dioxolan-2-ylmethyl)-2-benzofuran-1(3H)-one (61 g, 280 mmol) was combined with water (2.2 L) in a 5 L round bottomed flask equipped with a Claisen adapter, thermocouple, stir bar and nitrogen bubbler. Aqueous HCl solution (2M, 1.14 L, 2.29 mol) was added and the resulting mixture was heated at 40° C. for 8 h. Then the mixture was stirred overnight at room temperature. The mixture was extracted three times with 2 L of ethyl acetate. The combined organic layers were concentrated to give (1-oxo-1,3-dihydro-2-benzofuran-5-yl)acetaldehyde. MS: m/z 177 (M+1)$^+$.

Step C: 1,1-dimethylethyl-4-[2-(1-oxo-1,3-dihydro-2-benzofuran-5-yl)ethyl]piperazine-1-carboxylate A three neck 5 L round bottomed flask equipped with a nitrogen bubbler, thermocouple, and stirbar was charged with (1-oxo-1,3-dihydro-2-benzofuran-5-yl)acetaldehyde (46.1 g, 262 mmol) and dichloromethane (1 L). 1-Boc-piperazine (48.7 g, 262 mmol) in 1 L of dichloromethane was added and the mixture was stirred for 5 min. Sodium triacetoxyborohydride (111 g, 523 mmol) was added in portions at room temperature and the resulting mixture was stirred for 1 h.

Water (1 L) was added and the mixture was stirred for 10 min. After gas evolution subsided the organic layer was separated and the aqueous layer was extracted with methylene chloride (1 L). The organic layers were combined, washed with brine, and concentrated. The crude product was purified by silica gel MPLC eluting with a 0-100% gradient of 5% methanol/DCM solution (Solvent A) to pure DCM (Solvent B) to afford 1,1-dimethylethyl-4-[2-(1-oxo-1,3-dihydro-2-benzofuran-5-yl)ethyl]piperazine-1-carboxylate.

Step D: 5-(2-piperazin-1-ylethyl)-2-benzofuran-1(3H)-one hydrochloride

To 1,1-dimethylethyl-4-[2-(1-oxo-1,3-dihydro-2-benzofuran-5-yl)ethyl]piperazine-1-carboxylate (120 g, 347 mmol) in dioxane (800 mL) was added 4 N HCl in dioxane (87.0 mL, 347 mmol) and the resulting mixture was stirred at room temperature over night. The reaction mixture was concentrated and stored under vacuum overnight to afford 5-(2-piperazin-1-ylethyl)-2-benzofuran-1(3H)-one hydrochloride. This can be used as is or converted to the free base by partitioning between an organic solvent and saturated NaHCO3 solution. MS: m/z 247 (M+1)$^+$.

INTERMEDIATE 17

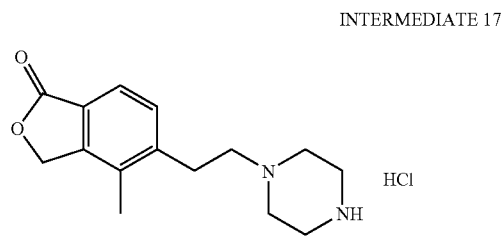 [SMILES: Cc1c(CCN2CCNCC2)ccc2c1COC2=O ; Cl]

4-methyl-5(2-piperazin-1-ylethyl)-2-benzofuran-1(3H)-one hydrochloride

Step A: 4-methyl-5-prop-2-en-1-yl-2-benzofuran-1(3H)-one

To a flask charged with 5-bromo-4-methyl-2-benzofuran-1(3H)-one (320 mg, 1.409 mmol) and a stir bar was added allyl tri-n-butyltin (0.655 ml, 2.11 mmol), Pd(PPh$_3$)$_4$ (244 mg, 0.211 mmol), lithium chloride (179 mg, 4.23 mmol), and toluene (15 mL). The reaction was purged with nitrogen 2 times then was heated at reflux for 4 hours. The product was separated by silica gel chromatography to give 4-methyl-5-prop-2-en-1-yl-2-benzofuran-1(3H)-one.

Step B: (4-methyl-1-oxo-1,3-dihydro-2-benzofuran-5-yl)acetaldehyde

A solution of the above olefin (220 mg, 1.2 mmol) in MeOH (20 mL) was cooled to −78° C. To this solution was bubbled ozone until the reaction turned blue. Nitrogen was bubbled through the reaction to drive off excess ozone, followed by addition of DMS (0.870 mL, 11.7 mmol). The reaction was allowed to warm up to RT. The crude product was purified by flash chromatography to afford (4-methyl-1-oxo-1,3-dihydro-2-benzofuran-5-yl)acetaldehyde.

$^1$H-NMR (500 MHz, CDCl$_3$) δ ppm 9.78 (s, 1H), 7.75 (d, J=7.5 Hz, 1H), 7.34 (d, J=7.5 Hz, 1H), 5.27 (s, 2H), 3.90 (s, 2H), 2.23 (s, 3H).

Step C: 1,1-dimethylethyl-4-[2-(4-methyl-1-oxo-1,3-dihydro-2-benzofuran-5-yl)ethyl]piperazine-1-carboxylate To a solution of (4-methyl-1-oxo-1,3-dihydro-2-benzofuran-5-yl)acetaldehyde (160 mg, 0.84 mmol) and 1-Boc Piperazine (234 mg, 1.26 mmol) in MeOH (5 mL) was added NaCNBH$_3$ (149 mg, 2.52 mmol) and a few drops of acetic acid. The reaction was allowed to stir at RT for 16 hours. TLC at that point showed good and complete reaction. The reaction was diluted with EtOAc (100 mL), washed with aq. NaHCO$_3$ solution and brine, dried over Na$_2$SO$_4$, adsorbed onto silica gel, and purified by MPLC. 1,1-Dimethylethyl-4-[2-(4-methyl-1-oxo-1,3-dihydro-2-benzofuran-5-yl)ethyl]piperazine-1-carboxylate was collected after removal of solvents.

LCMS: m/z 361 (M+1)$^+$.

Step D: 4-methyl-5-(2-piperazin-1-ylethyl)-2-benzofuran-1(3H)-one hydrochloride 1,1-Dimethylethyl-4-[2-(4-methyl-1-oxo-1,3-dihydro-2-benzofuran-5-yl)ethyl]piperazine-1-carboxylate (245 mg) was treated with 4N HCl in dioxane solution and the reaction was monitored until completion. The mixture was concentrated to afford 4-methyl-5-(2-piperazin-1-ylethyl)-2-benzofuran-1(3H)-one hydrochloride. The hydrochloride can be converted to free base as needed by partitioning between organic solvent (EtOAc, DCM, or 30% IPA/CHCl3) and saturated Na2CO3 solution.

$^1$H-NMR (500 MHz, DMSO) δ ppm 12.4 (broad, 1H), 9.80 (broad, 2H), 7.71 (d, J=7.5 Hz, 1H), 5.53 (d, J=7.5 Hz, 1H), 5.44 (s, 2H), 3.81 (m, 2H), 3.64-3.27 (m, 10H).

INTERMEDIATE 18

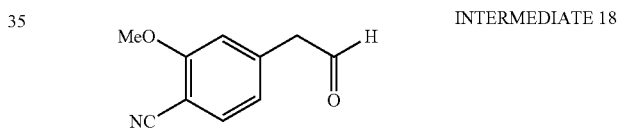

2-(methyloxy)-4-(2-oxoethyl)benzonitrile

Step A: Ethyl(3-methoxy-4-{[(trifluoromethyl)sulfonyl]oxy}phenyl)acetate

Ethyl(4-hydroxy-3-methoxyphenyl)acetate, 12 g, 57 mmol] was dissolved in anhydrous dichloromethane (200 mL). 4-Dimethylaminopyridine (0.70 g, 0.10 equiv) was added, followed by triethylamine (9.6 mL, 69 mmol). The solution was then cooled to −78° C. in a dry ice and acetone bath while under nitrogen. Trifluoromethanesulfonic anhydride (9.6 mL, 57 mmol) was slowly added and the reaction mixture was allowed to warm to ambient temperature. The reaction mixture was then diluted with dichloromethane (200 mL) and washed with water (2×100 mL). The organic layer was dried over MgSO$_4$, filtered, and concentrated to dryness under reduced pressure to yield ethyl(3-methoxy-4-{[(trifluoromethyl)sulfonyl]oxy}phenyl)acetate, which was used without further purification. LC/MS [(M+1)-CO$_2$Et]$^+$=269.0; t$_R$=3.5 min.

Step B: Ethyl(4-cyano-3-methoxyphenyl)acetate

Ethyl(3-methoxy-4-{[(trifluoromethyl)sulfonyl]oxy}phenyl)acetate (16.6 g) was dissolved in anhydrous dimethylformamide (100 mL). Zinc cyanide (3.4 g, 29 mmol)

was added, and the solution was purged thoroughly with nitrogen. Tetrakis(triphenylphosphine)palladium(0) (5.6 g, 4.9 mmol) was then added and the reaction mixture was heated to 80° C. for 4 h. After allowing the reaction mixture to cool to ambient temperature and diluting with water (200 mL), ethyl acetate (400 mL) was added and the mixture was filtered to remove any solids. The filtrate was transferred to a separatory funnel, and the layers separated. The aqueous layer was re-extracted with ethyl acetate (2×100 mL). The organic layers were combined and dried over magnesium sulfate. The dry organics were then filtered and evaporated to dryness under reduced pressure and excess dimethylformamide was removed by evaporation in vacuo at 65° C. for 1.5 h to yield crude product. The crude product was purified through silica gel chromatography (ethyl acetate/hexanes, 2:3) to yield ethyl(4-cyano-3-methoxyphenyl)acetate. $^1$H NMR (500 MHz, DMSO-$d_6$), δ 7.67 (d, J=8.0 Hz, 1H), 7.18 (s, 1H), 7.0 (d, J=8.0 Hz, 1H), 4.10 (q, J=7.1 Hz, 2H), 3.89 (s, 3H), 3.78 (s, 2H), 1.19 (t, J=7.1 Hz, 3H); LC/MS (M+1)$^+$=220.17; $t_R$=1.36 min.

Step C: 4-(2-Hydroxyethyl)-2-methoxybenzonitrile

LiBH$_4$ (1.7 mL, 3.4 mmol, 2 M in THF) was added to a stirred solution of ethyl(4-cyano-3-methoxyphenyl)acetate (0.50 g, 2.4 mmol) in THF (25 mL) at 0° C. The resulting solution was stirred for 12 h. Water (15 ml) was added, and the resulting solution was extracted with dichloromethane (2×50 ml). The combined organic layers were dried over MgSO$_4$, filtered, and evaporated under reduced pressure. The residue was purified by column chromatography eluting with EtOAc-Hexanes (7:3→1:1) to give 4-(2-hydroxyethyl)-2-methoxybenzonitrile. $^1$H NMR (500 MHz, CDCl$_3$) δ 7.52 (d, 1H, J=7.0 Hz), 6.91 (d, 1H, J=7.8 Hz), 6.88 (s, 1H), 3.95 (s, 3H), 3.92 (t, 2H, J=6.4 Hz), 2.93 (t, 2H, J=6.4 Hz); LCMS: [(M+1)]$^+$=178.3; $t_R$=2.1 min.

Step D: 2-Methoxy-4-(2-oxoethyl)benzonitrile

To a stirred solution of 4-(2-hydroxyethyl)-2-methoxybenzonitrile (1.5 g, 8.5 mmol) in dry CH$_2$Cl$_2$ (30 mL) at 0° C. was added Dess-Martin periodinane (3.6 g, 8.5 mmol) in one portion. The mixture was stirred for 12 h at rt and quenched with a 1:1 mixture of saturated Na$_2$S$_2$O$_3$ (40 mL) and saturated NaHCO$_3$ (40 mL). The resulting mixture was diluted with CH$_2$Cl$_2$ (70 mL) and the layers were separated. The aqueous phase was extracted with CH$_2$Cl$_2$ (2×50 mL). The combined organic phases were washed with brine, dried (Na$_2$SO$_4$), and concentrated in vacuo to give 2-methoxy-4-(2-oxoethyl)benzonitrile. The residue was used in the next step without further purification. $^1$H NMR (500 MHz, CDCl$_3$) δ 9.77 (s, 1H), 7.52 (d, 1H, J=8.8 Hz), 6.86 (dd, 1H, J=1.1 Hz), 6.79 (s, 1H), 3.92 (s, 3H), 3.76 (s, 2H); LCMS: [(M+1)]$^+$=176.26; $t_R$=1.98 min.

INTERMEDIATE 18

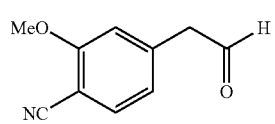

(method 2)

2-(methyloxy)-4-(2-oxoethyl)benzonitrile

Step A: 2-(methyloxy)-4-prop-2-en-1-ylbenzonitrile

To a 50 mL flask containing a stir bar were added 2-methoxy-4-bromobenzonitrile (0.30 g, 1.4 mmol), palladium tetrakis (82 mg, 0.071 mmol), allyltri-n-butyltin (0.877 mL, 2.83 mmol), and lithium chloride (0.120 g, 2.83 mmol). The resulting mixture was then dissolved in anhydrous toluene (16 mL); the flask was placed in an oil bath and heated at 130° C.; LC as well as TLC (hexanes/EtOAc=1/0.3) indicated that reaction had gone to completion. The flask was taken out of the oil bath and cooled to room temperature. To the flask was poured EtOAc (40 mL) and the mixture was transferred into a separatory funnel and washed with aqueous NaCl. The organic phase was dried over Na$_2$SO$_4$, filtered and concentrated to dryness. It was then dissolved in DCM and absorbed into silica gel. The slica gel was then loaded onto a silica column for separation with the solvent systems of hexanes/EtOAc (1/0.3); this gave 2-(methyloxy)-4-prop-2-en-1-ylbenzonitrile. LC-MS (IE, m/z): 174 [M+1]$^+$; $t_R$=2.10 min.

Step B: 2-(methyloxy)-4-(2-oxoethyl)benzonitrile

To a 25 mL flask containing a stir bar was added compound 2-(methyloxy)-4-prop-2-en-1-ylbenzonitrile (0.150 g, 0.866 mmol) and MeOH (8 mL). The flask was placed in a cold bath of −78° C. Ozone was bubbled through the flask for about 10 min. followed by addition of dimethyl sulfide (1.5 mL, 0.024 mmol). The flask was taken out of the cold bath and stirred at room temperature for 1 h; LC indicated completion of the reaction. The reaction mixture was concentrated to dryness to give 2-(methyloxy)-4-(2-oxoethyl)benzonitrile.
LC-MS (IE, m/z): 176 [M+1]$^+$; $t_R$=1.49 min.

INTERMEDIATE 19

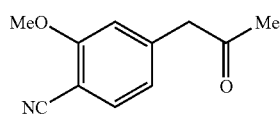

2-(methyloxy)-4-(2-oxopropyl)benzonitrile

Step A: 4-(2-Hydroxypropyl)-2-methoxybenzonitrile

To a stirred solution of 2-methoxy-4-(2-oxoethyl)benzonitrile (1.5 g, 8.5 mmol) in dichloromethane (30 mL) at 0° C. was added 2.8 mL (8.5 mmol) of a 3.0 M solution of methylmagnesium bromide in THF. The reaction mixture was allowed to warm up to rt and stirred for 12 h. The reaction was then quenched by the addition of 10 mL of 1 N hydrochloric acid and extracted with dichloromethane (2×30 mL). The combined organic extracts were dried with magnesium sulfate, filtered, and concentrated in vacuo. The crude residue was purified on silica (30% EtOAc/hexanes as eluent) to afford 4-(2-hydroxypropyl)-2-methoxybenzonitrile. $^1$H NMR (500 MHz, CDCl$_3$) δ 7.47 (d, 1H, J=7.8 Hz), 6.85 (dd, 1H, J=3.4 Hz), 6.82 (s, 1H), 4.05 (m, 1H), 3.93 (d, 2H), 3.91 (s, 3H), 1.25 (d, 2H, J=6.1 Hz); LCMS: [(M+1)]$^+$=192.30; $t_R$=2.39 min.

Step B: 2-Methoxy-4-(2-oxopropyl)benzonitrile

To a stirred solution of 4-(2-hydroxypropyl)-2-methoxybenzonitrile (1.5 g, 7.6 mmol) in dry CH$_2$Cl$_2$ (30 mL) at 0° C.

was added Dess-Martin periodinane (4.2 g, 9.9 mmol) in one portion. The mixture was stirred for 12 h at rt and quenched with a 1:1 mixture of saturated Na$_2$S$_2$O$_3$ (20 mL) and saturated NaHCO$_3$ (20 mL). The resulting mixture was diluted with CH$_2$Cl$_2$ (50 mL) and the layers were separated. The aqueous phase was extracted with CH$_2$Cl$_2$ (2×50 mL). The combined organic phases were washed with brine, dried (Na$_2$SO$_4$), and concentrated in vacuo to give 2-methoxy-4-(2-oxopropyl)benzonitrile. The crude residue was used in the next step without further purification. $^1$H NMR (500 MHz, CDCl$_3$) δ 7.55 (dd, 1H, J=1.6 Hz), 6.87 (d, 1H, J=7.8 Hz), 6.83 (s, 1H), 3.96 (s, 3H), 3.79 (s, 2H), 2.25 (s, 3H); LCMS: [(M+1)]$^+$=190.32; t$_R$=2.31 min.

for 12 hr. The starting material was consumed as indicated by TLC (25% ethyl acetate/hexanes). The reaction mixture was cooled to 0° C. and quenched by drop-wise addition of water. The mixture was extracted with ethyl acetate (2×70 mL). The combined organic layers were washed with water, brine, then dried (MgSO$_4$) and filtered. The filtrate was concentrated in vacuo. The residue was purified via column chromatography (silica gel, 10-30% EtOAc-hexanes) to afford 2-methoxy-4-(oxiran-2-yl)benzonitrile. $^1$H NMR (CDCl$_3$, 500 MHz) δ 7.57 (d, J=8 Hz, 1H), 6.99 (dd, J=1.1 Hz, J=1.2 Hz, 1H), 6.89 (s, 1H), 3.97 (s, 3H), 3.94-3.92 (m, 1H), 3.22 (dd, J=5.2, Hz, J=4.1 Hz, 1H), 2.77 (J=2.5 Hz, 1H); LC/MS (IE, m/z) 176.33 [M+1]$^+$; t$_R$=2.55 min.

INTERMEDIATE 20

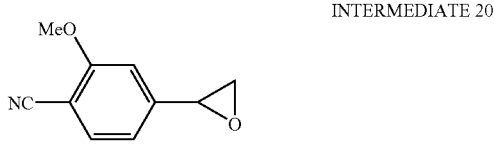

2-(methyloxy)-4-oxiran-2-ylbenzonitrile

INTERMEDIATE 21

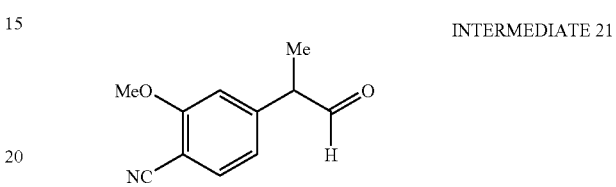

4-(1-methyl-2-oxoethyl)-2-(methyloxy)benzonitrile

Step A: 4-Formyl-2-methoxyphenyl trifluoromethanesulfonate

To a solution of vanillin (20.0 g, 131 mmol) in DMF (200 mL) at room temperature was added potassium carbonate (36 g, 263 mmol) and 4-nitrophenyl trifluoromethanesulfonate (54.0 g, 197 mmol) and the reaction mixture was stirred for 8 h. EtOAc (600 mL) was added to the reaction mixture and the organic layer was washed three times with water, dried, filtered, and concentrated. The crude compound was then purified by flash chromatography (ethylacetate/hexanes 1:9→3:7) to provide 4-formyl-2-methoxyphenyl trifluoromethanesulfonate.

$^1$H NMR (CDCl$_3$, 500 MHz) δ 10.02 (s, 1H), 7.60 (s, 1H), 7.55 (d, J=8.1 Hz, 1H), 7.45 (d, J=8.0 Hz, 1H), 4.04 (s, 3H); LC/MS (IE, m/z) 284.98 [M+1]$^+$; t$_R$=3.31 min.

Step B: 4-Formyl-2-methoxybenzonitrile

A mixture of 4-formyl-2-methoxyphenyl trifluoromethanesulfonate (37.0 g, 130 mmol), zinc cyanide (61.0 g, 521 mmol) and tetrakis triphenylphosphine palladium (0) (22.6 g, 19.5 mmol) in DMF (300 mL) were stirred at 110° C. for 8 h. EtOAc was added to the reaction mixture and the organic layer was washed two times with water, dried, filtered and concentrated. The crude product was then purified by column chromatography (silica gel, ethylacetate/hexanes 3:7) which afforded 4-formyl-2-methoxybenzonitrile.

$^1$H NMR (CDCl$_3$, 500 MHz) δ 10.08 (s, 1H), 7.80 (d, J=7.5 Hz, 1H), 7.55 (d, J=7.5 Hz. 1H), 7.51 (s, 1H), 4.06 (s, 3H); LC/MS (IE, m/z) 162.07 [M+1]$^+$.

Step C: 2-Methoxy-4-(oxiran-2-yl)benzonitrile

To a cool solution of NaH (0.16 g, 3.9 mmol) in THF (40 ml) was added dropwise a solution of trimethylsulfonium iodide (0.91 g, 4.5 mmol) in DMSO (20 ml). The resulting mixture was stirred at 0° C. under N$_2$ for 20 min. The solution of 4-formyl-2-methoxybenzonitrile (0.60 g, 3.7 mmol) in THF (20 ml) was added. The resulting reaction mixture was stirred at 0° C. under N$_2$ for 1 hr, and then it was warmed gradually to room temperature and stirred at that temperature Step A: Ethyl 2-(4-cyano-3-methoxyphenyl)propanoate To a suspension solution of NaH (0.18 g, 4.6 mmol, 60% dispersion in mineral oil) in THF (50 mL) at ° C. under N$_2$ atm was added a solution of ethyl(4-cyano-3-methoxyphenyl)acetate (1.0 g, 4.6 mmol) in THF (10 mL) drop-wise and the mixture was stirred for 30 min at the same temperature. The mixture was then allowed to warm to ambient temperature. The mixture was then allowed to cool back to 0° C. Methyl iodide (0.28 mL, 4.6 mmol) was added and the reaction mixture was stirred for 1 h. The reaction mixture was acidified with 1 M hydrochloric acid and extracted with EtOAc. The organic layer was washed with brine, dried over anhydrous sodium sulfate, and concentrated in vacuo. The residue was purified by silica gel column chromatography (hexane/EtOAc 15/1) to give ethyl 2-(4-cyano-3-methoxyphenyl)propanoate. $^1$H NMR (500 MHz, CDCl$_3$) δ 7.53 (d, 1H, J=8 Hz), 6.98 (d, 1H, J=8 Hz), 6.95 (s, 1H), 4.17 (q, 2H, J=3.4 Hz), 3.97 (s, 3H), 3.76 (q, 1H, J=9.1 Hz), 1.53 (d, 3H, J=7.1 Hz), 1.25 (t, 3H, J=7.1 Hz); LCMS: [(M+1)]$^+$=234.28; t$_R$=3.12 min.

Step B: 4-(1-Hydroxypropan-2-yl)-2-methoxybenzonitrile

LiBH$_4$ (0.55 mL, 1.1 mmol, 2 M in THF) was added to a stirred solution of ethyl 2-(4-cyano-3-methoxyphenyl)propanoate (0.17 g, 0.73 mmol) in THF (25 mL) at 0° C. The resulting solution was stirred for 12 h. Water (15 mL) was added, and the resulting solution was extracted with dichloromethane (2×50 mL). The combined organic layers were dried over MgSO$_4$, filtered, and evaporated under reduced pressure. The residue was purified by column chromatography eluting with EtOAc-Hexanes (7:3→1:1) to give 4-(1-hydroxypropan-2-yl)-2-methoxybenzonitrile.

$^1$H NMR (500 MHz, CDCl$_3$) δ 7.49 (d, 1H, J=7.9 Hz), 6.88 (dd, 1H, J=1.4 Hz), 6.83 (s, 1H), 3.92 (s, 3H), 3.72 (d, 2H, J=6.8 Hz), 2.97 (q, 1H, J=6.8 Hz), 1.28 (d, 3H, J=6.9 Hz);
LCMS: [(M+1)]$^+$=192.32; t$_R$=2.32 min.

Step C: 2-Methoxy-4-(1-oxopropan-2-yl)benzonitrile

To a stirred solution of 4-(1-hydroxypropan-2-yl)-2-methoxybenzonitrile (0.12 g, 0.63 mmol) in dry CH$_2$Cl$_2$ (30 mL) at 0° C. was added Dess-Martin periodinane (0.35 g, 0.82 mmol) in one portion. The mixture was stirred for 12 h at rt and quenched with a 1:1 mixture of saturated $Na_2S_2O_3$ (20 mL) and saturated $NaHCO_3$ (20 mL). The resulting mixture was diluted with $CH_2Cl_2$ (50 mL) and the layers were separated. The aqueous phase was extracted with $CH_2Cl_2$ (2×50 mL). The combined organic phases were washed with brine, dried ($Na_2SO_4$), and concentrated in vacuo to give crude 2-methoxy-4-(1-oxopropan-2-yl)benzonitrile. The crude residue was used in subsequent reactions without further purification.

LCMS: $[(M+1)]^+$=190.32; $t_R$=2.47 min

INTERMEDIATE 22

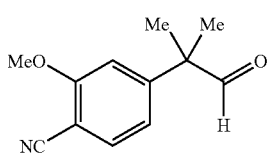

4-(1,1-dimethyl-2-oxoethyl)-2-(methyloxy)benzonitrile

Step A: Ethyl(3-methoxy-4-{[(trifluoromethyl)sulfonyl]oxy}phenyl)acetate

Ethyl(4-hydroxy-3-methoxyphenyl)acetate (12.0 g, 57.1 mmol) was dissolved in anhydrous dichloromethane (200 mL). 4-Dimethylaminopyridine (0.70 g, 0.10 equiv) was added, followed by triethylamine (9.55 mL, 68.5 mmol). The solution was then cooled to in a dry ice and acetone bath while under nitrogen. Trifluoromethanesulfonic anhydride (9.60 mL, 57.1 mmol) was slowly added and the reaction mixture was allowed to warm to ambient temperature. The reaction mixture was then diluted with dichloromethane (200 mL) and washed with water (2×100 mL). The organic layer was dried over magnesium sulfate, filtered, and concentrated to dryness under reduced pressure to yield the crude ethyl(3-methoxy-4-{[(trifluoromethyl)sulfonyl]oxy}phenyl)acetate. LC/MS $[(M+1)-CO_2Et]^+$=269.0; $t_R$=3.5 min.

Step B: Ethyl(4-cyano-3-methoxyphenyl)acetate

The crude ethyl(3-methoxy-4-{[(trifluoromethyl)sulfonyl]oxy}phenyl)acetate (16.61 g) was subsequently dissolved in anhydrous dimethylformamide (100 mL). Zinc cyanide (3.42 g, 29.1 mmol) was added, and the solution was purged thoroughly with nitrogen. Tetrakis(triphenylphosphine)palladium(0) (5.61 g, 4.85 mmol) was then added and the reaction mixture was heated to 80° C. for 4 h. After allowing the reaction mixture to cool to ambient temperature and diluting with water (200 mL), ethyl acetate (400 mL) was added. The combined layers were filtered to remove any solids, the filtrate transferred to a separatory funnel, and the layers separated. The aqueous layer was re-extracted with ethyl acetate (2×100 mL), the organic portions were combined and dried over magnesium sulfate. The dry organics were then filtered and evaporated to dryness under reduced pressure and excess dimethylformamide was removed by evaporation in vacuo at 65° C. for 1.5 h to yield the crude title compound (20 g). The crude product was purified through silica gel chromatography (ethyl acetate/hexanes, 2:3) to yield ethyl(4-cyano-3-methoxyphenyl)acetate. NMR (500 MHz, DMSO-$d_6$), δ 7.67 (d, J=8.0 Hz, 1H), 7.18 (s, 1H), 7.0 (d, J=8.0 Hz, 1H), 4.10 (q, J=7.1 Hz, 2H), 3.89 (s, 3H), 3.78 (s, 2H), 1.19 (t, J=7.1 Hz, 3H); LC/MS $(M+1)^+$=220.17; $t_R$=1.36 min.

Step C: Ethyl 2-(4-cyano-3-methoxyphenyl)-2-methylpropanoate

To a suspension solution of NaH (0.365 g, 9.12 mmol, 60% dispersion in mineral oil) in THF (50 mL) at ° C. under $N_2$ atm was added a solution of ethyl(4-cyano-3-methoxyphenyl)acetate (1.0 g, 4.56 mmol) in THF (10 mL) dropwise and the mixture was stirred for 30 min at the same temperature. The mixture was then allowed to warm to ambient temperature. The mixture was then allowed to cool back to ° C. Methyl iodide (0.570 mL, 9.12 mmol) was added and the reaction mixture was stirred for 1 h. The reaction mixture was acidified by 1 M hydrochloric acid and extracted with EtOAc. The organic layer was washed with brine, dried over anhydrous sodium sulfate, and concentrated in vacuo. The residue was purified by silica gel column chromatography (hexane/EtOAc 15/1) to give ethyl 2-(4-cyano-3-methoxyphenyl)-2-methylpropanoate. $^1$H NMR (500 MHz, CDCl$_3$) δ 7.54 (d, 1H, J=8.0 Hz), 7.02 (dd, 1H, J=1.6 Hz), 6.95 (d, 1H, J=1.4 Hz), 4.17 (q, 2H, J=7.2 Hz), 3.96 (s, 3H), 1.61 (s, 6H), 1.23 (t, 3H, J=7.1 Hz); LCMS: $[(M+1)]^+$=248.33; $t_R$=3.28 min.

Step D: 4-(1-Hydroxy-2-methylpropan-2-yl)-2-methoxybenzonitrile

LiBH$_4$ (0.485 mL, 0.971 mmol, 2 M in THF) was added to a stirred solution of ethyl 2-(4-cyano-3-methoxyphenyl)-2-methylpropanoate (0.160 g, 0.647 mmol) in THF (25 mL) at 0° C. The resulting solution was stirred for 12 h. Water (15 mL) was added, and the resulting solution was extracted with dichloromethane (2×50 mL). The combined organic layers were dried over MgSO$_4$, filtered, and evaporated under reduced pressure. The residue was purified by column chromatography eluting with EtOAc-Hexanes (7:3→1:1) to give an inseparable mixture containing primarily 4-(1-hydroxy-2-methylpropan-2-yl)-2-methoxybenzonitrile.

$^1$H NMR (500 MHz, CDCl$_3$) δ 7.55 (d, 1H, J=8.0 Hz), 6.88 (d, 1H, J=8.0 Hz), 7.02 (s, 1H), 3.98 (s, 3H), 3.69 (s, 2H), 1.38 (s, 6H); LCMS: $[(M+1)]^+$=206.35; $t_R$=2.65 min.

Step E: 2-methoxy-4-(2-methyl-1-oxopropan-2-yl) benzonitrile

To a stirred solution of 4-(1-hydroxy-2-methylpropan-2-yl)-2-methoxybenzonitrile (0.120 g, 0.585 mmol) in dry CH$_2$Cl$_2$ (30 mL) at 0° C. was added Dess-Martin periodinane (0.322 g, 0.760 mmol) in one portion. The mixture was stirred for 12 h at rt and quenched with a 1:1 mixture of saturated Na$_2$S$_2$O$_3$ (20 mL) and saturated NaHCO$_3$ (20 mL). The resulting mixture was diluted with CH$_2$Cl$_2$ (50 mL) and the layers were separated. The aqueous phase was extracted with CH$_2$Cl$_2$ (2×50 mL). The combined organic phases were washed with brine, dried (Na$_2$SO$_4$), and concentrated in vacuo to give crude aldehyde. The crude residue was used in the next step without further purification. LCMS: $[(M+1)]^+$=204; $t_R$=2.95 min.

INTERMEDIATE 23

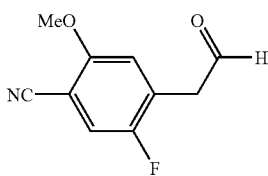

5-fluoro-2-(methyloxy)-4-(2-oxoethyl)benzonitrile

Step A: di-tert-Butyl(4-cyano-2-fluoro-5-methoxyphenyl)propanedioate

A suspension of NaH (60% in mineral oil, 0.33 g, 8.3 mmol) in dry DMF (20 mL) was stirred and cooled to 0° C., and di-tert-butyl malonate (1.5 g, 7.1 mmol) was added. The mixture was allowed to warm to room temperature before addition of 4,5-difluoro-2-methoxybenzonitrile (1.0 g, 5.9 mmol). The mixture was heated at 80° C. for 4 h with stirring, then the reaction mixture was cooled to room temperature and poured into a mixture of ice-water (100 mL) and AcOEt (100 mL). The layers were separated, and the organic layer was washed successively with water, and brine, then dried over $Na_2SO_4$ and concentrated. The residue was purified by flash chromatography (silica gel, EtOAc/hexanes, 0→10%) to give the di-tert-butyl(4-cyano-5-fluoro-2-methoxyphenyl)propanedioate. LCMS: $[(M+1)-t-Bu,CO2-t-Bu]^+=210.1$; $t_R=2.2$ min.

Step B: (4-Cyano-2-fluoro-5-methoxyphenyl)acetic acid

Trifluoroacetic acid (5 mL) was added to a solution of di-tert-butyl(4-cyano-5-fluoro-2-methoxyphenyl)propanedioate (1.3 g, 28 mmol) in dichloromethane (5 mL) at room temperature. The reaction mixture was stirred overnight, then concentrated under reduced pressure, and the residue was treated with $Et_2O$ (10 mL) to induce crystallization. The crystals were collected by filtration to give (4-cyano-2-fluoro-5-methoxyphenyl)acetic acid.

$^1$H NMR (500 MHz, $CD_3OD$) δ 7.44 (d, J=5.3 Hz, 1H), 7.19 (d, J=5.4 Hz, 1H), 3.96 (s, 3H), 3.78 (s, 2H); LC/MS: $[(M+1)]^+=210.1$; $t_R=0.62$ min.

Step C: Methyl(4-Cyano-2-fluoro-5-methoxyphenyl)acetate

To a solution of (4-cyano-2-fluoro-5-methoxyphenyl)acetic acid (5.0 g, 24 mmol) in methanol (50 mL) at 0° C. was added thionyl chloride (2.3 mL, 31 mmol) drop-wise. The mixture warmed slowly to rt and stirred 12 h, then was concentrated in vacuo and dried under high vacuum to provide methyl(4-Cyano-2-fluoro-5-methoxyphenyl)acetate. $^1$H NMR (500 MHz, $CD_3OD$) δ 7.35 (d, J=5.3 Hz, 1H), 7.19 (d, J=5.4 Hz, 1H), 3.96 (s, 3H), 3.82 (s, 3H), 3.81 (s, 2H).

Step D: 5-Fluoro-4-(2-hydroxyethyl)-2-methoxybenzonitrile

To a solution of methyl(4-Cyano-2-fluoro-5-methoxyphenyl)acetate (5.0 g, 22 mmol) in THF (50 mL) at 0° C. was added lithium borohydride (14.6 mL, 29.1 mmol). The reaction was stirred for 12 h, then was diluted with saturated ammonium chloride solution and extracted three times with ethyl acetate. The combined organic layers were washed with brine, dried (Na2SO4), filtered, and concentrated. Silica gel column chromatography (50→100% EtOAc:hex.) provided 5-fluoro-4-(2-hydroxyethyl)-2-methoxybenzonitrile. $^1$H NMR (500 MHz, $CD_3OD$) δ 7.19 (d, J=5.3 Hz, 1H), 6.89 (d, J=5.4 Hz, 1H), 4.21 (br s, 1H), 3.88 (s, 3H), 3.82 (m, 2H), 2.92 (m, 2H); LC/MS: $[(M+1)]^+=196.2$; $t_R=0.58$ min.

Step E: 5-Fluoro-2-methoxy-4-(2-oxoethyl)benzonitrile

To a solution of 5-fluoro-4-(2-hydroxyethyl)-2-methoxybenzonitrile (175 mg, 0.900 mmol) in Dichloromethane (4 mL) was added Dess-Martin Periodinane (0.53 g, 1.2 mmol). The solution was stirred for 2 h at ambient temperature, then was diluted with $NaHCO_3$ (sat.) and $Na_2S_2O_3$ (sat.) and stirred for 30 min. The layers were separated and the aqueous layer was extracted with dichloromethane twice. The combined organics were washed with brine, dried (MgSO4), filtered, and concentrated to provide the desired aldehyde, which was used directly without further purification.

INTERMEDIATE 24

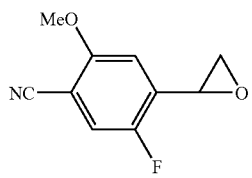

5-Fluoro-2-methoxy-4-oxiran-2-ylbenzonitrile

To a solution of 5-fluoro-4-(2-hydroxyethyl)-2-methoxybenzonitrile (0.68 g, 3.5 mmol) and $Et_3N$ (0.82 mL, 5.9 mmol) in dichloromethane (5 mL) was added methanesulfonyl chloride (0.33 mL, 4.2 mmol) at 0° C. After 15 min. the reaction mixture was poured into saturated ammonium chloride and extracted with dichloromethane. The combined organics were washed with 1 N HCl, saturated sodium bicarbonate solution, and brine, then dried (MgSO4) and concentrated in vacuo. The residue was re-dissolved in dichloromethane (5 mL), treated with DBU (0.79 mL, 5.2 mmol) and stirred for 2 h. TLC monitoring showed conversion to the olefin. The reaction mixture was diluted with water and extracted with dichloromethane. The combined organics were washed with 1 N HCl, saturated sodium bicarbonate solution, and brine, then dried (MgSO4) and concentrated in vacuo. The resulting olefin was dissolved in dichloromethane (5 mL) and treated with meta-chloro perbenzoic acid (0.72 g, 4.2 mmol) at 0° C. After 3 h, the mixture was diluted with saturated sodium bicarbonate solution and extracted with dichloromethane (twice). The combined organic extracts were washed with brine, dried (MgSO4), filtered and concentrated in vacuo. The crude epoxide was purified by silica gel column chromatography (5→80% EtOAc:hexane) to provide 5-fluoro-2-methoxy-4-oxiran-2-ylbenzonitrile. $^1$H NMR (500 MHz, $CD_3OD$) δ 7.32 (d, J=5.3 Hz, 1H), 6.82 (d, J=5.4 Hz, 1H), 4.19 (m, 1H), 3.96 (s, 3H), 3.27 (m, 1H), 2.76 (m, 1H);

LC/MS: $[(M+1)]^+=194.1$; $t_R=0.58$ min.

INTERMEDIATE 25

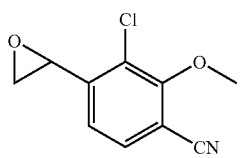

(2-Chloro-4-cyano-3-methoxyphenyl)ethylene oxide

Step A: t-Butyl, methyl(R,S)-2-(2-chloro-4-cyano-3-fluorophenyl)malonate t-Butyl, methyl malonate (7.5 g, 43 mmol) in DMF (50 mL) was cooled in an ice bath before NaH (60% in mineral oil, 1.0 g, 42 mmol) was added portionwise over 5 minutes with hydrogen evolution. The suspension was allowed to warm to RT for 30 minutes at which time everything was in solution. 3-Chloro-2,4-difluorobenzonitrile (5.0 g, 28.8 mmol) was added as a solid and the reaction was heated to 90° C. for 4 hours and then at RT for 12 hours. TLC (15% ethyl acetate/hexanes) indicated still some starting material but mostly product at a slightly lower $R_f$. The reaction was diluted with ether and quenched into water containing 2N HCl. The mixture was extracted twice with ether and the ether layers were washed with brine, dried over sodium sulfate and concentrated in vacuo. The crude product was taken up in 1:1 methanol:dichloromethane (50 mL) and 2M trimethylsilyldiazomethane in ether was added until the yellow color persisted to re-esterify any acid. The excess diazomethane was quenched with acetic acid and the mixture was reconcentrated. The product mixture was separated by flash chromatography (5-10% ethyl acetate/hexanes, then 10-20%) to afford first some recovered starting material, then a mixture of product and isomeric t-butyl, methyl(R,S)-2-(2-chloro-6-cyano-3-fluorophenyl)malonate by NMR (900 mg), followed by clean title product isomer. $^1$H-NMR (400 MHz, CDCl$_3$) δ ppm 1.46 (s, 9H), 3.79 (s, 3H), 5.15 (s, 1H), 7.448 (d, J=8.3 Hz, 1H), 7.56 (dd, J=6.0, 8.2, 1H).

Step B: Methyl(2-chloro-4-cyano-3-fluorophenyl)acetate

A solution of t-butyl, methyl(R,S)-2-(2-chloro-4-cyano-3-fluorophenyl)malonate (4.80 g, 14.6 mmol) in 1:1 TFA:dichloromethane (50:50 mL) was stirred at RT for 20 hours and then concentrated in vacuo. The residue was taken up in methanol and heated to reflux until the decarboxylation was complete by HPLC/MS and TLC. The mixture was reconcentrated and the residue was purified by flash chromatography (10-40% ethyl acetate/hexanes) to afford clean title product isomer. $^1$H-NMR (400 MHz, CDCl$_3$) δ ppm 3.73 (s, 3H), 3.86 (s, 2H), 7.234 (d, J=8.0 Hz, 1H), 7.56 (dd, J=6.1, 8.0 Hz, 1H).

Step C: Methyl(2-chloro-4-cyano-3-methoxyphenyl)acetate

A solution of methyl(2-chloro-4-cyano-3-fluorophenyl)acetate (1.40 g, 6.15 mmol) in methanol (30 mL) was divided into two 20 mL microwave (MW) vials. Potassium carbonate (2×850 mg) was added to each MW vial. Each was heated in a microwave at 130° C. for 60 minutes at which time HPLC/MS indicated no starting material was left and the product was all hydrolyzed to the acid. Most of the methanol was removed in vacuo and the residue was diluted with water, acidified with 2M HCl and the mixture was extracted twice with ethyl acetate. The organic layers were washed with brine, dried over sodium sulfate and concentrated in vacuo. The crude product was taken up in 1:1 methanol:dichloromethane (50 mL) and 2M trimethylsilyldiazomethane in ether was added until the yellow color persisted to re-esterify the acid. The excess diazomethane was quenched with acetic acid and the mixture was concentrated. The residue was purified by flash chromatography (40% DCM/hexanes to 100% DCM) to give the title product. $^1$H-NMR (400 MHz, CDCl$_3$) δ ppm 3.73 (s, 3H), 3.83 (s, 2H), 4.07 (s, 3H), 7.139 (d, J=8.1 Hz, 1H), 7.468 (d, J=8.0, 1H).

Step D: 2-(2-Chloro-4-cyano-3-methoxyphenyl)ethanol

To a solution of methyl(2-chloro-4-cyano-3-methoxyphenyl)acetate (700 mg, 2.92 mmol) in THF (30 mL) was added 2M lithium borohydride (1.46 mL, 2.92 mmol) and the reaction was stirred at RT for 16 hours. The reaction was diluted with ether and quenched into water containing 2N HCl. The mixture was extracted twice with ethyl acetate and the organic layers were washed with brine, dried over sodium sulfate and concentrated in vacuo. The product mixture was separated by flash chromatography (10-40% ethyl acetate/hexanes) to afford the title product. $^1$H-NMR (400 MHz, CDCl$_3$) δ ppm 3.10 (t, J=6.4 Hz, 2H), 3.94 (t, J=6.4 Hz, 2H), 4.08 (s, 3H), 7.175 (d, J=7.8 Hz, 1H), 7.46 (d, J=7.8 Hz, 1H).

Step E: 2-(2-Chloro-4-cyano-3-methoxyphenyl)ethyl methanesulfonate

A solution of 2-(2-chloro-4-cyano-3-methoxyphenyl)ethanol (205 mg, 0.969 mmol) DIPEA (0.846 mL, 4.84 mmol) and pyridine (0.078 mL, 0.969 mmol) in DCM (3 mL) was treated dropwise with mesyl chloride (0.110 mL, 1.417 mmol). The reaction was stirred for 2 hours and was then diluted with DCM and washed twice with aq. citric acid, then washed with brine, and dried over sodium sulfate. The residue was purified by flash chromatography (20-50% ethyl acetate/hexanes) to afford the title intermediate.
$^1$H-NMR (500 MHz, CDCl$_3$) δ ppm 3.00 (s, 3H), 3.30 (t, J=6.6 Hz, 2H), 4.11 (s, 3H), 4.50 (t, J=6.6 Hz, 2H), 7.189 (d, J=8.0 Hz, 1H), 7.508 (d, J=8.0 Hz, 1H).

Step F: (2-Chloro-4-cyano-3-methoxyphenyl)ethylene

A solution of 2-(2-chloro-4-cyano-3-methoxyphenyl)ethyl methanesulfonate (207 mg, 0.714 mmol) in DCM (4 mL) was treated with DBU (0.538 mL, 3.57 mmol) and stirred overnight at 40° C. TLC (50% ethyl acetate/hexanes) showed complete conversion to a faster intense UV band for product. The reaction was then diluted with DCM and aq. citric acid and the mixture was extracted twice with DCM. The organic layers were washed with brine, dried over sodium sulfate and concentrated in vacuo. Purification of the residue by flash chromatography (5-20% ethyl acetate/hexanes) afforded the title intermediate.
$^1$H-NMR (500 MHz, CDCl$_3$) δ ppm 4.09 (s, 3H), 5.59 (d, J=11 Hz, 1H), 5.87 (d, J=17.4 Hz, 1H), 7.11 (dd, J=11, 17.4 Hz, 1H), 7.40 (d, J=8.3 Hz, 1H), 7.47 (d, J=8.3 Hz, 1H).

Step G: (2-Chloro-4-cyano-3-methoxyphenyl)ethylene oxide

A solution of (2-chloro-4-cyano-3-methoxyphenyl)ethylene (120 mg, 0.620 mmol) in DCM (6 mL) was treated with 85% m-CPBA (208 mg, 0.930 mmol) and stirred for 5 hours at RT. The reaction was then diluted with DCM and stirred with sat'd sodium bicarbonate containing some sodium bisulfate. The mixture was then extracted twice with DCM and the organic layers were washed with another portion of sodium bicarbonate and brine, dried over sodium sulfate and concentrated in vacuo to afford the crude title epoxide. $^1$H-NMR (500 MHz, CDCl$_3$) δ ppm 2.68 (dd, J=2.6, 5.8 Hz, 1H), 3.28 (dd, J=4.1, 5.5 Hz, 1H), 4.12 (s, 3H), 4.24 (dd, J=2.5, 3.9 Hz, 1H), 7.13 (d, J=8.0 Hz, 1H), 7.52 (d, J=8.0 Hz, 1H).

INTERMEDIATE 26

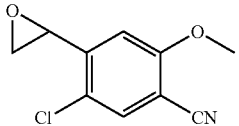

(2-Chloro-4-cyano-5-methoxyphenyl)ethylene oxide

Step A: Di-t-Butyl 2-(2-chloro-4-cyano-5-fluorophenyl)malonate

To sodium hydride (60% in mineral oil, 3.75 g, 94 mmol) under nitrogen was added dry DMF (150 mL) and the suspension was cooled in an ice bath. Di-t-butyl malonate (8.1 g, 37.5 mmol) was added dropwise over 15 minutes via syringe with hydrogen evolution. The suspension was stirred for 30 minutes after which time 5-chloro-2,4-difluorobenzonitrile (5.0 g, 28.8 mmol) in DMF (10 mL) was added dropwise over 15 minutes and the reaction was heated to 80° C. for 12 hours when TLC (15% ethyl acetate/hexanes) indicated mostly product. The reaction was diluted with ether and quenched into water containing aq. ammonium chloride. The mixture was extracted twice with ethyl acetate and the organic layers were washed with brine, dried over sodium sulfate and concentrated in vacuo. The residue was purified on silica gel (2-10% ethyl acetate/hexanes) to give the title product. NMR indicated about a 6:1 mixture of product and the isomeric di-t-butyl, 2-(4-chloro-2-cyano-5-fluorophenyl)malonate. $^1$H-NMR (400 MHz, CDCl$_3$) δ ppm 1.46 (s, 18H), 5.05 (s, 1H), 7.55 (d, J=8.3 Hz, 1H), 7.71 (d, J=6.0, 1H) (major isomer) and 1.46 (s, 18H), 4.95 (s, 1H), 7.63 (d, J=8.3 Hz, 1H), 7.78 (d, J=6.0, 1H) (minor isomer).

Step B: Methyl(2-chloro-4-cyano-5-fluorophenyl)acetate

A solution of di-t-butyl 2-(2-chloro-4-cyano-5-fluorophenyl)malonate (9.10 g, 24.6 mmol) in 1:2 TFA:dichloromethane (25:50 mL) was stirred at RT for 3 hours and then concentrated in vacuo to give a solid (5.05 g) after twice evaporating toluene. An aliquot of 4 g of solid was taken up in 1:1 methanol:dichloromethane (50 mL) and 2M trimethylsilyldiazomethane in ether was added until the yellow color persisted. Excess diazomethane was quenched with acetic acid and the mixture was concentrated. The residue was purified by flash chromatography (5-15% ethyl acetate/hexanes containing 5% DCM for solubility) to give separation from the higher R$_f$ 4-chloro-2-cyano-5-fluorophenyl isomer and still impure title product isomer. Flash chromatography was repeated (50-100% DCM/hexanes) to afford clean title product by NMR. $^1$H-NMR (400 MHz, CDCl$_3$) δ ppm 3.72 (s, 3H), 3.79 (s, 2H), 7.21 (d, J=8.9 Hz, 1H), 7.62 (d, J=5.8 Hz, 1H).

Step C: Methyl(2-chloro-4-cyano-5-methoxyphenyl)acetate

A solution of methyl(2-chloro-4-cyano-5-fluorophenyl)acetate (1.40 g, 6.15 mmol) in methanol (30 mL) was divided into two 20 mL microwave vials. Potassium carbonate (2×850 mg) was added to each vial. Each was heated in a microwave at 130° C. for 60 minutes at which time HPLC/MS indicated no starting material was left and the product was all hydrolyzed to the acid. Most of the methanol was removed in vacuo and the residue was diluted with water, acidified with 2M HCl and the mixture was extracted twice with ethyl acetate. The organic layers were washed with brine, dried over sodium sulfate and concentrated in vacuo. The crude product was taken up in 1:1 methanol:dichloromethane (50 mL) and 2M trimethylsilyldiazomethane in ether was added until the yellow color persisted to re-esterify the acid. The excess diazomethane was quenched with acetic acid and the mixture was concentrated. Flash chromatography (40% DCM/hexanes to 100% DCM) gave the methyl(2-chloro-4-cyano-5-methoxyphenyl)acetate. $^1$H-NMR (400 MHz, CDCl$_3$) δ ppm 3.73 (s, 3H), 3.83 (s, 2H), 4.07 (s, 3H), 7.139 (d, J=8.1 Hz, 1H), 7.468 (d, J=8.0, 1H).

Step D: 2-(2-chloro-4-cyano-5-methoxyphenyl)ethanol

To a solution of methyl(2-chloro-4-cyano-5-methoxyphenyl)acetate (200 mg, 0.835 mmol) in THF (5 mL) was added 2M lithium borohydride (0.835 mL, 1.67 mmol) and the reaction was stirred at RT for 16 hours. The reaction was diluted with ether and quenched into water containing 2N HCl. The mixture was extracted twice with ethyl acetate and the organic layers were washed with brine, dried over sodium sulfate and concentrated in vacuo. The product mixture was separated by MPLC (40+S; 20-60% ethyl acetate/hexanes) to afford the title product. $^1$H-NMR (400 MHz, CDCl$_3$) δ ppm 3.04 (t, J=6.4 Hz, 2H), 3.93 (t, J=6.4 Hz, 2H), 3.93 (s, 3H), 6.927 (s, 1H), 7.536 (s, 1H).

Step E: 2-(2-Chloro-4-cyano-5-methoxyphenyl)ethyl methanesulfonate

A solution of 2-(2-chloro-4-cyano-5-methoxyphenyl) ethanol (205 mg, 0.969 mmol) DIPEA (0.846 mL, 4.84 mmol) and pyridine (0.0780 mL, 0.969 mmol) in DCM (3 mL) was treated dropwise with mesyl chloride (0.110 mL, 1.42 mmol). The reaction was stirred for 2 hours and was then diluted with DCM and washed twice with aq. citric acid, then washed with brine, and dried over sodium sulfate. Purification of the residue by flash chromatography (20-50% ethyl acetate/hexanes) afforded the title intermediate. $^1$H-NMR (500 MHz, CDCl$_3$) δ ppm 2.99 (s, 3H), 3.24 (t, J=6.6 Hz, 2H), 3.95 (s, 3H), 4.49 (t, J=6.6 Hz, 2H), 6.962 (s, 1H), 7.563 (s, 1H).

Step F: (2-Chloro-4-cyano-5-methoxyphenyl)ethylene

A solution of 2-(2-chloro-4-cyano-5-methoxyphenyl) ethyl methanesulfonate (274 mg, 0.945 mmol) in DCM (4 mL) was treated with DBU (0.712 mL, 4.73 mmol) and stirred for 3 hours at 50° C., then at RT for 12 hours. TLC (50% ethyl acetate/hexanes) showed complete conversion to a faster intense UV band for the product. The reaction was then diluted with DCM and aq. citric acid and the mixture was extracted twice with DCM. The organic layers were washed with brine, dried over sodium sulfate and concentrated in vacuo. Purification of the residue by flash chromatography (10-20% ethyl acetate/hexanes) afforded the title intermediate.

$^1$H-NMR (500 MHz, CDCl$_3$) δ ppm 3.98 (s, 3H), 5.59 (d, J=11 Hz, 1H), 5.86 (d, J=17.4 Hz, 1H), 7.09 (dd, J=11, 17.4 Hz, 1H), 7.115 (s, 1H), 7.557 (s, 1H).

Step G: (2-Chloro-4-cyano-5-methoxyphenyl)ethylene oxide

A solution of (2-chloro-4-cyano-5-methoxyphenyl)ethylene (130 mg, 0.671 mmol) in DCM (6 mL) was treated with 85% m-CPBA (226 mg, 1.10 mmol) and stirred for 5 hours at RT when another portion of m-CPBA (115 mg) was added. The reaction stirred at room temperature for another 16 hours and was then diluted with DCM and stirred with sat'd sodium bicarbonate containing some sodium bisulfate. The mixture was then extracted twice with DCM and the organic layers were washed with another portion of sodium bicarbonate and brine, dried over sodium sulfate and concentrated in vacuo to afford the crude title epoxide.

$^1$H-NMR (500 MHz, CDCl$_3$) δ ppm 2.67 (dd, J=2.6, 5.8 Hz, 1H), 3.28 (dd, J=4.1, 5.5 Hz, 1H), 3.95 (s, 3H), 4.22 (dd, J=2.5, 3.9 Hz, 1H), 6.91 (s, 1H), 7.564 (s, 1H).

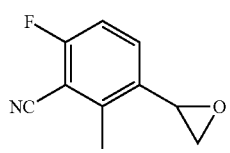

INTERMEDIATE 27

6-fluoro-2-methyl-3-oxiran-2-ylbenzonitrile

Step A: 3-bromo-6-fluoro-2-methylbenzonitrile

To a cooled (0° C.) solution of 2-fluoro-6-methylbenzonitrile (5.0 g, 37 mmol) in 100 mL of concentrated H$_2$SO$_4$ was added NBS (6.93 g, 38.9 mmol). Then the mixture was stirred at 0° C. for 3 hrs and poured into ice-water (1 L). The solution was extracted three times with EtOAc (200 mL) and the combined organic layers were washed with water and brine, dried over anhydrous sodium sulfate, filtered and concentrated. The residue was purified by silica gel flash chromatography to give 3-bromo-6-fluoro-2-methylbenzonitrile.

$^1$H-NMR (400 MHz, CDCl$_3$) δ ppm 7.71~7.74 (m, 1H), 6.95 (t, J=8.6 Hz, 1H), 2.62 (s, 3H).

Step B: 3-ethenyl-6-fluoro-2-methylbenzonitrile

A mixture of 3-bromo-6-fluoro-2-methylbenzonitrile (8.8 g, 41 mmol), tributyl(vinyl)tin (14.3 g, 45.2 mmol), LiCl (5.20 g, 123 mmol) and Pd(PPh$_3$)$_4$ (2.3 g, 2.0 mmol) in toluene (200 mL) was heated at 100-110° C. under N$_2$ overnight. The mixture was concentrated and the residue was purified by column chromatography to obtain 3-ethenyl-6-fluoro-2-methylbenzonitrile.

$^1$H-NMR (400 MHz, CDCl$_3$) δ ppm 7.54~7.58 (m, 1H), 6.95 (t, J=8.6 Hz, 1H), 6.73~6.81 (m, 1H), 5.54 (d, J=17.2 Hz, 1H), 5.34 (d, J=11.0 Hz, 1H), 2.47 (s, 3H).

Step C: 6-fluoro-2-methyl-3-oxiran-2-ylbenzonitrile

To a cooled (0° C.) solution of 3-ethenyl-6-fluoro-2-methylbenzonitrile (6.05 g, 37.6 mmol) in 200 mL of DCM was added m-CPBA (15.30 g, 85% purity, 75.16 mmol). Then the mixture was stirred at r.t. for 12 hrs and diluted with DCM (300 mL), washed with saturated Na$_2$SO$_3$ (4×300 mL) and brine, dried over anhydrous sodium sulfate, filtered and concentrated. The residue was purified by column chromatography to obtain 6-fluoro-2-methyl-3-oxiran-2-ylbenzonitrile.

$^1$H-NMR (400 MHz, CDCl$_3$) δ ppm 7.41~7.44 (m, 1H), 7.02 (t, J=8.6 Hz, 1H), 3.95 (t, J=3.1 Hz, 1H), 3.16~3.19 (m, 1H), 2.60~2.62 (m, 4H).

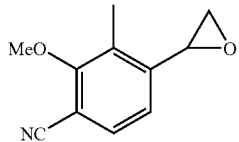

INTERMEDIATE 28

3-methyl-2-(methyloxy)-4-oxiran-2-ylbenzonitrile

Step A: 4-bromo-2-fluoro-3-methylbenzonitrile

To a solution of DIPA (12.1 g, 0.120 mmol) in 20 mL of dry THF was added 2.5M of n-BuLi (44 mL, 0.11 mmol) dropwise under Ar at −78° C., and then the reaction was allowed to warm to 0° C. After stirring for 1 hour, the solution was added to a solution of 4-bromo-2-fluorobenzonitrile (20 g, 0.1 mmol) in 200 mL of dry THF dropwise at −78° C. under Ar and the mixture was stirred for 3 hours, then MeI (15.6 g, 0.110 mmol) was added at one portion and the mixture was stirred for another 30 minutes. Then the reaction was quenched with aq. NH$_4$Cl and extracted with EtOAc (200 mL×3). The combined organic layers were washed with water, brine, dried and concentrated to brown oil, which was purified by silica gel column to give 4-bromo-2-fluoro-3-methylbenzonitrile.

Step B: 4-bromo-3-methyl-2-(methyloxy)benzonitrile

Sodium (3.00 g, 130 mmol) was added in portions into 80 mL of methanol and the mixture was stirred for 20 min until the sodium was completely dissolved. Then 4-bromo-2-fluoro-3-methylbenzonitrile (8.00 g, 37.3 mmol) was added and the solution was refluxed for 4 hours before cooling down. The reaction mixture was poured into ice/water (300 mL) and the resulting precipitate was collected by filtration. The solid afforded was dried under reduced pressure at 40° C. to give 4-bromo-3-methyl-2-(methyloxy)benzonitrile.

$^1$H-NMR (400 MHz, CDCl$_3$) δ ppm 7.39 (d, J=8.0 Hz, 1H), 7.28 (d, J=8.0 Hz, 1H), 4.00 (s, 3H), 2.37 (s, 3H).

Step C: 4-ethenyl-3-methyl-2-(methyloxy)benzonitrile

The mixture of 4-bromo-3-methyl-2-(methyloxy)benzonitrile (8.10 g, 35.8 mmol), potassium vinyl trifluoroborate (6.24 g, 46.6 mmol) and PdCl2(dppf)2 (0.55 g, 0.70 mmol) in 160 mL of EtOH and 40 mL of TEA was refluxed under Ar for 4 hours. The mixture was concentrated, and the residue was purified by column chromatography (PE:EtOAc=20:1) to afford 4-ethenyl-3-methyl-2-(methyloxy)benzonitrile.

$^1$H-NMR (400 MHz, CDCl$_3$) δ ppm 7.38 (d, J=8.4 Hz, 1H), 7.26 (d, J=8.4 Hz, 1H), 6.85-6.92 (m, 1H), 5.70 (d, J=17.6 Hz, 1H), 5.45 (d, J=10.8 Hz, 1H), 3.94 (s, 3H), 2.26 (s, 3H).

Step D:
3-methyl-2-(methyloxy)-4-oxiran-2-ylbenzonitrile

A mixture of 4-ethenyl-3-methyl-2-(methyloxy)benzonitrile (3.90 g, 22.5 mmol) and m-CPBA (85%, 11.7 g, 67.6 mmol) in 300 mL of DCM was stirred at room temperature for 120 hours. The reaction mixture was cooled to 0° C. and was washed subsequently with saturated NaHCO$_3$ (50 mL), saturated Na$_2$SO$_3$ (50 mL), 5% NaOH (50 mL×2) and brine (50 mL), dried over anhydrous Na$_2$SO$_4$ and concentrated. The residue was purified by column chromatography (PE:EtOAc=20:1) to afford 3-methyl-2-(methyloxy)-4-oxiran-2-ylbenzonitrile.

$^1$H-NMR (400 MHz, CDCl$_3$) δ ppm 7.39 (d, J=8.8 Hz, 1H), 7.03 (d, J=8.8 Hz, 1H), 3.95-3.97 (m, 4H), 3.17-3.19 (m, 1H), 2.60-2.62 (m, 1H).

INTERMEDIATE 29

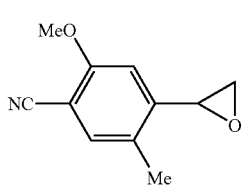

5-methyl-2-(methyloxy)-4-oxiran-2-ylbenzonitrile

Step A:
4-Hydroxy-5-methoxy-2-methylbenzaldehyde

To a solution of 2-methoxy-5-methylphenol (50.0 g, 362 mmol) in CH$_2$Cl$_2$ (1000 mL) at −5° C. were added titanium (IV) chloride (80.0 mL, 724 mmol) slowly via syringe (internal temperature was kept below 0° C. during addition) and dichloromethyl methyl ether (52.9 mL, 593 mmol). After being stirred at room temperature for 3 h, the mixture was poured into ice water. The resulting precipitate was collected by filtration and then washed with EtOAc and Et$_2$O to afford 4-Hydroxy-5-methoxy-2-methylbenzaldehyde. $^1$H NMR (CDCl$_3$) δ 10.22 (s, 1H), 7.38 (s, 1H), 6.81 (s, 1H), 6.14 (s, 1H), 3.96 (s, 3H), 2.62 (s, 3H); LC/MS: (IE, m/z) (M+1)$^+$=16.0; t$_R$=2.06 min.

Step B: 4-Formyl-2-methoxy-5-methylphenyl trifluoromethanesulfonate

To a solution of 4-Hydroxy-5-methoxy-2-methylbenzaldehyde (20.0 g, 122 mmol) in DMF (200 mL) at room temperature was added potassium carbonate (33.3 g, 241 mmol) and 4-nitrophenyl trifluoromethanesulfonate (49.0 g, 181 mmol) and the reaction mixture was stirred for 8 hr. EtOAc (600 mL) was added to the reaction mixture and the organic layer was washed three times with water, dried, filtered, and concentrated. The crude compound was then purified by flash chromatography (ethylacetate/hexanes 1:9→3:7) to provide 4-Formyl-2-methoxy-5-methylphenyl trifluoromethanesulfonate. $^1$H NMR (CDCl$_3$, 500 MHz) δ 10.34 (s, 1H), 7.53 (s, 1H), 7.16 (s, 1H), 3.99 (s, 3H), 2.67 (s, 3H); LC/MS: (IE, m/z) [M+1]$^+$=298.97; t$_R$=3.44 min.

Step C: 4-Formyl-2-methoxy-5-methylbenzonitrile

A mixture of 4-formyl-2-methoxy-5-methylphenyl trifluoromethanesulfonate (35.0 g, 117 mmol), zinc cyanide (55.1 g, 469 mmol) and tetrakis triphenylphosphine palladium (0) (20.34 g, 17.60 mmol) in DMF (300 mL) were stirred at 110° C. under nitrogen atmosphere for 8 hr. EtOAc was added to the reaction mixture and the organic layer was washed two times with water, dried, filtered and concentrated. The crude product was then purified by column chromatography (silica gel, ethylacetate/hexanes 3:7) which afforded 4-formyl-2-methoxy-5-methylbenzonitrile. $^1$H NMR (CDCl$_3$, 500 MHz) δ 10.39 (s, 1H), 7.47 (s, 1H), 7.44 (s, 1H), 4.02 (s, 3H), 2.66 (s, 3H); LC/MS: (IE, m/z) [M+1]$^+$=176.06; t$_R$=2.71 min.

Step D:
2-Methoxy-5-methyl-4-(oxiran-2-yl)benzonitrile

To a cool solution of NaH (1.20 g, 30.0 mmol) in THF (300 ml) was added dropwise a solution of trimethylsulfonium iodide (8.74 g, 42.8 mmol) in DMSO (80 mL). The resulting mixture was stirred at 0° C. under N$_2$ for 20 min. The solution of 4-formyl-2-methoxy-5-methylbenzonitrile (5.00 g, 28.5 mmol) in THF (60 mL) was added. The resulting reaction mixture was stirred at 0° C. under N$_2$ for 1 hr, and then it was warmed gradually to room temperature and stirred at that temperature for 12 hr. The starting material was consumed as indicated by TLC (25% ethyl acetate/hexanes). The reaction mixture was cooled to 0° C. and quenched with dropwise addition of water. The mixture was extracted with ethyl acetate (2×200 ml). The combined organic layers were washed with water, brine, then dried (MgSO$_4$) and filtered. The filtrate was concentrated in vacuo. The residue was purified via column chromatography (silica gel, 10-30% EtOAc-hexanes) to afford 2-methoxy-5-methyl-4-(oxiran-2-yl)benzonitrile. $^1$H NMR (CDCl$_3$, 500 MHz) δ 7.35 (s, 1H), 6.88 (s, 1H), 4.01 (s, 1H), 3.92 (s, 3H), 3.25 (s, 1H), 2.65 (d, J=2.6 Hz, 1H), 2.37 (s, 3H); LC/MS: (IE, m/z) [M+1]$^+$=190.0; t$_R$=2.85 min.

INTERMEDIATE 30

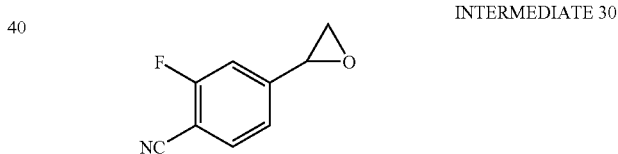

2-fluoro-4-oxiran-2-ylbenzonitrile

Step A: (4-cyano-3-fluorophenyl)acetic acid

A solution of dry diisopropylamine (16.5 g, 163 mmol) in dry THF (150 mL) under nitrogen was cooled with a −78° C. dry ice/acetone bath, and n-butyl lithium (2.50 M in hexane, 65.2 mL) was added slowly. The resulting solution was warmed to ambient temperature for 10 min and then cooled to −78° C. again. HMPA (30.0 mL, 168 mmol) was added, followed by a solution of 2-fluoro-4-methylbenzonitrile (20.0 g, 148 mmol) in 50 mL of dry THF. After stirring at −78° C. for 2 hours, CO$_2$ was bubbled through the solution for 20 min, and then the mixture was warmed slowly to 0° C. Then 1 N HCl was added until pH=2 and the mixture was extracted with EtOAc. The organic layers were washed with brine and dried over anhydrous sodium sulphate and concentrated to afford (4-cyano-3-fluorophenyl)acetic acid.

$^1$H-NMR (400 MHz, CDCl$_3$) δ ppm 7.58~7.61 (m, 1H), 7.19-7.21 (m, 2H), 3.72 (s, 2H).

Step B: 2-fluoro-4-(2-hydroxyethyl)benzonitrile

To a solution of (4-cyano-3-fluorophenyl)acetic acid (25.6 g, 143 mmol) in 150 mL of dry THF was cooled by ice/water, and then BH$_3$/Me$_2$S (10 M, 15.7 mL, 157 mmol) was added slowly. The reaction was warmed to ambient temperature and stirred overnight. The mixture was quenched with MeOH and concentrated to dryness. The residue was partitioned between water and EtOAc. The organic layers were washed with brine, dried over anhydrous sodium sulfate and concentrated to afford 2-fluoro-4-(2-hydroxyethyl)benzonitrile. $^1$H-NMR (400 MHz, CDCl$_3$) δ ppm 7.52~7.56 (m, 1H), 7.11~7.15 (m, 2H), 3.89 (t, J=6.3 Hz, 2H), 2.92 (t, J=6.3 Hz, 2H).

Step C: 2-(4-cyano-3-fluorophenyl)ethyl methanesulfonate

A solution of 2-fluoro-4-(2-hydroxyethyl)benzonitrile (22.5 g, 136 mmol) and MsCl (23.3 g, 205 mmol) in 200 mL of dry DCM was added dropwise TEA (27.5 g, 273 mmol) at 0° C. The resulting mixture was stirred at room temperature overnight before concentrating to dryness. The residue was dissolved in 300 mL of EtOAc and washed with 1 N HCl and brine, dried over anhydrous Na$_2$SO$_4$ and concentrated to afford crude 2-(4-cyano-3-fluorophenyl)ethyl methanesulfonate. MS m/z 244 (M+1)$^+$.

Step D: 4-ethenyl-2-fluorobenzonitrile

A solution of 2-(4-cyano-3-fluorophenyl)ethyl methanesulfonate (35.0 g, 144 mmol) and triethylamine (50 mL) in DCM (200 mL) was added DBU (50 mL) dropwise to at 0° C. After stirring at room temperature overnight, the solution was diluted with DCM, washed with 1 N HCl and brine, and dried over anhydrous sodium sulphate and concentrated. The residue was purified by column chromatography to give 4-ethenyl-2-fluorobenzonitrile. $^1$H-NMR (400 MHz, CDCl$_3$) δ ppm 7.53~7.57 (m, 1H), 7.20~7.26 (m, 2H), 6.64~6.71 (m, 1H), 5.48~5.90 (m, 2H).

Step E: 2-fluoro-4-oxiran-2-ylbenzonitrile

To a solution of 4-ethenyl-2-fluorobenzonitrile (18.0 g, 122 mmol) in 200 mL of DCM was slowly added mCPBA (74.8 g, 367.347 mmol) in portions at 0° C. The mixture was warmed to room temperature and stirred overnight. The solution was washed with aqueous Na$_2$SO$_3$ until KI paper didn't change color. The organic layers was washed with brine and then concentrated. The residue was purified via column chromatography to give 2-fluoro-4-oxiran-2-ylbenzonitrile. $^1$H-NMR (400 MHz, CDCl$_3$) δ ppm 7.59~7.62 (m, 1H), 7.12~7.22 (m, 2H), 3.89~3.91 (m, 1H), 3.20~3.22 (m, 1H), 2.72~2.74 (m, 1H).

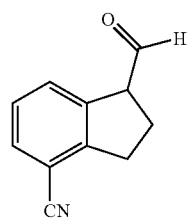

INTERMEDIATE 31

1-formyl-2,3-dihydro-1H-indene-4-carbonitrile

Step A: 1-oxo-2,3-dihydro-1H-indene-4-carbonitrile

To a solution of 4-bromo-2,3-dihydro-1H-inden-1-one (1.00 g, 4.74 mmol) in 5 mL of DMF was added Zn(CN)$_2$ (556 mg, 4.74 mmol) and Pd(PPh$_3$)$_4$ (77 mg, 0.14 mmol), and the reaction mixture was stirred under microwave irradiation for 1 h at 165° C. The solvent was removed in vacuum to afford the crude compound, which was purified via column chromatography to afford 1-oxo-2,3-dihydro-1H-indene-4-carbonitrile.

Step B: (1E)-1-[(methyloxy)methylidene]-2,3-dihydro-1H-indene-4-carbonitrile Sodium bis(trimethylsilyl)amide (2 mL, 4 mmol, 2M in THF) was added to a stirred suspension of (methoxy methyl)triphenylphosphonium chloride (1.47 g, 4.29 mmol) in dry THF (20 mL) at 0° C. for 35 min and a solution of 1-oxo-2,3-dihydro-1H-indene-4-carbonitrile (450 mg, 2.86 mmol) in THF (10 mL) added over 10 min. The mixture was stirred at 0° C. for 2 h and at room temperature for 1 h. Water was added and the mixture was partitioned between EtOAc and brine. The organic layer was dried and concentrated. The crude product was purified via prep-TLC (PE:EtOAc=10:1) to afford (1E)-1-[(methyloxy)methylidene]-2,3-dihydro-1H-indene-4-carbonitrile. $^1$H-NMR (400 MHz, CDCl$_3$) δ ppm 8.00 (d, J=8.3 Hz, 0.4H), 7.42 (d, J=8.3 Hz, 0.6H), 7.30-7.40 (m, 1H), 7.18-7.22 (m, 1H), 6.70 (s, 0.6H), 6.22 (s, 0.4H), 3.72 (s, 3H), 3.15 (t, J=5.7 Hz, 2H), 2.70-2.82 (m, 2H).

Step C: 1-formyl-2,3-dihydro-1H-indene-4-carbonitrile

A solution of (1E)-1-[(methyloxy)methylidene]-2,3-dihydro-1H-indene-4-carbonitrile (250 mg, 1.05 mmol) in DCM (5 mL) was added BBr$_3$ dropwise at −78° C. under N$_2$. Then the mixture was stirred at this temperature for 3 h. It was poured into ice-saturated NaHCO$_3$ solution, and extracted with DCM. The organic layer was washed with brine and dried over Na$_2$SO$_4$. The solvent was removed in vacuo to give crude 1-formyl-2,3-dihydro-1H-indene-4-carbonitrile (150 mg, crude), which is used for next step directly.

$^1$H-NMR (400 MHz, CDCl$_3$) δ ppm 9.72 (s, 1H), 7.54 (d, J=7.6 Hz, 2H), 7.34 (t, J=7.6 Hz, 1H), 3.76 (s, 1H), 3.18-3.24 (m, 2H), 2.42-2.58 (m, 2H).

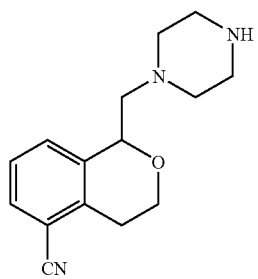

INTERMEDIATE 32

1-(piperazin-1-ylmethyl)-3,4-dihydro-1H-isochromene-5-carbonitrile

Step A: 2-(2-bromophenyl)ethanol

A solution of (2-bromophenyl)acetic acid (100 g, 0.46 mmol) in dry THF (2 L) was added NaBH$_4$ (29 g, 0.77 mol) in portions. The contents were cooled to 0° C., and BF₃. Et₂O (123 mL, 0.77 mol) was added drop wise over 1 h. The mixture was allowed to warm to 25° C. and stirred for 16 h. The reaction was cooled to 0° C. and cautiously quenched with aqueous sodium hydroxide. The contents were stirred for 3 h, and then extracted with EtOAc. The organic layer was dried and concentrated to give 2-(2-bromophenyl)ethanol.

¹H-NMR (400 MHz, CDCl₃) δ 7.54~7.56 (m, 1H), 7.23~7.28 (m, 2H), 7.07~7.11 (m, 1H), 3.88 (s, J=6.6 Hz, 2H), 3.03 (t, J=6.8 Hz, 2H).

Step B: methyl 5-bromo-3,4-dihydro-1H-isochromene-1-carboxylate

TiCl₄ (76 g, 0.4 mol) was added over a period of 10 min to an ice-cooled mixture of 2-(2-bromophenyl)ethanol (20 g, 0.1 mol) and ethyl bis(ethyloxy)acetate (21.1 g, 0.120 mol) in 120 mL of CH₃NO₂. After stirring for 10 min, the ice bath was removed and the mixture was allowed to stire at room temperature overnight. The mixture was poured into ice/aqueous 1N HCl. Extracted with DCM and backwashed with 1N HCl and brine, dried over anhydrous sodium sulfate and concentrated. The residue was purified with silica gel cloumn chromatography to give the product methyl 5-bromo-3,4-dihydro-1H-isochromene-1-carboxylate.

¹H-NMR (400 MHz, CDCl₃) δ 7.42~7.47 (m, 1H), 7.29 (d, J=8.0 Hz, 1H), 7.02 (t, J=8.0 Hz, 1H), 5.22 (s, 1H), 4.16~4.26 (m, 3H), 3.95~4.01 (m, 1H), 3.46~3.63 (m, 1H), 2.99~3.03 (m, 1H), 1.24 (t, J=8.0 Hz, 3H).

Step C: 5-bromo-3,4-dihydro-1H-isochromene-1-carboxylic acid

To a solution of methyl 5-bromo-3,4-dihydro-1H-isochromene-1-carboxylate (12.1 g, 42.4 mmol) in 200 mL of MeOH/THF/H₂O (2/2/1) was added LiOH.H₂O (5.34 g, 0.127 mol), and the mixture was stirred at ambient temperature for 30 min. The solvents were removed under vacuum, and the residue was added 100 mL of water and extracted with ether. The aqueous layer was then acidified with 4 N HCl to pH=4~5 in ice bath, and extracted with EtOAc. The combined organic phase was washed with brine, dried over anhydrous sodium sulfate and concentrated to afford 5-bromo-3,4-dihydro-1H-isochromene-1-carboxylic acid.

¹H-NMR (400 MHz, CDCl₃) δ 7.41~7.47 (m, 2H), 7.05 (t, J=8.0 Hz, 1H), 5.27 (s, 1H), 4.19~4.25 (m, 1H), 3.95~4.00 (m, 1H), 2.80 (t, J=6.0 Hz, 2H).

Step D: 5-bromo-N-methyl-N-(methyloxy)-3,4-dihydro-1H-isochromene-1-carboxamide

A mixture of 5-bromo-3,4-dihydro-1H-isochromene-1-carboxylic acid (9.10 g, 35.4 mmol) and CDI (4.14 g, 42.5 mmol) in 200 mL of dry DCM was stirred at r.t. for 30 min and then O,N-dimethyl-hydroxylamine (5.99 g, 42.5 mmol) was added. The resulting mixture was stirred overnight. The solvents were removed under vacuum, and the residue was purified with silica gel column chromatography to give 5-bromo-N-methyl-N-(methyloxy)-3,4-dihydro-1H-isochromene-1-carboxamide. ¹H-NMR (400 MHz, CDCl₃) δ 7.40 (d, J=8.0 Hz, 1H), 6.99 (t, J=8.0 Hz, 1H), 6.93 (d, J=8.0 Hz, 1H), 5.63 (s, 1H), 4.23~4.28 (m, 1H), 3.87~3.92 (m, 1H), 3.71 (s, 3H), 3.19 (s, 3H), 2.71~2.87 (m, 2H).

Step E: 5-bromo-3,4-dihydro-1H-isochromene-1-carbaldehyde

A solution of 5-bromo-N-methyl-N-(methyloxy)-3,4-dihydro-1H-isochromene-1-carboxamide (3.0 g, 10 mmol) in 60 mL of anhydrous THF was cooled to −30° C. and then DIBAL-H (20 mmol) was added. The mixture was stirred at −30° C. for 1 hours. The reaction was quenched with water, extract with DCM. The organic layer was washed with brine, dried over anhydrous sodium sulfate and concentrated. The crude 5-bromo-3,4-dihydro-1H-isochromene-1-carbaldehyde was used for next step without purification.

Step F: 1,1-dimethylethyl-4-[(5-bromo-3,4-dihydro-1H-isochromen-1-yl)methyl]piperazine-1-carboxylate A solution of 5-bromo-3,4-dihydro-1H-isochromene-1-carbaldehyde (1.62 g, 6.72 mmol), amine (1.25 g, 6.72 mmol) and NaBH(OAc)₃ (7.12 g, 33.6 mmol) in 50 mL of anhydrous DCM was stirred at ambient temperature overnight. The reaction mixture was added 50 mL of DCM and washed with brine. The organic layer was dried over anhydrous sodium sulfate and concentrated. The residue was purified with silica gel column chromatography to give 1,1-dimethylethyl-4-[(5-bromo-3,4-dihydro-1H-isochromen-1-yl)methyl]piperazine-1-carboxylate. ¹H-NMR (400 MHz, CDCl₃) δ 7.43 (d, J=8.0 Hz, 1H), 7.14 (d, J=8.0 Hz, 1H), 7.04 (t, J=8.0 Hz, 1H), 4.90 (d, J=8.0 Hz, 1H), 4.15~4.21 (m, 1H), 3.71~3.77 (m, 1H), 3.48~3.49 (m, 4H), 3.36 (t, J=4.0 Hz, 1H), 2.76~2.81 (m, 2H), 2.50~2.54 (m, 4H), 2.41 (s, 1H), 1.45 (s, 9H).

Step G: 1,1-dimethylethyl4-[(5-cyano-3,4-dihydro-1H-isochromen-1-yl)methyl]piperazine-1-carboxylate A solution of 1,1-dimethylethyl-4-[(5-bromo-3,4-dihydro-1H-isochromen-1-yl)methyl]piperazine-1-carboxylate (210 mg, 0.51 mmol), Pd(PPh₃)₄ (118 mg, 0.100 mmol) and Zn(CN)₂ (120 mg, 1.0 mmol) in 10 mL of anhydrous DMF was to 120° C. at N₂ atmosphere for 2 hours. After cooled to r.t., the mixture was partitioned between EtOAc and water. The organic layer was dried over anhydrous sodium sulfate and concentrated. The residue was purified with prep-TLC to afford 1,1-dimethylethyl4-[(5-cyano-3,4-dihydro-1H-isochromen-1-yl)methyl]piperazine-1-carboxylate.

Step H: 1-(piperazin-1-ylmethyl)-3,4-dihydro-1H-isochromene-5-carbonitrile

A solution of 1,1-dimethylethyl4-[(5-cyano-3,4-dihydro-1H-isochromen-1-yl)methyl]piperazine-1-carboxylate (150 mg, 0.42 mmol) in 10 mL of DCM was added 5 mL of 4N HCl/dioxane, and the mixture was stirred at room temperature for 2 hours. The solvents was removed off under vacuum to afford 1-(piperazin-1-ylmethyl)-3,4-dihydro-1H-isochromene-5-carbonitrile.

¹H-NMR (400 MHz, MeOD) δ 7.77 (d, J=8.0 Hz, 1H), 7.72 (d, J=8. Hz, 1H), 7.45 (t, J=8.0 Hz, 1H), 4.11~4.17 (m, 1H), 3.82~3.88 (m, 9H), 3.55~3.61 (m, 2H), 2.87~2.99 (m, 2H).

INTERMEDIATE 33

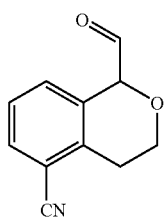

1-formyl-3,4-dihydro-1H-isochromene-5-carbonitrile

Step A: 2-(2-bromophenyl)ethanol

A solution of (2-bromophenyl)acetic acid (100 g, 0.46 mmol) in dry THF (2 L) was added NaBH₄ (29 g, 0.77 mol) in portions. The contents were cooled to 0° C., and BF₃. Et₂O (123 mL, 0.770 mol) was added drop-wise over 1 h. The mixture was allowed to warm to 25° C. and stirred for 16 h. The reaction was cooled to 0° C. and cautiously quenched with aqueous sodium hydroxide. The contents were stirred for 3 h, and then extracted with EtOAc. The organic layer was dried and concentrated to give 2-(2-bromophenyl)ethanol. ¹H-NMR (400 MHz, CDCl₃) δ 7.54~7.56 (m, 1H), 7.23~7.28 (m, 2H), 7.07~7.11 (m, 1H), 3.88 (s, J=6.6 Hz, 2H), 3.03 (t, J=6.8 Hz, 2H).

Step B:
5-bromo-3,4-dihydro-1H-isochromene-1-carboxylic acid

A solution of 2-(2-bromophenyl)ethanol (40 g, 0.2 mol) and glyoxylic acid (16 g, 0.22 mol) in 100 mL of trifluoacetic acid was refluxed overnight. The solvent was concentrated. Water and ammonium hydroxide was added to the residue to adjust the pH of the solution over 7. The solution was extracted with diethyl ether, and the aqueous layer was adjusted to about 3 with 1M HCl, and then the solution was extracted with ethyl acetate. The organic layer was dried and evaporated. The residue was without purification to give 5-bromo-3,4-dihydro-1H-isochromene-1-carboxylic acid. ¹H-NMR (400 MHz, CDCl₃) δ 7.52 (d, J=7.6 Hz, 1H), 7.12 (t, J=7.8 Hz, 2H), 5.33 (s, 1H), 4.27~4.33 (m, 1H), 3.99~4.06 (m, 1H), 2.87~2.89 (m, 2H).

Step C:
(5-bromo-3,4-dihydro-1H-isochromen-1-yl)methanol

A solution of 5-bromo-3,4-dihydro-1H-isochromene-1-carboxylic acid (0.500 g, 1.94 mmol) in 1 mL of THF was added BH₃. THF (3.88 mL, 3.88 mmol) drop wise at 0° C. The mixture was stirred at 0° C. for 2 h. The reaction was quenched with water and aqueous sodium hydroxide (1 N, 2 mL). The contents were stirred for 3 h, and then extracted with EtOAc. The organic layer was dried and concentrated to give (5-bromo-3,4-dihydro-1H-isochromen-1-yl)methanol
¹H-NMR (400 MHz, CDCl₃) δ 7.41 (t, J=2.4 Hz, 1H), 6.97~7.04 (m, 2H), 4.75~4.77 (m, 1H), 3.88~3.92 (m, 1H), 3.73~3.79 (m, 2H), 2.71~2.86 (m, 2H).

Step D: 1-(hydroxymethyl)-3,4-dihydro-1H-isochromene-5-carbonitrile

A mixture of (5-bromo-3,4-dihydro-1H-isochromen-1-yl)methanol (390 mg, 1.6 mmol), Zn(CN)₂ (113 mg, 0.960 mmol), TMEDA (0.37 mg), xantphose (4.6 mg) and Pd(dba)₃ (2.6 mg) in anhydrous DMF was microwaved 10 min at 100° C. The reaction was quenched with water and extracted with EtOAc. The organic layer was washed with brine, dried and concentrated. The residue was purified with prep-HPLC to give 1-(hydroxymethyl)-3,4-dihydro-1H-isochromene-5-carbonitrile. ¹H-NMR (400 MHz, CDCl₃) δ: 7.49~7.50 (m, 1H), 7.24~7.48 (m, 2H), 4.76~14.78 (m, 1H), 4.17~4.22 (m, 1H), 3.76~3.95 (m, 3H), 3.01~3.09 (m, 1H), 2.89~2.95 (m, 1H).

Step E:
1-formyl-3,4-dihydro-1H-isochromene-5-carbonitrile

A solution of 1-(hydroxymethyl)-3,4-dihydro-1H-isochromene-5-carbonitrile (0.16 g, 0.85 mmol) in 4 mL of DCM was added Dess-Martin reagent (0.72 g, 1.7 mmol) in one portion at 0° C. The mixture was stirred at 0° C. for 1 hour, and then stirred at rt. overnight. The reaction mixture was filtered and the filtrate was concentrated to give 1-formyl-3,4-dihydro-1H-isochromene-5-carbonitrile. ¹H-NMR (400 MHz, CDCl₃) δ 9.71 (s, 1H), 7.93~7.95 (m, 1H), 7.64~7.68 (m, 1H), 4.99 (s, 1H), 4.03~4.09 (m, 2H), 2.99~3.04 (m, 2H).

INTERMEDIATE 34

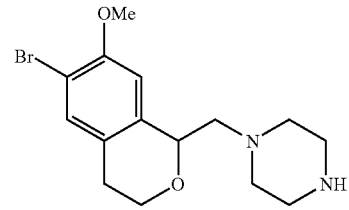

1-{[6-bromo-7-(methyloxy)-3,4-dihydro-1H-isochromen-1-yl]methyl}piperazine

Step A: 2-[3-bromo-4-(methyloxy)phenyl]ethanol

To a solution of [3-bromo-4-(methyloxy)phenyl]acetic acid (10.0 g, 40.8 mmol) in anhydrous THF (50 mL) was added BH₃.(CH₃)₂S (5.3 mL, 53 mmol) dropwise at 0° C. The resulting mixture was stirred at 0° C. for 3 h. The mixture was then treated with MeOH until gas evolution subsided, and then concentrated under reduced pressure. The residue was then partitioned between water and EtOAc. The organic layers were washed with brine, dried over Na₂SO₄ and concentrated to give crude 2-[3-bromo-4-(methyloxy)phenyl]ethanol, which was used without further purification for the next step.

Step B: methyl 6-bromo-7-(methyloxy)-3,4-dihydro-1H-isochromene-1-carboxylate

To an ice-cooled mixture of 2-[3-bromo-4-(methyloxy)phenyl]ethanol (9.5 g, 41 mmol) and ethyl bis(ethyloxy)acetate (8.7 g, 48 mmol) in 60 mL of CH₃NO₂ was added TiCl₄ (31.2 g, 169 mmol) over a period of 20 min. After stirring for 10 min, the ice bath was removed and the mixture was allowed to stir at room temperature over night. The mixture was poured onto ice/aqueous 1N HCl. Extracted by DCM and backwashed with 1N HCl and brine, dried over anhydrous sodium sulfate and concentrated. The residue was purified via column chromatography to give methyl 6-bromo-7-(methyloxy)-3,4-dihydro-1H-isochromene-1-carboxylate.

Step C: 6-bromo-7-(methyloxy)-3,4-dihydro-1H-isochromene-1-carboxylic acid

To a solution of 6-bromo-7-(methyloxy)-3,4-dihydro-1H-isochromene-1-carboxylate (12 g, 38 mmol) in 50 mL of MeOH/THF/H$_2$O (2/2/1) was added LiOH.H$_2$O (4.79 g, 114 mmol), and the mixture was stirred at ambient temperature overnight. The solvents were removed under vacuum, and to the residue was added 50 mL of water and the mixture was extracted with ether. The aqueous layer was then acidified with 4 N HCl to pH=3 in ice bath, and extracted with EtOAc. The combined organic phase was washed with brine, dried over anhydrous sodium sulfate and concentrated to give 6-bromo-7-(methyloxy)-3,4-dihydro-1H-isochromene-1-carboxylic acid.

Step D: 6-bromo-N-methyl-N,7-bis(methyloxy)-3,4-dihydro-1H-isochromene-1-carboxamide A mixture of 6-bromo-7-(methyloxy)-3,4-dihydro-1H-isochromene-1-carboxylic acid (5.9 g, 21 mmol) and CDI (4.0 g, 25 mmol) in 60 mL of dry DCM was stirred at r.t. for 0.5 hours and then O,N-dimethyl-hydroxylamine (2.4 g, 25 mmol) was added. The result mixture was stirred overnight. The solvents were removed under vacuum, and the residue was purified by column to give 6-bromo-N-methyl-N,7-bis(methyloxy)-3,4-dihydro-1H-isochromene-1-carboxamide.

Step E: 6-bromo-7-(methyloxy)-3,4-dihydro-1H-isochromene-1-carbaldehyde

A solution of 6-bromo-N-methyl-N,7-bis(methyloxy)-3,4-dihydro-1H-isochromene-1-carboxamide (800 mg, 2.4 mmol) in 20 mL of anhydrous THF was cooled to –78° C. and then DIBAL-H (4.8 mL, 4.8 mmol, 1M) was added. The mixture was stirred at –78° C. for 1 h. The reaction was quenched with water and extracted with DCM. The orgainc layer was washed with brine, dried over anhydrous sodium sulfate and concentrated. The resulting 6-bromo-7-(methyloxy)-3,4-dihydro-1H-isochromene-1-carbaldehyde was used without further purification.

Step F: 1,1-dimethylethyl4-{[6-bromo-7-(methyloxy)-3,4-dihydro-1H-isochromen-1-yl]methyl}piperazine-1-carboxylate To a solution of 6-bromo-7-(methyloxy)-3,4-dihydro-1H-isochromene-1-carbaldehyde (700 mg, 2.6 mmol) in 20 mL of DCM was added 1,1-dimethylethyl piperazine-1-carboxylate (481 mg, 2.60 mmol) and NaBH(OAc)$_3$ (2.7 g, 12 mmol), and the mixture was stirred at room temperature overnight. The reaction was diluted with DCM, and washed with brine. The organic layer was dried over anhydrous Na$_2$SO$_4$ and concentrated. The residue was purified by prep-TLC to give 1,1-dimethylethyl-4-{[6-bromo-7-(methyloxy)-3,4-dihydro-1H-isochromen-1-yl]methyl}piperazine-1-carboxylate.

Step G: 1-{[6-bromo-7-(methyloxy)-3,4-dihydro-1H-isochromen-1-yl]methyl}piperazine To a solution of 1,1-dimethylethyl-4-{[6-bromo-7-(methyloxy)-3,4-dihydro-1H-isochromen-1-yl]methyl}piperazine-1-carboxylate (150 mg, 0.34 mmol) in 5 mL of DCM was added 5 mL of TFA and the mixture was stirred at room temperature for 1 h. The reaction was concentrated and the 1-{[6-bromo-7-(methyloxy)-3,4-dihydro-1H-isochromen-1-yl]methyl}piperazine was directly used in next step.

INTERMEDIATE 35

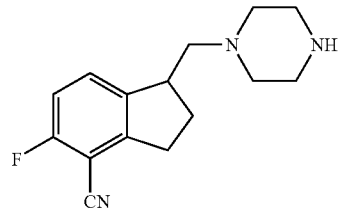

5-fluoro-1-(piperazin-1-ylmethyl)-2,3-dihydro-1H-indene-4-carbonitrile

Step A: 3-(2-bromo-3-fluorophenyl)propanoic acid

To a flask charged with 2-bromo-1-(bromomethyl)-3-fluorobenzene (2.0 g, 7.5 mmol) and a stir bar was added dimethyl malonate (20.0 mL, 174 mmol). The solution was cooled to 0° C. in an ice bath. To this solution was carefully added sodium hydride (0.597 g, 14.9 mmol) in small portions. When the addition was done, the reaction was kept stirring for another 30 minutes. The reaction was quenched with NH4Cl, extracted with EtOAc, washed with brine, dried over Na2SO4, and concentrated. The residue was dissolved in acetic acid (50 mL). To this solution was added HCl (50 ml, 330 mmol), and the reaction was heated to reflux for 16 hours. Analysis by LC showed formation of the desired acid. Most of the solvent was removed on a rotary evaporator. The remaining solution was diluted with 50 mL of water, and extracted with ether (50 mL×3). The extracts were combined, and washed with 1N NaOH (50 mL×2). At that point, all the acid was in the aqueous as the salt. The aqueous washes were combined, acidified, and back extracted with DCM (100 mL×2). The extracts were combined, dried over Na$_2$SO$_4$, and concentrated to afford 3-(2-bromo-3-fluorophenyl)propanoic acid.

Step B: 4-bromo-5-fluoro-2,3-dihydro-1H-inden-1-one

A flask charged with PPA (20 mL) and a stir bar was heated to 90° C. 3-(2-Bromo-3-fluorophenyl)propanoic acid (2.0 g) was charged to the mixture. The reaction mixture was heated to 100° C., and all the solids slowly dissolved. The reaction mixture was poured into ice water, and some fluffy solids precipitated. The solids were collected by filtration to afford 4-bromo-5-fluoro-2,3-dihydro-1H-inden-1-one. LC-MS M+1 (calc. 229, found 229).

Step C: 5-fluoro-1-oxo-2,3-dihydro-1H-indene-4-carbonitrile

To a microwave tube charged with 4-bromo-5-fluoro-2,3-dihydro-1H-inden-1-one (500 mg, 2.2 mmol) and a stir bar was added Pd$_2$(dba)$_3$ (40.0 mg, 0.044 mmol), S-phos (45 mg, 0.11 mmol), zinc cyanide (333 mg, 2.84 mmol), DMF (15 mL), and Water (0.15 mL). The tube was sealed, and purged three times with nitrogen. The reaction was then heated to 175° C. for 3 minutes in a microwave reactor. TLC showed formation of the desired product, along with a small amount of the dimethylaniline adduct. The crude product mixture was diluted with EtOAc, washed with brine, dried over sodium sulfate, adsorbed onto silica, and purified by MPLC. After removal of solvent, 5-fluoro-1-oxo-2,3-dihydro-1H-indene-4-carbonitrile was collected.

LC-MS M+1 (calc. 176.05, found 276.17).

Step D: 5-fluoro-1-methylidene-2,3-dihydro-1H-indene-4-carbonitrile

Methyl triphenylphosphine bromide (816 mg, 2.28 mmol) was dissolved in THF (10 mL) and placed in a cool bath at −20° C. The mixture was then treated with n-butyl lithium (913 μl, 2.28 mmol), and stirred for 20 min. at −20° C. To the mixture was then added 5-fluoro-1-oxo-2,3-dihydro-1H-indene-4-carbonitrile (200 mg, 1.14 mmol) via cannula and subsequently stirred for 20 min at −20° C.; LC as well as TLC (hexanes/EtOAc=1/0.3) indicated that reaction was half complete. To the mixture was poured $NH_4Cl$, and the solution was transferred into separatory funnel, diluted with EtOAc, washed with $NH_4Cl$, NaCl, dried over $Na_2SO_4$, filtered and concentrated to dryness. The residue was then absorbed into silica gel and separated over a silica column with the solvent systems of hexanes/EtOAc (1/0.3) to give 5-fluoro-1-methylidene-2,3-dihydro-1H-indene-4-carbonitrile. LC-MS (IE, m/z): 174 $[M+1]^+$; $t_R$=2.10 min.

Step E: 5-fluoro-1-(hydroxymethyl)-2,3-dihydro-1H-indene-4-carbonitrile

5-Fluoro-1-methylidene-2,3-dihydro-1H-indene-4-carbonitrile (100 mg, 0.577 mmol) in THF (6 mL) at 0° C. was treated with borane tetrahydrofuran (1 M, 0.751 ml, 0.751 mmol). The resulting mixture was stirred for overnight at room temperature; LC analysis indicated consumption of starting material. To the mixture was added a combination of hydrogen peroxide (0.083 ml, 0.81 mmol) and 2M NaOH (0.404 ml, 0.808 mmol). The resulting mixture was then stirred for 2 hours. LC analysis indicated completion of the reaction. The reaction mixture was diluted with EtOAc, washed with brine, dried over Na2SO4, filtered and concentrated to dryness. The residue was absorbed into silica gel and loaded into silica column for separation with the solvent systems of hexanes/EtOAc (1/1) to give the desired product 5-fluoro-1-(hydroxymethyl)-2,3-dihydro-1H-indene-4-carbonitrile.

Step F: 1,1-dimethylethyl-4-[(4-cyano-5-fluoro-2,3-dihydro-1H-inden-1-yl)methyl]piperazine-1-carboxylate 5-Fluoro-1-(hydroxymethyl)-2,3-dihydro-1H-indene-4-carbonitrile (0.055 g, 0.29 mmol) in DCM (4 mL) was added to a flask containing a stir bar; the flask was then placed in a cooling bath at 0° C. To the mixture was then added Dess-Martin Periodinane (0.183 g, 0.431 mmol) and the resulting solution was subsequently stirred for 2 h; LC analysis indicated completion of the reaction. To the mixture was then added DCM (10 mL) and aq. $Na_2S_2O_3$ (10 mL) and the mixture was subsequently stirred for 2 h. The organic layer was separated and the aqueous layer was extracted with DCM, washed with NaCl, dried over Na2SO4, filtered and concentrated to dryness; the resulting organic residue (0.060 g, 0.13 mmol) was dissolved in MeOH (10 mL). To this solution was added tert-butyl piperazine-1-carboxylate (0.118 g, 0.634 mmol), sodium cyanoborohydride (0.199 g, 3.17 mmol) and few drops of AcOH. The reaction mixture was then stirred overnight under $N_2$. LC analysis indicated completion of the reaction. The reaction mixture was concentrated to dryness, re-dissolved in EtOAc, washed with $NaHCO_3$, dried over $Na_2SO_4$, filtered, and concentrated to dryness. The residue was absorbed into silica gel and loaded onto a silica column for separation with the solvent system of 5% DCM in MeOH to give the desired product, 1,1-dimethylethyl-4-[(4-cyano-5-fluoro-2,3-dihydro-1H-inden-1-yl)methyl]piperazine-1-carboxylate. LC-MS (IE, m/z): 360 $[M+1]^+$; $t_R$=2.55 min.

Step G: 5-fluoro-1-(piperazin-1-ylmethyl)-2,3-dihydro-1H-indene-4-carbonitrile To a solution 1,1-dimethylethyl-4-[(4-cyano-5-fluoro-2,3-dihydro-1H-inden-1-yl)methyl]piperazine-1-carboxylate (0.060 g) in DCM (2 mL) was added 4N HCl (2 mL) at RT. The mixture was allowed to stir at RT for 2 hours. The solvents were removed on a rotary evaporator, and the residue was redissolved in aq $NaHCO_3$ solution. The solution was extracted with IPA-CHCl3 (3:1) twice (50 mL each). The extractions were combined, dried over sodium sulfate, and concentrated to give 5-fluoro-1-(piperazin-1-ylmethyl)-2,3-dihydro-1H-indene-4-carbonitrile. LC-MS (IE, m/z): 260 $[M+1]^+$.

INTERMEDIATE 36

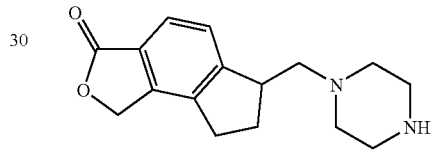

6-(piperazin-1-ylmethyl)-1,6,7,8-tetrahydro-3H-indeno[4,5-c]furan-3-one

Step A: methyl 3-bromo-2-but-3-en-1-ylbenzoate

To a flask charged with freshly prepared LDA (42 mmol) from n-BuLi and i-$Pr_2$NH was dropped a solution of 3-bromo-2-methylbenzoic acid (3.0 g, 14 mmol) at −78° C. The reaction turned red right away. After stirring the mixture for 15 minutes, allyl bromide (8.4 g, 70 mmol) was dropped into the reaction. The reaction was allowed to warm up to 0° C. The reaction was quenched with 1N HCl, and extracted with EtOAc (100 mL×2). The extracts were combined, washed with brine, dried over sodium sulfate, and concentrated to give a light yellow oil. The oil was dissolved in toluene (30 mL) and methanol (10 mL) and treated with excess TMSdiazo methane (10 mL, 2.0 M in ether). Excess TMSdiazomethane was quenched with acetic acid when TLC indicated the reaction was done. The mixture was concentrated and crude product was purified by silica gel chromatography to afford methyl 3-bromo-2-but-3-en-1-ylbenzoate. $^1$H-NMR (500 MHz, $CDCl_3$) δ ppm 7.78 (d, J=8.0 Hz, 1H), 7.76 (d, J=8.0 Hz, 1H), 7.15 (t, J=8.0 Hz, 1H), 5.98 (m, 1H), 5.12 (d, 17 Hz, 1H), 5.04 (d, J=10 Hz, 1H), 3.94 (s, 3H), 3.18 (m, 2H), 2.41 (m, 2H).

Step B: methyl 1-methylidene-2,3-dihydro-1H-indene-4-carboxylate

To a microwave tube charged with methyl 3-bromo-2-but-3-en-1-ylbenzoate (800 mg, 3.0 mmol) and a stir bar was added palladium(II) acetate (67 mg, 0.30 mmol), triphenylphosphine (310 mg, 1.19 mmol), potassium carbonate (2.46 g, 18.0 mmol), and acetonitrile (20 mL). The reaction tube was sealed, and the solution was purged three times with nitrogen, and heated in a microwave apparatus to 120° C. for 10 minutes. TLC showed a big blue spot right below the SM. The product was isolated by silica gel chromatography. LC-MS M+1 (calc. 189, found 189).

Step C: 2,3-dihydro-1H-indene-1,4-diyldimethanol

To a solution of methyl 1-methylidene-2,3-dihydro-1H-indene-4-carboxylate (1.4 g, 7.4 mmol) in THF (15 mL) was added borane THF complex (1.0 M, 9.7 mL, 9.7 mmol) at 0° C. The mixture was allowed to stir for 3 hours. To the reaction was added 2N sodium hydroxide (7.5 mL, 15 mmol) and 30% hydrogen peroxide (1.7 mL, 15 mmol). The mixture was then allowed to warm to RT. LC analysis showed complete reaction within 30 minutes. The reaction was neutralized with NH4Cl, diluted with water, extracted with EtOAc, dried over sodium sulfate, and purified by silica gel chromatography. The intermediate hydroxyester (1.1 g) was collected after removal of solvents. To a DCM (10 mL) solution of the hydroxyester (750 mg, 3.6 mmol) was added DIBAL-H (18 mL, 18 mmol) at −78° C. The reaction was allowed to stir for 16 h, warming to RT slowly. The reaction was diluted with DCM (30 mL), and worked up with Roschelle's salt. The organic layer was separated using a separatory funnel, dried over sodium sulfate, and the crude product was purified by silica gel chromatography to afford 2,3-dihydro-1H-indene-1,4-diyldimethanol. $^1$H-NMR (500 MHz, CDCl$_3$) δ ppm 7.25-7.30 (m, 3H), 4.72 (s, 3H), 3.85 (m, 2H), 3.42 (m, 1H), 3.03 (m, 1H), 2.95 (m, 1H), 2.34 (m, 1H), 2.04 (m, 1H).

Step D: 6-(hydroxymethyl)-1,6,7,8-tetrahydro-3H-indeno[4,5-c]furan-3-one

To a flask charged with 2,3-dihydro-1H-indene-1,4-diyldimethanol (210 mg, 1.2 mmol) and a stir bar was added thallium trifluoroacetate (770 mg, 1.4 mmol) and TFA (2 mL) at 0° C. The mixture was allowed to stir for 16 hours. LC showed no SM left at that point. The volatiles were removed under reduced pressure, and the residue was dissolved in DCM and concentrated twice to affect azeotropic removal of all TFA. After pumping the residue under high vacuum for 20 minutes, palladium chloride (21 mg, 0.18 mmol), lithium chloride (75 mg, 1.8 mmol), magnesium oxide (190 mg, 4.7 mmol), and MeOH (10 mL) were added to the flask. The mixture was treated under an atmosphere of CO for 2 hours. To this mixture was added DCM and EtOAc to precipitate all the inorganic solids. The crude solution was filtered through a celite pad, and the filtrate was collected, adsorbed onto silica gel, and purified by MPLC to afford 6-(hydroxymethyl)-1,6,7,8-tetrahydro-3H-indeno[4,5-c]furan-3-one.
$^1$H-NMR (500 MHz, CDCl$_3$) δ ppm 7.79 (d, J=8.0 Hz, 1H), 7.52 (d, J=8.0 Hz, 1H), 5.27 (s, 2H), 3.91 (d, J=6.0 Hz, 2H), 3.85 (dd, J=6.0, 3.5 Hz, 1H), 3.50 (m, 1H), 3.00 (m, 1H), 2.93 (m, 1H), 2.45 (m, 1H), 2.14 (m, 1H).

Step E: 3-oxo-3,6,7,8-tetrahydro-1H-indeno[4,5-c]furan-6-carbaldehyde

To a solution of 6-(hydroxymethyl)-1,6,7,8-tetrahydro-3H-indeno[4,5-c]furan-3-one (55 mg, 0.27 mmol) in DCM (5 mL) was added Dess-Martin Periodate (171 mg, 0.400 mmol). The reaction was allowed to stir at RT for 3 hours. LC analysis showed formation of the desired product, and there was little SM left. The solution was diluted with DCM (30 mL), and to that was added Na2S2O3 (10% aq solution, 15 mL) to consume the excess Dess-Martin reagent. The mixture was stirred until the two layers separated. The bottom DCM layer was collected, washed with aq Na2CO3, dried over sodium sulfate, and concentrated to give 3-oxo-3,6,7,8-tetrahydro-1H-indeno[4,5-c]furan-6-carbaldehyde. LC-MS (IE, m/z): 203 [M+1]$^+$; t$_R$=0.58 min.

Step F: 1,1-dimethylethyl-4-[(3-oxo-3,6,7,8-tetrahydro-1H-indeno[4,5-c]furan-6-yl)methyl]piperazine-1-carboxylate To 3-oxo-3,6,7,8-tetrahydro-1H-indeno[4,5-c]furan-6-carbaldehyde obtained above was added 1-Boc Piperazine (110 mg, 0.59 mmol), NaCNCH3 (186 mg, 3.0 mmol), MeOH (6 mL), and three drops of acetic acid. The mixture was then allowed to stir at RT overnight. LC analysis showed complete reaction. The crude solution was then concentrated to dryness, redissolved in EtOAc (50 mL), washed with NaHCO3 and brine, dried over sodium sulfate, and purified by silica gel flash chromatography to furnish 1,1-dimethylethyl-4-[(3-oxo-3,6,7,8-tetrahydro-1H-indeno[4,5-c]furan-6-yl)methyl]piperazine-1-carboxylate. LC-MS (IE, m/z): 373 [M+1]$^+$; t$_R$=2.51 min.

Step G: 6-(piperazin-1-ylmethyl)-1,6,7,8-tetrahydro-3H-indeno[4,5-c]furan-3-one

To a solution of the SM (0.050 g) in DCM (2 mL) was added 4N HCl (2 mL) at RT. The mixture was allowed to stir at RT for 3 hours. The solvents were removed on a rotary evaporator, and the residue was redissolved in aq NaHCO$_3$ solution. The solution was extracted with IPA-CHCl3 (3:1) twice (50 mL each). The extractions were combined, dried over sodium sulfate, and concentrated to give 6-(piperazin-1-ylmethyl)-1,6,7,8-tetrahydro-3H-indeno[4,5-c]furan-3-one. LC-MS (IE, m/z): 273 [M+1]$^+$.

INTERMEDIATE 37A and 37B

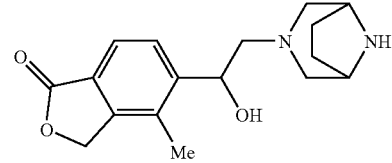

5-[2-(3,8-diazabicyclo[3.2.1]oct-3-yl)-1-hydroxyethyl]-4-methyl-2-benzofuran-1(3H)-one Step A: 5-{1-hydroxy-2-[8-(phenylmethyl)-3,8-diazabicyclo[3.2.1]oct-3-yl]ethyl}-4-methyl-2-benzofuran-1(3H)-one A mixture of 4-methyl-5-oxiran-2-yl-2-benzofuran-1(3H)-one (1.0 g, 3.7 mmol) and 8-(phenylmethyl)-3,8-diazabicyclo[3.2.1]octane (748 mg, 3.68 mmol) in 2 mL DMSO was heated under microwave condition (150° C.) for 1 hr. After cooling to rt., the mixture was diluted with water (50 mL), extracted with EtOAc (3×50 mL). The combined organic layers were washed with brine and dried over Na$_2$SO$_4$, then concentrated. The residue was purified by TLC (MeOH/DCM=1:15) to obtain 5-{1-hydroxy-2-[8-(phenylmethyl)-3,8-diazabicyclo[3.2.1]oct-3-yl]ethyl}-4-methyl-2- benzofuran-1(3H)-one. The two isomers were separated by SFC chiral chromatography to obtain two single isomers, isomer A and isomer B with the same MS m/z 393 (M+1)⁺.

Step B: 5-[2-(3,8-diazabicyclo[3.2.1]oct-3-yl)-1-hydroxyethyl]-4-methyl-2-benzofuran-1(3H)-one To a solution of isomer A from Step A (230 mg, 0.585 mmol) in 50 mL of EtOAc was added 100 mg of Pd/C, and the mixture was stirred at ambient temperature under $H_2$ atmosphere overnight. The reaction mixture was filtered and the filtrate was concentrated. The residue was purified by pep-TLC (MeOH/DCM=1:15) to give one isomer (37A) of 5-[2-(3,8-diazabicyclo[3.2.1]oct-3-yl)-1-hydroxyethyl]-4-methyl-2-benzofuran-1(3H)-one. MS m/z 303 (M+1)⁺.

To a solution of isomer B from Step A (210 mg, 0.536 mmol) in 50 mL of EtOAc was added 100 mg of Pd/C under Ar, and the mixture was stirred at ambient temperature under $H_2$ atmosphere overnight. The reaction mixture was filtered and the filtrate was concentrated. The residue was purified by prep-TLC (MeOH/DCM=1:15) to give the second isomer (37B) of 5-[2-(3,8-diazabicyclo[3.2.1]oct-3-yl)-1-hydroxyethyl]-4-methyl-2-benzofuran-1(3H)-one.
MS m/z 303 (M+1)⁺.

INTERMEDIATE 38

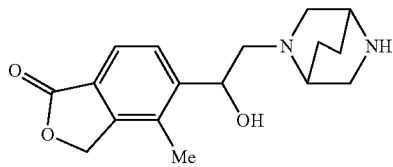

5-[2-(2,5-diazabicyclo[2.2.2]oct-2-yl)-1-hydroxyethyl]-4-methyl-2-benzofuran-1(3H)-one (and separated isomers)

Step A: 1,1-dimethylethyl5-[2-hydroxy-2-(4-methyl-1-oxo-1,3-dihydro-2-benzofuran-5-yl)ethyl]-2,5-diazabicyclo[2.2.2]octane-2-carboxylate A mixture of 4-methyl-5-oxiran-2-yl-2-benzofuran-1(3H)-one (700 mg, 3.68 mmol) and 1,1-dimethylethyl 2,5-diazabicyclo[2.2.2]octane-2-carboxylate (748 mg, 3.68 mmol) in 2 mL DMSO was heated under microwave condition (150° C.) for 1 hr. After cooling to rt., the mixture was diluted with water (50 mL), extracted with EtOAc (3×50 mL). The combined organic layers were washed with brine and dried over $Na_2SO_4$, then concentrated. The residue was purified by TLC (MeOH/DCM=1:15) to obtain 1,1-dimethylethyl5-[2-hydroxy-2-(4-methyl-1-oxo-1,3-dihydro-2-benzofuran-5-yl)ethyl]-2,5-diazabicyclo[2.2.2]octane-2-carboxylate as a mixture of 4 isomers, which was separated by SFC chiral chromatography to obtain four chiral isomers or isomer mixtures A, B, C and D with the same MS m/z 403 (M+1)⁻.

Step B: 5-[2-(2,5-diazabicyclo[2.2.2]oct-2-yl)-1-hydroxyethyl]-4-methyl-2-benzofuran-1(3H)-one A solution of isomers A, B, C, and D from Step A above (150~190 mg) in 5 mL of DCM were added 5 mL of TFA and the mixture was stirred for 2 h before concentrating. The residues were then dissolved in 20 mL of $CH_3CN$ and added 500 mg of $Na_2CO_3$. The mixture was stirred at r.t. overnight and then filtered. The filtrate was concentrated to give the corresponding free amines single isomers of 5-[2-(2,5-diazabicyclo[2.2.2]oct-2-yl)-1-hydroxyethyl]-4-methyl-2-benzofuran-1(3H)-one (38A, 38B, 38C, and 38D) with same MS m/z 303 (M+1)⁺.

INTERMEDIATE 39

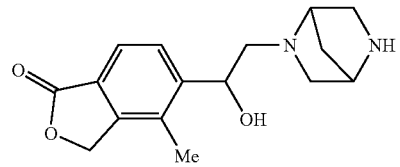

5-[2-(2,5-diazabicyclo[2.2.1]hept-2-yl)-1-hydroxyethyl]-4-methyl-2-benzofuran-1(3H)-one Step A: phenylmethyl-5-[2-hydroxy-2-(4-methyl-1-oxo-1,3-dihydro-2-benzofuran-5-yl)ethyl]-2,5-diazabicyclo[2.2.1]heptane-2-carboxylate A mixture of 4-methyl-5-oxiran-2-yl-2-benzofuran-1(3H)-one (700 mg, 3.68 mmol) and phenylmethyl 2,5-diazabicyclo[2.2.1]heptane-2-carboxylate (748 mg, 3.68 mmol) in 2 mL DMSO was heated under microwave condition (150° C.) for 1 hr. After cooling to it, the mixture was diluted with water (50 mL), extracted with EtOAc (3×50 mL). The combined organic layers were washed with brine and dried over $Na_2SO_4$, then concentrated. The residue was purified by TLC (MeOH/DCM=1:15) to obtain the racemic product (950 mg), which was separated by SFC chiral chromatography to obtain two isomer mixtures of phenylmethyl-5-[2-hydroxy-2-(4-methyl-1-oxo-1,3-dihydro-2-benzofuran-5-yl)ethyl]-2,5-diazabicyclo[2.2.1]heptane-2-carboxylate Isomers A and Isomers B with the same MS m/z 423 (M+1)⁺.

Step B: 5-[2-(2,5-diazabicyclo[2.2.1]hept-2-yl)-1-hydroxyethyl]-4-methyl-2-benzofuran-1(3H)-one A solution of isomers A of phenylmethyl-5-[2-hydroxy-2-(4-methyl-1-oxo-1,3-dihydro-2-benzofuran-5-yl)ethyl]-2,5-diazabicyclo[2.2.1]heptane-2-carboxylate (340 mg, 0.804 mmol) in 50 mL of EtOAc was added 100 mg of Pd/C under Ar, and the mixture was stirred at ambient temperature under $H_2$ atmosphere overnight. The reaction mixture was filtered and the filtrate was concentrated. The residue was purified by prep-TLC (MeOH/DCM=1:15) to give isomers A of 5-[2-(2,5-diazabicyclo[2.2.1]hept-2-yl)-1-hydroxyethyl]-4-methyl-2-benzofuran-1(3H)-one. MS m/z 289 (M+1)⁺.

A solution of isomers B of phenylmethyl-5-[2-hydroxy-2-(4-methyl-1-oxo-1,3-dihydro-2-benzofuran-5-yl)ethyl]-2,5-diazabicyclo[2.2.1]heptane-2-carboxylate (470 mg, 1.114 mmol) in 50 mL of EtOAc was added 100 mg of Pd/C under Ar, and the mixture was stirred at ambient temperature under $H_2$ atmosphere overnight. The reaction mixture was filtered and the filtrate was concentrated. The residue was purified by prep-TLC (MeOH/DCM=1:15) to give isomers B of 5-[2-(2,5-diazabicyclo[2.2.1]hept-2-yl)-1-hydroxyethyl]-4-methyl-2-benzofuran-1(3H)-one. MS m/z 289 (M+1)⁻.

INTERMEDIATE 40

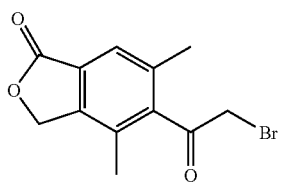

5-(bromoacetyl)-4,6-dimethyl-2-benzofuran-1(3H)-one

Step A: 5-acetyl-4,6-dimethyl-2-benzofuran-1(3H)-one

To a 20 mL microwave tube containing a stir bar were added 4,6-dimethyl-5-oxiran-2-yl-2-benzofuran-1(3H)-one (from the synthesis of INTERMEDIATE 9, 1.0 g, 4.2 mmol), tetrakis(triphenylphosphine)palladium (0) (0.240 g, 0.207 mmol), and tributyl(1-ethoxy-vinyl)tin (2.20 g, 6.22 mmol); to the mixture was added anhydrous toluene (18 mL) and the tube was capped, degassed and purged with $N_2$. The tube was then placed in an oil bath and heated at 110° C. for 12 h; LC indicated some product formation. The tube was taken out of the oil bath and cooled to room temperature. The solution was concentrated to dryness under reduced pressure and the resulting residue was then treated with 4M HCl (10 mL); the resulting solution was stirred at room temperature for 1 h; LC analysis indicated completion of the reaction. The solution was concentrated to dryness and the residue was re-dissolved in DCM, was absorbed in silica gel and was then loaded into silica column for separation with the solvent systems of Hexanes/EtOAc (1/1); this yielded 5-acetyl-4,6-dimethyl-2-benzofuran-1(3H)-one.

$^1$H-NMR (CDCl$_3$, 500 MHz), δ 7.645 (s, 1H), 5.271 (s, 2H), 2.558 (s, 3H), 2.393 (s, 3H), 2.623 (s, 3H). LC-MS (IE, m/z): 205 [M+1]$^-$; $t_R$=3.08 min.

Step B: 5-(bromoacetyl)-4,6-dimethyl-2-benzofuran-1(3H)-one

To a solution of 5-acetyl-4,6-dimethyl-2-benzofuran-1(3H)-one (370 mg, 1.8 mmol) in THF (4 mL) was added Copper(II) dibromide (486 mg, 2.20 mmol) at RT. The mixture was allowed to stir at RT for 16 hours. TLC showed formation of the desired product. The reaction was diluted with EtOAc (100 mL), washed with brine, dried over sodium sulfate, and purified by silica gel flash chromatography. 5-(Bromoacetyl)-4,6-dimethyl-2-benzofuran-1(3H)-one was collected after removal of solvent. $^1$H-NMR (CDCl$_3$, 500 MHz), δ 7.671 (s, 1H), 5.286 (s, 2H), 4.314 (s, 2H), 2.414 (s, 3H), 2.288 (s, 3H)

INTERMEDIATE 41

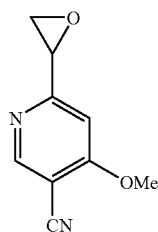

4-Methoxy-6-(oxiran-2-yl)pyridine-3-carbonitrile

Step A: 5-Bromo-2-chloro-4-methoxypyridine

To a solution of 2-chloro-4-methoxypyridine (10.0 g, 69.7 mmol) in 50 mL of sulfuric acid at 0° C. was added NBS. The reaction mixture was allowed to stir and warm up to room temperature for 2 hour and then heated at 60° C. for 5 h. Then it was cooled to room temperature and neutralized with 1 N NaOH (pH ~7), diluted with water (50 mL) and the aqueous layer was extracted with ethyl acetate (2×100 mL). The organic layers were washed with water (2×50 mL), sat. NaHCO$_3$, brine, dried over Mg$_2$SO$_4$ and concentrated to provide an oil, which was chromatographed. On elution with 0-25% EtOAc/hexanes, of the final product was obtained. $^1$H NMR (500 MHz, DMSO-d$_6$), δ 8.4 (s, 1H), 7.29 (s, 1H), 3.97 (s, 3H);

LC/MS (M+1)$^+$=223.81; $t_R$=2.75 min.

Step B: 6-Chloro-4-methoxypyridine-3-carbonitrile

A solution of 5-bromo-2-chloro-4-methoxypyridine (5.0 g, 22.48 mmol) in DMF (80 mL) was purged with nitrogen for 15 min. At this point, Zn(CN)$_2$ (3.96 g, 33.7 mmol) and Pd(Ph$_3$P)$_4$ (2.60 g, 2.25 mmol) were added, successively. The resulting suspension was stirred at 95° C. for 12 h under nitrogen atm. The reaction mixture was cooled to ambient temperature, filtered to remove inorganic solid. The solvent (DMF) was evaporated to provide the crude residue as an oil, which was purified on silica gel and eluted with 0-30% ethyl acetate/hexanes to afford the product. $^1$H NMR (500 MHz, DMSO-d$_6$), δ 8.69 (s, 1H), 7.50 (s, 1H), 4.04 (s, 3H);

LC/MS (M+1)$^+$=168.96; $t_R$=2.05 min.

Step C: 6-Ethenyl-4-methoxypyridine-3-carbonitrile

A 20 mL microwave tube was charged with 6-chloro-4-methoxypyridine-3-carbonitrile (200.0 mg, 1.2 mmol), bis (diphenylphosphino)ferrocene]dichloropalladium(II), complex with dichloromethane (97.0 mg, 0.12 mmol), potassium vinyl trifluoroborate (318.0 mg, 2.37 mmol), and triethylamine (0.33 mL, 2.37 mmol), and EtOH (6 mL). The microwave tube was evacuated and filled with nitrogen (two times) and heated to 140° C. After 1 h, the reaction mixture was diluted with water and extracted with EtOAc. The combined organic layers were washed with brine and dried over Na$_2$SO$_4$. The extracts were concentrated and chromatographed over a column of SiO$_2$ (0-30% EtOAc/hexanes as eluent). Evaporation of the solvent yielded the title compound. $^1$H NMR (500 MHz, DMSO-d$_6$), δ 8.65 (s, 1H), 6.89 (s, 1H), 6.83 (dd, J=10.7 Hz, 1H), 6.42 (d, J=7.3 Hz, 1H), 5.70 (d, J=10.6 Hz, 1H) 4.05 (s, 3H);

LC/MS (M+1)$^+$=161.03; $t_R$=1.67 min.

Step D: 6-(2-Bromo-1-hydroxyethyl)-4-methoxypyridine-3-carbonitrile

A solution of 6-ethenyl-4-methoxypyridine-3-carbonitrile (80.0 mg, 0.499 mmol) in 1,4-dioxane (8 mL) and H$_2$O (4 mL) was treated with N-bromosuccinimide (89.0 mg, 0.499 mmol, 1.0 equiv). The reaction mixture was allowed to stir at room temperature overnight. The reaction mixture was poured into H$_2$O (8 mL) and extracted with EtOAc (3×30 mL). The combined organic layers were washed with saturated aqueous NaCl (1×30 mL), dried over Na$_2$SO$_4$. Evaporation of the solvent gave an oil that was purified over SiO$_2$ (0-30% EtOAc/hexanes as eluent) yielding 6-(2-bromo-1-hydroxyethyl)-4-methoxypyridine-3-carbonitrile.

$^1$H NMR (500 MHz, DMSO-d$_6$), δ 8.65 (s, 1H), 7.19 (s, 1H), 5.05 (t, J=5.4 Hz, 1H), 4.05 (s, 3H), 3.85 (dd, J=4.5 Hz, 1H), 3.75 (dd, J=6.1 Hz, 1H);
LC/MS (M+1)$^+$=240.89; t$_R$=1.31 min.

Step E:
4-Methoxy-6-(oxiran-2-yl)pyridine-3-carbonitrile

A solution of 6-(2-bromo-1-hydroxyethyl)-4-methoxypyridine-3-carbonitrile (74.0 mg, 0.288 mmol) in anhydrous methanol (7 mL) was treated with sodium carbonate (61.0 mg, 0.576 mmol, 2.0 equiv), and allowed to stir at room temperature overnight. The solvent was evaporated. The residue was taken up in EtOAc (30 mL) and washed with water and brine. After drying over Na$_2$SO$_4$, the organic layer was removed and the residue was purified over SiO$_2$ (10-45% EtOAc/hexanes as eluent) to yield 4-methoxy-6-(oxiran-2-yl)pyridine-3-carbonitrile.

$^1$H NMR (500 MHz, DMSO-d$_6$), δ 8.64 (s, 1H), 6.87 (s, 1H), 4.08 (dd, J=2.6 Hz, J=2.3 Hz, 1H), 4.03 (s, 3H), 3.26 (dd, J=4.6 Hz, J=5.4 Hz, 1H), 2.87 (dd, J=2.2 Hz, J=2.4 Hz, 1H); LC/MS (M+1)$^+$=177.11; t$_R$=1.68 min.

INTERMEDIATE 42

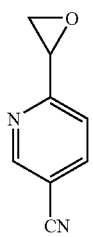

6-(Oxiran-2-yl)pyridine-3-carbonitrile

Step A: 6-Ethenylpyridine-3-carbonitrile

To a stirring solution of 6-bromopyridine-3-carbonitrile (2.0 g, 10.9 mmol), in EtOH (70 mL) were added bis[(diphenylphosphino)ferrocene]dichloropalladium(II), complex with dichloromethane (0.892 mg, 0.10 mmol), potassium vinyl trifluoroborate (2.93 g, 21.9 mmol), triethylamine (3.0 mL, 21.9 mmol), and water (0.5 mL). The reaction mixture was heated to reflux. Upon completion as determined by reverse phase HPLC-MS (1-2 h) and TLC (eluent: 10% ethyl acetate in hexanes), the reaction was cooled to room temperature, and then was diluted with water and extracted with EtOAc. The combined organic layers were washed with brine and dried over MgSO$_4$. The extracts were concentrated and chromatographed over a column of SiO$_2$ (0-20% EtOAc/hexanes as eluent). Evaporation of the solvent yielded 6-ethenylpyridine-3-carbonitrile.

$^1$H NMR (500 MHz, CDCl$_3$), δ 8.85 (s, 1H), 7.94-7.93 (m, 1H), 6.89-6.83 (m, 1H), 7.45 (d, J=8.2 Hz, 1H), 6.85 (dd, J=10.8, Hz, 1H), 6.42 (d, J=17.4 Hz, 1H); LC/MS (M+1)$^+$=131.06.

Step B: 6-(Oxiran-2-yl) pyridine-3-carbonitrile

A solution of 6-ethenylpyridine-3-carbonitrile (0.742 g, 5.70 mmol) in a 2:1 ratio of H$_2$O:t-BuOH (30 mL) was treated with N-bromosuccinimide in portions over 5 min (1.07 g, 5.99 mmol) and stirred at 40° C. for 1 h. After cooling to 5° C., the reaction was basified with drop wise addition of solution of sodium hydroxide (0.684 g in 5 mL of H$_2$O, 17.1 mmol) and stirred for another 1 h. The reaction mixture was poured into H$_2$O (10 mL) and extracted with EtOAc (2×50 mL). The combined organic layers were washed with saturated aqueous NaCl (1×30 mL) and dried over MgSO$_4$. Evaporation of the solvent and purification over SiO$_2$ (0-30% EtOAc/hexanes as eluent) provided 6-(oxiran-2-yl) pyridine-3-carbonitrile.

$^1$H NMR (500 MHz, CDCl$_3$), δ 8.87 (s, 1H), 7.99 (d, J=8.1 Hz, 1H), 7.40 (d, J=8.1 Hz, 1H), 4.11 (s, 1H), 4.08 (dd, J=2.6 Hz, J=2.3 Hz, 1H), 3.29 (m, 1H), 2.94 (m, 1H); LC/MS (M+1)$^+$=147.09.

Resolution of the epoxides was carried out (prep SFC, 160 mL/min., 10% MeOH in SC CO$_2$, AD-H) to provide: Isomer A: (M+1)$^+$=147.09. Isomer B: (M+1)$^+$=147.09.

INTERMEDIATE 43

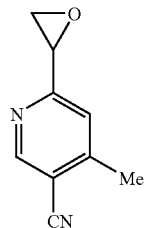

4-Methyl-6-(oxiran-2-yl)pyridine-3-carbonitrile

4-Methyl-6-(oxiran-2-yl) pyridine-3-carbonitrile was prepared in a similar fashion to that described for the synthesis of INTERMEDIATE 42 starting from 6-chloro-4-methylpyridine-3-carbonitrile. LC/MS (M+1)$^+$=161.13.

INTERMEDIATE 44

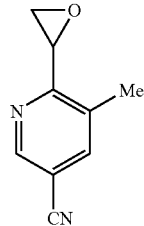

5-Methyl-6-(oxiran-2-yl)pyridine-3-carbonitrile

5-Methyl-6-(oxiran-2-yl)pyridine-3-carbonitrile was prepared in a similar fashion to that described for the synthesis of INTERMEDIATE 42 starting from 6-chloro-5-methylpyridine-3-carbonitrile.

LC/MS (M+1)$^+$=161.10.

INTERMEDIATE 45

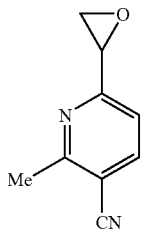

2-Methyl-6-(oxiran-2-yl)pyridine-3-carbonitrile

2-Methyl-6-(oxiran-2-yl)pyridine-3-carbonitrile was prepared in a similar fashion to that described for the synthesis of INTERMEDIATE 42 starting from 6-chloro-2-methylpyridine-3-carbonitrile.
LC/MS (M+1)$^+$=161.16.

INTERMEDIATE 46

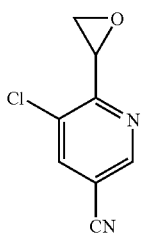

5-chloro-6-(oxiran-2-yl)pyridine-3-carbonitrile

5-Chloro-6-(oxiran-2-yl)pyridine-3-carbonitrile was prepared in a similar fashion to that described for the synthesis of INTERMEDIATE 42 starting from 5,6-dichloropyridine-3-carbonitrile.
LC/MS (M+1)$^+$=180.99.

INTERMEDIATE 47

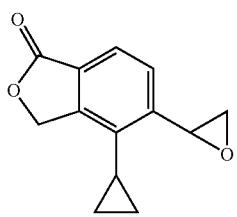

4-cyclopropyl-5-oxiran-2-yl-2-benzofuran-1(3H)-one

Step A: 5-bromo-4-iodo-2-benzofuran-1(3H)-one

To a cooled (0° C.) solution of 5-bromo-2-benzofuran-1(3H)-one (50 g, 0.235 mol) in trifluoromethanesulfonic acid (400 mL) was added N-iodosuccinimide (55.5 g, 0.247 mol). The resulting mixture was stirred at room temperature overnight, then poured slowly into ice water (2 L), filtered and the filtrate extracted with EtOAc. The combined organic layers were washed with water and brine, dried and concentrated to give 5-bromo-4-iodo-2-benzofuran-1(3H)-one.

Step B: 5-bromo-4-vinyl-2-benzofuran-1(3H)-one

A mixture of 5-bromo-4-iodo-2-benzofuran-1(3H)-one (1 g, 2.95 mmol), potassium vinyltrifluoroborate (474 mg, 3.54 mmol) and Pd(dppf)Cl$_2$ (200 mg) in 20 mL of TEA and 20 mL of EtOH was heated to reflux under N$_2$ for 2 hours. TLC showed complete reaction. Most of the solvent was removed, and the residue was dissolved in EtOAc (100 mL). The solution was washed with 0.1 N HCl, sodium bicarbonate, and brine, dried over sodium sulfate, filtered and concentrated to provide 5-bromo-4-vinyl-2-benzofuran-1(3H)-one.

Step C: 5-bromo-4-cyclopropyl-2-benzofuran-1(3H)-one

To a cooled (0° C.) mixture of 5-bromo-4-vinyl-2-benzofuran-1(3H)-one (2.2 g, 9.21 mol) and Pd(OAc)$_2$ (100 mg) in EtOAc (50 mL) was added a solution of CH$_2$N$_2$ in ether (100 mL) slowly. The resulting mixture was stirred at room temperature overnight, then quenched with acetic acid, filtered and the filtrate washed with water and brine, dried and concentrated to provide 5-bromo-4-cyclopropyl-2-benzofuran-1(3H)-one.

Step D: 4-cyclopropyl-5-vinyl-2-benzofuran-1(3H)-one

A mixture of 5-bromo-4-cyclopropyl-2-benzofuran-1(3H)-one (760 mg, 3.004 mmol), potassium vinyltrifluoroborate (805 mg, 6.008 mmol) and Pd(dppf)Cl$_2$ (100 mg) in 20 mL of TEA and 20 mL of EtOH was heated to reflux under N$_2$ for 8 hours. When TLC showed complete reaction most of the solvent was removed, and the residue was dissolved in EtOAc (100 mL). The solution was washed with 0.1 N HCl, sodium bicarbonate, and brine, dried over sodium sulfate, filtered and concentrated. The resulting oil was purified by column chromatography to give 4-cyclopropyl-5-vinyl-2-benzofuran-1(3H)-one.
$^1$H-NMR (400 MHz, CDCl$_3$) δ ppm 7.74 (d, J=8.6 Hz, 1H), 7.67 (d, J=7.8 Hz, 1H), 7.34-7.41 (m, 1H), 5.81 (d, J=17.2 Hz, 1H), 5.50 (d, J=11.0 Hz, 1H), 5.38 (s, 2H), 1.84-1.90 (m, 1H), 1.04-1.09 (m, 2H), 0.61-0.65 (m, 2H).

Step E: 4-cyclopropyl-5-oxiran-2-yl-2-benzofuran-1(3H)-one

To a solution of 4-cyclopropyl-5-vinyl-2-benzofuran-1(3H)-one (440 mg, 2.2 mmol) in 50 mL of DCM was slowly added mCPBA (1.14 g, 6.6 mmol) in 50 mL of DCM at 0° C. After warming to room temperature, the mixture was stirred for 12 hours. The mixture was washed with aqueous Na$_2$SO$_3$ until KI paper didn't change color. The organic layers were combined, washed with brine and then concentrated. The residue was purified via prep-TLC to give product 4-cyclopropyl-5-oxiran-2-yl-2-benzofuran-1(3H)-one.
$^1$H-NMR (400 MHz, CDCl$_3$) δ ppm 7.77 (d, J=8.6 Hz, 1H), 7.39 (d, J=7.8 Hz, 1H), 5.39 (s, 2H), 4.43-4.45 (m, 1H), 3.26-3.28 (m, 1H), 2.68-2.70 (m, 1H), 1.94-2.01 (m, 1H), 1.08-1.12 (m, 2H), 0.65-0.75 (m, 2H).

INTERMEDIATE 48

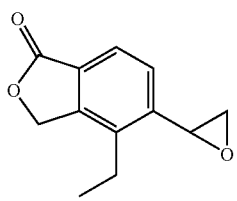

4-ethyl-5-oxiran-2-yl-2-benzofuran-1(3H)-one

Step A: 5-bromo-4-ethyl-2-benzofuran-1(3H)-one

A mixture of 5-bromo-4-vinyl-2-benzofuran-1(3H)-one (2.0 g, 8.37 mmol) and Pd/C (400 mg) in 50 mL of MeOH was stirred at rt. under $H_2$ (1 atm) overnight, and then filtered. The filtrate was concentrated. The resulting oil was purified by column chromatography to give 5-bromo-4-ethyl-2-benzofuran-1(3H)-one.
$^1$H-NMR (400 MHz, CDCl$_3$) δ ppm 7.71 (d, J=7.8 Hz, 1H), 7.59 (d, J=7.8 Hz, 1H), 5.28 (s, 2H), 2.76 (q, J=7.4 Hz, 2H), 1.21 (t, J=7.4 Hz, 3H).

Step B: 4-ethyl-5-vinyl-2-benzofuran-1(3H)-one

A mixture of 5-bromo-4-ethyl-2-benzofuran-1(3H)-one (1.81 g, 7.51 mmol), potassium vinyltrifluoroborate (1.21 g, 9.01 mmol) and Pd(dppf)Cl$_2$ (200 mg) in 20 mL of TEA and 20 mL of EtOH was heated to reflux under $N_2$ overnight and then concentrated. The resulting oil was purified by column chromatography to give 4-ethyl-5-vinyl-2-benzofuran-1(3H)-one.
$^1$H-NMR (400 MHz, CDCl$_3$) δ ppm 7.73 (d, J=7.8 Hz, 1H), 7.66 (d, J=7.8 Hz, 1H), 7.00-7.07 (m, 1H), 5.82 (d, J=17.2 Hz, 1H), 5.51 (d, J=11.0 Hz, 1H), 5.28 (s, 2H), 2.69 (q, J=7.4 Hz, 2H), 1.19 (t, J=7.4 Hz, 3H).

Step C: 4-ethyl-5-oxiran-2-yl-2-benzofuran-1(3H)-one

A solution of 4-ethyl-5-vinyl-2-benzofuran-1(3H)-one (1.1 g, 5.85 mmol) in 50 mL of DCM was slowly added mCPBA (3.60 g, 85% purity, 17.6 mmol) in 50 mL of DCM at 0° C. Warmed to room temperature, the mixture was stirred for 3 days. The mixture was washed with aqueous Na$_2$SO$_3$ until KI paper didn't change color. The organic layers were combined, washed with brine and concentrated. The residue was purified by column chromatography to give product 4-ethyl-5-oxiran-2-yl-2-benzofuran-1(3H)-one. $^1$H-NMR (400 MHz, CDCl$_3$) δ ppm 7.75 (d, J=8.6 Hz, 1H), 7.41 (d, J=7.8 Hz, 1H), 5.30 (s, 2H), 4.11-4.13 (m, 1H), 3.23-3.25 (m, 1H), 2.75-2.82 (m, 2H), 2.70-2.72 (m, 1H), 1.27 (t, J=7.4 Hz, 3H).

INTERMEDIATE 49

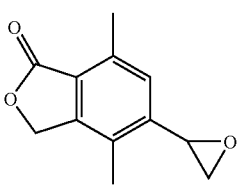

4,7-dimethyl-5-oxiran-2-yl-2-benzofuran-1(3H)-one

Step A: 3-Bromo-2,5-dimethylbenzoic acid

A solution of 2,5-dimethylbenzoic acid (20 g, 133 mmol) in 100 mL of conc. sulfuric acid was cooled to 0° C., and then N-bromosuccinimide (24 g, 139 mmol) was added. The reaction was stirred at 0° C. for 1.5 hours. The mixture was poured onto ice/water, extracted with EtOAc, washed with brine, dried over anhydrous sodium sulfate and concentrated. The crude product was purified by column chromatography to afford 3-bromo-2,5-dimethylbenzoic acid.
$^1$H-NMR (400 MHz, CDCl$_3$) δ ppm 7.73 (s, 1H), 7.60 (s, 1H), 2.66 (s, 3H), 2.343 (s, 3H).

Step B: (3-bromo-2,5-dimethylphenyl)methanol

To a solution of 3-bromo-2,5-dimethylbenzoic acid (3.5 g, 15 mmol) in anhydrous THF was added borane THF complex (1.0 M, 25 mL, 25 mmol) at 0° C., then the reaction was warmed to ambient temperature overnight. The reaction was quenched with MeOH and concentrated to afford (3-bromo-2,5-dimethylphenyl)methanol.

Step C: 5-bromo-4,7-dimethyl-2-benzofuran-1(3H)-one

To a solution of (3-bromo-2,5-dimethylphenyl)methanol (1.6 g, 7.4 mmol) in trifluoroacetic acid (20 mL) was added Tl(OOCF$_3$)$_3$ (4 g, 7.4 mmol) at r.t, then the reaction was stirred at r.t overnight under $N_2$. The mixture was concentrated under pressure. The residue solids, LiCl (0.6 g, 14.9 mmol), MgO (0.6 g, 14.9 mmol) and PdCl$_2$ (0.13 g, 0.74 mmol) in MeOH were stirred under CO at 1 Mpa over night. EtOAc was added to the mixture and filtered. The organic phase was concentrated to afford 5-bromo-4,7-dimethyl-2-benzofuran-1(3H)-one.

Step D: 4,7-dimethyl-5-vinyl-2-benzofuran-1(3H)-one

A mixture of 5-bromo-4,7-dimethyl-2-benzofuran-1(3H)-one (0.7 g, 2.9 mmol), potassium vinyltrifluoroborate (0.544 g, 4 mmol) and Pd(dppf)$_2$Cl$_2$ (0.07 g) in 20 mL of EtOH and 20 mL of TEA was refluxed under $N_2$ for 4 hours. The mixture was concentrated and the residue was purified by column chromatography to afford 4,7-Dimethyl-5-vinyl-2-benzofuran-1(3H)-one. $^1$H-NMR (400 MHz, CDCl$_3$) δ ppm 7.30 (s, 1H), 6.85-6.92 (m, 1H), 5.70 (d, J=17.3 Hz, 1H), 5.40 (d, J=11.0 Hz, 1H), 5.18 (s, 2H), 2.64 (s, 3H), 2.24 (s, 3H).

Step E: 4,7-dimethyl-5-oxiran-2-yl-2-benzofuran-1(3H)-one

To a solution of 4,7-dimethyl-5-vinyl-2-benzofuran-1(3H)-one (0.4 g, 2.1 mmol) in 60 mL of DCM was slowly added mCPBA (85%, 0.7 g, 4.2 mmol) at 0° C. After warming to room temperature, the mixture was stirred for 48 hours. The mixture was washed subsequently with saturated NaHCO$_3$, aqueous Na$_2$SO$_3$, 5% NaOH and brine. The mixture was concentrated and the residue was purified by column chromatography to afford 4,7-dimethyl-5-oxiran-2-yl-2-benzofuran-1(3H)-one as white solid.
$^1$H-NMR (400 MHz, CDCl$_3$) δ ppm 7.07 (s, 1H), 5.13 (s, 2H), 3.96-3.98 (m, 1H), 3.14-3.16 (m, 1H), 2.61-2.63 (m, 1H), 2.56 (s, 3H), 2.24 (s, 3H).

INTERMEDIATE 50

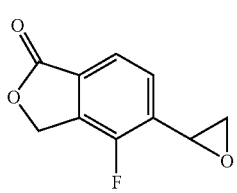

4-fluoro-5-oxiran-2-yl-2-benzofuran-1(3H)-one

Step A: 5-Bromo-4-fluoro-2-benzofuran-1(3H)-one

A solution of n-BuLi (40 mL, 100 mmol) was added dropwise to a solution of diisopropylamine (10.6 g, 105 mmol) in 150 mL of THF at −70° C. The mixture was stirred at 0° C. for 15 minutes and then cooled to −70° C. again. A solution of 4-bromo-3-fluorobenzoic acid (10 g, 45.7 mmol, in 50 mL of THF) was added dropwise. The resulting mixture was stirred at −70° C. for 1 hour then CH$_2$O gas (generated by heating 5.1 g of Para formaldehyde to 200° C.) was bubbled into the mixture. The resulting mixture was stirred at −70° C. for 1 hour then allowed to warm to room temperature and stirred for another 2 hours. HCl gas was bubbled into the suspension for 15 minutes to give a clear solution. The mixture was diluted with 1 L of EtOAc and washed subsequently with water, saturated Na$_2$CO$_3$ and brine, dried over anhydrous Na$_2$SO$_4$ and concentrated to give 5-bromo-4-fluoro-2-benzofuran-1(3H)-one as white solid.

$^1$H-NMR (400 MHz, CDCl3) δ ppm 7.72-7.75 (m, 1H), 7.58 (d, J=8.0 Hz, 1H), 5.36 (s, 2H).

Step B: 4-fluoro-5-vinyl-3H-isobenzofuran-1-one

A mixture of 5-bromo-4-fluoro-2-benzofuran-1(3H)-one (5.0 g, 21.6 mmol), potassium vinyltrifluoroborate (4.4 g, 32.5 mmol) and Pd(dppf)Cl$_2$ (500 mg) in 100 mL of TEA and 100 mL of EtOH was heated to reflux under N$_2$ for 4 hrs and then concentrated. The resulting oil was purified by column chromatography to give 4-fluoro-5-vinyl-3H-isobenzofuran-1-one. $^1$H-NMR (400 MHz, CDCl$_3$) δ ppm 7.67-7.68 (m, 2H), 6.90-6.97 (m, 1H), 6.00 (d, J=17.2 Hz, 1H), 5.60 (d, J=11.0 Hz, 1H), 5.35 (s, 2H).

Step C: 4-fluoro-5-oxiranyl-3H-isobenzofuran-1-one

To a solution of 4-fluoro-5-vinyl-3H-isobenzofuran-1-one (4.0 g, 17.3 mmol) in 100 mL of DCM was slowly added mCPBA (6.0 g, 85% purity, 34.6 mmol) in 50 mL of DCM at 0° C. After warming to room temperature, the mixture was stirred overnight. The mixture was washed with aqueous Na$_2$SO$_3$ until KI paper didn't change color. The organic layers were washed with brine and then concentrated. The residue was purified by column chromatography to give product 4-fluoro-5-oxiranyl-3H-isobenzofuran-1-one.

$^1$H-NMR (400 MHz, CDCl$_3$) δ ppm 7.71 (d, J=7.8 Hz, 1H), 7.37-7.40 (m, 1H), 5.37 (s, 2H), 4.21-4.22 (m, 1H), 3.25-3.27 (m, 1H), 2.80-2.82 (m, 1H).

INTERMEDIATE 51

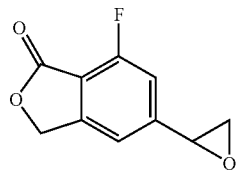

7-fluoro-5-oxiran-2-yl-2-benzofuran-1(3H)-one

Step A: 2,4-dibromo-6-fluorobenzoic acid

A solution of n-BuLi (20 mL, 50.0 mmol) was added dropwise to a solution of diisopropylamine (5.6 g, 55.0 mmol) in 200 mL of THF at −70° C. The mixture was stirred at 0° C. for 15 minutes and then recooled to −70° C. A solution of 1,3-dibromo-5-fluorobenzene (12.7 g, 50.0 mmol, in 50 mL of THF) was added dropwise. The resulting mixture was stirred at −70° C. for 2 hours then poured into fresh dry ice and stirred overnight. The mixture was diluted with 1 L of ether and washed with water twice. The combined water layer was washed with ether then acidified to pH=2 with hydrochloric acid and extracted with EtOAc twice. The combined EtOAc layer was washed with brine, dried over anhydrous Na$_2$SO$_4$ and concentrated to give 2,4-dibromo-6-fluorobenzoic acid as white solid.

$^1$H-NMR (400 MHz, d6-DMSO) δ ppm 7.85 (s, 1H), 7.76 (d, J=8.8 Hz, 1H).

Step B: 5-bromo-7-fluoro-2-benzofuran-1(3H)-one

A solution of n-BuLi (36.7 mL, 91.6 mmol) was added dropwise to a solution of 2,4-dibromo-6-fluorobenzoic acid (13.0 g, 43.6 mmol, in 200 mL of THF) at −70° C. The resulting solution was stirred for 15 minutes before CH$_2$O gas (generated by heating 5.1 g of Para formaldehyde to 200° C.) was bubbled into the mixture at −70° C. The suspension was stirred for 1 hour then warmed to room temperature and stirred for another 2 hours. HCl gas was bubbled into the suspension for 15 minutes to give a clear solution. The mixture was diluted with 1 L of EtOAc and washed subsequently with water, saturated Na$_2$CO$_3$ and brine, then dried over anhydrous Na$_2$SO$_4$ and concentrated. The residue was purified by column chromatography (PE:EtOAc=5:1) to give 5-bromo-7-fluoro-2-benzofuran-1(3H)-one as white solid.

$^1$H-NMR (400 MHz, CDCl3) δ ppm 7.46 (s, 1H), 7.36 (d, J=8.0 Hz, 1H), 5.29 (s, 2H).

Step C: 7-fluoro-5-vinyl-2-benzofuran-1(3H)-one

A mixture of 5-bromo-7-fluoro-2-benzofuran-1(3H)-one (4.6 g, 20.0 mmol), potassium vinyltrifluoroborate (2.9 g, 22 mmol) and Pd (dppf)$_2$Cl$_2$ (0.5 g) in 40 mL of EtOH and 40 mL of TEA was refluxed under Ar for 4 hours. After concentration, the residue was purified by column chromatography (PE:EtOAc=20:1) to afford 7-fluoro-5-vinyl-2-benzofuran-1(3H)-one. $^1$H-NMR (400 MHz, CDCl3) δ ppm 7.23 (s, 1H), 7.17 (d, J=10.0 Hz, 1H), 6.70-6.77 (m, 1H), 5.89 (d, J=17.2 Hz, 1H), 5.51 (d, J=11.2 Hz, 1H), 5.28 (s, 2H).

Step D: 7-fluoro-5-oxiran-2-yl-2-benzofuran-1(3H)-one mCPBA (85%, 9.9 g, 48.9 mmol) was added to a solution of 7-fluoro-5-vinyl-2-benzofuran-1(3H)-one (2.9 g, 16.3 mmol) in 300 mL of DCM at 0° C. The mixture was stirred at room temperature for 16 hours before being cooled to 0° C. The mixture was washed sequentially with saturated NaHCO₃ (50 mL), aqueous Na₂SO₃ (50 mL×2), 5% NaOH (50 mL) and brine, then concentrated. The residue was purified by column chromatography eluted with DCM to afford 7-fluoro-5-oxiran-2-yl-2-benzofuran-1(3H)-one as white solid.

$^1$H-NMR (400 MHz, CDCl₃) δ ppm 7.20 (s, 1H), 7.09 (d, J=9.6 Hz, 1H), 5.29 (s, 2H), 3.94-3.96 (m, 1H), 3.21-3.24 (m, 1H), 2.75-2.77 (m, 1H); MS m/z 195 (M+1)$^+$.

INTERMEDIATE 52

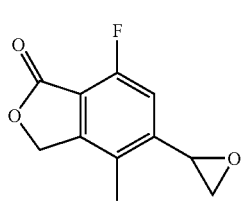

7-fluoro-4-methyl-5-oxiran-2-yl-2-benzofuran-1(3H)-one

Step A: 3-bromo-5-fluoro-2-methyl-benzoic acid

To a cooled (0° C.) solution of 5-fluoro-2-methyl-benzoic acid (20 g, 130 mmol) in conc. sulfuric acid (200 mL) was added N-bromosuccinimide (24.3 g, 136 mmol) portionwise. The resulting mixture was stirred at 0° C. for 3 hrs, then warmed to room temperature and stirred for 16 hrs. Then the mixture was poured slowly into ice water (2 L), and extracted with EtOAc. The combined organic layers were washed with water and brine, dried and concentrated to provide 3-bromo-5-fluoro-2-methyl-benzoic acid, which was used directly in the next step.

Step B: (3-bromo-5-fluoro-2-methyl-phenyl)-methanol

To a cooled (0° C.) solution of 3-bromo-5-fluoro-2-methyl-benzoic acid (3 g, 12.9 mmol) in dry THF (20 mL) was added borane THF complex (25.8 mL, 1 M in THF, 25.8 mmol) slowly. The resulting mixture was stirred at room temperature overnight, then quenched with MeOH and concentrated. The residue was purified by column chromatography to give (3-bromo-5-fluoro-2-methyl-phenyl)-methanol. $^1$H-NMR (400 MHz, CDCl₃) δ ppm 7.25 (dd, J=8.6 Hz, J=3.1 Hz, 1H), 7.15 (dd, J=8.6 Hz, J=2.3 Hz, 1H), 4.71 (s, 2H), 2.33 (s, 3H).

Step C: 5-Bromo-7-fluoro-4-methyl-3H-isobenzofuran-1-one

To a solution of (3-bromo-5-fluoro-2-methyl-phenyl)-methanol (1.7 g, 7.76 mmol) in trifluoroacetic acid (20 mL) was added Tl(CF₃COO)₃ (4.2 g, 7.76 mmol). The resulting mixture was stirred at room temperature overnight, then concentrated to dryness. The residue was dissolved in MeOH (50 mL). To the mixture was added PdCl₂ (137 mg, 0.776 mmol), LiCl (652 mg, 15.5 mmol) and MgO (652 mg, 15.5 mmol). The resulting mixture was reacted under a CO (50 psi) atmosphere at room temperature overnight, and then filtered. The filtrate was concentrated and the residue was purified by column chromatography to give 5-bromo-7-fluoro-4-methyl-3H-isobenzofuran-1-one.

Step D: 7-Fluoro-4-methyl-5-vinyl-3H-isobenzofuran-1-one

A mixture of 5-bromo-7-fluoro-4-methyl-3H-isobenzofuran-1-one (0.6 g, 2.45 mmol), potassium vinyltrifluoroborate (492 mg, 3.67 mmol) and Pd(dppf)Cl₂ (100 mg) in 20 mL of TEA and 20 mL of EtOH was heated to reflux under N₂ for 4 hrs and then concentrated. The resulting oil was purified by prep-TLC to give 7-fluoro-4-methyl-5-vinyl-3H-isobenzofuran-1-one.

$^1$H-NMR (400 MHz, CDCl₃) δ ppm 7.26 (d, J=9.4 Hz, 1H), 6.89-6.97 (m, 1H), 5.80 (d, J=17.2 Hz, 1H), 5.60 (d, J=11.0 Hz, 1H), 5.23 (s, 2H), 2.24 (s, 3H).

Step E: 7-Fluoro-4-methyl-5-oxiran-2-yl-2-benzofuran-1(3H)-one

A solution of 7-fluoro-4-methyl-5-vinyl-3H-isobenzofuran-1-one (420 mg, 1.71 mmol) in 10 mL of DCM was slowly added mCPBA (741 mg, 85% purity, 3.43 mmol) in 10 mL of DCM at 0° C. After warming to room temperature, the mixture was stirred overnight. The mixture was washed with aqueous Na₂SO₃ until KI paper didn't change color. The organic layers was washed with brine and then concentrated. The residue was purified by column chromatography to give product 7-fluoro-4-methyl-5-oxiranyl-3H-isobenzofuran-1-one. The enantiomers of the product were resolved via SFC (Column: Chiralpak AD-H 250*4.6 mm ID, 5 um; Mobile phase: methanol (0.05% DEA) in CO₂ from 5% to 40%; Flow rate: 2.35 mL/min; Wavelength: 220 nm). MS m/z 209 (M+1)$^-$.

INTERMEDIATE 53

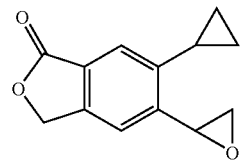

6-Cyclopropyl-5-oxiran-2-yl-2-benzofuran-1(3H)-one

Step A: 5-(2-Hydroxyethyl)-6-vinyl-2-benzofuran-1(3H)-one

To a 500 ml flask containing a stir bar was added 5-(2-hydroxyethyl)-6-iodo-2-benzofuran-1(3H)-one (5 g, 16.4 mmol), Potassium vinyltrifluoroborate (3.3 g, 24.7 mmol), Pd(dppf)Cl₂ (0.6 g, 0.822 mmol) and TEA (2.3 mL). The mixture was then dissolved in EtOH (50 mL) and heated at 100° C. in a silicon oil bath for 2 h; TLC showed complete reaction. The flask was cooled to room temperature, treated with EtOAc (150 mL) and poured into a separatory funnel and washed with brine (2×100 mL). The organic layer was then separated, dried (Na₂SO₄), filtered and concentrated to dryness. The resulting organic residue was dissolved in DCM and absorbed into silica gel and purified by MPLC (hexanes/EtOAc; 1/1 eluent) to provide 5-(2-Hydroxyethyl)-6-vinyl-2-benzofuran-1(3H)-one.

¹H NMR (500 MHz, CD₃Cl) δ 8.03 (s, 1H), 7.38 (s, 1H), 7.023-7.08 (m, 1H), 5.79 (d, J=17 Hz, 1H), 5.47 (d, J=11 Hz, 1H), 5.31-5.36 (m, 3H), 3.91-3.94 (m, 2H), 3.08-3.11 (m, 2H).

Step B: 6-Cyclopropyl-5-(2-hydroxyethyl)-2-benzofuran-1(3H)-one

To a 100 ml flask containing a stir bar was added 5-(2-Hydroxyethyl)-6-vinyl-2-benzofuran-1(3H)-one (0.9 g, 4.41 mmol), and Palladium diacetate (0.049 g, 0.220 mmol), followed by addition of a freshly prepared diazomethane (3.7 g, 88 mmol) in diethyl ether (10 mL) over a course of 20 minutes. The resulting mixture was then stirred at room temperature in a shielded environment for 1 h. When the reaction was complete, the solvent was concentrated to dryness, dissolved in EtOAc, and washed with brine, dried (Na₂SO₄), filtered and concentrated to dryness. The resulting residue was used for the next step without further purification.

¹H NMR (500 MHz, CD₃Cl) δ 7.56 (s, 1H), 7.38 (s, 1H) 5.28-5.32 (m, 3H), 3.97-4.03 (m, 3H), 3.23-3.26 (m, 2H), 1.81-1.73 (m, 4H); LC/MS: [(M+1)]⁺=219.

Step C: 6-Cyclopropyl-5-vinyl-2-benzofuran-1(3H)-one

To a 100 ml flask containing a stir bar was added compound 6-cyclopropyl-5-(2-hydroxyethyl)-2-benzofuran-1(3H)-one, (0.5 g, 2.29 mmol), TEA (20 mL) followed by addition of dichloromethane (25 mL). The flask was placed in a cool bath of 0° C., and slowly treated with methanesulfonyl chloride (6.5 mL, 83 mmol). The resulting mixture was then stirred for 20 min. TLC (hexanes/EtOAc=1/1) indicated completion of the reaction. The mixture was poured into saturated ammonium chloride and extracted with DCM. The combined organics were washed with 1 N HCl, saturated sodium bicarbonate solution, and brine, then dried (Na₂SO₄) and concentrated in vacuo. The residue (LC/MS: [(M+1)]⁺=297; t_R=1.01 min) was dissolved in dichloromethane (25 mL) and treated with DBU (0.7 mL, 4.72 mmol) and stirred for 2 h. TLC monitoring showed conversion to the olefin. The reaction mixture was diluted with water and extracted with dichloromethane. The combined organics were washed with 1N HCl, saturated sodium bicarbonate solution, and brine, then dried (Na₂SO₄) and concentrated in vacuo. The material was used in the next step without further purification.

Step D: 6-Cyclopropyl-5-oxiran-2-yl-2-benzofuran-1(3H)-one

6-Cyclopropyl-5-vinyl-2-benzofuran-1(3H)-one (0.45 g, 2.25 mmol) was dissolved in dichloromethane (10 mL) and treated with meta-chloro perbenzoic acid (1 g, 6.3 mmol) at 0° C. and stirred for 12 h. TLC indicated completion of the reaction; the mixture was diluted with saturated sodium bicarbonate solution and extracted with dichloromethane (2×). The combined organic extracts were washed with brine, dried (Na₂SO₄), filtered and concentrated in vacuo. The epoxide was purified by silica gel column chromatography (hexanes/EtOAc=1/1) to give 6-Cyclopropyl-5-oxiran-2-yl-2-benzofuran-1(3H)-one. The oxirane was further resolved over a chiral column giving two isomers:

Oxirane A—¹H NMR (500 MHz, CD₃Cl) δ 7.63 (s, 1H), 7.41 (s, 1H), 5.29-5.33 (m, 2H), 4.21-4.42 (m, 1H), 3.16-3.34 (m, 1H), 2.71-2.72 (m, 1H) 2.09-2.11 (m, 1H), 1.07-1.14 (m, 2H), 0.76-0.88 (m, 2H).

Oxirane B—¹H NMR (500 MHz, CD₃Cl) δ 7.63 (s, 1H), 7.41 (s, 1H), 5.29-5.30 (m, 2H), 4.412-4.42 (m, 1H), 3.31-3.33 (m, 1H), 2.71-2.72 (m, 1H), 2.09-2.12 (m, 1H), 1.07-1.60 (m, 2H), 0.76-0.87 (m, 2H)

INTERMEDIATE 54

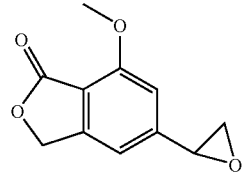

7-Methoxy-5-oxiran-2-yl-2-benzofuran-1(3H)-one

Step A: Methyl 4-allyl-2-formyl-6-methoxybenzoate

To a flask containing 5-allyl-2-hydroxy-3-methoxybenzaldehyde (5.0 g, 26.0 mmol) and N-phenyl-trifluoromethanesulfonimide was added DCM (75 mL). The flask was placed at 0° C. and treated with Et₃N (4 mL) and stirred for 2 days at room temp. The mixture was diluted with dichloromethane and washed with 1N HCl, saturated sodium bicarbonate solution, and brine, then dried (Na₂SO₄) and concentrated. The residue in a flask was treated with dppf (0.18 g, 0.45 mmol), PdOAc₂ (0.1 g, 0.44 mmol), and Et₃N (8 mL, 56 mmol) followed by addition of DMF (45 mL) and MeOH (30 mL). The reaction mixture was then degassed and purged with CO 3 times and stirred under CO for 6 h at 70° C. When LC indicated consumption of starting material, the solution was concentrated to dryness. The organic residue was purified by MPLC (hexanes/EtOAc=1/0.2) to provide methyl 4-allyl-2-formyl-6-methoxybenzoate.

LC/MS: [(M+1)]⁺=236.

Step B: 5-Allyl-7-methoxy-2-benzofuran-1(3H)-one

To a flask charged with methyl 4-allyl-2-formyl-6-methoxybenzoate (0.77 g, 1 mmol) was added sodium borohydride (0.36 g, 9.33 mmol); the mixture was then dissolved in MeOH (10 mL) and stirred for 18 h at room temp. LC indicated completion of the reaction. The mixture was diluted with EtOAc (150 mL) and washed with brine (2×100 mL). The organic layer was then separated, dried(Na₂SO₄), filtered and concentrated in vacuo. The resulting residue was purified by MPLC (hexanes/EtOAc=1/0.5) to provide 5-allyl-7-methoxy-2-benzofuran-1(3H)-one.

LC/MS: [(M+1)]⁺=205.

Step C: (7-Methoxy-1-oxo-1,3-dihydro-2-benzofuran-5-yl)acetaldehyde

To a flask containing 5-allyl-7-methoxy-2-yl-2-benzofuran-1(3H)-one (0.24 g, 1.18 mmol) in MeOH (10 mL) at −78° C. was bubbled ozone for 10 min. followed by addition of dimethyl sulfide (5 mL). The resulting mixture was stirred for 1 h at room temp. LC indicated that reaction had gone to completion. The mixture was diluted with saturated sodium bicarbonate solution and extracted with EtOAc (2×). The combined organic extracts were washed with brine, dried (Na₂SO₄), filtered and concentrated in vacuo to give (7-methoxy-1-oxo-1,3-dihydro-2-benzofuran-5-yl)acetaldehyde.

LC/MS: [(M+1)]⁺=207.

Step D: 5-(2-Hydroxyethyl)-7-methoxy-2-benzofuran-1(3H)-one

A solution of (7-methoxy-1-oxo-1,3-dihydro-2-benzofuran-5-yl)acetaldehyde (0.12 g, 0.58 mmol) was treated with sodium borohydride (0.05 g, 1.45 mmol) and methanol (10 mL); the resulting mixture was stirred at room temperature for 1 h. The solution was concentrated to dryness, dissolved in EtOAc and washed with water, dried (Na$_2$SO$_4$), filtered and concentrated in vacuo to give 5-(2-hydroxyethyl)-7-methoxy-2-benzofuran-1(3H)-one. LC/MS: [(M+1)]$^+$=209.

Step E: 7-Methoxy-5-vinyl-2-benzofuran-1(3H)-one

A dichloromethane solution of 5-(2-hydroxyethyl)-7-methoxy-2-benzofuran-1(3H)-one was placed cooled to 0° C., and slowly treated with methanesulfonyl chloride (0.11 mL, 1.4 mmol) and TEA (0.2 mL, 1.44 mmol). The resulting mixture was then stirred for 20 min. TLC (hexanes/EtOAc=1/1) indicated completion of the reaction. The mixture was poured into saturated ammonium chloride and extracted with dichloromethane. The combined organics were washed with 1 N HCl, saturated sodium bicarbonate solution, and brine, then dried (Na$_2$SO$_4$) and concentrated in vacuo. To the residue (LC/MS: [(M+1)]$^+$=287; t$_R$=0.81 min) (0.16 g, 0.56 mmol) was added DBU (0.19 mL, 1.26 mmol) and dichloromethane (2 mL) and stirred for 2 h. TLC monitoring showed conversion to the olefin. The reaction mixture was diluted with water and extracted with dichloromethane. The combined organics were washed with 1N HCl, saturated sodium bicarbonate solution, and brine, then dried (Na$_2$SO$_4$) and concentrated to dryness. The resulting oil was used in the next step without further purification.

Step F: 7-Methoxy-5-oxiran-2-yl-2-benzofuran-1(3H)-one

To a solution of 7-methoxy-5-vinyl-2-benzofuran-1(3H)-one in DCM (5 mL) was added meta-chloro perbenzoic acid (0.18 g, 1.05 mmol) at 0° C. and stirred for 12 h. TLC indicated completion of the reaction; the mixture was diluted with saturated sodium bicarbonate solution and extracted with DCM (2×). The combined organic extracts were washed with brine, dried (Na$_2$SO$_4$), filtered and concentrated in vacuo. The resulting epoxide was purified by silica gel column chromatography (hexanes/EtOAc=1/1) to give 7-methoxy-5-oxiran-2-yl-2-benzofuran-1(3H)-one. LC/MS: [(M+1)]$^+$=207.

INTERMEDIATE 55

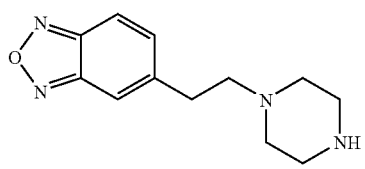

5-[2-(piperazin-1-yl)ethyl]-2,1,3-benzoxadiazole

Step A: 5-(prop-2-en-1-yl)-2,1,3-benzoxadiazole

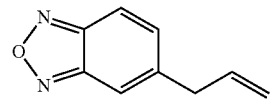

5-Bromo-2,1,3-benzoxadiazole (10 g, 50.3 mmol) was dissolved in toluene (300 mL) and treated with lithium chloride (6.39 g, 151 mmol), Pd(Ph3P)4 (2.90 g, 2.51 mmol), and allyltributylstannane (18.66 ml, 60.3 mmol). Degassed and refluxed the mixture under N2 for 3 hrs. The reaction mixture turned black. Poured the reaction mixture into water and extracted with ethyl acetate. The organic layer was separated, washed with brine, dried, and evaporated to dryness. The residue was chromatographed through 120 g ISCO Redi-Sep column and eluted with 0-10% ethyl acetate/hexane to yield 5-(prop-2-en-1-yl)-2,1,3-benzoxadiazole.

Step B: 5-[2-(piperazin-1-yl)ethyl]-2,1,3-benzoxadiazole

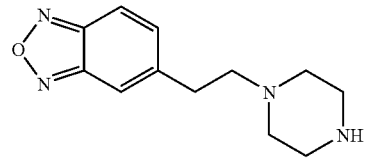 [SMILES: c1cc2nonc2cc1CCN1CCNCC1]

5-(Prop-2-en-1-yl)-2,1,3-benzoxadiazole (480, 3.0 mmole) was dissolved in DCM and cooled to −78° C. Ozone was bubbled in until the reaction mixture reached a bluish tint, then nitrogen was bubbled through the mixture to get rid of excess ozone. Boc-piperazine (558 mg, 3.0 mmol) was then added followed by sodium triacetoxyborohydride (2541 mg, 11.99 mmol). The reaction mixture was warmed up to RT and stirred overnight. The reaction mixture was poured into 1 N NaOH and extracted with ethyl acetate twice. The ethyl acetate layer was dried over MgSO4, filtered, and evaporated to dryness. The residue was purified through a 40 g Redi-sep column to yield tert-butyl 4-[2-(2,1,3-benzoxadiazol-5-yl)ethyl]piperazine-1-carboxylate, which was dissolved in dioxane and treated with 7 mL of 4M HCl in dioxane. The reaction mixture was stirred at RT overnight. The solvent was evaporated, then the residue was taken up in ethyl acetate and made alkaline by addition of 1N NaOH. The ethyl acetate was separated, washed with brine, then dried over Na2SO4 and evaporated to dryness. The residue was purified by MPLC chromatography using 5% (1 NH4OH:10 MeOH) in 95% DCM to yield 5-[2-(piperazin-1-yl)ethyl]-2,1,3-benzoxadiazole.

$^1$H-NMR (600 MHz, CDCl3): δ 7.72 (d, J=9.2 Hz, 1H), 7.28 (d, J=9.2 Hz, 1H), 2.92 (t, J=4.9 Hz, 2H), 2.88 (t, J=7.6 Hz, 1H), 2.65 (t, J=7.6 Hz, 1H)

LC-MS: M+1=233.

INTERMEDIATE 56

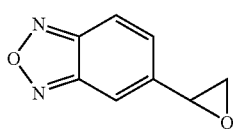

5-(oxiran-2-yl)-2,1,3-benzoxadiazole

Step A: 5-ethenyl-2,1,3-benzoxadiazole

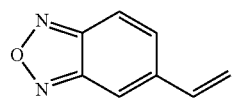

5-Bromo-2,1,3-benzoxadiazole (5.5 g, 27.6 mmol)), potassium vinylfluoroborate (7.40 g, 55.3 mmol), and PdCl2 (dppf)-CH2Cl2Adduct (1.088 g, 1.332 mmol) were suspended in ethanol (75 ml) then added TEA (7.70 ml, 55.3 mmol). The reaction mixture was then degassed and heated to reflux for 3 hrs. The reaction was diluted with ethyl acetate and washed with brine. The organic layer was dried over Na2SO4, filtered and evaporated to dryness. The residue was purified through a 330 g ISCO Redi-Sep silica gel plug and eluted with 20% ETOAc/hexane to yield 5-ethenyl-2,1,3-benzoxadiazole.

$^1$H-NMR (600 MHz, CDCl$_3$): δ ppm 7.81 (d, J=9.3 Hz, 1H), 7.66 (s, 1H), 7.63 (d, J=9.3 Hz, 1H), 6.35 (d, J=10.9 Hz, 0.5H), 6.80 (d, J=10.9 Hz, 0.5H), 5.94 (d. J=17.5 Hz, 1H), 5.55 (d, J=11 Hz, 1H).

Step B: 5-(oxiran-2-yl)-2,1,3-benzoxadiazole

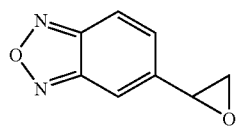

5-Ethenyl-2,1,3-benzoxadiazole (2.82 g, 19.30 mmol) was dissolved in DCM (100 ml) then added mCpBA (9.99 g, 57.9 mmol) and stirred for 48 hrs. The reaction mixture was washed with 10% aqueous NaS2O3 (1×25 ml), then with 1N NaOH (1×25 ml), followed by brine (1×25 ml) and dried over Na2SO4. The mixture was filtered and evaporated to dryness. The residue was purified by MPLC using 120 g ISCO Redi-sep column and eluted with 0%-100% EtOAc/hexane solvent system to yield 5-(oxiran-2-yl)-2,1,3-benzoxadiazole.

$^1$H-NMR (600 MHz, CDCl$_3$): δ ppm 7.83 (d, J=9.8 Hz, 1H), 7.82 (s, 1H), 7.24 (d, J=9.3 Hz, 1H), 3.98 (t, J=3.8 Hz, 1H), 3.24 (t, J=4.5 Hz, 1H), 2.84 (dd. J=5.2 Hz, J=2.5 Hz, 1H).

INTERMEDIATES 57 A and 57 B

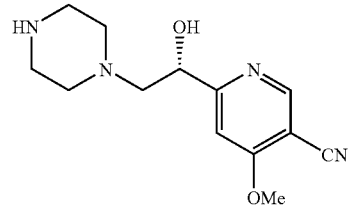

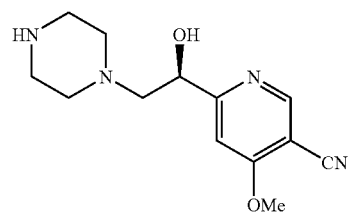

Step A: tert-Butyl 4-[2-(5-cyano-4-methoxy-2-pyridyl)-2-hydroxy-ethyl]piperazine-1-carboxylate

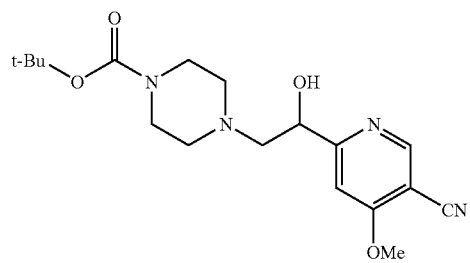 [SMILES: COc1cc(C(O)CN2CCN(C(=O)OC(C)(C)C)CC2)ncc1C#N]

A 20 mL Pyrex vessel was charged with magnetic stirring bar, (1.68 g, 9.54 mmol) of 4-methoxy-6-(oxiran-2-yl)pyridine-3-carbonitrile, (2.66 g, 14.3 mmol) of tert-butyl piperazine-1-carboxylate, and 10 mL of EtOH. Then it was introduced in the microwave reactor and irradiated at 150° C. for 1 h. The mixture was cooled to room temperature and the solvent was evaporated and the resulting residue was purified by column chromatography (silica gel, 1-10% MeOH/dichloromethane) which afforded the product as an isomeric mixtures. LC/MS: (IE, m/z) 307.09 [(M+1)–t-Bu]$^+$.

This mixture was further separated into its enantiomers using SFC-HPLC a 21×250 mm on a Chiralpak AD-H column, eluting with 10% MeOH/CO$_2$+0.2% IBA with a flow rate of 70 mL/min, 100 bar, 50 mg/mL in (1:1 MeOH:MeCN), 40 C, 220 nm, Thr=200. Enantiomer A eluted around 4.56 min, and Enantiomer B eluted around 5.72 min.

Isomer A: Analytical chiral HPLC (4.6×250 mm Chiralpak AD-H column, 15% MeOH(0.2% IBA)/CO$_2$, eluting at 2.4 mL/min): $t_R$=4.56 min. LC/MS: (IE, m/z) $t_R$=2.25 min; [(M+1)–t-Bu]$^+$=307.07.

Isomer B: Analytical chiral HPLC (4.6×250 mm Chiralpak AD-H column, 15% MeOH(0.2% IBA)/$CO_2$, eluting at 2.4 mL/min): $t_R$=5.72 min. LC/MS: (IE, m/z) $t_R$=2.25 min; [(M+1)–t-Bu]$^+$=307.07.

Step B: 6-(1-Hydroxy-2-piperazin-1-yl-ethyl)-4-methoxy-pyridine-3-carbonitrile

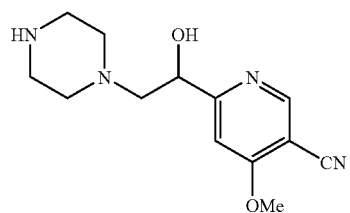 [SMILES: COc1cc(C(O)CN2CCNCC2)ncc1C#N]

Enantiomer A of tert-Butyl 4-[2-(5-cyano-4-methoxy-2-pyridyl)-2-hydroxy-ethyl]piperazine-1-carboxylate (1.30 g, 3.59 mmol) was dissolved in 5 mL of TFA and stirred at room temperature for 2 h. The mixture was concentrated to ¼ the original volume and diluted with 10 mL of diethyl ether. The precipitate was filtered and dried under high vacuum to offer amine TFA salt. This intermediate was diluted with 5% aqueous sodium bicarbonate with follow up addition of 10 N NaOH to bring the pH of extraction above 10. The aqueous layer was extracted with ethyl acetate. The organic layers were dried over $MgSO_4$, filtered, and concentrated under reduced pressure to provide the product. LC/MS: (IE, m/z) $t_R$=0.39 min; [M+1]$^+$=263.12

Enantiomer B of tert-Butyl 4-[2-(5-cyano-4-methoxy-2-pyridyl)-2-hydroxy-ethyl]piperazine-1-carboxylate (1.0 g, 2.76 mmol) was dissolved in 5 mL of TFA and stirred at room temperature for 2 h. The mixture was concentrated to ¼ the original volume and diluted with 10 mL of diethyl ether. The precipitate was filtered and dried under high vacuum to offer amine TFA salt. This intermediate was diluted with 5% aqueous sodium bicarbonate with follow up addition of 10 N NaOH to bring the pH of extraction above 10. The aqueous layer was extracted with ethyl acetate. The organic layers were dried over $MgSO_4$, filtered, and concentrated under reduced pressure to provide the product. LC/MS: (IE, m/z) $t_R$=0.62 min; [M+1]$^+$=263.09

Example 1

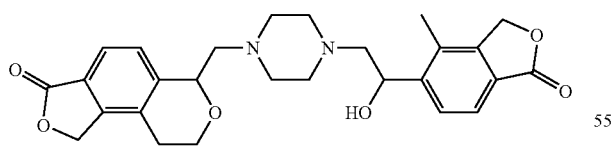

6-({4-[2-hydroxy-2-(4-methyl-1-oxo-1,3-dihydro-2-benzofuran-5-yl)ethyl]piperazin-1-yl}methyl)-8,9-dihydro-1H-furo[3,4-f]isochromen-3(6H)-one Step A: 5-bromo-4-iodo-2-benzofuran-1(3H)-one To a solution of 5-bromo-2-benzofuran-1(3H)-one (5.00 g, 23.5 mmol) at 0° C. in TfOH (100 mL) was added NIS (5.55 g, 24.6 mmol). The mixture was stirred at room temperature over night; LC analysis of the reaction mixture indicated completion of the reaction. The reaction mixture was then poured slowly into ice-water (1 L) with stirring. To the solution was then added EtOAc (500 mL) and subsequently stirred for 10 min. The mixture was filtered and the organic layer separated. The aqueous layer was extracted with EtOAc (2×200 mL). The combined organic layers were washed with water (500 mL), brine (500 mL), dried over $Na_2SO_4$, filtered, concentrated to dryness; it was absorbed into silica gel and separated with the solvent systems of (hexanes/EtOAc=1/1) to yield 5-bromo-4-iodo-2-benzofuran-1(3H)-one. $^1$H-NMR (400 MHz, $CDCl_3$) δ ppm 7.80 (d, J=7.8 Hz, 1H), 7.74 (d, J=8.5 Hz, 1H), 5.07 (s, 2H).

Step B: 5-bromo-4-prop-2-en-1-yl-2-benzofuran-1(3H)-one

A mixture of 5-bromo-4-iodo-2-benzofuran-1(3H)-one (2.42 g, 7.13 mmol), allyltributyltin (2.36 g, 7.13 mmol), LiCl (1.50 g, 35.7 mmol) and Pd $(PPh_3)_4$ (200 g, 0.173 mmol) in toluene (50 mL) was heated at 90-100° C. under $N_2$ overnight; LC indicated that reaction had gone to completion, to the solution was poured EtOAc (100 mL) and washed with brine. The organic layer was dried over $Na_2SO_4$, filtered and concentrated to dryness, absorbed into silica gel and was then separated over silica gel column to give 5-bromo-4-prop-2-en-1-yl-2-benzofuran-1(3H)-one. $^1$H-NMR (400 MHz, $CDCl_3$) δ ppm 7.795 (d, J=8 Hz, 1H), 7.680 (d, J=8 Hz, 8.5 Hz, 1H), 5.938-5.925 (m, 1H), 5.302 (s, 2H), 5.192-5.172 (m, 1H), 5.075-5.041 (m, 1H), 3.611-3.599 (m, 2H)

Step C: 5-bromo-4-(2-hydroxyethyl)-2-benzofuran-1(3H)-one

To a solution of 5-bromo-4-prop-2-en-1-yl-2-benzofuran-1(3H)-one (1.27 g, 5.02 mmol) in MeOH (50 mL) and DCM (50 mL) was bubbled $O_3$ at −78° C. until the solution turned blue; excess ozone was removed on high vacuum. After the solution's color changed into colorless, $NaBH_4$ (0.8 g, 20 mmol) was added to the reaction mixture and subsequently stirred at room temperature for 30 min; LC and TLC indicated that reaction had gone to completion; solvent was removed on high vacuum, the residue was then re-dissolved in EtOAc and washed with water, dried over $Na_2SO_4$, filtered and concentrated to dryness. The organic residue was absorbed into silica gel and was separated on silica gel column to give 5-bromo-4-(2-hydroxyethyl)-2-benzofuran-1(3H)-one. $^1$H-NMR (400 MHz, $CDCl_3$) δ ppm 7.7 (d, J=7.8 Hz, 1H), 7.5 (d, J=7.8 Hz, 1H), 5.37 (s, 2H), 3.94 (t, J=6.3 Hz, 2H), 2.98 (t, J=6.3 Hz, 2H)

Step D: 5-ethenyl-4-(2-hydroxyethyl)-2-benzofuran-1(3H)-one

A mixture of 5-bromo-4-(2-hydroxyethyl)-2-benzofuran-1(3H)-one (0.460 g, 1.78 mmol), tributyl(vinyl)tin (0.676 g, 2.13 mmol), LiCl (0.224 g, 5.33 mmol) and Pd $(PPh_3)4$ (0.10 g, 0.087 mmol) in toluene (50 mL) was heated at 100-110° C. under $N_2$ overnight; TLC indicated that reaction had gone to completion and to the solution was poured EtOAc (100 mL) and washed with brine, water, dried over $Na_2SO_4$, filtered and concentrated to dryness. The residue was then absorbed into silica gel and separated over silica column to give 5-ethenyl-4-(2-hydroxyethyl)-2-benzofuran-1(3H)-one. $^1$H-NMR (400 MHz, $CDCl_3$) δ ppm 7.74 (d, J=7.8 Hz, 1H), 7.67 (d, J=7.8

Hz, 1H), 7.00-7.07 (m, 1H), 5.79-5.84 (m, 1H), 5.50-5.53 (m, 1H), 5.35 (s, 2H), 3.86 (t, J=6.3 Hz, 2H), 2.93 (t, J=6.3 Hz, 2H).

Step E: 4-(2-hydroxyethyl)-5-oxiran-2-yl-2-benzofuran-1(3H)-one

5-Ethenyl-4-(2-hydroxyethyl)-2-benzofuran-1(3H)-one (1.2 g, 5.9 mmol) was added to a flask containing a stir bar. To the flask was then added dichloromethane (20 mL). The flask was placed in a cool bath of 0° C.; to the flask was poured mCPBA (1.5 g, 8.8 mmol) and the resulting mixture was stirred at room temperature for overnight; LC as well as TLC (hexanes/EtOAc=1/1) indicated that reaction had gone to completion. The solution was treated with dichloromethane and washed with $NaHCO_3$, $Na_2S_2O_3$, and water, the organic layer was then dried over $Na_2SO_4$, filtered and concentrated to dryness, it was then treated with AcOH (20 mL) and stirred overnight; LC indicated formation of cyclized product. The solvent was removed and the resulting residue was absorbed into silica gel and 6-(hydroxymethyl)-8,9-dihydro-1H-furo[3,4-f]isochromen-3(6H)-one was isolated with the solvent systems of hexanes/EtOAc (1/1). $^1$H-NMR (400 MHz, $CDCl_3$) δ ppm 7.807 (d, J=8 Hz, 1H), 7.337 (d, J=8 Hz, 1H), 5.279 (s, 2H), 4.985 (s, 1H), 4.302-4.302 (m, 1H), 4.183-4.084 (m, 2H), 3.954-3.912 (m, 2H), 3.006-2.944 (m, 1H), 2.717-2.686 (m, 1H), 2.179-2.172 (m, 2H)

Step F: (3-oxo-3,6,8,9-tetrahydro-1H-furo[3,4-f]isochromen-6-yl)methyl-4-methylbenzenesulfonate 6-(Hydroxymethyl)-8,9-dihydro-1H-furo[3,4-f]isochromen-3(6H)-one, in DCM (10 mL) was treated with p-Toluenesulfonyl chloride (0.40 g, 2.3 mmol); to the mixture was added pyridine (2 mL) and the resulting mixture stirred at room temperature for 12 h. TLC (hexanes/EtOAc=1/0.5) and LC indicated the consumption of starting material and formation of the desired product. Reaction mixture was treated with dichloromethane and washed with NaCl, water and dried over $Na_2SO_4$, filtered and concentrated to dryness, absorbed into silica gel and was then subjected for purification over silica gel; (3-oxo-3,6,8,9-tetrahydro-1H-furo[3,4-f]isochromen-6-yl)methyl-4-methylbenzenesulfonate was isolated with the solvent system of hexanes/EtOAc (1/0.5). $^1$H-NMR (400 MHz, $CDCl_3$) δ ppm 7.781 (d, J=8 Hz, 1H), 7.727 (d, J=8 Hz, 1H), 7.367 (d, J=8 Hz, 1H), 7.257 (d, J=8.5 Hz, 1H), 7.206 (d, J=8 Hz, 1H), 5.253 (s, 2H), 5.110 (s, 1H), 4.481-4.452 (m, 2H), 4.419-4.385 (m, 2H), 4.196-4.153 (m, 2H), 2.495 (s, 3H).

Step G: 6-({4-[2-hydroxy-2-(4-methyl-1-oxo-1,3-dihydro-2-benzofuran-5-yl)ethyl]piperazin-1-yl}methyl)-8,9-dihydro-1H-furo[3,4-f]isochromen-3(6H)-one To a 5 mL microwave tube were added (3-oxo-3,6,8,9-tetrahydro-1H-furo[3,4-f]isochromen-6-yl)methyl-4-methylbenzenesulfonate (50 mg, 0.13 mmol), the free base generated by aqueous bicarbonate wash of 1-[2-hydroxy-2-(4-methyl-1-oxo-1,3-dihydro-2-benzofuran-5-yl)ethyl]piperazin-1-ium chloride (55 mg, 0.20 mmol), and a stir bar; the mixture was dissolved in acetonitrile (2.5 mL). The tube was capped, degassed and purged with $N_2$. The tube was then placed in a microwave reactor and heated at 120° C. for 1 h; LC indicated formation of the desired product. The solution was concentrated to dryness, dissolved in MeOH (3.5 mL), filtered and was then subjected to mass-directed HPLC for purification to give 6-({4-[2-hydroxy-2-(4-methyl-1-oxo-1,3-dihydro-2-benzofuran-5-yl)ethyl]piperazin-1-yl}methyl)-8,9-dihydro-1H-furo[3,4-f]isochromen-3(6H)-one, as a mixture of isomers which could be partially separated under the purification conditions. LC-MS (IE, m/z): 478 $[M+1]^+$.

Example 1A and 1B

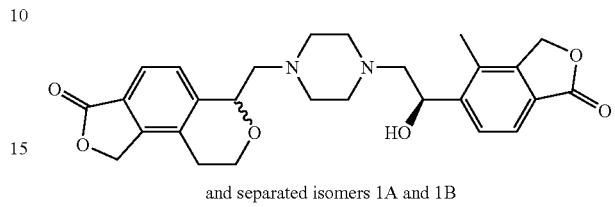

and separated isomers 1A and 1B (6S)-6-({4-[(2R)-2-hydroxy-2-(4-methyl-1-oxo-1,3-dihydro-2-benzofuran-5-yl)ethyl]piperazin-1-yl}methyl)-8,9-dihydro-1H-furo[3,4-f]isochromen-3(6H)-one and (6R)-6-({4-[(2R)-2-hydroxy-2-(4-methyl-1-oxo-1,3-dihydro-2-benzofuran-5-yl)ethyl]piperazin-1-yl}methyl)-8,9-dihydro-1H-furo[3,4-f]isochromen-3(6H)-one (6S)-6-({4-[(2R)-2-hydroxy-2-(4-methyl-1-oxo-1,3-dihydro-2-benzofuran-5-yl)ethyl]piperazin-1-yl}methyl)-8,9-dihydro-1H-furo[3,4-f]isochromen-3(6H)-one and (6R)-6-({4-[(2R)-2-hydroxy-2-(4-methyl-1-oxo-1,3-dihydro-2-benzofuran-5-yl)ethyl]piperazin-1-yl}methyl)-8,9-dihydro-1H-furo[3,4-f]isochromen-3(6H)-one as two single isomers was prepared in the same way as EXAMPLE 1 (mixture isomers) except that 4-methyl-5-[(2R)-oxiran-2-yl]-2-benzofuran-1(3H)-one was used as the epoxide reagent and the final mixture of two isomers was separated using SFC chromatography with an OJ-H column.

Example 2

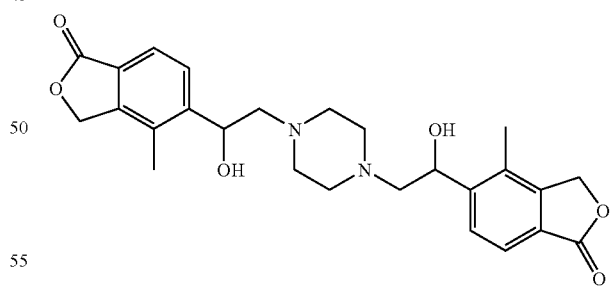

5,5'-[piperazine-1,4-diylbis(1-hydroxyethane-2,1-diyl)]bis(4-methyl-2-benzofuran-1(3H)-one)

To a microwave tube charged with 4-methyl-5-oxiran-2-yl-2-benzofuran-1(3H)-one (194 mg, 1.00 mmol) and piperazine (40 mg, 0.46 mmol) was added a stir bar and EtOH (4 mL). The tube was sealed and heated in a microwave apparatus to 150° C. for 90 minutes. The crude product was adsorbed onto silica gel, and purified by flash chromatography (MeOH-DCM 0~7% gradient). After removal of solvents, 5,5'-[piperazine-1,4-diylbis(1-hydroxyethane-2,1-diyl)]bis(4-methyl-2-benzofuran-1(3H)-one) was collected.

¹H-NMR (500 MHz, CDCl₃) δ ppm 7.79 (s, 4H), 5.25 (s, 4H), 5.10 (dd, J=10.5, 3.0 Hz, 2H), 4.01 (broad, 2H), 2.90 (broad, 4H), 2.69-2.50 (m, 6H), 2.44 (dd, J=10.5, 13 Hz, 2H), 2.29 (s, 6H). LCMS M+1 (calc. 467, found 467).

The three isomers of 5,5'-[piperazine-1,4-diylbis(1-hydroxyethane-2,1-diyl)]bis(4-methyl-2-benzofuran-1(3H)-one), were resolved on an analytical IA column (5 u), with the R,R-isomer (EXAMPLE 2A) eluting first at 17.4 min, R,S-isomer (EXAMPLE 2C) eluting next at 21.0 min, and S,S-isomer (EXAMPLE 2B) eluting last at 22.6 min.

Example 2A

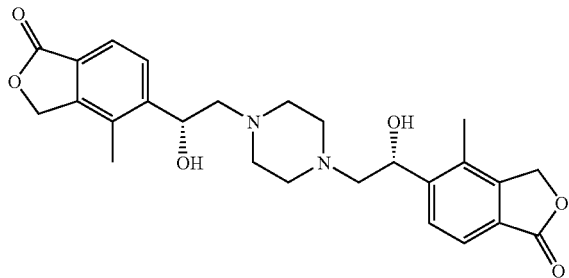 [SMILES: Cc1c([C@@H](O)CN2CCN(C[C@H](O)c3ccc4c(c3C)COC4=O)CC2)ccc2c1COC2=O]

5,5'-{piperazine-1,4-diylbis[(1R)-1-hydroxyethane-2,1-diyl]}bis(4-methyl-2-benzofuran-1 (3H)-one)

Method 1:
To a 20 mL microwave tube charged with 4-methyl-5-[(2R)-oxiran-2-yl]-2-benzofuran-1(3H)-one (972 mg, 5.11 mmol) and piperazine (200 mg, 2.3 mmol) was added a stir bar and EtOH (16 mL). The tube was sealed and heated in a microwave apparatus to 150° C. for 90 minutes. The crude product was adsorbed onto silica gel, and purified by flash chromatography (MeOH-DCM 0~7% gradient). After removal of solvents, 5,5'-{piperazine-1,4-diylbis[(1R)-1-hydroxyethane-2,1-diyl]}bis(4-methyl-2-benzofuran-1(3H)-one) was collected. ¹H-NMR (500 MHz, CDCl₃) δ ppm 7.80 (s, 4H), 5.25 (s, 4H), 5.11 (d, J=10.5 Hz, 2H), 4.00 (broad, 2H), 2.90 (broad, 4H), 2.69-2.50 (m, 6H), 2.44 (t, J=11 Hz, 2H), 2.29 (s, 6H); LCMS M+1 (calc. 467, found 467).

Method 2:
Piperazine (4.51 g, 52.4 mmol) and 4-methyl-5-[(2R)-oxiran-2-yl]-2-benzofuran-1(3H)-one (20.0 g, 105 mmol) were charged to a 3-neck 500-mL roundbottom flask, equipped with a reflux condenser, under nitrogen. Toluene (80.0 mL, 751 mmol) and N,N-dimethylacetamide (80 mL, 854 mmol) were added to provide a suspension. The reaction mixture was warmed to 110° C., becoming homogeneous at 25° C. After stirring for 4.5 h at 110° C., the temperature was increased to 115° C. to drive the reaction forward. After stirring for 48 h, the reaction mixture was cooled to RT. On cooling, crystallization occurred. Water was added via addition funnel (45 mL), generating a thick slurry. The suspension was filtered and the solids were washed with 4:1 water:DMA (60 mL), followed by water (2×35 mL). The solid was dried on the funnel under vacuum with a nitrogen sweep to constant mass. 5,5'-{Piperazine-1,4-diylbis[(1R)-1-hydroxyethane-2,1-diyl]}bis(4-methyl-2-benzofuran-1(3H)-one) was isolated. ¹H-NMR (500 MHz, CDCl₃) δ ppm 7.80 (s, 4H), 5.25 (s, 4H), 5.11 (d, J=11 Hz, 2H), 4.30-3.51 (broad, 2H), 2.90 (broad, 4H), 2.69-2.50 (m, 6H), 2.44 (t, J=11 Hz, 2H), 2.30 (s, 6H).

Compounds of the present invention are amines and can therefore be converted to a variety of salts by treatment with any of a number of acids. For example, the compound of Example 2A can be converted to several different salt forms as shown in the following representative examples. These are selected examples and are not meant to be an exhaustive list; numerous additional salts can be prepared in a similar fashion using a variety of acids.

Example 2A-1

(di-HCl salt): 5,5'-{piperazine-1,4-diylbis[(1R)-1-hydroxyethane-2,1-diyl]}bis(4-methyl-2-benzofuran-1(3H)-one)dihydrochloride To a 250 mL pear shape flask charged with the free base (1.2 g, 2.6 mmol) and a stir bar was added DCM. The solution was stirred until all solids were gone. To this solution was added 4N HCl in dioxane (2.6 mL, 4.0 eq), and the mixture was allowed to stir for another 15 minutes. The solvent was removed on a rotary evaporator, and the product was left dry on a high vacuum pump until there was no weight change. The product was determined to be 5,5'-{piperazine-1,4-diylbis[(1R)-1-hydroxyethane-2,1-diyl]}bis(4-methyl-2-benzofuran-1(3H)-one)dihydrochloride.

Example 2A-2

(HCl salt): 5,5'-{piperazine-1,4-diylbis[(1R)-1-hydroxyethane-2,1-diyl]}bis(4-methyl-2-benzofuran-1(3H)-one)hydrochloride To a 20 dram vial charged with the free base (160 mg, 0.34 mmol) and a stir bar was added 0.1 M HCl in IPA. The solution was allowed to stir at RT for 30 minutes, and then heated to 40° C. for 1 hour. The solvent was removed under vacuum, and the resulting product was left on a high vacuum pump for 16 hours. The product corresponded to 5,5'-{piperazine-1,4-diylbis[(1R)-1-hydroxyethane-2,1-diyl]}bis(4-methyl-2-benzofuran-1(3H)-one)hydrochloride.

Example 2A-3

(mono-hydrate of the di-HCl salt): 5,5'-{piperazine-1,4-diylbis[(1R)-1-hydroxyethane-2,1-diyl]}bis(4-methyl-2-benzofuran-1(3H)-one)dihydrochloride hydrate To a flask charged with the free base (1.0 g, 2.1 mmol) and a stir bar was added 1 N HCl (50 mL). The mixture was allowed to stir until all solids dissolved. The solvent was removed on a rotary evaporator, and the resulting product was left on a high vacuum pump for 16 hours. The product was determined to be 5,5'-{piperazine-1,4-diylbis[(1R)-1-hydroxyethane-2,1-diyl]}bis(4-methyl-2-benzofuran-1(3H)-one)dihydrochloride hydrate.

Example 2A-4

(H₂SO₄ salt): 5,5'-{piperazine-1,4-diylbis[(1R)-1-hydroxyethane-2,1-diyl]}bis(4-methyl-2-benzofuran-1(3H)-one)sulfate (salt)

To a 100 mL flask charged with a solution of the free base (154 mg, 0.330 mmol) in DMF:MeOH (3:1) (20 mL) and a stir bar was added 0.1 M H₂SO₄ (3.3 mL). The solution was allowed to stir at RT for 30 minutes, and then heated to 40° C. for 2 hours. A lot of solids formed during that time. The solvent was removed under vacuum, and the white solids were left on high vacuum for 16 hours to afford 5,5'-{piperazine-1,4-diylbis[(1R)-1-hydroxyethane-2,1-diyl]}bis(4-methyl-2-benzofuran-1(3H)-one)sulfate (salt).

Example 2B

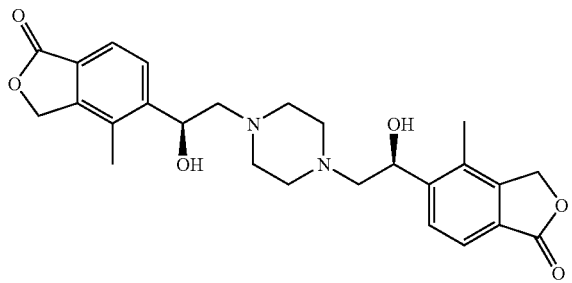 [SMILES: Cc1c([C@H](O)CN2CCN(C[C@@H](O)c3ccc4c(c3C)COC4=O)CC2)ccc2c1COC2=O]

5,5'-{piperazine-1,4-diylbis[(1S)-1-hydroxyethane-2,1-diyl]}bis(4-methyl-2-benzofuran-1(3H)-one)

To a 20 mL microwave tube charged with 4-methyl-5-[(2S)-oxiran-2-yl]-2-benzofuran-1(3H)-one (980 mg, 5.15 mmol) and piperazine (200 mg, 2.3 mmol) was added a stir bar and EtOH (16 mL). The tube was sealed and heated in a microwave apparatus to 150° C. for 90 minutes. The crude product was adsorbed onto silica gel, and purified by flash chromatography (MeOH-DCM 0~7% gradient). After removal of solvents, 5,5'-{piperazine-1,4-diylbis[(1S)-1-hydroxyethane-2,1-diyl]}bis(4-methyl-2-benzofuran-1(3H)-one) was collected (560 mg).
$^1$H-NMR (500 MHz, CDCl₃) δ ppm 7.80 (s, 4H), 5.25 (s, 4H), 5.11 (d, J=11 Hz, 2H), 4.30-3.51 (broad, 2H), 2.90 (broad, 4H), 2.69-2.50 (m, 6H), 2.44 (t, J=11 Hz, 2H), 2.30 (s, 6H); LCMS M+1 (calc. 467, found 467).

Example 2C

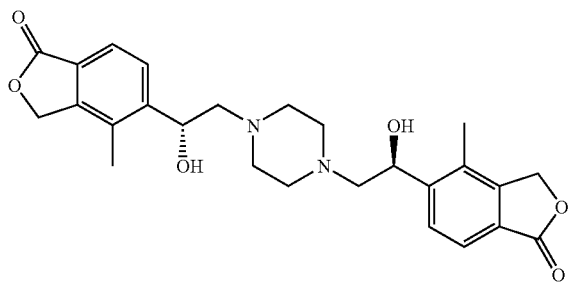 [SMILES: Cc1c([C@H](O)CN2CCN(C[C@H](O)c3ccc4c(c3C)COC4=O)CC2)ccc2c1COC2=O]

5-((1R)-1-hydroxy-2-{4-[(2S)-2-hydroxy-2-(4-methyl-1-oxo-1,3-dihydro-2-benzofuran-5-yl)ethyl]piperazin-1-yl}ethyl)-4-methyl-2-benzofuran-1(3H)-one To a 20 mL microwave tube charged with 5-[(1R)-1-hydroxy-2-piperazin-1-ylethyl]-4-methyl-2-benzofuran-1 (3H)-one (166 mg, 0.600 mmol) and a stir bar was added 4-methyl-5-[(2S)-oxiran-2-yl]-2-benzofuran-1(3H)-one (171 mg, 0.900 mmol) and ethanol (10 mL). The mixture was heated in a microwave apparatus to 150° C. for 90 minutes. After the reaction cooled down, DCM (5 mL) was added to the tube. The mixture was allowed to sit at RT overnight. A lot of solids precipitated during that time; these were collected by filtration. Chiral HPLC analysis showed the material was over 95% ee pure 5-((1R)-1-hydroxy-2-{4-[(2S)-2-hydroxy-2-(4-methyl-1-oxo-1,3-dihydro-2-benzofuran-5-yl)ethyl]piperazin-1-yl}ethyl)-4-methyl-2-benzofuran-1(3H)-one.
$^1$H-NMR (500 MHz, DMSO-d⁶) δ ppm 7.74 (s, 4H), 5.43 (m, 4H), 6.60-5.80 (broad, 2H), 5.33 (s, 2H), 3.40 (broad, 8H), 3.09 (broad, 4H), 2.32 (s, 6H); LCMS M+1 (calc. 467, found 467).

Example 3

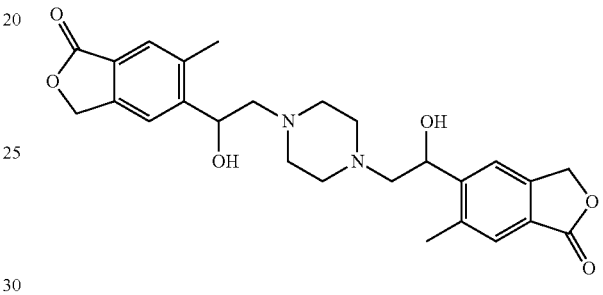

5,5'-[piperazine-1,4-diylbis(1-hydroxyethane-2,1-diyl)]bis(6-methyl-2-benzofuran-1(3H)-one)

The reaction was run in a similar fashion to the general epoxide opening conditions as shown for EXAMPLE 2 starting from 6-methyl-5-oxiran-2-yl-2-benzofuran-1(3H)-one. 5,5'-[Piperazine-1,4-diylbis(1-hydroxyethane-2,1-diyl)]bis(6-methyl-2-benzofuran-1(3H)-one), was purified by preparative reverse phase HPLC. $^1$H-NMR (500 MHz, CDCl₃) δ ppm 7.77 (s, 2H), 7.67 (s, 2H), 5.27 (s, 4H), 5.07 (m, 2H), 4.30-3.70 (broad, 2H), 2.95-2.80 (m, 3H), 2.65-2.50 (m, 5H), 2.42 (s, 6H), 2.37 (m, 2H); LCMS M+1 (calc. 467, found 467).

Example 4

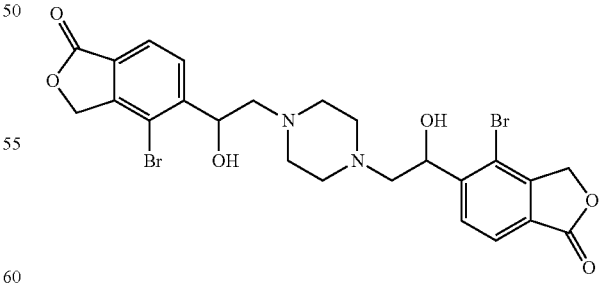

5,5'-[piperazine-1,4-diylbis(1-hydroxyethane-2,1-diyl)]bis(4-bromo-2-benzofuran-1(3H)-one)

The reaction was run in a similar fashion to the general epoxide opening conditions shown for EXAMPLE 2 starting from 4-bromo-5-oxiran-2-yl-2-benzofuran-1(3H)-one. 5,5'-[Piperazine-1,4-diylbis(1-hydroxyethane-2,1-diyl)]bis(4-bromo-2-benzofuran-1(3H)-one), a mixture of three diastereomers was purified by preparative reverse phase HPLC.

LCMS M+1 (calc. 597, found 597).

$^1$H NMR (500 MHz, CD$_3$OD) diastereomer A: δ 7.78 (d, J=8.5 Hz, 2H), 7.64 (s, 1H), 7.55 (d, J=7.5 Hz, 2H), 5.40 (s, 4H), 4.84 (m, 2H), 2.41-2.69 (overlapping m's, 12H); diastereomer B: δ 7.78 (d, J=8.5 Hz, 2H), 7.64 (s, 1H), 7.55 (d, J=7.5 Hz, 2H), 5.30 (s, 4H), 4.03 (m, 2H), 2.41-2.69 (overlapping m's, 12H); LC/MS: [(M+1)]$^+$=438.5.

Example 5

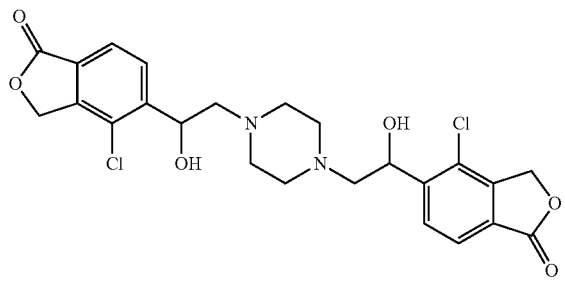 [SMILES: O=C1OCc2c1ccc(C(O)CN1CCN(CC(O)c3ccc4c(c3Cl)COC4=O)CC1)c2Cl]

5,5'-[piperazine-1,4-diylbis(1-hydroxyethane-2,1-diyl)]bis(4-chloro-2-benzofuran-1(3H)-one The reaction was run in a similar fashion to the general epoxide opening conditions shown in EXAMPLE 2 starting from 4-chloro-5-oxiran-2-yl-2-benzofuran-1(3H)-one. Purification by preparative reverse phase HPLC afforded 5,5'-[piperazine-1,4-diylbis(1-hydroxyethane-2,1-diyl)]bis(4-chloro-2-benzofuran-1(3H)-one. LCMS M+1 (calc. 507, found 507).

Example 6

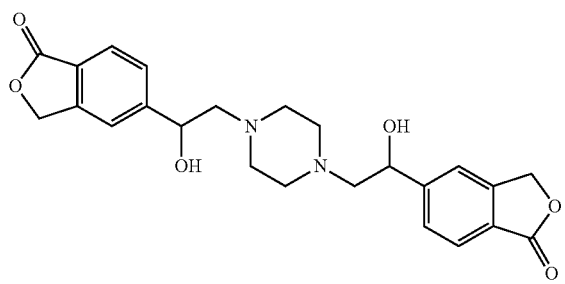 [SMILES: O=C1OCc2cc(C(O)CN3CCN(CC(O)c4ccc5c(c4)COC5=O)CC3)ccc21]

5,5'-[piperazine-1,4-diylbis(1-hydroxyethane-2,1-diyl)]bis(2-benzofuran-1(3H)-one)

The reaction was run in a similar fashion to the general epoxide opening conditions shown for EXAMPLE 2 starting from 5-oxirane-2-yl-2-benzofuran-1(3H)-one. Purification by preparative reverse phase HPLC afforded 5,5'-[piperazine-1,4-diylbis(1-hydroxyethane-2,1-diyl)]bis(2-benzofuran-1(3H)-one).

Example 7

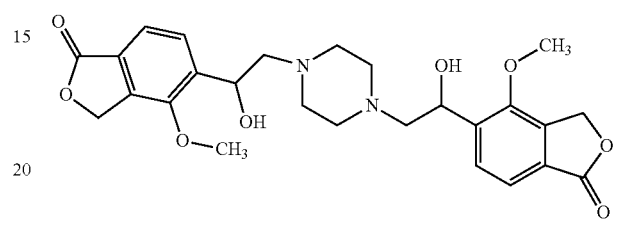

5,5'-[piperazine-1,4-diylbis(1-hydroxyethane-2,1-diyl)]bis[4-(methyloxy)-2-benzofuran-1(3H)-one]

The reaction was run under the general epoxide opening conditions as shown for EXAMPLE 2 (at 130° C. for 60 min) starting from 4-(methyloxy)-5-oxiran-2-yl-2-benzofuran-1(3H)-one. Purification by preparative TLC afforded 5,5'-[piperazine-1,4-diylbis(1-hydroxyethane-2,1-diyl)]bis[4-(methyloxy)-2-benzofuran-1(3H)-one].

$^1$H NMR (500 MHz, CDCl$_3$) δ in ppm: 7.88 (2H, aromatic, d, J=7.6 Hz), 7.64 (2H, aromatic, d, J=7.6 Hz), 5.48 (4H, s), 5.14 (2H, m), 3.96 (6H, s), 3.0-2.1 (12H, m).

LC-MS (IE, m/z): 499.02 [M+1]$^+$.

Example 8

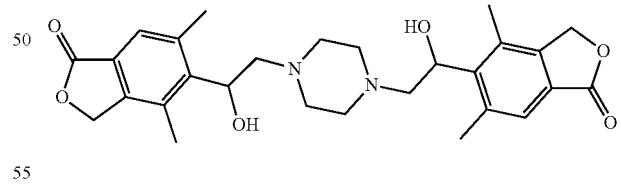

5,5'-[piperazine-1,4-diylbis(1-hydroxyethane-2,1-diyl)]bis(4,6-dimethyl-2-benzofuran-1(3H)-one)

The reaction was run under the general epoxide opening conditions as shown for EXAMPLE 2 (at 160° C. for 60 min) The crude product was purified by mass-directed preparative HPLC to give the desired product, 5,5'-[piperazine-1,4-diylbis(1-hydroxyethane-2,1-diyl)]bis(4,6-dimethyl-2-benzofuran-1(3H)-one).

LC-MS (IE, m/z): 495 [M+1]$^+$.

Example 9

And Separated Isomers

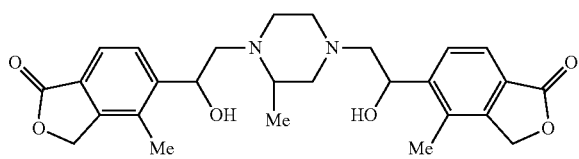 [SMILES: Cc1c(C(O)CN2CCN(CC(O)c3ccc4c(c3C)COC4=O)C(C)C2)ccc2c1COC2=O]

5,5'-[(2-methylpiperazine-1,4-diyl)bis(1-hydroxy-ethane-2,1-diyl)]bis(4-methyl-2-benzofuran-1(3H)-one)

A mixture of 4-methyl-5-oxiran-2-yl-2-benzofuran-1(3H)-one (700 mg, 3.684 mmol) and 2-methylpiperazine (184 mg, 1.842 mmol) in 2 mL DMSO was heated under microwave condition (150° C.) for 1 hr. After cooling to rt., the mixture was diluted with water (50 mL), extracted with EtOAc (3×50 mL). The combined organic layers were washed with brine and dried over $Na_2SO_4$, then concentrated. The residue was purified by prep-HPLC to obtain two peaks (peak 1 and peak 2). Each peak was further separated by SFC chiral chromatography to obtain three chiral isomers for each (of 8 isomers six were obtained, though two may be mixtures of 2 isomers).

Isomer A $^1$H-NMR (400 MHz, CDCl$_3$) δ ppm 7.76 (s, 4H), 5.20 (s, 4H), 5.00~5.16 (m, 2H), 2.30~3.30 (m, 11H), 2.26 (s, 6H), 1.16~1.18 (m, 3H). MS m/e 481 (M+1)$^+$.

Isomer B $^1$H-NMR (400 MHz, CDCl$_3$) δ ppm 7.78 (s,s, 4H), 5.24 (s, 4H), 5.06~5.15 (m, 2H), 3.02~3.26 (m, 2H), 2.28~2.82 (m, 9H), 2.26 (s, 6H), 1.16~1.18 (m, 3H). MS m/e 481 (M+1)$^+$.

Isomer C $^1$H-NMR (400 MHz, CDCl$_3$) δ ppm 7.78 (s, 4H), 5.24 (s, 4H), 5.09~5.12 (m, 2H), 3.22~3.28 (m, 1H), 3.12~3.18 (m, 1H), 2.72~2.80 (m, 3H), 2.35~2.68 (m, 6H), 2.28 (s, 6H), 1.13 (d, J=6.3 Hz, 3H). MS m/e 481 (M+1)$^+$.

Isomer D $^1$H-NMR (400 MHz, CD3OD) δ ppm 7.68~7.74 (m, 4H), 5.32 (s, 4H), 5.18~5.24 (m, 2H), 2.50~3.38 (m, 11H), 2.32 (s,s, 6H), 1.04 (d, J=6.4 Hz, 3H). MS m/e 481 (M+1)$^+$.

Isomer E $^1$H-NMR (400 MHz, CD3OD) δ ppm 7.68~7.76 (m, 4H), 5.34 (s, 4H), 5.18~5.24 (m, 2H), 2.50~2.96 (m, 11H), 2.32 (s,s, 6H), 1.02 (d, J=6.4 Hz, 3H). MS m/e 481 (M+1)$^+$.

Isomer F $^1$H-NMR (400 MHz, CD3OD) δ ppm 7.70~7.80 (m, 4H), 5.35 (s, 4H), 5.20~5.30 (m, 2H), 2.50~3.35 (m, 11H), 2.33 (s,s, 6H), 1.22 (d, J=6.4 Hz, 3H). MS m/e 481 (M+1)$^+$.

Example 10

Three Separated Isomers

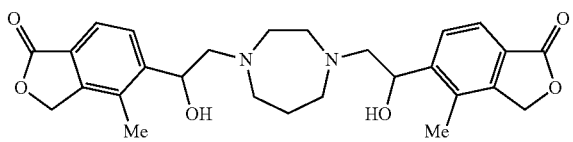 [SMILES: Cc1c(C(O)CN2CCCN(CC(O)c3ccc4c(c3C)COC4=O)CC2)ccc2c1COC2=O]

5,5'-[1,4-diazepane-1,4-diylbis(1-hydroxyethane-2,1-diyl)]bis(4-methyl-2-benzofuran-1(3H)-one The reaction was run in a similar fashion to general epoxide opening conditions as shown for EXAMPLE 2 (at 150° C. for 60 min) starting from 4-methyl-5-oxiran-2-yl-2-benzofuran-1(3H)-one and 1,4-diazepane. Purification by preparative TLC (MeOH/DCM=1:15) afforded 5,5'-[1,4-diazepane-1,4-diylbis(1-hydroxyethane-2,1-diyl)]bis(4-methyl-2-benzofuran-1(3H)-one) The resulting mixture of isomers was then separated to all three pure diastereomers by SFC chiral chromatography.

Isomer 1 $^1$H-NMR (400 MHz, CDCl$_3$) δ ppm 7.76 (s, 4H), 5.22 (s, 4H), 4.98~5.00 (m, 2H), 2.98~3.04 (m, 4H), 2.78~2.84 (m, 6H), 2.38~2.44 (m, 2H), 2.26 (s, 6H), 1.92~1.98 (m, 2H); MS m/e 481 (M+1)$^-$ Isomer 2 $^1$H-NMR (400 MHz, CDCl$_3$) δ ppm 7.78 (s, 4H), 5.23 (s, 4H), 4.98~5.02 (m, 2H), 2.97~3.05 (m, 4H), 2.78~2.85 (m, 6H), 2.36~2.45 (m, 2H), 2.24 (s, 6H), 1.90~1.97 (m, 2H); MS m/e 481 (M+1)$^-$.

Isomer 3 $^1$H-NMR (400 MHz, CDCl$_3$) δ ppm 7.72 (s, 4H), 5.20 (s, 4H), 4.92~4.96 (m, 2H), 2.88~3.00 (m, 4H), 2.70~2.82 (m, 6H), 2.32~2.38 (m, 2H), 2.20 (s, 6H), 1.82~1.94 (m, 2H); MS m/e 481 (M+1)$^-$.

Example 11

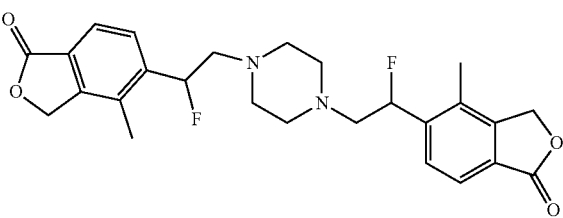 [SMILES: Cc1c(C(F)CN2CCN(CC(F)c3ccc4c(c3C)COC4=O)CC2)ccc2c1COC2=O]

5,5'-[Piperazine-1,4-diylbis(1-fluorethane-2,1-diyl)]bis(4-methyl-2-benzofuran-1(3H)-one)

5,5'-[Piperazine-1,4-diylbis(1-hydroxyethane-2,1-diyl)]bis(4-methyl-2-benzofuran-1(3H)-one) (28 mg, 0.060 mmol, 1.0 eq) was dissolved in THF (5 ml). The solution was cooled to 0° C. To the above solution was added DAST (17 μL, 0.13 mmol, 2.2 eq). The reaction was warmed to r.t. and stirred at that temperature for 30 min. The reaction was quenched with addition of aqueous NH$_4$Cl. The mixture was diluted with DCM, washed with aqueous bicarbonate, water and brine. The organic phase was dried over MgSO$_4$, filtered and concentrated. The product was obtained after purification by flash column chromatography.

$^1$H NMR (500 MHz, CDCl$_3$, δ in ppm): 7.79 (2H, s), 7.61 (2H, d, J=8.0 Hz), 5.93 (2H, m), 5.26 (4H, s), 4.0-2.5 (m), 2.30 (6H, s);

LC-MS (IE, m/z): 471.1 [M+1]$^+$.

Example 12

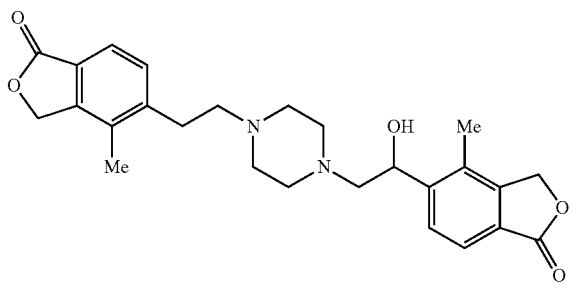 [SMILES: Cc1c(CCN2CCN(CC(O)c3ccc4c(c3C)COC4=O)CC2)ccc2c1COC2=O]

5-(1-hydroxy-2-{4-[2-4-methyl-1-oxo-1,3-dihydro-2-benzofuran-5-yl)ethyl]piperazin-1-yl}ethyl)-4-methyl-2-benzofuran-1(3H)-one 4-Methyl-5-oxiran-2-yl-2-benzofuran-1(3H)-one (60 mg, 0.31 mmol, 1.2 mmol) and 4-methyl-5-(2-piperazin-1-yl-ethyl)-2-benzofuran-1(3H)-one (68 mg, 0.26 mmol, 1.0 eq) were suspended in ethanol (5 ml) in a microwave tube. The tube was capped, degassed under vacuum, and purged with nitrogen gas. The mixture was heated to 150° C. for 30 min under microwave irradiation. The mixture was then concentrated and purified by flash column chromatography (0-10% MeOH/DCM).

$^1$H NMR (500 MHz, CDCl$_3$, δ in ppm): 7.80 (2H, br-s), 7.70 (1H, d, J=7.8 Hz), 7.35 (1H, d, J=7.8 Hz), 5.25 (4H, br-s), 5.10 (1H, dd, J=3.1 Hz, J=10.6 Hz), 3.0-2.4 (14H, m), 2.30 (3H, s), 2.29 (3H, s); LC-MS (IE, m/z): 451.4 [M+1].

Example 13

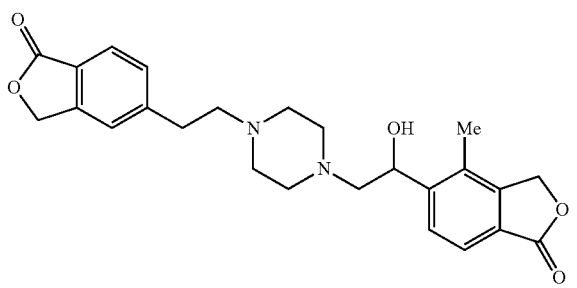 [SMILES: Cc1c(C(O)CN2CCN(CCc3ccc4c(c3)COC4=O)CC2)ccc2c1COC2=O]

5-(1-hydroxy-2-{4-[2-(1-oxo-1,3-dihydro-2-benzofuran-5-yl)ethyl]piperazin-1-yl}ethyl)-4-methyl-2-benzofuran-1(3H)-one 5-(1-Hydroxy-2-{4-[2-(1-oxo-1,3-dihydro-2-benzofuran-5-yl)ethyl]piperazin-1-yl}ethyl)-4-methyl-2-benzofuran-1(3H)-one was prepared in a similar fashion to that described for the synthesis of EXAMPLE 12 starting from 4-methyl-5-oxiran-2-yl-2-benzofuran-1(3H)-one and 5-(2-piperazin-1-ylethyl)-2-benzofuran-1(3H)-one.

$^1$H NMR (500 MHz, CDCl$_3$, δ in ppm): 7.80 (2H, m), 7.70 (1H, d, J=7.8 Hz), 7.35 (1H, d, J=7.8 Hz), 5.25 (4H, br-s), 5.10 (1H, dd, J=3.1 Hz, J=10.6 Hz), 3.0-2.4 (14H, m), 2.30 (3H, s), 2.29 (3H, s); LC-MS (IE, m/z): 437.4 [M+1]$^-$.

Example 14

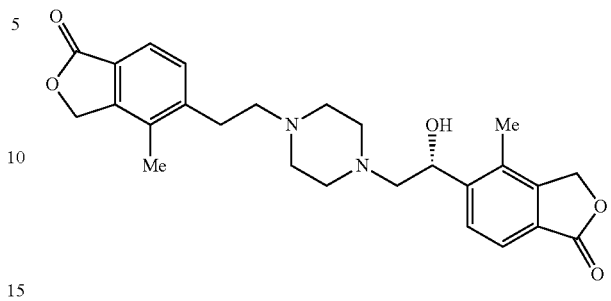

5-((1R)-1-hydroxy-2-{4-[2-(4-methyl-1-oxo-1,3-dihydro-2-benzofuran-5-yl)ethyl]piperazin-1-yl}ethyl)-4-methyl-2-benzofuran-1(3H)-one 5-((1R)-1-hydroxy-2-{4-[2-(4-methyl-1-oxo-1,3-dihydro-2-benzofuran-5-yl)ethyl]piperazin-1-yl}ethyl)-4-methyl-2-benzofuran-1(3H)-one was prepared in a similar fashion to that described for the synthesis of EXAMPLE 12 starting from 4-methyl-5-[(2R)-oxiran-2-yl]-2-benzofuran-1(3H)-one and 4-methyl-5-(2-piperazin-1-ylethyl)-2-benzofuran-1(3H)-one.

$^1$H NMR (500 MHz, CDCl$_3$, δ in ppm): 7.79 (2H, m), 7.70 (1H, d, J=7.9 Hz), 7.35 (1H, d, J=7.9 Hz), 5.25 (4H, br-s), 5.10 (1H, dd, J=2.8 Hz, J=10.2 Hz), 3.0-2.4 (14H, m), 2.30 (3H, s), 2.28 (3H, s); LC-MS (IE, m/z): 451.53 [M+1]$^+$.

Example 15

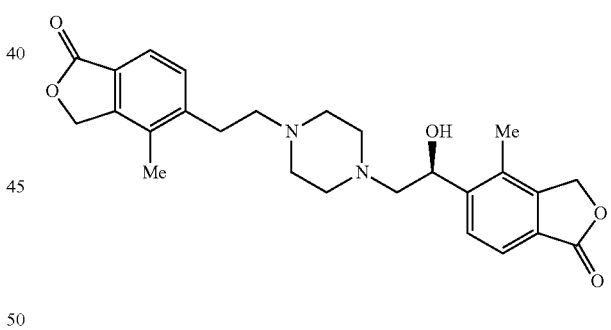

5-((1S)-1-hydroxy-2-{4-[2-(4-methyl-1-oxo-1,3-dihydro-2-benzofuran-5-yl)ethyl]piperazin-1-yl}ethyl)-4-methyl-2-benzofuran-1(3H)-one 5-((1S)-1-hydroxy-2-{4-[2-(4-methyl-1-oxo-1,3-dihydro-2-benzofuran-5-yl)ethyl]piperazin-1-yl}ethyl)-4-methyl-2-benzofuran-1(3H)-one was prepared in a similar fashion to that described for the synthesis of EXAMPLE 12 starting from 4-methyl-5-[(2S)-oxiran-2-yl]-2-benzofuran-1(3H)-one and 4-methyl-5-(2-piperazin-1-ylethyl)-2-benzofuran-1(3H)-one.

$^1$H NMR (500 MHz, CDCl$_3$, δ in ppm): 7.79 (2H, m), 7.70 (1H, d, J=7.9 Hz), 7.35 (1H, d, J=7.9 Hz), 5.25 (4H, br-s), 5.10 (1H, dd, J=2.8 Hz, J=10.2 Hz), 3.0-2.4 (14H, m), 2.30 (3H, s), 2.28 (3H, s); LC-MS (IE, m/z): 451.52 [M+1]$^+$.

Example 16

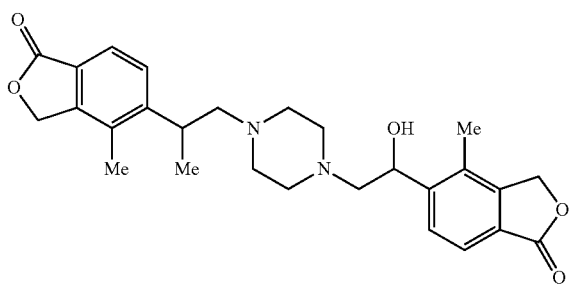 [SMILES: Cc1c(C(C)CN2CCN(CC(O)c3ccc4c(c3C)COC4=O)CC2)ccc2c1COC2=O]

5-(2-{4-[2-hydroxy-2-4-methyl-1-oxo-1,3-dihydro-2-benzofuran-5-yl)ethyl]piperazin-1-yl}-1-methylethyl)-4-methyl-2-benzofuran-1(3H)-one 5-(2-{4-[2-Hydroxy-2-(4-methyl-1-oxo-1,3-dihydro-2-benzofuran-5-yl)ethyl]piperazin-1-yl}-1-methylethyl)-4-methyl-2-benzofuran-1(3H)-one was prepared in a similar fashion to that described for the synthesis of EXAMPLE 12 starting from 4-methyl-5-oxiran-2-yl-2-benzofuran-1(3H)-one (58 mg, 0.31 mmol, 1.2 mmol) and 4-methyl-5-(1-methyl-2-piperazin-1-ylethyl)-2-benzofuran-1(3H)-one.

$^1$H NMR (500 MHz, CDCl$_3$, δ in ppm): 7.78 (4H, br-s), 7.34 (2H, d, J=7.9 Hz), 7.40 (2H, d, J=7.9 Hz), 5.25 (2H, s), 5.23 (2H, s), 5.06 (2H, m), 3.4-2.3 (m), 2.30 (3H, s), 2.26 (3H, s);

LC-MS (IE, m/z): 465.40 [M+1]$^+$.

Example 17

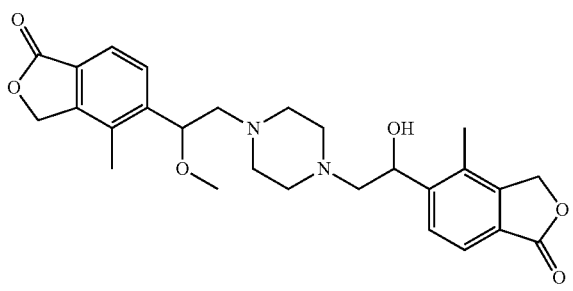 [SMILES: COC(CN1CCN(CC(O)c2ccc3c(c2C)COC3=O)CC1)c1ccc2c(c1C)COC2=O]

5-[2-{4-[2-hydroxy-2-(4-methyl-1-oxo-1,3-dihydro-2-benzofuran-5-yl)ethyl]piperazin-1-yl}-1-(methyloxy)ethyl]-4-methyl-2-benzofuran-1(3H)-one 4-Methyl-5-[1-(methyloxy)-2-piperazin-1-ylethyl]-2-benzofuran-1(3H)-one hydrochloride (40 mg, 0.14 mmol), 4-methyl-5-oxiran-2-yl-2-benzofuran-1(3H)-one (79 mg, 0.41 mmol), were added to a 5 mL microwave tube containing a stir bar; to the mixture was added EtOH (2 mL) and THF (0.5 Ml). The tube was capped, degassed and purged with N$_2$. It was then placed in a microwave reactor and heated at 120° C. for 1 hour; LC indicated completion of the reaction. The solution was concentrated to dryness, dissolved in MeOH (3.5 Ml), filtered and was then purified by mass-directed HPLC to give 5-[2-{4-[2-hydroxy-2-(4-methyl-1-oxo-1,3-dihydro-2-benzofuran-5-yl)ethyl]piperazin-1-yl}-1-(methyloxy)ethyl]-4-methyl-2-benzofuran-1(3H)-one. LC-MS (IE, m/z): 481 [M+1]$^+$.

Examples 18 and 19

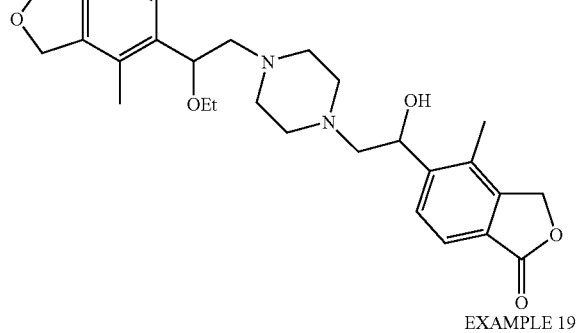

EXAMPLE 18

EXAMPLE 19

Example 18

5-(1-(ethyloxy)-2-{4-[2-hydroxy-2-(4-methyl-1-oxo-1,3-dihydro-2-benzofuran-5-yl)ethyl]piperazin-1-yl}ethyl)-4-methyl-2-benzofuran-1(3H)-one

Example 19

5-(1-fluoro-2-{4-[2-hydroxy-2-(4-methyl-1-oxo-1,3-dihydro-2-benzofuran-5-yl)ethyl]piperazin-1-yl}ethyl)-4-methyl-2-benzofuran-1(3H)-one 4-Methyl-5-oxiran-2-yl-2-benzofuran-1(3H)-one (75 mg, 0.394 mmol, 1.2 mmol) and 5-(1-fluoro-2-piperazin-1-ylethyl)-4-methyl-2-benzofuran-1(3H)-one (90 mg, 0.323 mmol, 1.0 eq) were suspended in ethanol (30 ml). The mixture was heated to 150° C. for 30 min under microwave irradiation. The mixture was concentrated and purify by flash column chromatograph (0-10% MeOH/DCM) to afford the expected product 5-(1-fluoro-2-{4-[2-hydroxy-2-(4-methyl-1-oxo-1,3-dihydro-2-benzofuran-5-yl)ethyl]piperazin-1-yl}ethyl)-4-methyl-2-benzofuran-1(3H)-one as well as byproduct 5-(1-(ethyloxy)-2-{4-[2-hydroxy-2-(4-methyl-1-oxo-1,3-dihydro-2-benzofuran-5-yl)ethyl]piperazin-1-yl}ethyl)-4-methyl-2-benzofuran-1(3H)-one.

Example 19: $^1$H NMR (500 MHz, CDCl$_3$, δ in ppm): 7.81 (1H, d, J=8.0 Hz), 7.79 (2H, br-s), 7.63 (1H, d, J=8.0 Hz), 5.96 (1H, dd, J=8.0 Hz, J=48.3 Hz), 5.27 (2H, s), 5.25 (2H, s), 5.09 (1H, m), 3.00-2.36 (m), 2.31 (3H, s), 2.28 (3H, s);

LC-MS (IE, m/z): 469.1 [M+1]$^+$.

Example 18: $^1$H NMR (500 MHz, CDCl$_3$, δ in ppm): 7.76 (2H, d, J=5.5 Hz), 7.75 (4H, m), 7.61 (2H, d, J=8.1 Hz), 5.24 (2H, s), 5.22 (2H, s), 5.06 (1H, m), 4.83 (1H, m), 3.35 (2H, m), 2.8-2.2 (18H, m), 1.19 (3H, m). LC-MS (IE, m/z): 495.1 [M+1]$^+$.

Example 20

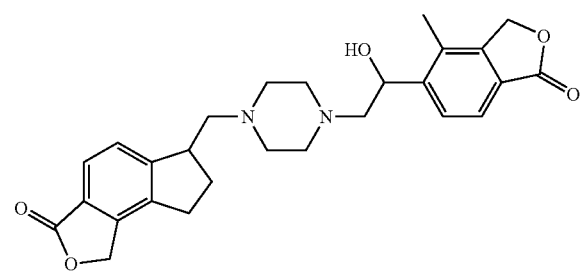 [SMILES: Cc1c(C(O)CN2CCN(CC3CCc4c3ccc3c4COC3=O)CC2)ccc2c1COC2=O]

6-({4-[2-hydroxy-2-(4-methyl-1-oxo-1,3-dihydro-2-benzofuran-5-yl)ethyl]piperazin-1-yl}methyl)-1,6,7,8-tetrahydro-3H-indeno[4,5-c]furan-3-one 6-(Piperazin-1-ylmethyl)-1,6,7,8-tetrahydro-3H-indeno[4,5-c]furan-3-one (40 mg, 0.15 mmol) and 4-methyl-5-oxiran-2-yl-2-benzofuran-1(3H)-one (55 mg, 0.29 mmol), were added to a 5 mL microwave tube containing a stir bar; to the mixture was added EtOH (2.5 mL). The tube was capped, degassed and purged with N$_2$. It was then placed in a microwave reactor and heated at 150° C. for 30 min; LC indicated formation of the desired product. The solution was concentrated to dryness, dissolved in MeOH (3.5 mL), filtered and was then subjected to purification by mass-directed HPLC to give 6-({4-[2-hydroxy-2-(4-methyl-1-oxo-1,3-dihydro-2-benzofuran-5-yl)ethyl]piperazin-1-yl}methyl)-1,6,7,8-tetrahydro-3H-indeno[4,5-c]furan-3-one. LC-MS (IE, m/z): 463 [M+1]$^+$.

Example 21

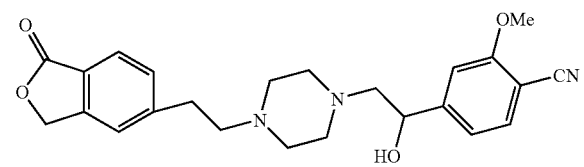

4-(1-hydroxy-2-{4-[2-(1-oxo-1,3-dihydro-2-benzofuran-5-yl)ethyl]piperazin-1-yl}ethyl)-2-(methyloxy)benzonitrile 4-(1-Hydroxy-2-{4-[2-(1-oxo-1,3-dihydro-2-benzofuran-5-yl)ethyl]piperazin-1-yl}ethyl)-2-(methyloxy)benzonitrile was prepared in a similar fashion to that described for the synthesis of EXAMPLE 12 starting from 5-(2-piperazin-1-ylethyl)-2-benzofuran-1(3H)-one and 2-(methyloxy)-4-oxiran-2-ylbenzonitrile.

$^1$H NMR (500 MHz, DMSO-d$_6$), δ 7.84 (d, J=8.0 Hz, 1H), 7.18 (s, 1H), 7.6 (d, J=7.7 Hz, 1H), 7.60 (s, 1H), 7.54 (d, J=7.8 Hz, 1H), 7.33 (s, 1H), 7.18 (d, J=8.0 Hz, 1H), 5.4 (s, 2H), 5.26 (d, J=8.0 Hz, 1H), 3.94 (s, 3H), 3.82 (bs, 4H), 3.42 (bs, 4H), 3.25 (bs, 4H);

LC/MS (M+1)$^+$=422.33.

Example 22

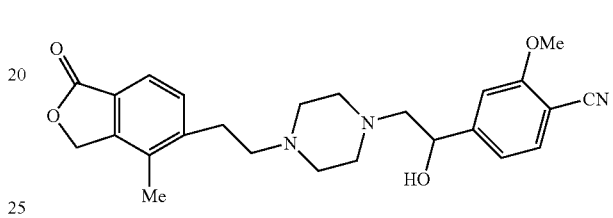

4-(1-hydroxy-2-{4-[2-(4-methyl-1-oxo-1,3-dihydro-2-benzofuran-5-yl)ethy2-(methyloxy)-4-oxiran-2-ylbenzonitrile 4-(1-hydroxy-2-{4-[2-(4-methyl-1-oxo-1,3-dihydro-2-benzofuran-5-yl)ethy2-(methyloxy)-4-oxiran-2-ylbenzonitrile was prepared in a similar fashion to that described for the synthesis of EXAMPLE 12 starting from 4-methyl-5-(1-methyl-2-piperazin-1-ylethyl)-2-benzofuran-1(3H)-one and 2-(methyloxy)-4-oxiran-2-ylbenzonitrile.

$^1$H NMR (500 MHz, DMSO-d$_6$), δ 7.76 (d, J=8.0 Hz, 1H), 7.67 (d, J=7.8 Hz, 1H), 7.50 (d, J=7.8 Hz, 1H), 7.35 (s, 1H), 7.19 (d, J=8.0 Hz, 1H), 5.40 (s, 2H), 5.27 (d, J=9.8 Hz, 1H), 4.40 (bs, 1H), 3.95 (s, 3H), 3.85-3.43 (m, 8H), 3.38-3.22 (m, 6H), 2.33 (s, 3H);

LC/MS (M+1)$^+$=436.40.

The 2 individual isomers of 4-(1-hydroxy-2-{4-[2-(4-methyl-1-oxo-1,3-dihydro-2-benzofuran-5-yl)ethy2-(methyloxy)-4-oxiran-2-ylbenzonitrile were obtained by SFC chiral chromatography (Method Info: 4.6×150 mm ChiralCel OJ-H, 2.5 mL/min, 100 bar, 30% MeOH+ IBA/CO$_2$ at 35° C.). Characterization for Isomer 1 (faster eluting from chiral HPLC) and Isomer 2 (slower eluting from chiral HPLC) are below.

Isomer 1: $^1$H NMR (500 MHz, DMSO-d$_6$), δ 7.65 (d, J=7.7 Hz, 1H), 7.59 (d, J=7.8 Hz, 1H), 7.41 (d, J=7.7 Hz, 1H), 7.22 (s, 1H), 7.08 (d, J=7.8 Hz, 1H), 5.37 (s, 2H), 5.29 (d, J=3.8 Hz, 1H), 4.77 (bs, 1H), 3.91 (s, 3H), 2.87 (t, J=7.6 Hz, J=8.0 Hz, 2H), 2.40-2.38 (m, 12H), 2.25 (s, 3H); LC/MS (M+1)$^+$=436.53.

Isomer 2: $^1$H NMR (500 MHz, DMSO-d$_6$), δ 7.65 (d, J=7.8 Hz, 1H), 7.59 (d, J=7.5 Hz, 1H), 7.41 (d, J=7.8 Hz, 1H), 7.22 (s, 1H), 7.08 (d, J=7.7 Hz, 1H), 5.37 (s, 2H), 5.29 (d, J=3.9 Hz, 1H), 4.76 (bs, 1H), 3.91 (s, 3H), 2.87 (t, J=7.5 Hz, J=8.0 Hz, 2H), 2.55-2.38 (m, 12H), 2.25 (s, 3H); LC/MS (M+1)$^+$=436.50.

Example 23

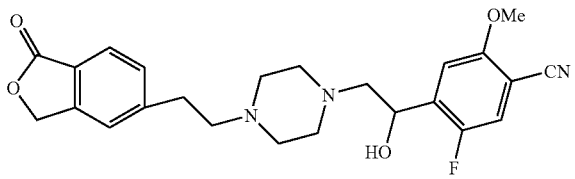 [SMILES: COc1cc(C(O)CN2CCN(CCc3ccc4c(c3)COC4=O)CC2)c(F)cc1C#N]

5-fluoro-4-(1-hydroxy-2-{4-[2-(1-oxo-1,3-dihydro-2-benzofuran-5-yl)ethyl]piperazin-1-yl}ethyl)-2-(methyloxy)benzonitrile 5-fluoro-4-(1-hydroxy-2-{4-[2-(1-oxo-1,3-dihydro-2-benzofuran-5-yl)ethyl]piperazin-1-yl}ethyl)-2-(methyloxy)benzonitrile was prepared in a similar fashion to that described for the synthesis of EXAMPLE 12 starting from 5-(2-piperazin-1-ylethyl)-2-benzofuran-1(3H)-one and 5-fluoro-2-(methyloxy)-4-oxiran-2-ylbenzonitrile.

LC/MS (M+1)$^+$=440.54.

Example 24

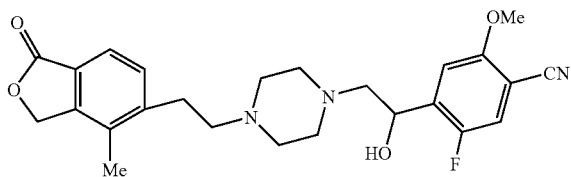 [SMILES: COc1cc(C(O)CN2CCN(CCc3ccc4c(c3C)COC4=O)CC2)c(F)cc1C#N]

5-fluoro-5-(1-hydroxy-2-{4-[2-(4-methyl-1-oxo-1,3-dihydro-2-benzofuran-5-yl)ethyl]piperazin-1-yl}ethyl)-2-(methyloxy)benzonitrile 5-fluoro-4-(1-hydroxy-2-{4-[2-(4-methyl-1-oxo-1,3-dihydro-2-benzofuran-5-yl)ethyl]piperazin-1-yl}ethyl)-2-(methyloxy)benzonitrile was prepared in a similar fashion to that described for the synthesis of EXAMPLE 12 starting from 4-methyl-5-(1-methyl-2-piperazin-1-ylethyl)-2-benzofuran-1(3H)-one and 5-fluoro-2-(methyloxy)-4-oxiran-2-ylbenzonitrile.

LC/MS (M+1)$^+$=454.55.

Example 25

All Four Separated Isomers

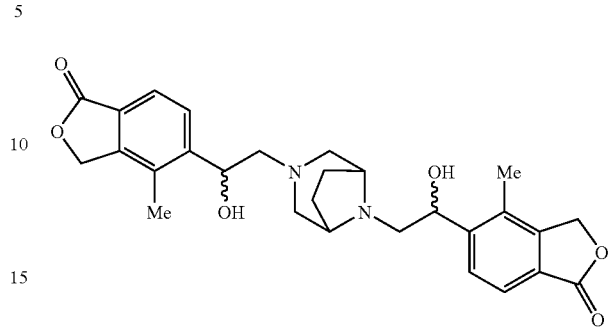

5,5'-[3,8-diazabicyclo[3.2.1]octane-3,8-diylbis(1-hydroxyethane-2,1-diyl)]bis(4-methyl-2-benzofuran-1(3H)-one)

A mixture of isomer (37A) of 5-[2-(3,8-diazabicyclo[3.2.1]oct-3-yl)-1-hydroxyethyl]-4-methyl-2-benzofuran-1(3H)-one (53 mg, 0.175 mmol) and 4-methyl-5-oxiran-2-yl-2-benzofuran-1(3H)-one (57 mg, 0.210 mmol) in 2 mL DMSO was heated under microwave condition (150° C.) for 1 hr. After cooling to rt., the mixture was diluted with water (50 mL), and extracted with EtOAc (3×50 mL). The combined organic layers were washed with brine and dried over Na$_2$SO$_4$, then concentrated. The residue was purified by prep-TLC (MeOH/DCM=1:15) and then separated by SFC chiral chromatography to obtain two separated isomers A and B of 5,5'-[3,8-diazabicyclo[3.2.1]octane-3,8-diylbis(1-hydroxyethane-2,1-diyl)]bis(4-methyl-2-benzofuran-1(3H)-one).

Isomer A $^1$H-NMR (400 MHz, CDCl$_3$) δ ppm 7.78 (d, J=3.1 Hz, 4H), 5.24 (s, 4H), 5.05~5.10 (m, 2H), 3.50 (bs, 1H), 3.26 (bs, 1H), 3.00~3.05 (m, 1H), 2.55~2.85 (m, 5H), 2.30~2.42 (m, 2H), 2.28 (s, 3H), 2.26 (s, 3H), 1.85~2.01 (m, 4H). MS m/z 493 (M+1)$^+$.

Isomer B $^1$H-NMR (400 MHz, CDCl$_3$) δ ppm 7.78 (s, 4H), 5.22 (s, 4H), 4.95~5.06 (m, 2H), 3.42 (bs, 1H), 3.20 (bs, 1H), 2.96~3.00 (m, 1H), 2.64~2.72 (m, 3H), 2.48~2.58 (m, 2H), 2.26~2.38 (m, 2H), 2.25 (s, 6H), 1.90~2.00 (m, 4H). MS m/z 493 (M+1)$^+$.

A mixture of isomer (37B) of 5-[2-(3,8-diazabicyclo[3.2.1]oct-3-yl)-1-hydroxyethyl]-4-methyl-2-benzofuran-1(3H)-one (45 mg, 0.149 mmol) and 4-methyl-5-oxiran-2-yl-2-benzofuran-1(3H)-one (57 mg, 0.210 mmol) in 2 mL DMSO was heated under microwave condition (150° C.) for 1 hr. After cooling to rt., the mixture was diluted with water (50 mL), and extracted with EtOAc (3×50 mL). The combined organic layers were washed with brine and dried over Na$_2$SO$_4$, then concentrated. The residue was purified by prep-TLC (MeOH/DCM=1:15) and then separated by SFC chiral chromatography to obtain two separated isomers C and D of 5,5'-[3,8-diazabicyclo[3.2.1]octane-3,8-diylbis(1-hydroxyethane-2,1-diyl)]bis(4-methyl-2-benzofuran-1(3H)-one).

Isomer C $^1$H-NMR (400 MHz, CDCl$_3$) δ ppm 7.78 (s, 4H), 5.24 (s, 4H), 5.05~5.10 (m, 2H), 3.52 (bs, 1H), 3.00~3.04 (m, 1H), 2.62~2.74 (m, 4H), 2.34~2.44 (m, 2H), 2.28 (s, 3H), 2.26 (s, 3H), 2.14~2.26 (m, 2H), 1.96~2.04 (m, 4H).

MS m/z 493 (M+1)$^-$.

Isomer D $^1$H-NMR (400 MHz, CDCl$_3$) δ ppm 7.76 (s, 4H), 5.22 (s, 4H), 5.06~5.12 (m, 2H), 3.50 (bs, 1H), 3.42 (bs, 1H), 3.00~3.05 (m, 1H), 2.58~2.88 (m, 5H), 2.32~2.44 (m, 2H), 2.28 (s, 3H), 2.26 (s, 3H), 1.90~2.02 (m, 4H).
MS m/z 493 (M+1)⁻.

Example 26

All 8 Separated Isomers

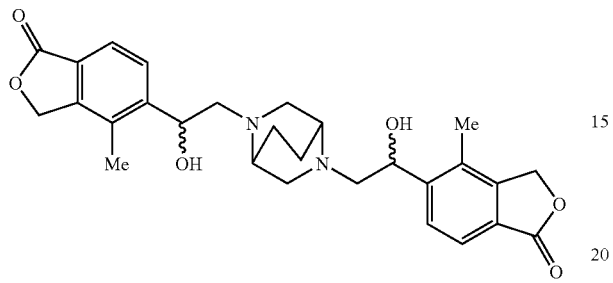

5,5'-[2,5-diazabicyclo[2.2.2]octane-2,5-diylbis(1-hydroxyethane-2,1-diyl)]bis(4-methyl-2-benzofuran-1(3H)-one)

In four separate reactions, isomers A-D of 5-[2-(2,5-diazabicyclo[2.2.2]oct-2-yl)-1-hydroxyethyl]-4-methyl-2-benzofuran-1(3H)-one (about 100 mg, 0.33 mmol) and 4-methyl-5-oxiran-2-yl-2-benzofuran-1(3H)-one (95 mg, 0.50 mmol) in 2 mL DMSO was heated under microwave condition (150° C.) for 1 hr. After cooling to it, the mixtures were diluted with water (20 mL), extracted with EtOAc (3×20 mL). The combined organic layers were washed with brine and dried over Na₂SO₄, then concentrated. The residues were purified by preparative TLC (MeOH/DCM=1:15) to obtain 5,5'-[2,5-diazabicyclo[2.2.2]octane-2,5-diylbis(1-hydroxyethane-2,1-diyl)]bis(4-methyl-2-benzofuran-1(3H)-one) as 4 mixtures of two isomers, which were separated by SFC chiral chromatography to obtain two single isomers for each (eight total).

Isomer A ¹H-NMR (400 MHz, CDCl₃) δ ppm 7.68~7.72 (m, 4H), 5.15 (s, 4H), 5.09~5.13 (m, 2H), 3.60~3.66 (m, 2H), 2.96 (s, 2H), 2.86~2.90 (m, 2H), 2.75~2.77 (m, 2H), 2.47~2.61 (m, 4H), 2.23 (s, 6H), 1.93~2.03 (m, 2H), 1.66~1.73 (m, 2H). MS m/z 493 (M+1)⁺.

Isomer B ¹H-NMR (400 MHz, CDCl₃) δ ppm 7.68~7.72 (m, 4H), 5.18 (s, 4H), 4.95~5.01 (m, 2H), 3.38~3.44 (m, 1H), 3.07~3.18 (m, 2H), 2.76~2.91 (m, 4H), 2.67~2.69 (m, 1H), 2.41~2.52 (m, 2H), 2.24 (d, J=9.7 Hz, 6H), 1.94~2.07 (m, 4H). MS m/z 493 (M+1)⁺.

Isomer C ¹H-NMR (400 MHz, CDCl₃) δ ppm 7.68~7.72 (m, 4H), 5.15 (s, 4H), 4.90~4.93 (m, 2H), 3.04~3.07 (m, 2H), 2.92~2.95 (m, 4H), 2.81~2.85 (m, 2H), 2.40~2.45 (m, 2H), 2.22 (s, 6H), 1.97~2.06 (m, 2H), 1.69~1.75 (m, 2H). MS m/z 493 (M+1)⁺.

Isomer D ¹H-NMR (400 MHz, CDCl₃) δ ppm 7.68~7.72 (m, 4H), 5.18 (s, 4H), 4.86~4.93 (m, 2H), 3.28~3.31 (m, 1H), 3.13~3.15 (m, 1H), 2.97~2.99 (m, 1H), 2.80~2.87 (m, 2H), 2.63~2.71 (m, 3H), 2.32~2.44 (m, 2H), 2.23 (d, J=9.5 Hz, 6H), 1.87~2.00 (m, 2H), 1.61~1.73 (m, 2H). MS m/z 493 (M+1).

Isomer E ¹H-NMR (400 MHz, CDCl₃) δ ppm 7.68~7.72 (m, 4H), 5.15 (s, 4H), 4.88~4.93 (m, 2H), 3.04~3.07 (m, 2H), 2.80~2.95 (m, 4H), 2.66~2.72 (m, 2H), 2.40~2.45 (m, 2H), 2.22 (s, 6H), 1.97~2.06 (m, 2H), 1.66~1.77 (m, 2H). MS m/z 493 (M+1)⁺.

Isomer F ¹H-NMR (400 MHz, CDCl₃) δ ppm 7.68~7.72 (m, 4H), 5.15 (s, 4H), 5.00~5.07 (m, 2H), 3.48~3.51 (m, 1H), 3.11~3.33 (m, 3H), 2.83~2.99 (m, 4H), 2.48~2.57 (m, 2H), 2.23 (d, J=6.4 Hz, 6H), 1.89~2.00 (m, 2H), 1.64~1.79 (m, 2H). MS m/z 493 (M+1)⁺.

Isomer G ¹H-NMR (400 MHz, CDCl₃) δ ppm 7.68~7.72 (m, 4H), 5.18 (s, 4H), 4.93~4.96 (m, 2H), 3.38~3.41 (m, 2H), 2.84~2.88 (m, 2H), 2.71~2.73 (m, 2H), 2.37~2.42 (m, 2H), 2.22 (s, 6H), 1.90~2.00 (m, 2H), 1.60~1.66 (m, 2H). MS m/z 493 (M+1)⁺.

Isomer H ¹H-NMR (400 MHz, CDCl₃) δ ppm 7.68~7.72 (m, 4H), 5.15 (s, 4H), 4.91~4.98 (m, 2H), 3.35~3.38 (m, 1H), 3.14~3.17 (m, 2H), 2.81~2.90 (m, 2H), 2.74~2.77 (m, 2H), 2.66~2.68 (m, 1H), 2.37~2.49 (m, 2H), 2.23 (d, J=10.1 Hz, 6H), 1.90~2.60 (m, 2H), 1.61~1.73 (m, 2H). MS m/z 493 (M+1)⁻.

Example 27

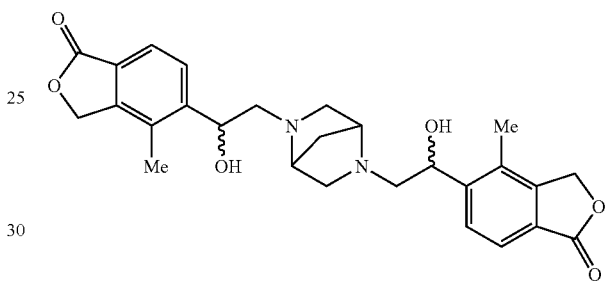

5,5'-[2,5-diazabicyclo[2.2.1]heptane-2,5-diylbis(1-hydroxyethane-2,1-diyl)]bis(4-methyl-2-benzofuran-1(3H)-one)

In separate vessels Isomers A and B of 5,5'-[2,5-diazabicyclo[2.2.1]heptane-2,5-diylbis(1-hydroxyethane-2,1-diyl)]bis(4-methyl-2-benzofuran-1(3H)-one) (80 mg~250 mg, 0.33 mmol) and 4-methyl-5-oxiran-2-yl-2-benzofuran-1(3H)-one (1.5 eq.) in 2 mL DMSO was heated under microwave conditions (150° C.) for 1 hr. After cooling to it, the mixture was diluted with water (20 mL), extracted with EtOAc (3×20 mL). The combined organic layers were washed with brine and dried over Na₂SO₄, then concentrated. The residue was purified by TLC (MeOH/DCM=1:15) to obtain 5,5'-[2,5-diazabicyclo[2.2.1]heptane-2,5-diylbis(1-hydroxyethane-2,1-diyl)]bis(4-methyl-2-benzofuran-1(3H)-one) as mixtures of isomers, which were separated by SFC chiral chromatography to afford three single isomers for each.

Isomer A: MS m/z 479 (M+1)⁺.

Isomer B: ¹H-NMR (400 MHz, CDCl₃) δ ppm 7.68~7.74 (m, 4H), 5.18 (s, 4H), 4.02~5.18 (m, 2H), 3.60~3.66 (m, 2H), 2.90~3.28 (m, 6H), 2.50~2.60 (m, 2H), 2.26 (s, 6H), 1.52~1.60 (m, 2H). MS m/z 479 (M+1)⁻.

Isomer C: ¹H-NMR (400 MHz, CDCl₃) δ ppm 7.68~7.72 (m, 4H), 5.18~5.20 (m, 4H), 5.04~5.12 (m, 2H), 2.500~3.70 (m, 10H), 2.24~2.28 (m, 6H), 1.50~1.65 (m, 2H). MS m/z 479 (M+1)⁺.

Isomer D: ¹H-NMR (400 MHz, CDCl₃) δ ppm 7.68~7.72 (m, 4H), 5.14~5.20 (s, 4H), 4.78~4.82 (m, 1H), 3.96~4.00 (m, 1H), 3.68~3.82 (m, 2H), 3.14~3.30 (m, 2H), 2.35~3.00 (m, 6H), 2.18 (s, s, 6H), 1.54~1.74 (m, 2H). MS m/z 479 (M+1)⁺.

Isomer E: ¹H-NMR (400 MHz, CDCl₃) δ ppm 7.72~7.80 (m, 4H), 5.22 (s, 4H), 4.90~5.00 (m, 2H), 3.40~3.50 (m, 2H), 3.00~3.10 (m, 2H), 2.64~2.78 (m, 6H), 2.26 (s, 6H), 1.74~1.78 (m, 2H). MS m/z 479 (M+1).

Isomer F: ¹H-NMR (400 MHz, CD3OD) δ ppm 7.68~7.74 (m, 4H), 5.18 (s, 4H), 5.00~5.12 (m, 2H), 3.62~3.74 (m, 2H), 3.14~3.40 (m, 2H), 2.50~2.86 (m, 6H), 2.26 (s, 3H), 2.24 (s, 3H), 1.82~1.96 (m, 2H). MS m/z 479 (M+1)⁺.

Example 28

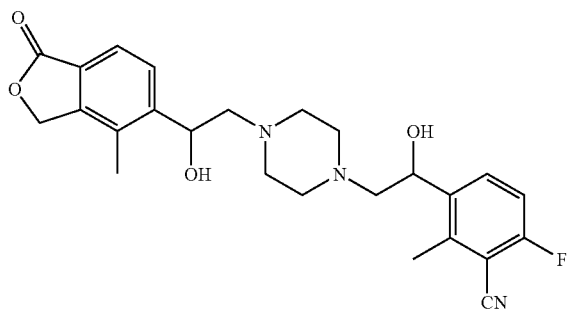 [SMILES: Cc1c(C(O)CN2CCN(CC(O)c3ccc4c(c3C)COC4=O)CC2)ccc(F)c1C#N]

6-fluoro-3-(1-hydroxy-2-{4-[2-hydroxy-2-(4-methyl-1-oxo-1,3-dihydro-2-benzofuran-5-yl)ethyl]piperazin-1-yl}ethyl)-2-methylbenzonitrile 6-Fluoro-2-methyl-3-oxiran-2-ylbenzonitrile (69.2 mg, 0.391 mmol), 5-(1-hydroxy-2-piperazin-1-ylethyl)-4-methyl-2-benzofuran-1(3H)-one (54.0 mg, 0.195 mmol) was dissolved in EtOH (5 ml) then microwaved at 150° C. for 1 hr. Evaporated off ethanol and the residue was purified by mass directed hplc to yield 6-fluoro-3-(1-hydroxy-2-{4-[2-hydroxy-2-(4-methyl-1-oxo-1,3-dihydro-2-benzofuran-5-yl)ethyl]piperazin-1-yl}ethyl)-2-methylbenzonitrile.

¹H-NMR (500 MHz, DMSO₄): δ ppm 7.83 (t, J=8 Hz, 1H), 7.72 (s, 2H), 7.38 (t, d=8.5 Hz, 1H), 5.35-5.43 (q, 2H), 5.28 (d, J=7.5 Hz, 1H), 5.16 (t, J=6 Hz, 1H), 3.16-3.41 (b, 7H), 3.06-3.07 (m, 5H), 2.55 (s, 3H), 2.29 (s, 3H).

LC-MS: M+1=454.

Example 29

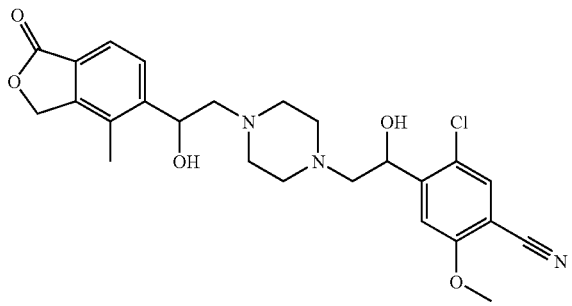 [SMILES: COc1cc(C(O)CN2CCN(CC(O)c3ccc4c(c3C)COC4=O)CC2)c(Cl)cc1C#N]

5-chloro-4-(1-hydroxy-2-{4-[2-hydroxy-2-(4-methyl-1-oxo-1,3-dihydro-2-benzofuran-5-yl)ethyl]piperazin-1-yl}ethyl)-2-(methyloxy)benzonitrile A solution of (2-chloro-4-cyano-5-methoxyphenyl)ethylene oxide (45.50 mg, 0.22 mmol) and 5-(1-hydroxy-2-piperazin-1-ylethyl)-4-methyl-2-benzofuran-1(3H)-one (0.50 mg, 0.18 mmol) in DMSO (2.00 mL) was stirred at 150° C. via microwave for 1 hour. Added brine and EtOAc, the organic layer was separated and the aqueous layer was extracted with EtOAc. The organic layers were dried over Na₂SO₄ and concentrated. The residue was purified via prep-TLC to give pure product as a mixture of isomers which were separated via chiral prep-HPLC to afford the resolved 4 isomers of 5-chloro-4-(1-hydroxy-2-{4-[2-hydroxy-2-(4-methyl-1-oxo-1,3-dihydro-2-benzofuran-5-yl)ethyl]piperazin-1-yl}ethyl)-2-(methyloxy)benzonitrile.

Isomer 1: ¹H-NMR (400 MHz, CDCl₃) δ ppm 7.78 (s, 2H), 7.48 (s, 1H), 7.34 (s, 1H), 5.24 (s, 2H), 5.08~5.11 (m, 2H), 3.95 (s, 3H), 2.81~2.89 (m, 6H), 2.53~2.58 (m, 6H), 2.28 (s, 3H); MS m/e 486 (M+1)⁻.

Isomer 2: ¹H-NMR (400 MHz, CDCl₃) δ ppm 7.79 (s, 2H), 7.49 (s, 1H), 7.35 (s, 1H), 5.25 (s, 2H), 5.09~5.11 (m, 2H), 3.96 (s, 3H), 2.82~2.89 (m, 6H), 2.55~2.61 (m, 6H), 2.29 (s, 3H); MS m/e 486 (M+1)⁻.

Isomer 3: ¹H-NMR (400 MHz, CDCl₃) δ ppm 7.79 (s, 2H), 7.50 (s, 1H), 7.35 (s, 1H), 5.25 (s, 2H), 5.12 (d, 2H), 3.96 (s, 3H), 2.95~2.32 (m, 12H), 2.29 (s, 3H); MS m/e 486 (M+1)⁺.

Isomer 4: ¹H-NMR (400 MHz, CDCl₃) δ ppm 7.78 (s, 2H), 7.49 (s, 1H), 7.35 (s, 1H), 5.24 (s, 2H), 5.09~5.11 (m, 2H), 3.95 (s, 3H), 2.82~2.89 (m, 6H), 2.55~2.61 (m, 6H), 2.28 (s, 3H); MS m/e 486 (M+1)⁻.

Example 30

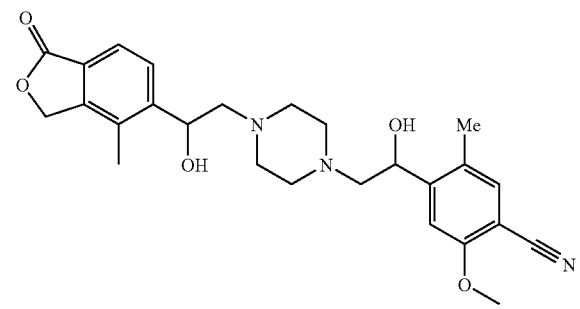 [SMILES: COc1cc(C(O)CN2CCN(CC(O)c3ccc4c(c3C)COC4=O)CC2)c(C)cc1C#N]

4-(1-hydroxy-2-{4-[2-hydroxy-2-(4-methyl-1-oxo-1,3-dihydro-2-benzofuran-5-yl)ethyl]piperazin-1-yl}ethyl)-5-methyl-2-(methyloxy)benzonitrile 4-(1-hydroxy-2-{4-[2-hydroxy-2-(4-methyl-1-oxo-1,3-dihydro-2-benzofuran-5-yl)ethyl]piperazin-1-yl}ethyl)-5-methyl-2-(methyloxy)benzonitrile was prepared in a similar fashion to that described for the synthesis of EXAMPLES 2C and 28-29 starting from 5-(1-hydroxy-2-piperazin-1-ylethyl)-4-methyl-2-benzofuran-1(3H)-one and 5-methyl-2-(methyloxy)-4-oxiran-2-ylbenzonitrile. LC/MS (M+1)+=466.02.

Example 31

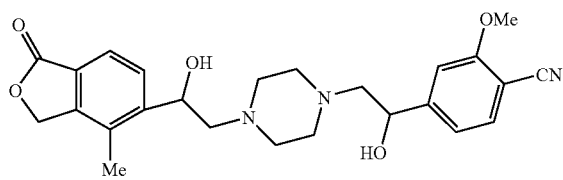 [SMILES: COc1cc(C(O)CN2CCN(CC(O)c3ccc4c(c3C)COC4=O)CC2)ccc1C#N]

4-(1-hydroxy-2-{4-[2-hydroxy-2-(4-methyl-1-oxo-1,3-dihydro-2-benzofuran-5-yl)ethyl]piperazin-1-yl}ethyl)-2-(methyloxy)benzonitrile 4-(1-hydroxy-2-{4-[2-hydroxy-2-(4-methyl-1-oxo-1,3-dihydro-2-benzofuran-5-yl)ethyl]piperazin-1-yl}ethyl)-2-(methyloxy)benzonitrile was prepared in a similar fashion to that described for the synthesis of EXAMPLES 2C and 28-29 starting from 5-(1-hydroxy-2-piperazin-1-ylethyl)-4-methyl-2-benzofuran-1(3H)-one and 2-(methyloxy)-4-oxiran-2-yl-benzonitrile.

$^1$H NMR (500 MHz, DMSO-d$_6$), δ 7.77 (bs, 1H), 7.74 (bs, 2H), 7.36 (bs, 1H), 7.19 (d, J=7.3 Hz, 1H), 6.48 (bs, 1H), 5.58 (bs, 1H), 5.42 (dd, J=8.7 Hz, 2H), 5.26 (bs, 1H), 3.95 (s, 3H), 3.92-3.76 (m, 5H), 3.75-3.42 (m, 4H), 3.40-3.21 (m, 4H), 2.36 (s, 3H); LC/MS (M+1)$^+$=452.35. The 4 individual isomers of 4-(1-hydroxy-2-{4-[2-hydroxy-2-(4-methyl-1-oxo-1,3-dihydro-2-benzofuran-5-yl)ethyl]piperazin-1-yl}ethyl)-2-(methyloxy)benzonitrile were obtained by SFC chiral chromatography (4.6×250 mm ChiralCel OJ-H, 2.4 mL/min, 100 bar, 4-40% MeOH: MeCN/CO$_2$ at 35° C.); isomer 1: t$_R$=7.049 min, isomer 2: t$_R$=7.308 min, isomer 3: t$_R$=7.740 min, isomer 4: t$_R$=7.869 min.

Example 32

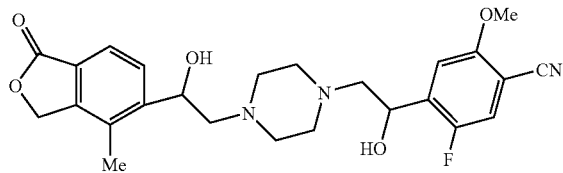 [SMILES: COc1cc(C(O)CN2CCN(CC(O)c3ccc4c(c3C)COC4=O)CC2)c(F)cc1C#N]

5-fluoro-4-(1-hydroxy-2-{4-[2-hydroxy-2-(4-methyl-1-oxo-1,3-dihydro-2-benzofuran-5-yl)ethyl]piperazin-1-yl}ethyl)-2-(methyloxy)benzonitrile 5-fluoro-4-(1-hydroxy-2-{4-[2-hydroxy-2-(4-methyl-1-oxo-1,3-dihydro-2-benzofuran-5-yl)ethyl]piperazin-1-yl}ethyl)-2-(methyloxy)benzonitrile was prepared in a similar fashion to that described for the synthesis of EXAMPLES 2C and 28-29 starting from 5-(1-hydroxy-2-piperazin-1-ylethyl)-4-methyl-2-benzofuran-1(3H)-one and 5-fluoro-2-(methyloxy)-4-oxiran-2-ylbenzonitrile. LC/MS (M+1)$^+$=470.56.

Example 33

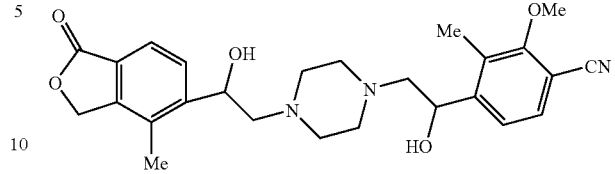

4-(1-hydroxy-2-{4-[2-hydroxy-2-(4-methyl-1-oxo-1,3-dihydro-2-benzofuran-5-yl)ethyl]piperazin-1-yl}ethyl)-3-methyl-2-(methyloxy)benzonitrile 4-(1-hydroxy-2-{4-[2-hydroxy-2-(4-methyl-1-oxo-1,3-dihydro-2-benzofuran-5-yl)ethyl]piperazin-1-yl}ethyl)-3-methyl-2-(methyloxy)benzonitrile was prepared in a similar fashion to that described for the synthesis of EXAMPLES 2C and 28-29 starting from 5-(1-hydroxy-2-piperazin-1-ylethyl)-4-methyl-2-benzofuran-1(3H)-one and 3-methyl-2-(methyloxy)-4-oxiran-2-ylbenzonitrile.

$^1$H NMR (500 MHz, DMSO-d$_6$), δ 7.72 (m, 3H), 7.46 (d, J=8.2 Hz, 1H), 5.60 (d, J=9.6 Hz, 1H), 5.46 (bs, 1H), 5.42 (dd, J=8.9 Hz, 2H), 4.12-3.73 (m, 4H), 3.65-3.45 (m, 4H), 3.42-3.22 (m, 5H), 2.37 (s, 3H), 2.32 (s, 3H);

LC/MS (M+1)$^+$=466.02.

Example 34

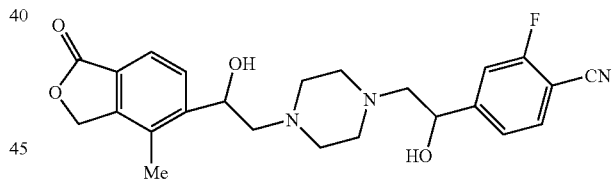

2-fluoro-4-(1-hydroxy-2-{4-[2-hydroxy-2-(4-methyl-1-oxo-1,3-dihydro-2-benzofuran-5-yl)ethyl]piperazin-1-yl}ethyl)benzonitrile 2-fluoro-4-(1-hydroxy-2-{4-[2-hydroxy-2-(4-methyl-1-oxo-1,3-dihydro-2-benzofuran-5-yl)ethyl]piperazin-1-yl}ethyl)benzonitrile was prepared in a similar fashion to that described for the synthesis of EXAMPLES 2C and 28-29 starting from 5-(1-hydroxy-2-piperazin-1-ylethyl)-4-methyl-2-benzofuran-1(3H)-one and 2-fluoro-4-oxiran-2-ylbenzonitrile. $^1$H NMR (500 MHz, DMSO-d$_6$), δ 7.98 (m, 1H), 7.74 (m, 1H), 7.71 (m, 1H), 7.60 (d, J=10.5 Hz, 1H), 7.52 (d, J=7.9 Hz, 1H), 5.56 (d, J=7.7 Hz, 1H), 5.42 (dd, J=8.3 Hz, 2H), 5.38 (bs, 1H), 3.95-3.42 (m, 6H), 3.40-3.18 (m, 6H), 2.36 (s, 3H); LC/MS (M+1)$^+$=440.02.

Example 35

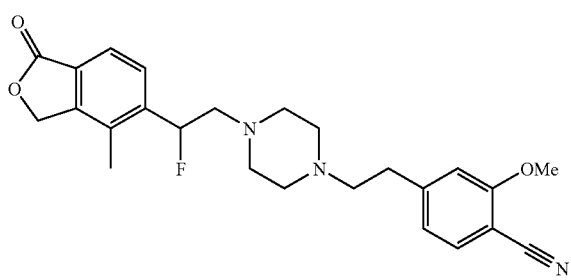

4-(2-{4-[2-fluoro-2-(4-methyl-1-oxo-1,3-dihydro-2-benzofuran-5-yl)ethyl]piperazin-1-yl}ethyl)-2-(methyloxy)benzonitrile 5-(1-Fluoro-2-piperazin-1-ylethyl)-4-methyl-2-benzofuran-1(3H)-one hydrochloride (30 mg, 0.11 mmol), 2-(methyloxy)-4-(2-oxoethyl)benzonitrile (37 mg, 0.22 mmol), sodium cyanoborohydride (67 mg, 1.078 mmol) were added to a 25 mL flask containing a stir bar; to the flask was added MeOH (3 mL) and few drops of AcOH. The reaction mixture was subsequently stirred for 12 h r; LC indicated that reaction had gone to completion. The solution was concentrated to dryness, redissolved in EtOAc (15 mL) and washed with aq. NaHCO$_3$ and aq. NaCl. The organic phase was dried over Na$_2$SO$_4$, filtered and concentrated to dryness. It was then re-dissolved in MeOH (3.5 mL) again, filtered and shot into mass-directed HPLC for separation to give the desired product. LC-MS (IE, m/z): 450 [M+1]$^+$.

Example 36

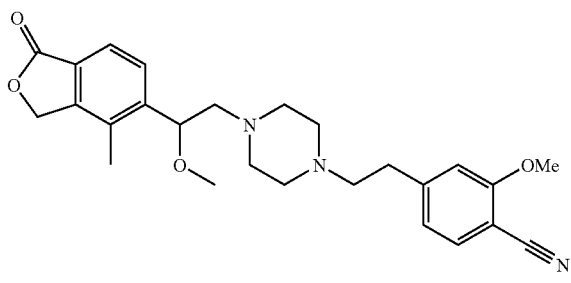 [SMILES: COc1cc(CCN2CCN(CC(OC)c3ccc4c(c3C)COC4=O)CC2)ccc1C#N]

4-(2-{4-[2-(4-methyl-1-oxo-1,3-dihydro-2-benzofuran-5-yl)-2-(methyloxy)ethyl]piperazin-1-yl}ethyl)-2-(methyloxy)benzonitrile 4-Methyl-5-[1-(methyloxy)-2-piperazin-1-ylethyl]-2-benzofuran-1(3H)-one hydrochloride (50 mg, 0.17 mmol), 2-(methyloxy)-4-(2-oxoethyl)benzonitrile (60 mg, 0.34 mmol), sodium cyanoborohydride (108 mg, 1.72 mmol) and a stir bar were added to a 25 mL flask and few drops of AcOH. The resulting mixture was then dissolved in MeOH (3 mL) and stirred for 12 h; analysis by LC indicated that reaction had gone to completion. The reaction mixture was treated with EtOAc (20 mL) and washed with aq. NaHCO$_3$, aq. NaCl. The organic phase was then dried over Na$_2$SO$_4$ and concentrated to dryness; the resulting residue was then dissolved in MeOH (3.5 mL), filtered and shot into Mass-directed HPLC for separation to give the desired product. LC-MS (IE, m/z): 481 [M+1]$^+$.

Example 37

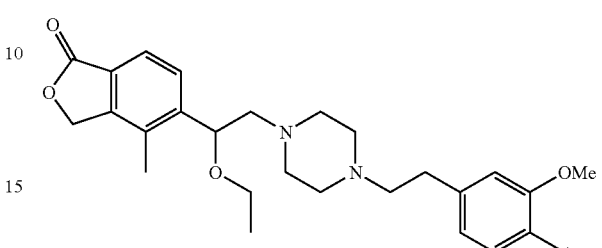

4-(2-{4-[2-(ethyloxy)-2-(4-methyl-1-oxo-1,3-dihydro-2-benzofuran-5-yl)ethyl]piperazin-1-yl}ethyl)-2-(methyloxy)benzonitrile 5-[1-(Ethyloxy)-2-piperazin-1-ylethyl]-4-methyl-2-benzofuran-1(3H)-one hydrochloride (50 mg, 0.16 mmol), 2-(methyloxy)-4-(2-oxoethyl)benzonitrile (40 mg, 0.23 mmol), sodium cyanoborohydride (14 mg, 1.7 mmol) and a stir bar were added to a 25 mL flask and few drops of AcOH. The resulting mixture was then dissolved in MeOH (3 mL) and stirred for 12 h; Analysis by LC indicated that reaction had gone to completion. The reaction mixture was treated with EtOAc (20 mL) and washed with aq. NaHCO$_3$ and aq. NaCl. The organic phase was then dried over Na$_2$SO$_4$, filtered and concentrated to dryness; the resulting residue was then dissolved in MeOH (3.5 mL), filtered and shot into Mass-directed HPLC for separation to give the desired product. LC-MS (IE, m/z): 464 [M+1]$^+$.

Example 38

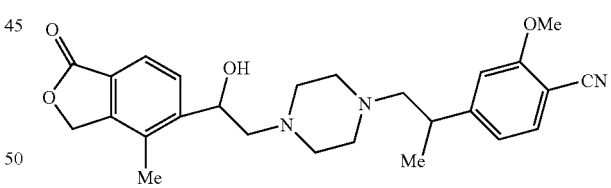

4-(2-{4-[2-hydroxy-2-(4-methyl-1-oxo-1,3-dihydro-2-benzofuran-5-yl)ethyl]piperazin-1-yl}-1-methylethyl)-2-(methyloxy)benzonitrile To 2-methoxy-4-(1-oxopropan-2-yl)benzonitrile (0.020 g, 0.106 mmol) were added dichloromethane (15 mL) and 5-[1-hydroxy-2-(piperazin-1-yl)ethyl]-4-methyl-2-benzofuran-1(3H)-one hydrochloride [(0.037 g, 0.116 mmol), in dichloromethane (2 mL), and triethylamine (0.029 mL, 0.211 mmol)], and the mixture was stirred at room temperature for 0.5 h. Sodium triacetoxyborohydride (0.112 g, 0.529 mmol) was added, and the reaction mixture was stirred at room temperature for 24 h. The reaction was quenched with water (5 mL), and the organics were extracted with EtOAc (2×40 mL). The combined organic layers were washed with water (20 mL) and brine (20 mL) and dried (MgSO$_4$). Filtration followed by concentration afforded an oily residue, which was purified via mass-directed reverse-phase HPLC followed by evaporation and drying of the pure fraction obtained which then converted to HCl salt by triturating in 1M HCl in diethyl ether (0.50 mL, 2 h). Evaporation and dried under vacuum provided 4-(2-{4-[2-hydroxy-2-(4-methyl-1-oxo-1,3-dihydro-2-benzofuran-5-yl)ethyl]piperazin-1-yl}-1-methyl-ethyl)-2-(methyloxy)benzonitrile.

$^1$H NMR (500 MHz, DMSO-d$_6$), δ 7.75 (bs, 1H), 7.73 (d, J=3.6 Hz, 1H), 7.70 (d, J=8.0 Hz, 1H), 7.29 (s, 1H), 7.10 (d, J=8.0 Hz, 1H), 5.53 (d, J=8.7 Hz, 1H), 5.41 (dd, J=8.5 Hz, 2H), 3.95 (s, 3H), 2.95-2.65 (m, 9H), 3.55-3.25 (m, 4H), 2.33 (s, 3H), 1.32 (bs, 3H);

LC/MS (M+1)$^+$=450.53.

Example 39

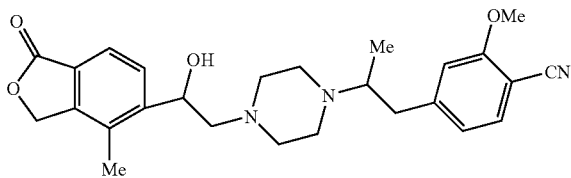 [SMILES: COc1cc(CC(C)N2CCN(CC(O)c3ccc4c(c3C)COC4=O)CC2)ccc1C#N]

4-(2-{4-[2-hydroxy-2-(4-methyl-1-oxo-1,3-dihydro-2-benzofuran-5-yl)ethyl]piperazin-1-yl}propyl)-2-(methyloxy)benzonitrile 4-(2-{4-[2-hydroxy-2-(4-methyl-1-oxo-1,3-dihydro-2-benzofuran-5-yl)ethyl]piperazin-1-yl}propyl)-2-(methyloxy)benzonitrile was prepared in a similar fashion as described for the preparation of EXAMPLE 38 starting from 5-[1-hydroxy-2-(piperazin-1-yl)ethyl]-4-methyl-2-benzofuran-1(3H)-one hydrochloride and 2-methoxy-4-(2-oxopropyl)benzonitrile.

LC/MS (M+1)$^+$=450.57.

Example 40

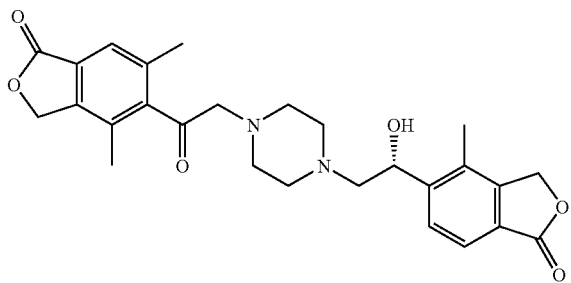 [SMILES: Cc1cc2c(c(C)c1C(=O)CN1CCN(C[C@H](O)c3ccc4c(c3C)COC4=O)CC1)COC2=O]

5-({4-[(2R)-2-hydroxy-2-(4-methyl-1-oxo-1,3-dihydro-2-benzofuran-5-yl)ethyl]piperazin-1-yl}acetyl)-4,6-dimethyl-2-benzofuran-1(3H)-one To a 5 ml microwave tube were added 5-(bromoacetyl)-4,6-dimethyl-2-benzofuran-1(3H)-one (0.220 g, 0.777 mmol), 1-[(2R)-2-hydroxy-2-(4-methyl-1-oxo-1,3-dihydro-2-benzofuran-5-yl)ethyl]piperazin-1-ium chloride (0.215 g, 0.777 mmol), and a stir bar; the mixture was dissolved in THF (2 mL). The tube was capped, degassed and purged with N$_2$. The tube was then placed in an oil bath and heated at 50° C. for 12 h; LC indicated formation of the desired product. The solution was concentrated to dryness, dissolved in MeOH (3.6 mL), filtered and was then subjected to purification by mass-directed HPLC to give 5-({4-[(2R)-2-hydroxy-2-(4-methyl-1-oxo-1,3-dihydro-2-benzofuran-5-yl)ethyl]piperazin-1-yl}acetyl)-4,6-dimethyl-2-benzofuran-1(3H)-one. LC-MS (IE, m/z): 479 [M+1]$^+$.

Example 41

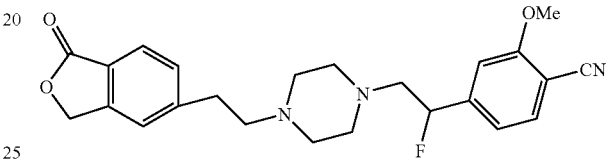

4-(1-fluoro-2-{4-[2-(1-oxo-1,3-dihydro-2-benzofuran-5-yl)ethyl]piperazin-1-yl}ethyl)-2-(methyloxy)benzonitrile Was prepared in a similar as described in EXAMPLE 11 starting from 4-(1-hydroxy-2-{4-[2-(1-oxo-1,3-dihydro-2-benzofuran-5-yl)ethyl]piperazin-1-yl}ethyl)-2-(methyloxy)benzonitrile.

$^1$H NMR (500 MHz, DMSO-d$_6$), δ 7.80 (d, J=3.9 Hz, 1H), 7.66 (s, 1H), 7.57 (bs, 1H), 7.49 (bs, 1H), 7.29 (bs, 1H), 7.13 (s, 1H), 7.18 (d, J=8.0 Hz, 1H), 4.11 (bs, 2H), 3.94 (bs, 2H), 3.60 (s, 3H), 3.45 (bs, 8H); LC/MS (M+1)$^+$=424.31.

Example 42

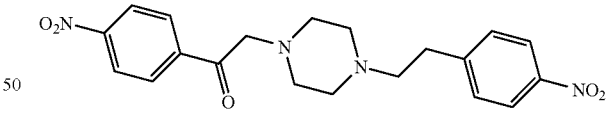

1-(4-nitrophenyl)-2-{4-[2-(4-nitrophenyl)ethyl]piperazin-1-yl}ethanone

Step A: 1-[2-(4-nitrophenyl)ethyl]piperazine hydrochloride

Triethylamine (22.6 mL, 161 mmol) was added to a stirred solution of BOC-piperazine (10.0 g, 53.7 mmol) and 4-Nitrophenethyl bromide (12.4 g, 53.7 mmol) in 100 mL DMF then the mixture was heated at 50° C. for 16 h. The reaction mixture was poured into water and extracted three times with ethyl acetate. The combined organic layers were washed three times with water, three times with 0.1 N HCl, again with water, then finally with brine. The organic layer was dried over MgSO4, filtered, most of the solvent was removed under reduced pressure, and hexane was added. The resulting precipitate was filtered and washed with hexane to yield the Boc-protected intermediate. Analysis by LC-MS showed M+H 336 and M-55 280 for the major peak at 2.4 min. The intermediate was treated with 4N HCl in dioxane (Aldrich) to yield 1-[2-(4-nitrophenyl)ethyl]piperazine hydrochloride.

$^1$H-NMR (500 MHz, DMSO): δ ppm 9.80 (b, 1H), 8.21 (d, J=8.5 Hz, 2H), 7.59 (d, J=8.5 Hz, 2H), 3.2-3.8 (m, 12H); LC-MS: M+1=236.

Step B: 1-(4-nitrophenyl)-2-{4-[2-(4-nitrophenyl)ethyl]piperazin-1-yl}ethanone 2-Bromo-1-(4-nitrophenyl)ethanone (269 mg, 1.10 mmol) was added to a stirred solution of 1-[2-(4-nitrophenyl)ethyl]piperazine hydrochloride (200 mg, 0.736 mmol) followed by Hünig's base, then was stirred at RT for 1 h. The reaction mixture was poured into saturated NH$_4$Cl solution and extracted twice with ethyl acetate. The combined organic layers were washed with water, then brine. The organic layer was dried over MgSO$_4$, filtered, and concentrated. The residue was purified by preparative TLC using 5% MeOH/DCM solvent system to yield 1-(4-nitrophenyl)-2-{4-[2-(4-nitrophenyl)ethyl]piperazin-1-yl}ethanone.

$^1$H-NMR (500 MHz, CDCl$_3$): δ ppm 8.32 (d, J=8.5 Hz, 2H), 8.19 (d, J=8.5 Hz, 2H, 7.50 (d, J=8.5 Hz, 2H), 3.87 (s, 2H), 3.31 (s, 4H), 2.86 (t, J=7.5 Hz, 2H), 2.55 (t, J=7.5 Hz, 2H), 2.45 (b, 4H); LC-MS: M+1=399.4.

Example 43

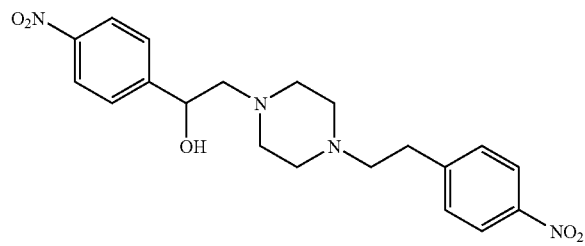 [SMILES: O=[N+]([O-])c1ccc(CCN2CCN(CC(O)c3ccc([N+](=O)[O-])cc3)CC2)cc1]

1-(4-nitrophenyl)-2-{4-[2-(4-nitrophenyl)ethyl]piperazin-1-yl}ethanol

Sodium borohydride (8.0 mg, 0.21 mmol) was added to 1-(4-nitrophenyl)-2-{4-[2-(4-nitrophenyl)ethyl]piperazin-1-yl}ethanone (20 mg, 0.050 mmol) in ethanol (1 mL) and stirred at RT for 2 h. The reaction mixture was poured into water and extracted twice with EtOAc, twice with brine, then was dried over MgSO4, and evaporated to dryness. The crude material was purified by preparative TLC using 5% (10% NH$_4$OH in MeOH): 95% DCM solvent system to yield 1-(4-nitrophenyl)-2-{4-[2-(4-nitrophenyl)ethyl]piperazin-1-yl}ethanol.

LC-MS: M+1=401.

Example 44

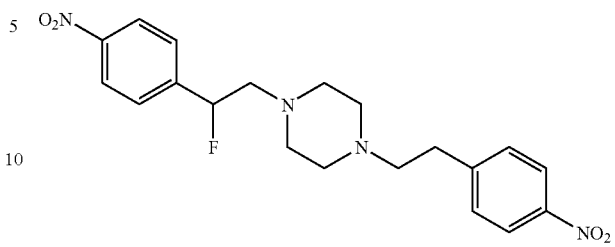

1-[2-fluoro-2-(4-nitrophenyl)ethyl]-4-[2-(4-nitrophenyl)ethyl]piperazine

DAST (6.6 μL, 0.050 mmol) was added to 1-(4-nitrophenyl)-2-{4-[2-(4-nitrophenyl)ethyl]piperazin-1-yl}ethanol (10 mg, 0.025 mmol) in DCM (1 mL) and the resulting mixture was stirred at RT for 72 h. Then 1 N NaOH was added and the mixture was extracted twice with DCM. The combined organic layers were dried over MgSO4, filtered, and evaporated to dryness. The crude product was purified by mass directed preparative HPLC to yield 1-[2-fluoro-2-(4-nitrophenyl)ethyl]-4-[2-(4-nitrophenyl)ethyl]piperazine.

LC-MS: M+1=403.

Example 45

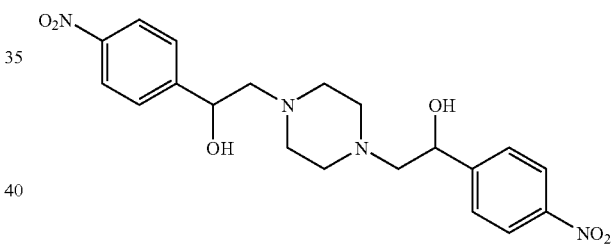

2,2'-piperazine-1,4-diylbis[1-(4-nitrophenyl)ethanol]

Step A: 2,2'-piperazine-1,4-diylbis[1-(4-nitrophenyl)ethanone]

2-bromo-1-(4-nitrophenyl)ethanone (3.117 g, 12.77 mmol) was added to a solution of piperazine (0.500 g, 5.80 mmol) and N,N-diisopropylethylamine (4.06 mL, 23.2 mmol) in THF (25 mL) at 0° C. The reaction mixture was allowed to warm up to room temperature and was stirred for ½ h. The reaction mixture was poured into water and extracted twice with DCM. The combined organic layers were dried over MgSO$_4$ then filtered and evaporated to dryness. The residue was purified by MPLC using a 120 g. Redi-sep column and eluting with 0%-5% MeOH/DCM solvent system to yield 2,2'-piperazine-1,4-diylbis[1-(4-nitrophenyl)ethanone] (1.9 g, 79%). LC-MS: M+1=413.

Step B: 2,2'-piperazine-1,4-diylbis[1-(4-nitrophenyl)ethanol]

NaBH$_4$ (308 mg, 8.15 mmol) was added to a 25 mL ethanol solution of 2,2'-piperazine-1,4-diylbis[1-(4-nitrophenyl)

ethanone] (400 mg, 0.970 mmol) at 0° C. The reaction mixture was allowed to warm up to room temperature and stir overnight. The reaction mixture was poured into water and extracted twice with EtOAc. The combined organic layers were washed with brine twice, then dried over $MgSO_4$, filtered, and evaporated to dryness. The residue was purified by preparative TLC using 5% methanol in DCM to yield 2,2'-piperazine-1,4-diylbis[1-(4-nitrophenyl)ethanol].

$^1$H-NMR (500 MHz, DMSO): δ ppm 8.25 (d, J=8.5 Hz, 4H), 7.69 (d, J=8.5 Hz, 4H), 5.19 (d, J=10 Hz, 2H), 3.77 (s, 2H), 3.56-3.59 (b, 6H), 3.37 (d, J=13 Hz, 2H), 3.28 (t, J=13 Hz, 2H). LC-MS: M+1=417.

Example 46

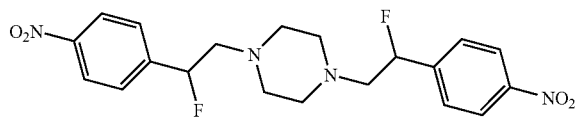 [SMILES: O=[N+]([O-])c1ccc(C(F)CN2CCN(CC(F)c3ccc([N+](=O)[O-])cc3)CC2)cc1]

1,4-bis[2-fluoro-2-(4-nitrophenyl)ethyl]piperazine

DAST (464 mg, 2.88 mmol) was added to 2,2'-piperazine-1,4-diylbis[1-(4-nitrophenyl)ethanol] (from EXAMPLE 44, 300 mg, 0.720 mmol) in DCM (10 mL) at 0° C. The reaction mixture was allowed to warm to room temperature and stir overnight. The reaction mixture was poured into cold water and extracted twice with DCM. The combined organic layers were washed with brine, dried over MgSO4, filtered, and evaporated to dryness. The crude material was purified by preparative TLC using 5% (10% $NH_4OH$ in MeOH): 95% DCM solvent system to yield 1,4-bis[2-fluoro-2-(4-nitrophenyl)ethyl]piperazine.

$^1$H-NMR (500 MHz, DMSO): δ ppm 8.29 (d, J=8.5 Hz, 4H), 7.70 (d, J=8.5 Hz, 4H), 6.17 (d, J=9 Hz, 1H), 6.07 (d, J=9 Hz, 1H), 3.40 (m, 2H), 3.25 (d, J=14.5 Hz, 2H), 3.03-3.20 (m, 8H). LC-MS: M+1=421.

Example 47

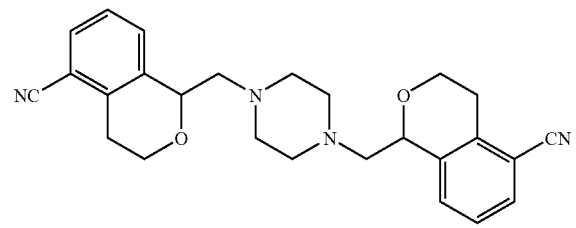

1,1'-(piperazine-1,4-diyldimethanediyl)bis(3,4-dihydro-1H-isochromene-5-carbonitrile)

Step A: 1-[(5-bromo-3,4-dihydro-1H-isochromen-1-yl)methyl]piperazine

A solution of 1,1-dimethylethyl-4-[(5-bromo-3,4-dihydro-1H-isochromen-1-yl)methyl]piperazine-1-carboxylate (480 mg, 1.2 mmol) in 10 mL of DCM was added 10 mL of 4N HCl/dioxane, and then stirred at room temperature for 2 hours. The solvents was removed under vacuum to afford 1-[(5-bromo-3,4-dihydro-1H-isochromen-1-yl)methyl]piperazine.

$^1$H-NMR (400 MHz, MeOD) δ 7.55 (d, J=8.0 Hz, 1H), 7.27 (d, J=8.0 Hz, 1H), 7.19 (t, J=8.0 Hz, 1H), 3.34 (d, J=8.0 Hz, 1H), 4.23~4.29 (m, 1H), 3.92~3.95 (m, 1H), 3.85~3.90 (m, 1H), 3.84 (brs, 4H), 3.64~3.71 (m, 6H), 3.58~3.61 (m, 1H).

Step B: 1,4-bis[(5-bromo-3,4-dihydro-1H-isochromen-1-yl)methyl]piperazine

To a solution of 1-[(5-bromo-3,4-dihydro-1H-isochromen-1-yl)methyl]piperazine (160 mg, 0.52 mmol) in DCM/MeOH (1:1, 5 mL) was added DIEA (134 mg, 1.03 mmol), and then mixture was stirred at r.t for 10 min. Then AcOH (62 mg, 1.03 mmol), $NaCNBH_3$ (65 mg, 1.03 mmol) and 5-bromo-3,4-dihydro-1H-isochromene-1-carbaldehyde (125 mg, 0.516 mmol) were added into the mixture. The reaction solution was stirred at ambient temperature overnight. The reaction mixture was added water and extracted with DCM. The organic layer was dried over anhydrous sodium sulfate and concentrated. The residue was purified with prep-TLC to give the product 1,4-bis[(5-bromo-3,4-dihydro-1H-isochromen-1-yl)methyl]piperazine.

Step C: 1,1'-(piperazine-1,4-diyldimethanediyl)bis(3,4-dihydro-1H-isochromene-5-carbonitrile)

A solution of 1,4-bis[(5-bromo-3,4-dihydro-1H-isochromen-1-yl)methyl]piperazine (130 mg, 0.24 mmol), $Pd(PPh_3)_4$ (56 mg, 0.050 mmol) and $Zn(CN)_2$ (85 mg, 0.73 mmol) in 5 mL of anhydrous DMF was to 120° C. at $N_2$ atmosphere for 6 hours. After cooled to r.t., the mixture was partitioned between EtOAc and water. The organic layer was dried over anhydrous sodium sulfate and concentrated. The residue was purified with prep-TLC to afford 1,1'-(piperazine-1,4-diyldimethanediyl)bis(3,4-dihydro-1H-isochromene-5-carbonitrile)

$^1$H-NMR (400 MHz, MeOD) δ: 7.64 (d, J=8.0 Hz, 2H), 7.53 (d, J=8.0 Hz, 2H), 7.39 (t, J=8.0 Hz, 2H), 5.13 (d, J=8.0 Hz, 2H), 4.22~4.27 (m, 2H), 3.83~3.89 (m, 2H), 3.37~3.41 (m, 2H), 3.20~3.25 (m, 10H), 3.10~3.12 (m, 2H), 2.92~3.08 (m, 2H).

Example 48

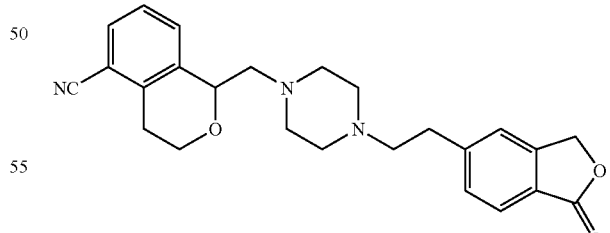

1-({4-[2-(1-oxo-1,3-dihydro-2-benzofuran-5-yl)ethyl]piperazin-1-yl}methyl)-3,4-dihydro-1H-isochromene-5-carbonitrile A mixture of 1-formyl-3,4-dihydro-1H-isochromene-5-carbonitrile (65 mg, 0.35 mmol), 5-(2-piperazin-1-ylethyl)-2-benzofuran-1(3H)-one hydrochloride (100 mg, 0.35 mmol), DIEA (45 mg, 0.35 mmol), AcOH (21 mg, 0.35 mmol) in 3 mL of DCM was stirred 30 min at room temperature and then NaBH(OAc)$_3$ (440 mg, 2.1 mmol) was added. The mixture was stirred over night at room temperature. Water was added and the mixture was extracted with DCM. The combined organic layers were washed with brine, dried over anhydrous Na$_2$SO$_4$, concentrated and the residue was purified by prep-HPLC to give 1-({4-[2-(1-oxo-1,3-dihydro-2-benzofuran-5-yl)ethyl]piperazin-1-yl}methyl)-3,4-dihydro-1H-isochromene-5-carbonitrile.

$^1$H-NMR (400 MHz, MeOD) δ 7.68-7.69 (m, 1H), 7.60~7.61 (m, 1H), 7.48~7.50 (m, 3H), 7.47~7.49 (m, 1H), 5.32 (s, 2H), 5.18~5.19 (m, 1H), 4.20~4.22 (m, 1H), 3.79~4.02 (m, 1H), 3.30~3.55 (m, 12H), 2.80~3.21 (m, 4H).

MS: m/z 418 (M+1)$^+$.

Example 49

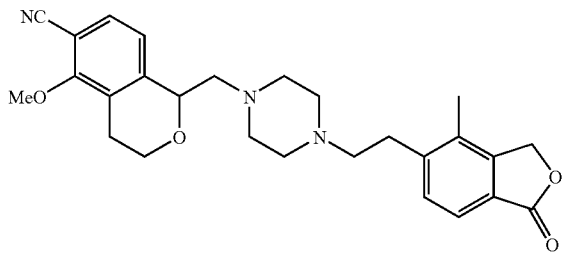

1-({4-[2-(4-methyl-1-oxo-1,3-dihydro-2-benzofuran-5-yl)ethyl]piperazin-1-yl}methyl)-5-(methyloxy)-3,4-dihydro-1H-isochromene-6-carbonitrile Step A: methyl(2-hydroxyphenyl)acetate To a solution of (2-hydroxyphenyl)acetic acid (11 g, 72.3 mmol) in 100 mL of MeOH was added SOCl$_2$ (17.2 g, 144.7 mmol) at 0° C. The mixture was stirred at 50° C. overnight. The reaction was concentrated. The residue was purified column chromatography to give methyl(2-hydroxyphenyl)acetate.

Step B: methyl(3-bromo-2-hydroxyphenyl)acetate

To a solution of methyl(2-hydroxyphenyl)acetate (14.0 g, 84.3 mmol) in 100 mL of DCM was added diisopropyl-amine (1.70 g, 16.8 mmol) and NBS (15 g, 84.2 mmol) at 0° C. The mixture was stirred at 0° C. for 1 h. The reaction was poured into 1N HCl, extracted with DCM, and concentrated to give crude methyl(3-bromo-2-hydroxyphenyl)acetate.

Step C: methyl[3-bromo-2-(methyloxy)phenyl]acetate

To a solution of methyl(3-bromo-2-hydroxyphenyl)acetate (18.7 g, 76.3 mmol) in 200 mL of DMF was added K$_2$CO$_3$ (52.7 g, 382 mmol), MeI (14.0 mL, 229 mmol). The mixture was stirred at 50° C. for 3 hours. The reaction solution was diluted with EtOAc and water. The organic layer was dried over anhydrous sodium sulfate and concentrated. The residue was purified column chromatography to give methyl[3-bromo-2-(methyloxy)phenyl]acetate.

Step D: 2-[3-bromo-2-(methyloxy)phenyl]ethanol

To a solution of methyl[3-bromo-2-(methyloxy)phenyl]acetate (8.20 g, 31.7 mmol) in 200 mL of dry THF under N$_2$ at room temperature was added LiBH$_4$ (32 mL, 63.32 mmol, 2M THF). After 1.5 hours, the reaction was warmed to reflux for 3 hours, and then cooled to room temperature. The solution was poured into EtOAc/1N HCl solution, and the layers were separated. The organic layer was washed with water, saturated Na$_2$CO$_3$ and brine, dried over anhydrous Na$_2$SO$_4$ and concentrated to give 2-[3-bromo-2-(methyloxy)phenyl]ethanol Step E: methyl 6-bromo-5-(methyloxy)-3,4-dihydro-1H-isochromene-1-carboxylate bromo-2-(methyloxy)phenyl]ethanol (6 g, 26.0 mmol) and ethyl bis(ethyloxy)acetate (5.50 g, 31.1 mmol) in 60 mL of CH$_3$NO$_2$. After stirred for 10 min, the ice bath was removed and the mixture was allowed to stir at room temperature over night. The mixture was poured onto ice/aqueous 1N HCl. Extracted by DCM and backwashed with 1N HCl and brine, dried over anhydrous sodium sulfate and concentrated. The residue was purified via column chromatograph to give methyl 6-bromo-5-(methyloxy)-3,4-dihydro-1H-isochromene-1-carboxylate.

Step F: 6-bromo-5-(methyloxy)-3,4-dihydro-1H-isochromene-1-carboxylic acid

To a solution of methyl 6-bromo-5-(methyloxy)-3,4-dihydro-1H-isochromene-1-carboxylate (650 mg, 2.06 mmol) in 20 mL of MeOH/THF/H$_2$O (2/2/1) was added LiOH.H$_2$O (347 mg, 8.25 mmol), and the mixture was stirred at ambient temperature overnight. The solvents were removed under vacuum, and the residue was added 50 mL of water and extracted with ether. The aqueous layer was then acidified with 4 N HCl to pH=3 in ice bath, and extracted with EtOAc. The combined organic phase was washed with brine, dried over anhydrous sodium sulfate and concentrated to give 6-bromo-5-(methyloxy)-3,4-dihydro-1H-isochromene-1-carboxylic acid.

Step G: 6-bromo-N-methyl-N,5-bis(methyloxy)-3,4-dihydro-1H-isochromene-1-carboxamide A mixture of 6-bromo-5-(methyloxy)-3,4-dihydro-1H-isochromene-1-carboxylic acid (600 mg, 2.08 mmol) and CDI (475 mg, 2.93 mmol) in 20 mL of dry DCM was stirred at r.t. for 0.5 hours and then O,N-dimethyl-hydroxylamine (285 mg, 2.93 mmol) was added. The result mixture was stirred overnight. The solvents were removed under vacuum, and the residue was purified by preparative TLC to give 6-bromo-N-methyl-N,5-bis(methyloxy)-3,4-dihydro-1H-isochromene-1-carboxamide.

Step H: 6-bromo-5-(methyloxy)-3,4-dihydro-1H-isochromene-1-carbaldehyde

To a solution of 6-bromo-N-methyl-N,5-bis(methyloxy)-3,4-dihydro-1H-isochromene-1-carboxamide (300 mg, 0.9 mmol) in 20 mL of anhydrous THF was cooled to −30° C. and then DIBAL-H (1.3 mL, 1.3 mmol, 1M) was added. The mixture was stirred at −30° C. for 2 hours. The reaction was quenched with water and extracted with DCM. The organic layer was washed with brine, dried over anhydrous sodium sulfate and concentrated. The crude 6-bromo-5-(methyloxy)-3,4-dihydro-1H-isochromene-1-carbaldehyde was used for next step without purification.

Step I: 1,1-dimethylethyl-4-{[6-bromo-5-(methyloxy)-3,4-dihydro-1H-isochromen-1-yl]methyl}piperazine-1-carboxylate To a solution of 6-bromo-5-(methyloxy)-3,4-dihydro-1H-isochromene-1-carbaldehyde (230 mg, 0.85 mmol) in 10 mL of DCM was added 1,1-dimethylethyl piperazine-1-carboxylate (189 mg, 1.02 mmol) and NaBH(OAc)$_3$ (720 mg, 3.4 mmol), and the mixture was stirred at room temperature overnight. The reaction was diluted with DCM, and washed with brine. The organic layer was dried over anhydrous Na$_2$SO$_4$ and concentrated. The residue was purified by prep-TLC to give 1,1-dimethylethyl-4-{[6-bromo-5-(methyloxy)-3,4-dihydro-1H-isochromen-1-yl]methyl}piperazine-1-carboxylate).

Step J: 1,1-dimethylethyl-4-{[6-cyano-5-(methyloxy)-3,4-dihydro-1H-isochromen-1-yl]methyl}piperazine-1-carboxylate To a solution of 1,1-dimethylethyl-4-{[6-bromo-5-(methyloxy)-3,4-dihydro-1H-isochromen-1-yl]methyl}piperazine-1-carboxylate (50 mg, 0.11 mmol), Pd(PPh$_3$)$_4$ (20 mg) and Zn(CN)$_2$ (26 mg, 0.23 mmol) in 5 mL of anhydrous DMF was to 110° C. at N$_2$ atmosphere overnight. The reaction was cooled to room temperature, extracted by EtOAc, washed by water then by brine. The organic layer was dried over anhydrous sodium sulfate and concentrated. The residue was purified with prep-TLC to afford 1,1-dimethylethyl-4-{[6-cyano-5-(methyloxy)-3,4-dihydro-1H-isochromen-1-yl]methyl}piperazine-1-carboxylate).

Step K: 5-(methyloxy)-1-(piperazin-1-ylmethyl)-3,4-dihydro-1H-isochromene-6-carbonitrile To a solution of 1,1-dimethylethyl-4-{[6-cyano-5-(methyloxy)-3,4-dihydro-1H-isochromen-1-yl]methyl}piperazine-1-carboxylate (30 mg, 0.08 mmol) in 5 mL of DCM was added 5 mL of TFA was stirred at room temperature for 1 hours, and the reaction was concentrated. The resulting crude 5-(methyloxy)-1-(piperazin-1-ylmethyl)-3,4-dihydro-1H-isochromene-6-carbonitrile was directly used in next step.

Step L: 1-({4-[2-(4-methyl-1-oxo-1,3-dihydro-2-benzofuran-5-yl)ethyl]piperazin-1-yl}methyl)-5-(methyloxy)-3,4-dihydro-1H-isochromene-6-carbonitrile To a solution of 5-(methyloxy)-1-(piperazin-1-ylmethyl)-3,4-dihydro-1H-isochromene-6-carbonitrile (0.04 mmol) in 5 mL of DCM was added (4-methyl-1-oxo-1,3-dihydro-2-benzofuran-5-yl)acetaldehyde (from Step B, Intermediate 17, 11 mg, 0.06 mmol) and NaBH(OAc)$_3$ (34 mg, 0.16 mmol), the mixture was stirred at room temperature overnight. The reaction was diluted with DCM and washed with brine. The organic layer was dried over anhydrous Na$_2$SO$_4$ and concentrated. The residue was purified by prep-TLC to give 1-({4-[2-(4-methyl-1-oxo-1,3-dihydro-2-benzofuran-5-yl)ethyl]piperazin-1-yl}methyl)-5-(methyloxy)-3,4-dihydro-1H-isochromene-6-carbonitrile.
$^1$H-NMR (400 MHz, CDCl3) δ ppm 7.62 (d, J=7.8 Hz, 1H), 7.33 (d, J=8.6 Hz, 1H), 7.28 (d, J=7.8 Hz, 1H), 6.98 (d, J=7.8 Hz, 1H), 5.17 (s, 2H), 4.80~4.90 (m, 1H), 4.08~4.13 (m, 1H), 3.98 (s, 3H), 3.60~3.67 (m, 1H), 2.49~2.79 (m, 16H), 2.24 (s, 3H).

Example 50

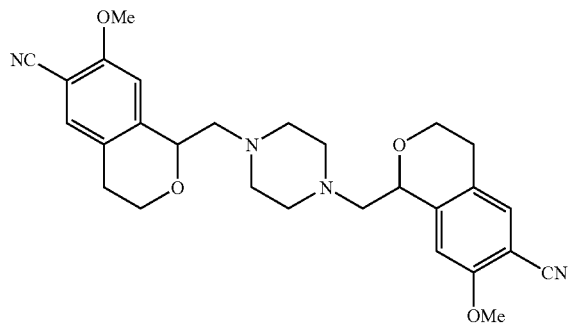

1,1'-(Piperazine-1,4-diyldimethanediyl)bis[7-(methyloxy)-3,4-dihydro-1H-isochromene-6-carbonitrile]

Step A: 1,4-bis{[6-bromo-7-(methyloxy)-3,4-dihydro-1H-isochromen-1-yl]methyl}piperazine To a solution of 1-{[6-bromo-7-(methyloxy)-3,4-dihydro-1H-isochromen-1-yl]methyl}piperazine (100 mg, 0.3 mmol) in 5 mL of DCM was added 6-bromo-7-(methyloxy)-3,4-dihydro-1H-isochromene-1-carbaldehyde (81 mg, 0.30 mmol) and NaBH(OAc)$_3$ (127 mg, 0.6 mmol). The mixture was stirred at room temperature overnight. The reaction mixture was diluted with DCM and washed with brine. The organic layer was dried over anhydrous Na$_2$SO$_4$ and concentrated. The residue was purified by prep-TLC to give 1,4-bis{[6-bromo-7-(methyloxy)-3,4-dihydro-1H-isochromen-1-yl]methyl}piperazine.

Step B: 1,1'-(Piperazine-1,4-diyldimethanediyl)bis[7-(methyloxy)-3,4-dihydro-1H-isochromene-6-carbonitrile]

A solution of 1,4-bis{[6-bromo-7-(methyloxy)-3,4-dihydro-1H-isochromen-1-yl]methyl}piperazine (30 mg, 0.05 mmol), Pd(PPh$_3$)$_4$ (10 mg) and Zn(CN)$_2$ (58 mg, 0.10 mmol) in 8 mL of anhydrous DMF was heated to 110° C. under a N$_2$ atmosphere overnight. The reaction mixture was cooled to room temperature, extracted with EtOAc, washed with water then with brine. The organic layer was dried over anhydrous sodium sulfate and concentrated. The residue was purified with prep-TLC to afford the title compound.
$^1$H-NMR (400 MHz, CDCl$_3$) δ ppm 7.22 (s, 2H), 6.94 (s, 2H), 4.11~4.02 (m, 2H), 3.71 (s, 6H), 3.59 (s, 4H), 2.51~2.89 (m, 14H).

Example 51

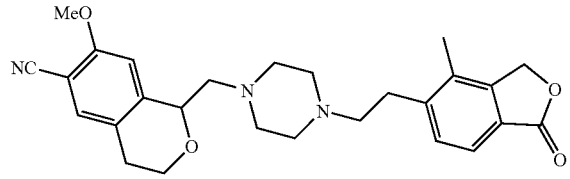

1-({4-[2-(4-methyl-1-oxo-1,3-dihydro-2-benzofuran-5-yl)ethyl]piperazin-1-yl}methyl)-7-(methyloxy)-3,4-dihydro-1H-isochromene-6-carbonitrile

Step A: 1,1-dimethylethyl-4-{[6-cyano-7-(methyloxy)-3,4-dihydro-1H-isochromen-1-yl]methyl}piperazine-1-carboxylate A solution of 1,1-dimethylethyl-4-{[6-bromo-7-(methyloxy)-3,4-dihydro-1H-isochromen-1-yl]methyl}piperazine-1-carboxylate (350 mg, 0.79 mmol), Pd(PPh$_3$)$_4$ (180 mg, 0.15 mmol) and Zn(CN)$_2$ (187 mg, 1.60 mmol) in 10 mL of anhydrous DMF was heated to 110° C. under a N$_2$ atmosphere overnight. The reaction was cooled to room temperature, extracted with EtOAc, washed with water then by brine. The organic layer was dried over anhydrous sodium sulfate and concentrated. The residue was purified with prep-TLC to afford 1,1-dimethylethyl-4-{[6-cyano-7-(methyloxy)-3,4-dihydro-1H-isochromen-1-yl]methyl}piperazine-1-carboxylate.

Step B: 7-(methyloxy)-1-(piperazin-1-ylmethyl)-3,4-dihydro-1H-isochromene-6-carbonitrile To a solution of 1,1-dimethylethyl-4-{[6-cyano-7-(methyloxy)-3,4-dihydro-1H-isochromen-1-yl]methyl}piperazine-1-carboxylate (270 mg, 0.697 mmol) in 5 mL of DCM was added 5 mL of TFA and the mixture was stirred at room temperature for 1 h. The reaction mixture was concentrated to afford 7-(methyloxy)-1-(piperazin-1-ylmethyl)-3,4-dihydro-1H-isochromene-6-carbonitrile. The residue was directly used in next step.

Step C: 1-({4-[2-(4-Methyl-1-oxo-1,3-dihydro-2-benzofuran-5-yl)ethyl]piperazin-1-yl}methyl)-7-(methyloxy)-3,4-dihydro-1H-isochromene-6-carbonitrile To a solution of 7-(methyloxy)-1-(piperazin-1-ylmethyl)-3,4-dihydro-1H-isochromene-6-carbonitrile (50 mg, 0.18 mmol) in 5 mL of DCM was added (4-methyl-1-oxo-1,3-dihydro-2-benzofuran-5-yl)acetaldehyde (from Step B, Intermediate 17, 33 mg, 0.18 mmol) and NaBH(OAc)$_3$ (100 mg, 0.5 mmol). The mixture was stirred at room temperature overnight. The reaction mixture was diluted with DCM and washed with brine. The organic layer was dried over anhydrous Na$_2$SO$_4$ and concentrated. The residue was purified by prep-TLC to give the title compound. $^1$H-NMR (400 MHz, MeOD) δ ppm 7.65 (d, J=7.8 Hz, 1H), 7.45 (d, J=7.0 Hz, 2H), 6.99 (s, 1H), 5.34 (s, 2H), 5.14~5.17 (m, 1H), 4.14~4.19 (m, 1H), 3.92 (s, 3H), 3.74~3.80 (m, 1H), 3.46~3.50 (m, 1H), 3.31~3.35 (m, 2H), 3.04~3.27 (m, 10H), 2.86~2.94 (m, 1H), 2.68~2.74 (m, 1H), 2.34 (s, 3H); MS m/e 462 (M+1)$^+$.

Example 52

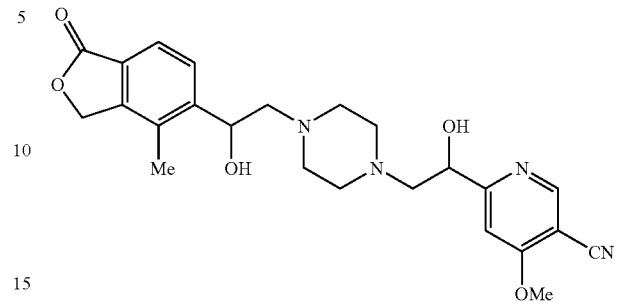

6-(1-Hydroxy-2-{4-[2-hydroxy-2-(4-methyl-1-oxo-1,3-dihydro-2-benzofuran-5-yl)ethyl]piperazin-1-yl}ethyl)-4-methoxypyridine-3-carbonitrile To a microwave tube were added 4-methoxy-6-(oxiran-2-yl)pyridine-3-carbonitrile (20.0 mg, 0.114 mmol), 5-[1-hydroxy-2-(piperazin-1-yl)ethyl]-4-methyl-2-benzofuran-1(3H)-one (37.6 mg, 0.136 mmol, as a free base), and EtOH (3.0 mL). The mixture was heated in the microwave for 30 min at 150° C. The solvent was evaporated and the crude product was purified by mass directed reverse-phase HPLC Chromatography to give the title compound as an off white foam (TFA salt). Further, the product was treated with 1 M HCl in diethyl ether (1 mL) to give the final product as an HCl salt.

$^1$H NMR (500 MHz, DMSO-d$_6$), δ 8.79 (s, 1H), 7.74 (m, 2H), 7.39 (s, 1H), 5.41 (dd, J=5.9 Hz, J=5.6 Hz, 1H), 5.38 (bs, 1H), 4.99 (bs, 1H), 4.03 (s, 3H), 3.99-3.42 (m, 8H), 3.05-2.99 (m, 4H), 2.31 (s, 3H); LC/MS: (IE, m/z) [(M+1)]$^+$=453.11.

Examples 52A and 52B

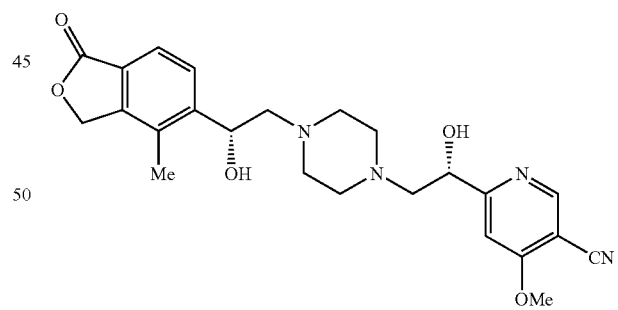

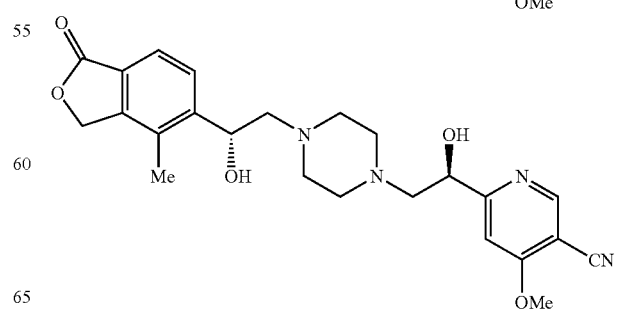

6-[(1S)-1-hydroxy-2-{4-[(2R)-2-hydroxy-2-(4-methyl-1-oxo-1,3-dihydro-2-benzofuran-5-yl)ethyl]piperazin-1-yl}ethyl]-4-methoxypyridine-3-carbonitrile and 6-[(1R)-1-hydroxy-2-{4-[(2R)-2-hydroxy-2-(4-methyl-1-oxo-1,3-dihydro-2-benzofuran-5-yl)ethyl]piperazin-1-yl}ethyl]-4-methoxypyridine-3-carbonitrile 6-[(1S)-1-Hydroxy-2-{4-[(2R)-2-hydroxy-2-(4-methyl-1-oxo-1,3-dihydro-2-benzofuran-5-yl)ethyl]piperazin-1-yl}ethyl]-4-methoxypyridine-3-carbonitrile and 6-[(1R)-1-hydroxy-2-{4-[(2R)-2-hydroxy-2-(4-methyl-1-oxo-1,3-dihydro-2-benzofuran-5-yl)ethyl]piperazin-1-yl}ethyl]-4-methoxypyridine-3-carbonitrile were each individually prepared in an analogous fashion to EXAMPLE 2C from 4-methyl-5-[(2R)-oxiran-2-yl]-2-benzofuran-1(3H)-one and either isomer A or B of 6-[1-hydroxy-2-(piperazin-1-yl)ethyl]-4-methoxypyridine-3-carbonitrile.

52A: LC/MS: (IE, m/z) [(M+1)]$^+$=453
52B: LC/MS: (IE, m/z) [(M+1)]$^+$=453

Example 53

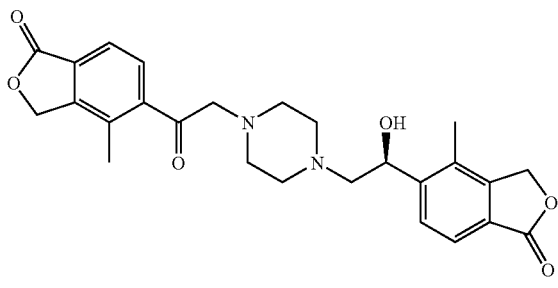 [SMILES: Cc1c(C(=O)CN2CCN(C[C@@H](O)c3ccc4c(c3C)COC4=O)CC2)ccc2c1COC2=O]

5-({4-[(2S)-2-hydroxy-2-(4-methyl-1-oxo-1,3-dihydro-2-benzofuran-5-yl)ethyl]piperazin-1-yl}acetyl)-4-methyl-2-benzofuran-1(3H)-one To a solution of oxalyl chloride (71 uL, 0.82 mmol) in DCM (30 mL) was dropped DMSO (120 uL, 1.6 mmol) at −78° C. After stirring the mixture for 10 minutes, a DCM solution of 5,5'-{piperazine-1,4-diylbis[(1S)-1-hydroxyethane-2,1-diyl]}bis(4-methyl-2-benzofuran-1(3H)-one) (380 mg, 0.82 mmol) was added into the reaction. The reaction was stir for another 20 minutes before TEA (570 uL, 4.1 mmol) was added to the reaction mixture. The reaction was then allowed to warm up to RT slowly. TLC analysis showed two new spots right above the SM. LC analysis suggested formation of the mono-ketone as well as the di-ketone. The reaction was diluted with DCM, washed with water, dried over sodium sulfate, and purified by flash chromatography. The title product was collected after removal of solvent.

$^1$H-NMR (500 MHz, CDCl$_3$) δ ppm 7.83 (d, J=8 Hz, 1H), 7.79-7.76 (m, 3H), 5.31 (s, 2H), 5.24 (s, 2H), 5.08 (dd, J=11, 2.5 Hz, 1H), 3.76 (s, 2H), 2.86 (broad, 2H), 2.70 (broad, 4H), 2.62-2.51 (m, 3H), 2.43 (s, 3H), 2.45-2.39 (m, 1H), 2.27 (s, 3H); LCMS M+1 (calc. 465.19, found 465.35).

Example 54

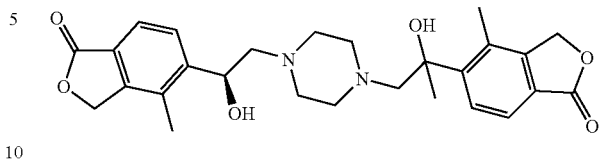

5-(1-hydroxy-2-{4-[(2S)-2-hydroxy-2-(4-methyl-1-oxo-1,3-dihydro-2-benzofuran-5-yl)ethyl]piperazin-1-yl}-1-methylethyl)-4-methyl-2-benzofuran-1(3H)-one To a solution of 5-({4-[(2S)-2-hydroxy-2-(4-methyl-1-oxo-1,3-dihydro-2-benzofuran-5-yl)ethyl]piperazin-1-yl}acetyl)-4-methyl-2-benzofuran-1(3H)-one (50 mg, 0.108 mmol) in THF (2 mL) in a 25 mL flask was added methyl lithium (2 mg, 0.1 mmol) at 0° C. The reaction mixture was stirred for 20 min.; LC analysis indicated formation of the desired product. The solution was concentrated to dryness, dissolved in MeOH (3.5 mL), filtered and was then purified by mass-directed HPLC to give 5-(1-hydroxy-2-{4-[(2S)-2-hydroxy-2-(4-methyl-1-oxo-1,3-dihydro-2-benzofuran-5-yl)ethyl]piperazin-1-yl}-1-methylethyl)-4-methyl-2-benzofuran-1(3H)-one. LC-MS (IE, m/z): 481 [M+1]$^+$.

Example 55

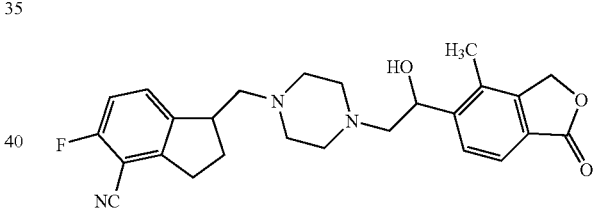

5-fluoro-1-({4-[2-hydroxy-2-(4-methyl-1-oxo-1,3-dihydro-2-benzofuran-5-yl)ethyl]piperazin-1-yl}methyl)-2,3-dihydro-1H-indene-4-carbonitrile 5-Fluoro-1-(piperazin-1-ylmethyl)-2,3-dihydro-1H-indene-4-carbonitrile (60 mg, 0.23 mmol), 4-methyl-5-oxiran-2-yl-2-benzofuran-1(3H)-one (88 mg, 0.46 mmol), were added to a 5 mL microwave tube containing a stir bar; to the mixture was added EtOH (2.5 mL). The tube was capped, degassed and purged with N$_2$. It was then placed in a microwave reactor and heated at 120° C. for 1 hour; LC indicated formation of some desired product. The tube was again placed in a microwave reactor and heated again at 150° C. for 30 min; LC indicated formation of more product. The solution was concentrated to dryness, re-dissolved in DCM (20 mL) and was then absorbed into silica gel. It was then loaded onto a silica column for separation with the solvent system of (10% MeOH in DCM), to give 5-fluoro-1-({4-[2-hydroxy-2-(4-methyl-1-oxo-1,3-dihydro-2-benzofuran-5-yl)ethyl]piperazin-1-yl}methyl)-2,3-dihydro-1H-indene-4-carbonitrile. LC-MS (IE, m/z): 450 [M+1]$^+$.

Example 56

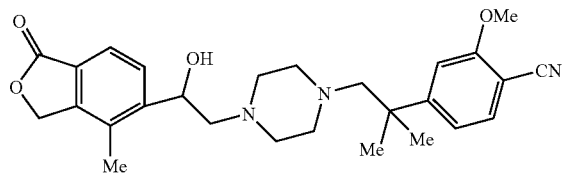 [SMILES: COc1cc(C(C)(C)CN2CCN(CC(O)c3ccc4c(c3C)COC4=O)CC2)ccc1C#N]

4-(2-{4-[2-hydroxy-2-(4-methyl-1-oxo-1,3-dihydro-2-benzofuran-5-yl)ethyl]piperazin-1-yl}-1,1-dimethylethyl)-2-(methyloxy)benzonitrile 4-(2-{4-[2-hydroxy-2-(4-methyl-1-oxo-1,3-dihydro-2-benzofuran-5-yl)ethyl]piperazin-1-yl}-1,1-dimethylethyl)-2-(methyloxy)benzonitrile was prepared in a similar fashion as described for the preparation of EXAMPLE 38. LC/MS (M+1)$^+$=464.56.

Example 57A and 57B

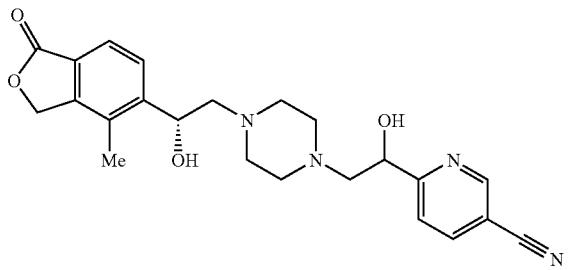 [SMILES: Cc1c([C@@H](O)CN2CCN(CC(O)c3ccc(C#N)cn3)CC2)ccc2c1COC2=O]

6-(1-Hydroxy-2-{4-[(2R)-2-hydroxy-2-(4-methyl-1-oxo-1,3-dihydro-2-benzofuran-5-yl)ethyl]piperazin-1-yl}ethyl)pyridine-3-carbonitrile To a microwave tube were added isomer B of 6-(oxiran-2-yl)pyridine-3-carbonitrile (330 mg, 2.26 mmol), 5-[(1R)-1-hydroxy-2-(piperazin-1-yl)ethyl]-4-methyl-2-benzofuran-1(3H)-one (686 mg, 2.48 mmol, as a free base), and EtOH (7.0 mL). The mixture was heated in the microwave for 60 min at 140° C. The solvent was evaporated and the crude product was purified by silica gel MPLC (0→10% CH$_2$CH$_2$:MeOH) to provide 6-(1-Hydroxy-2-{4-[(2R)-2-hydroxy-2-(4-methyl-1-oxo-1,3-dihydro-2-benzofuran-5-yl)ethyl]piperazin-1-yl}ethyl)pyridine-3-carbonitrile as a single isomer. Further, the product was treated with 1 M HCl in diethyl ether to give the final product as an HCl salt. $^1$H NMR (500 MHz, DMSO-d$_6$), δ 8.92 (s, 1H), 8.28 (dd, J=1.9 Hz, J=2.0 Hz, 1H), 7.68-7.63 (m, 3H), 5.48 (d, J=4.8 Hz, 1H), 5.37 (d, J=2.2 Hz, 2H), 5.20 (d, J=3.9 Hz, 1H), 5.03 (m, 1H), 4.78 (m, 1H), 2.64 (dd, J=4.1, 1H), 2.55-2.41 (m, 8H), 2.33 (dd, J=3.7 Hz, 1H), 2.24 (s, 3H); LC/MS: (IE, m/z) [(M+1)]$^+$=423.04 (57A).

The isomer corresponding to inversion of the benzylic hydroxyl stereocenter was also prepared in a similar fashion starting with isomer A of 6-(oxiran-2-yl)pyridine-3-carbonitrile (57B):

LC/MS: [(M+1)]$^+$=423.

Examples 58A and 58B

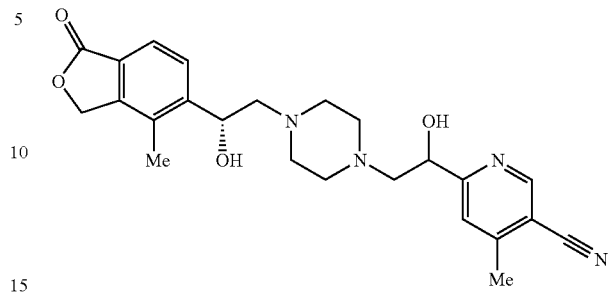

6-(1-Hydroxy-2-{4-[(2R)-2-hydroxy-2-(4-methyl-1-oxo-1,3-dihydro-2-benzofuran-5-yl)ethyl]piperazin-1-yl}ethyl)-4-methylpyridine-3-carbonitrile To a microwave tube were added 4-methyl-6-(oxiran-2-yl)pyridine-3-carbonitrile (40 mg, 0.25 mmol), 5-[(1R)-1-hydroxy-2-(piperazin-1-yl)ethyl]-4-methyl-2-benzofuran-1(3H)-one (69 mg, 0.25 mmol, as a free base), and EtOH (3.0 mL). The mixture was heated in the microwave for 60 min at 140° C. The solvent was evaporated and the crude product was purified by chiral prep SFC (30% MeOH (0.1% DEA)/CO2 on OJ column) to provide 6-(1-hydroxy-2-{4-[(2R)-2-hydroxy-2-(4-methyl-1-oxo-1,3-dihydro-2-benzofuran-5-yl)ethyl]piperazin-1-yl}ethyl)-4-methylpyridine-3-carbonitrile as individual isomers. Further, the products were treated with 1 M HCl in diethyl ether to give the final products as HCl salts.

Isomer A (58A): LC/MS: (IE, m/z) [(M+1)]$^+$=437.07 (Peak 1 from chiral HPLC).

Isomer B (58B): LC/MS: (IE, m/z) [(M+1)]$^+$=437.07 (Peak 2 from chiral HPLC).

Example 59

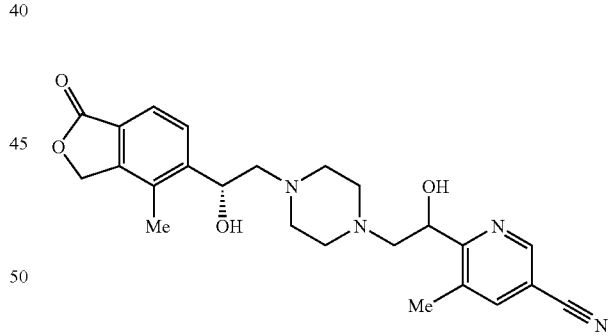

6-(1-Hydroxy-2-{4-[(2R)-2-hydroxy-2-(4-methyl-1-oxo-1,3-dihydro-2-benzofuran-5-yl)ethyl]piperazin-1-yl}ethyl)-5-methylpyridine-3-carbonitrile 6-(1-Hydroxy-2-{4-[(2R)-2-hydroxy-2-(4-methyl-1-oxo-1,3-dihydro-2-benzofuran-5-yl)ethyl]piperazin-1-yl}ethyl)-5-methylpyridine-3-carbonitrile was prepared in a similar fashion to that described for the synthesis of EXAMPLE 58 starting from 5-[(1R)-1-hydroxy-2-(piperazin-1-yl)ethyl]-4-methyl-2-benzofuran-1(3H)-one and 5-methyl-6-(oxiran-2-yl)pyridine-3-carbonitrile.

Isomer A: LC/MS: (IE, m/z) [(M+1)]$^+$=437.06.
Isomer B: LC/MS: (IE, m/z) [(M+1)]$^+$=437.06.

Examples 60A and 60B

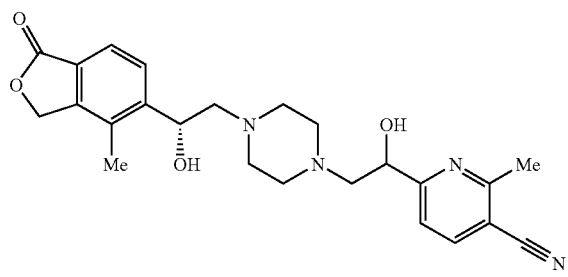 [SMILES: Cc1nc(C(O)CN2CCN(C[C@H](O)c3ccc4c(c3C)COC4=O)CC2)ccc1C#N]

6-[1-Hydroxy-2-[4-[(2R)-2-hydroxy-2-(4-methyl-1-oxo-3H-isobenzofuran-5-yl)ethyl]piperazin-1-yl]ethyl]-2-methyl-pyridine-3-carbonitrile 6-[1-Hydroxy-2-[4-[(2R)-2-hydroxy-2-(4-methyl-1-oxo-3H-isobenzofuran-5-yl)ethyl]piperazin-1-yl]ethyl]-2-methyl-pyridine-3-carbonitrile was prepared in a similar fashion to that described for the synthesis of EXAMPLE 58 starting from 5-[(1R)-1-hydroxy-2-(piperazin-1-yl)ethyl]-4-methyl-2-benzofuran-1(3H)-one and 2-methyl-6-(oxiran-2-yl)pyridine-3-carbonitrile.

Isomer A (60A): LC/MS: (IE, m/z) [(M+1)]$^+$=437.08 (Peak 1 from chiral HPLC).

Isomer B (60B): LC/MS: (IE, m/z) [(M+1)]$^+$=437.07 (Peak 2 from chiral HPLC).

Example 61

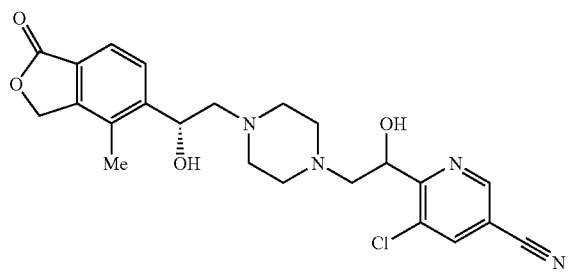 [SMILES: Cc1c([C@@H](O)CN2CCN(CC(O)c3ncc(C#N)cc3Cl)CC2)ccc2c1COC2=O]

5-Chloro-6-[1-hydroxy-2-[4-[(2R)-2-hydroxy-2-(4-methyl-1-oxo-3H-isobenzofuran-5-yl)ethyl]piperazin-1-yl]ethyl]pyridine-3-carbonitrile 5-Chloro-6-[1-hydroxy-2-[4-[(2R)-2-hydroxy-2-(4-methyl-1-oxo-3H-isobenzofuran-5-yl)ethyl]piperazin-1-yl]ethyl]pyridine-3-carbonitrile was prepared in a similar fashion to that described for the synthesis of EXAMPLE 58 starting from 5-[(1R)-1-hydroxy-2-(piperazin-1-yl)ethyl]-4-methyl-2-benzofuran-1(3H)-one and 5-chloro-6-(oxiran-2-yl)pyridine-3-carbonitrile.

Isomer A: LC/MS: (IE, m/z) [(M+1)]$^+$=457.17.
Isomer B: LC/MS: (IE, m/z) [(M+1)]$^+$=457.15.

Example 62

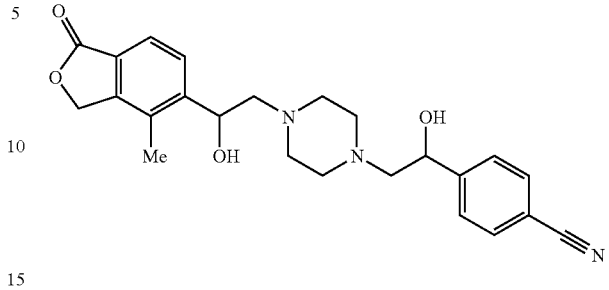

4-[1-Hydroxy-2-[4-[2-hydroxy-2-(4-methyl-1-oxo-3H-isobenzofuran-5-yl)ethyl]piperazin-1-yl]ethyl]benzonitrile 4-[1-Hydroxy-2-[4-[2-hydroxy-2-(4-methyl-1-oxo-3H-isobenzofuran-5-yl)ethyl]piperazin-1-yl]ethyl]benzonitrile was prepared in a similar fashion to that described for the synthesis of EXAMPLES 2C and 28-29 starting from 5-[(1R)-1-hydroxy-2-(piperazin-1-yl)ethyl]-4-methyl-2-benzofuran-1(3H)-one and 4-(oxiran-2-yl)benzonitrile.

LC/MS: (IE, m/z) [(M+1)]$^+$=422.07.

Example 63

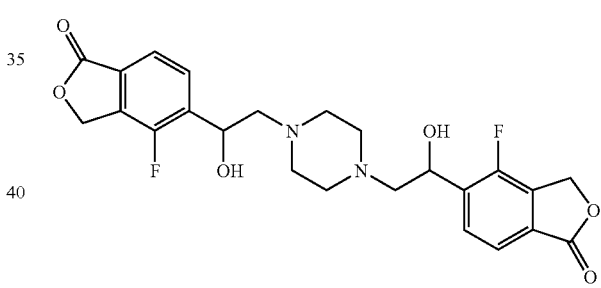

5,5'-[piperazine-1,4-diylbis(1-hydroxyethane-2,1-diyl)]bis(4-fluoro-2-benzofuran-1(3H)-one)

5,5'-[piperazine-1,4-diylbis(1-hydroxyethane-2,1-diyl)]bis(4-fluoro-2-benzofuran-1(3H)-one) was prepared in a similar fashion to that described for the synthesis of EXAMPLE 2 starting from 4-fluoro-5-oxiranyl-3H-isobenzofuran-1-one and piperazine. The isomers of the product were obtained via SFC resolution (Column: Chiralcel OJ-H 100*4.6 mm I.D., 5 um; Mobile phase: 40% iso-propanol (0.05% DEA) in $CO_2$; Flow rate: 4.5 mL/min; Wavelength: 220 nm).

Isomer A: $^1$H-NMR (400 MHz, MeOD) δ ppm 7.83-7.86 (m, 2H), 7.74 (d, J=8.0 Hz, 2H), 5.42-5.46 (m, 6H), 3.03-3.35 (m, 12H).

Isomer B: $^1$H-NMR (400 MHz, MeOD) δ ppm 7.86-7.89 (m, 2H), 7.77 (d, J=8.0 Hz, 2H), 5.45-5.48 (m, 6H), 3.13-3.33 (m, 12H).

Isomer C: $^1$H-NMR (400 MHz, MeOD) δ ppm 7.86-7.89 (m, 2H), 7.77 (d, J=8.0 Hz, 2H), 5.43-5.48 (m, 6H), 3.05-3.26 (m, 12H).

Example 64

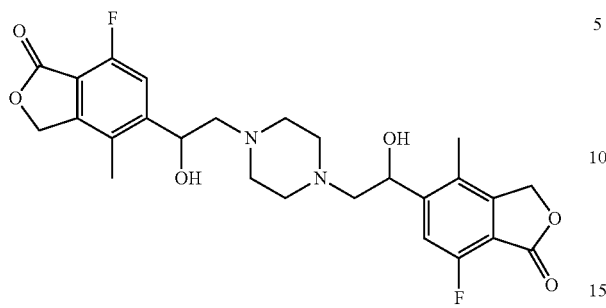

5,5'-[piperazine-1,4-diylbis(1-hydroxyethane-2,1-diyl)]bis(7-fluoro-4-methyl-2-benzofuran-1(3H)-one)

5,5'-[piperazine-1,4-diylbis(1-hydroxyethane-2,1-diyl)]bis(7-fluoro-4-methyl-2-benzofuran-1(3H)-one) was prepared in a similar fashion to that described for the synthesis of EXAMPLE 2 starting from 7-Fluoro-4-methyl-5-oxiran-2-yl-2-benzofuran-1(3H)-one and piperazine.

$^1$H-NMR (400 MHz, MeOD) δ ppm 7.47 (d, J=10.3 Hz, 1H), 5.34-5.44 (m, 6H), 3.51-3.58 (m, 8H), 3.17-3.19 (m, 4H), 2.31 (s, 6H).

Examples 65A and 65B

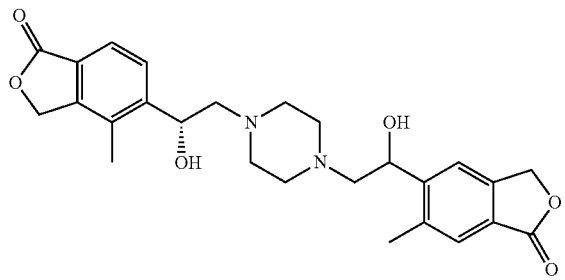 [SMILES: Cc1cc2c(cc1C(O)CN1CCN(C[C@H](O)c3ccc4c(c3C)COC4=O)CC1)COC2=O]

5-[(1R)-1-hydroxy-2-{4-[2-hydroxy-2-(6-methyl-1-oxo-1,3-dihydro-2-benzofuran-5-yl)ethyl]piperazin-1-yl}ethyl]-4-methyl-2-benzofuran-1(3H)-one 5-[(1R)-1-hydroxy-2-{4-[2-hydroxy-2-(6-methyl-1-oxo-1,3-dihydro-2-benzofuran-5-yl)ethyl]piperazin-1-yl}ethyl]-4-methyl-2-benzofuran-1(3H)-one was prepared in a similar fashion to that described for the synthesis of EXAMPLE 58 starting from 5-[(1R)-1-hydroxy-2-(piperazin-1-yl)ethyl]-4-methyl-2-benzofuran-1(3H)-one and isomer B of 6-methyl-5-oxiran-2-yl-2-benzofuran-1(3H)-one (65B).

$^1$H NMR 500 MHz, DMSO) δ 7.64-7.76 (m, 4H), 5.36-5.43 (m, 4H), 2.48-2.51 (m, 16H) 10H), 2.43 (s, 3H), 2.29 (s, 3H); LC/MS: [(M+1)]$^+$=467; $t_R$=1.99 min.

The product obtained from isomer A of 6-methyl-5-oxiran-2-yl-2-benzofuran-1(3H)-one was also prepared (65A): LC/MS: [(M+1)]$^+$=467.

Example 66

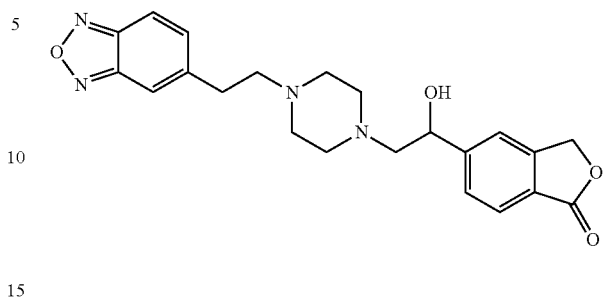

5-(2-{4-[2-(2,1,3-benzoxadiazol-5-yl)ethyl]piperazin-1-yl}-1-hydroxyethyl)-2-benzofuran-1(3H)-one 5-(2-{4-[2-(2,1,3-benzoxadiazol-5-yl)ethyl]piperazin-1-yl}-1-hydroxyethyl)-2-benzofuran-1(3H)-one was prepared in a similar fashion as to the synthesis described in EXAMPLE 12 starting from 5-[2-(piperazin-1-yl)ethyl]-2,1,3-benzoxadiazole and 5-oxiran-2-yl-2-benzofuran-1(3H)-one. LC/MS: [(M+1)]$^+$=409.

Example 67

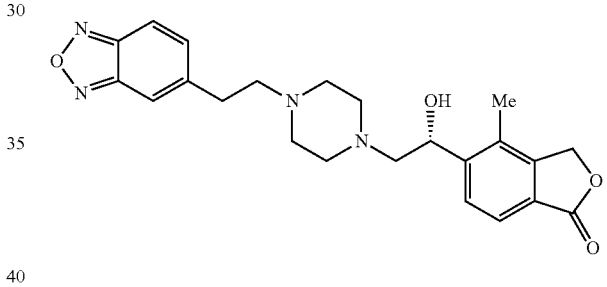

5-[(1R)-2-{4-[2-(2,1,3-benzoxadiazol-5-yl)ethyl]piperazin-1-yl}-1-hydroxyethyl]-4-methyl-2-benzofuran-1(3H)-one 5-[(1R)-2-{4-[2-(2,1,3-benzoxadiazol-5-yl)ethyl]piperazin-1-yl}-1-hydroxyethyl]-4-methyl-2-benzofuran-1(3H)-one was prepared in a similar fashion as to the synthesis described in EXAMPLE 12 starting from 5-[2-(piperazin-1-yl)ethyl]-2,1,3-benzoxadiazole and 4-methyl-5-[(2R)-oxiran-2-yl]-2-benzofuran-1(3H)-one. LC/MS: [(M+1)]$^+$=423.

Example 68A and 68B

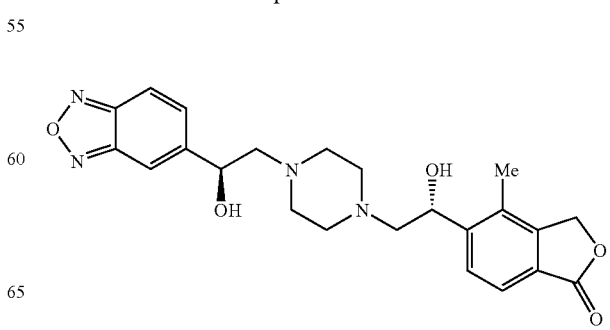

-continued

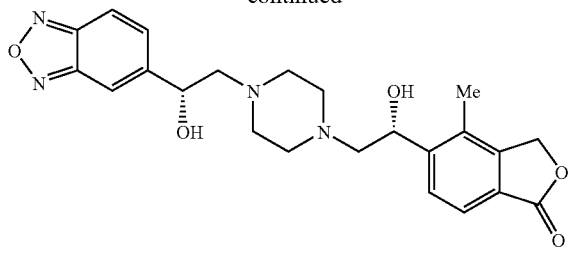

5-[(1R)-2-{4-[(2S)-2-(2,1,3-benzoxadiazol-5-yl)-2-hydroxyethyl]piperazin-1-yl}-1-hydroxyethyl]-4-methyl-2-benzofuran-1(3H)-one and 5-[(1R)-2-{4-[(2R)-2-(2,1,3-benzoxadiazol-5-yl)-2-hydroxyethyl]piperazin-1-yl}-1-hydroxyethyl]-4-methyl-2-benzofuran-1(3H)-one The title compounds were prepared as described for the synthesis of EXAMPLES 57-58 starting from 5-[(1R)-1-hydroxy-2-(piperazin-1-yl)ethyl]-4-methyl-2-benzofuran-1 (3H)-one and 5-(oxiran-2-yl)-2,1,3-benzoxadiazole. The resulting two diastereomers were resolved by prep SFC on Chiralcel OJ 30×200 mm column eluting with 70 mL/min of 30% methanol (0.2% DEA)/$CO_2$ at 35° C. with pressure of 100 bar.

Isomers A and B had retention times of 7.07 and 8.24 respectively.

Isomer A-TFA salt: $^1$H-NMR (500 MHz, $CDOD_3$): δ ppm 7.99 (s, 1H), 7.95 (d, J=9.3 Hz, 1H), 7.84 (d, J=8 Hz, 1H), 7.76 (d, J=8 Hz, 1H), 7.63 (dd, J=9.5 Hz, 1H), 5.52 (dd. J=9.75 Hz, 3.7 Hz, 1H), 5.38 (d, J=1.5 Hz, 2H), 5.24 (dd, J=9.5 Hz, 3.05 Hz, 1H) 3.68 (b, 4H), 3.63 (b, 4H), 3.27-3.41 (m, 4H), 2.4 (s, 3H). LC-MS: M+1=439.

Isomer B: $^1$H-NMR (500 MHz, DMSO): δ ppm 7.96 (d, J=9.3 Hz, 1H), 7.86 (d, J=0.8 Hz, 1H), 7.64 (q, 2H), 7.60 (dd, J=7.75 Hz, 0.75 Hz, 1H), 5.35 (d. J=4 Hz, 2H), 5.01-5.03 (m, 1H), 4.79-4.82 (m, 1H), 2.31-2.55 (m, 12H), 2.22 (s, 3H). LC-MS: M+1=439.

The following table contains additional examples which were prepared in a manner similar to that which has been described in the examples above using intermediates that are either known or for which the syntheses have been described above. Stereochemistry is as shown where indicated. In some cases the products were prepared as mixtures of isomers, which in some instances were separated.

TABLE 1

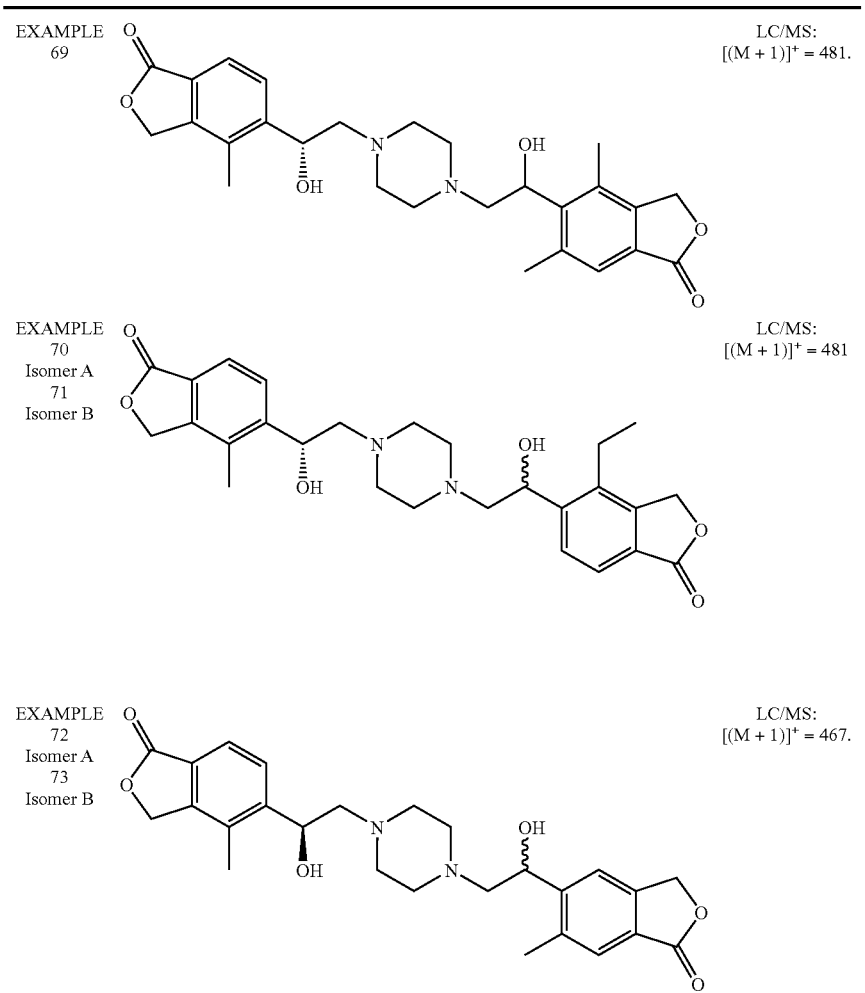

TABLE 1-continued
| EXAMPLE 74 | 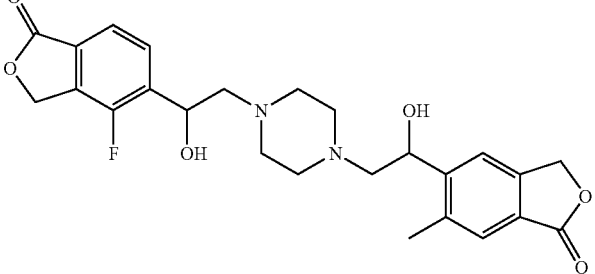 | LC/MS: [(M + 1)]⁺ = 471. |
| EXAMPLE 75 | 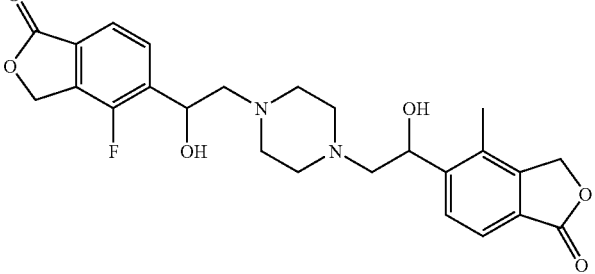 | LC/MS: [(M + 1)]⁺ = 471. |
| EXAMPLE 76 Isomer A 77 Isomer B | 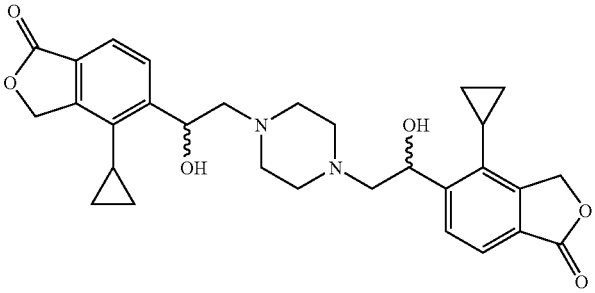 [SMILES: O=C1OCc2c1ccc(C(O)CN1CCN(CC(O)c3ccc4c(c3C3CC3)COC4=O)CC1)c2C1CC1] | LC/MS: [(M + 1)]⁺ = 519 |
| EXAMPLE 78 | 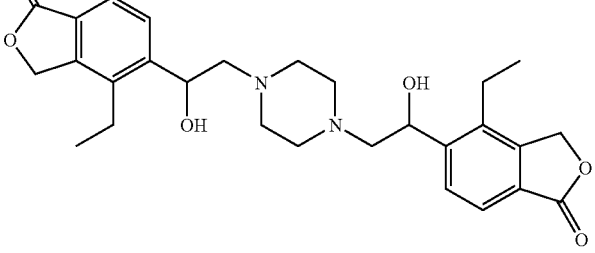 | LC/MS: [(M + 1)]⁺ = 495 |
| EXAMPLE 79 Isomer A 80 Isomer B | 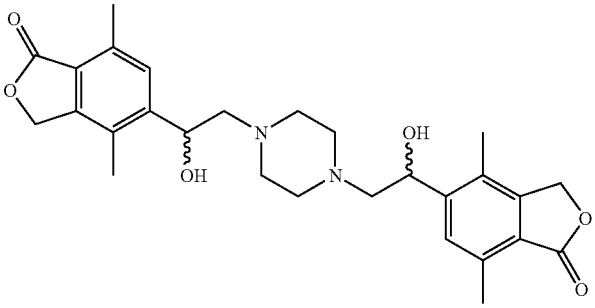 [SMILES: Cc1cc(C(O)CN2CCN(CC(O)c3cc(C)c4c(c3C)COC4=O)CC2)c(C)c2c1C(=O)OC2] | LC/MS: [(M + 1)]⁺ = 495 |

TABLE 1-continued
EXAMPLE 81
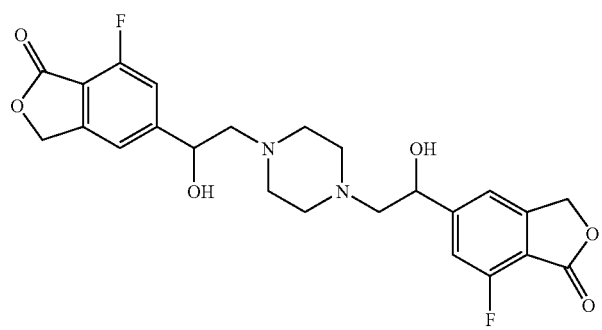 [SMILES: O=C1OCc2cc(C(O)CN3CCN(CC(O)c4cc(F)c5c(c4)COC5=O)CC3)cc(F)c21]
LC/MS: [(M + 1)]⁺ = 475
EXAMPLE 82
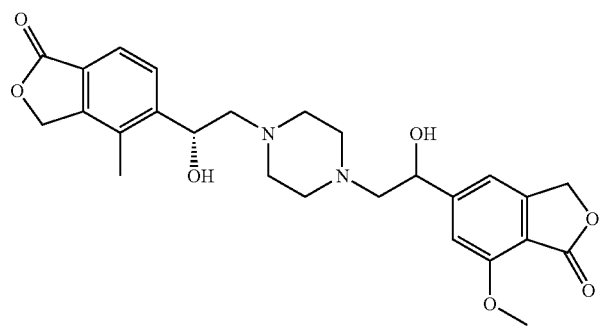 [SMILES: COc1cc(C(O)CN2CCN(C[C@H](O)c3ccc4c(c3C)COC4=O)CC2)cc2c1C(=O)OC2]
LC/MS: [(M + 1)]⁺ = 483.
EXAMPLE 83 Isomer A
84 Isomer B
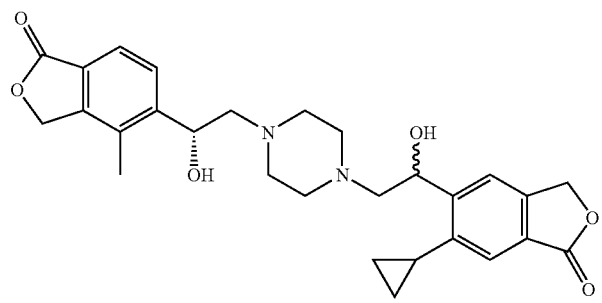 [SMILES: Cc1c([C@@H](O)CN2CCN(CC(O)c3cc4c(cc3C3CC3)C(=O)OC4)CC2)ccc2c1COC2=O]
LC/MS: [(M + 1)]⁺ = 493.
EXAMPLE 85
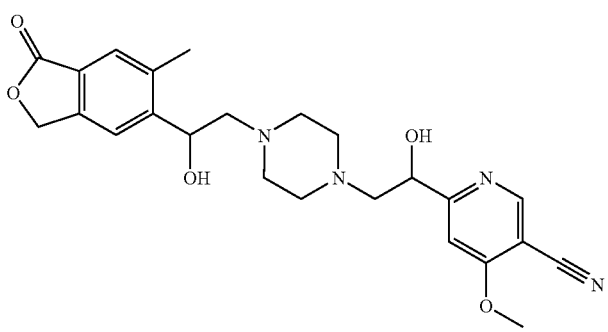 [SMILES: COc1cc(C(O)CN2CCN(CC(O)c3cc4c(cc3C)C(=O)OC4)CC2)ncc1C#N]
LC/MS: [(M + 1)]⁺ = 453.
EXAMPLE 86
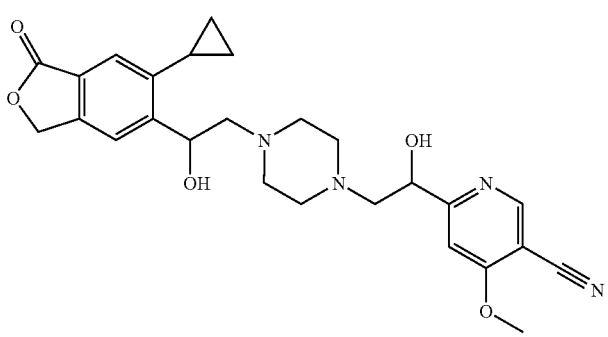 [SMILES: COc1cc(C(O)CN2CCN(CC(O)c3cc4c(cc3C3CC3)C(=O)OC4)CC2)ncc1C#N]
LC/MS: [(M + 1)]⁺ = 479

TABLE 1-continued

| EXAMPLE | | LC/MS: |
|---|---|---|
| 87 Isomer A | | $[(M + 1)]^+ = 493.$ |
| 88 Isomer B | | |

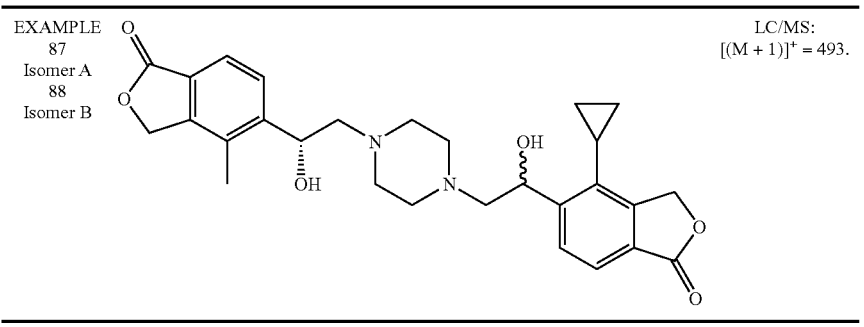

Several assays may be used to measure functional inhibition of the ROMK channel by compounds of the instant invention. One primary assay that can be used is a functional $^{86}Rb^+$ efflux assay that measures the ability of ROMK to permeate $^{86}Rb^+$, in the absence or presence of test compound. Under control conditions, cells loaded with $^{86}Rb^+$ and incubated in $Rb^+$-free medium display a time-dependent efflux of the isotope, the rate of which depends on number of functional channels. When cells are incubated in the presence of a channel inhibitor, efflux of $^{86}Rb^+$ is prevented in a concentration-dependent manner, and $IC_{50}$ values of inhibition by compounds can be accurately determined This assay has been established with cell lines expressing either human, rat or dog ROMK channels, and can operate in 96- or 384-well format. Importantly, the human, rat, and dog $^{86}Rb^+$ efflux assays can be carried out in the presence of up to 100% serum allowing, therefore, an accurate estimation of the effect of protein binding on the inhibitory activity of compounds of interest. Another ROMK functional assay makes use of the ability of thallium to permeate through open ROMK channels and increase the fluorescence of a dye previously loaded into the cells. Under control conditions, cells loaded with dye and exposed to thallium-containing medium display a time-dependent increase in fluorescence, the rate of which depends on number of functional channels. When cells are incubated in the presence of a channel inhibitor, the increase in fluorescence is attenuated in a concentration-dependent manner, and $IC_{50}$ values of inhibition by compounds can be accurately determined. This assay has been established with cell lines expressing either human, or rat ROMK channels, and operates in 384-well format. Another assay for evaluation of the compounds of the instant invention and for evaluation of mechanism of action of compounds of Formula I relies on the measurement of the electrical current that is generated as potassium permeates through the channel. For these electrophysiological experiments, three different platforms, IonWorks, QPatch, or manual patch clamp, are used, depending on the experimental protocol under consideration. IonWorks operates in a 384-well format and allows accurate determination of $IC_{50}$ values for inhibitors. Examples of compounds of the present invention (listed above) all had potencies of at least 1 µM or lower in one or more of the three assays described herein.

$^{86}Rb^+$ Efflux Assay

Cell Culture Conditions

CHO-DHFR-cells stably expressing hROMK1 ($K_{ir}1.1$) are grown at 37° C. in a 10% $CO_2$ humidified incubator in Iscove's Modified Dulbecco's Medium (Gibco 12440) supplemented with HT Supplement, Penicillin/Streptomycin/Glutamine, G418 (500 µg/ml) and 10% FBS. Cells are seeded in Sterile and Tissue Culture Treated Packard CulturPlate White Opaque Microplates at a concentration of 5.0 E5-7.0E5 cells/ml—PerkinElmer 6005680 (96-well); Corning 3707 (384 well) in complete media containing 1.5 µCi/ml Rubidium-86. Cells are incubated in 37° C.-10% $CO_2$ incubator overnight. On the day of the experiment, the media is removed and cells are washed with low K assay buffer. $^{86}Rb^+$ efflux is initiated after addition of assay buffer±test compound followed by 35 min incubation at room temperature. ROMK-sensitive component of efflux is defined in the presence of 10 mM $BaCl_2$. Assay buffer is removed and transferred to a plate and cells are solubilized in the presence of SDS. Radioactivity associated with assay and cell plate is determined.

Step Protocol
1. Remove cell media and wash cells with low K assay buffer (126.9 mM NaCl, 4.6 mM KCl, 2 mM $CaCl_2$, 1 mM $MgCl_2$, 10 mM Hepes/NaOH; pH 7.4)
   200 µl for 96-well plate; 70 µl for 384-well plate
2. Add assay buffer (121.5 mM NaCl, 10 mM KCl, 2 mM $CaCl_2$, 1 mM $MgCl_2$, 10 mM Hepes/NaOH; pH 7.4) ±test compound to cells
   100 µl for 96-well plate; 50 µl for 384-well plate
3. Incubate at ambient temperature (22-24° C.) for 35 min
4. Remove assay buffer add it to a 96- or 384-well plate containing Microscint-20
   96-well Plate: 100 µl buffer, 170 µl MicroScint 20 (for TopCount)
   384-well plate: 20 µl buffer, 50 µl Optiphase (for MicroLux)
5. Completely remove remaining assay buffer from cell plate
6. Solubilize cells with 1% SDS; than add MicroScint or Optiphase
   96-well Plate: 30 µl SDS, 170 µl MicroScint 20 (for TopCount)
   384-well plate: 20 µl SDS, 50 µl Optiphiase (for MicroLux)
7. Seal both cell and supernatant plates and count Data Calculation Radioactivity associated with the assay plate is normalized to the total radioactivity (assay+cell plates) to provide % efflux, under each condition. % efflux in the presence of 10 mM $BaCl_2$ is subtracted from each experimental point to provide the ROMK-sensitive component of $^{86}Rb^+$ efflux. In the absence of test compound, this number corresponds to 100% control efflux. $IC_{50}$ values represent the concentration of compound that inhibits 50% of ROMK efflux. Normally, a control compound is included to support that the assay is giving consistent results compared to previous measurements, although the control is not required to obtain the results for the test compounds. The control can be any compound of Formula I of the present invention, preferably with an $IC_{50}$ potency of less than 1 μM in this assay. Alternatively, the control could be another compound (outside the scope of Formula I) that has an $IC_{50}$ potency in this assay of less than 1 μM. Representative examples of data collected for compounds of the present invention using the $^{86}Rb^+$ Efflux Assay are shown in the Table 2 below.

TABLE 2

| EXAMPLE # | $^{86}Rb^+$ Efflux Assay $IC_{50}$ (μM) |
|---|---|
| 2A | 0.068 |
| 2B | 0.171 |
| 2C | 0.107 |
| 5 | 0.088 |
| 12 | 0.046 |
| 20 | 0.036 |
| 22 (isomer 2) | 0.042 |
| 24 | 0.130 |
| 52 | 0.370 |
| 55 | 0.047 |

Thallium Flux Assay

Cell Culture Conditions

HEK293 cells stably expressing hROMK ($hK_{ir}1.1$) are grown at 37° C. in a 10% $CO_2$ humidified incubator in complete growth media: Dulbecco's Modified Eagle Medium supplemented with non-essential amino acids, Penicillin/Streptomycin/Glutamine, G418 and FBS. At >80% confluency, aspirate the media from the flask and rinse with 10 ml Calcium/Magnesium-free PBS. Add 5 ml of 1× trypsin (prepared in Ca/Mg Free PBS) to T-225 flask and return flask to 37° C./$CO_2$ incubator for 2-3 minutes. To dislodge the cell, gently bang the side of the flask with your hand. Triturate the cells completely and then transfer the cells to 25 ml complete media. Centrifuge at 1,500 rpm for 6 min followed by resuspension in complete growth media and determine cell concentration. For typical re-seeding, 4E6 cells/T-225 flask will attain >80% confluency in 4 days. Under ideal growth conditions and appropriate tissue culture practices, this cell line is stable for 40-45 passages.

FluxOR Kit Components (Invitrogen F10017)
  FluxOR™ Reagent (Component A)
  FluxOR™ Assay Buffer (Component B)—10× Concentrate
  PowerLoad™ Concentrate (Component C)—100× Concentrate
  Probenecid (Component D)—Lyophilized sample is kept at −20° C. Water soluble, 100× after solubilization in 1 ml water. Store at 4° C.
  FluxOR™ Chloride-free Buffer (Component E)—5× Concentrate
  Potassium sulfate ($K_2SO_4$) Concentrate (Component F)—125 mM in water. Store at 4° C.
  Thallium sulfate ($Tl_2SO_4$) Concentrate (Component G)—50 mM in water. Store at 4° C.
  DMSO (dimethyl sulfoxide, Component H)—1 ml (100%)

Reagent Preparation
FluxOR Working Solutions
  1000× FluxOR™ Reagent: Reconstitute a vial of component A in 100 μl DMSO; Mix well; Store 10 μl aliquots at −20° C.
  1× FluxOR™ Assay Buffer: Dilute Component B 10-fold with water; Adjust pH to 7.4 with Hepes/NaOH; Filter and store at 4° C.
  Probenecid/Assay Buffer: 100 ml of 1× FluxOR™ Assay Buffer; 1 ml of reconstituted component D; Store at 4° C.
  Loading Buffer (per microplate): 10 μl 1000× FluxOR™ Reagent; 100 μl component C; 10 ml Probenecid/Assay Buffer
  Compound Buffer (per microplate): 20 ml Probenecid/Assay Buffer; 0.3 mM ouabain (10 mM ouabain in water can be stored in amber bottle/aluminum foil at room temperature); Test compound
  1× FluxOR™ Chloride-Free Buffer: Prepare 1× working solution in water. Can be stored at room temperature
  Stimulant Buffer (prepared at 5× final concentration in 1× FluxOR™ Chloride-Free Buffer): 7.5 mM Thallium sulfate and 0.75 mM Potassium sulfate (to give a final assay concentration of 3 mM Thallium/0.3 mM Potassium). Store at 4° C. when not in use. If kept sterile, this solution is good for months.

Assay Protocol

The ROMK channel functional thallium flux assay is performed in 384 wells, using the FLIPR-Tetra instrument. HEK-hKir1.1 cells are seeded in Poly-D-Lysine microplates and kept in a 37° C.-10% $CO_2$ incubator overnight. On the day of the experiment, the growth media is replaced with the FluxOR™ reagent loading buffer and incubated, protected from light, at ambient temperature (23-25° C.) for 90 min. The loading buffer is replaced with assay buffer±test compound followed by 30 min incubation at ambient temperature, where the Thallium/Potassium stimulant is added to the microplate.

Step Protocol
1. Seed HEK-hKir1.1 cells (50 μl at 20,000 cells/well) in 384-well PDL coated Microplates
2. Allow cells to adhere overnight in humidified 37° C./10% $CO_2$ incubator
3. Completely remove cell growth media from microplate and replace with 25 μl loading buffer
4. Incubate Microplate at room temperature, protected form light, for 90 min
5. Remove loading buffer and replace with 25 μl 1× Assay Buffer±test compound.
6. Incubate microplate at room temperature, protected form light, for 30 min
7. At FLIPR-Tetra 384: Add stimulant (Thallium/Potassium) solution to microplate and monitor fluorescence. Excitation=400 nm, Emission=460 & 580 nm. Collect data for ~10 min.

Data Calculation

The fluorescence intensity of wells containing 3 μM of a standard control ROMK inhibitor of the present invention is used to define the ROMK-sensitive component of thallium flux. Fluorescence in the presence of test compounds is normalized to control values to provide % fluorescence change. $IC_{50}$ values represent the concentration of compound that inhibits 50% of the ROMK thallium flux signal.

Assay Standard

Normally, a control compound is included to support that the assay is giving consistent results compared to previous measurements, although the control is not required to obtain the results for the test compounds. The control can be any compound of Formula I of the present invention, preferably with an $IC_{50}$ potency of less than 1 μM in this assay. Alternatively, the control could be another compound (outside the scope of Formula I) that has an $IC_{50}$ potency in this assay of less than 1 µM.

Representative examples of data collected for compounds of the present invention using the Thallium Flux Assay are shown in the Table 3 below.

TABLE 3

| EXAMPLE # | Thallium Flux Assay $IC_{50}$ (µM) |
|---|---|
| 2A | 0.006 |
| 2B | 0.029 |
| 2C | 0.011 |
| 5 | 0.013 |
| 12 | 0.006 |
| 20 | 0.007 |
| 22 (isomer 2) | 0.018 |
| 24 | 0.026 |
| 52 | 0.086 |
| 55 | 0.015 |

Electrophysiology Assay

Block of Kir1.1 (ROMK1) currents was examined by whole cell voltage clamp (Hamill et. al. Pfluegers Archives 391:85-100 (1981)) using the IonWorks Quattro automated electrophysiology platform (Molecular Devices, Sunnyvale, Calif.). Chinese hamster ovary cells stably expressing Kir1.1 channels were maintained in T-75 flasks in cell culture media in a humidified 10% $CO_2$ incubator at 37° C. Prior to an experiment, Kir1.1 expression was induced by overnight incubation with 1 mM sodium butyrate. On the day of the experiment, cells were dissociated with 2.5 ml of Versene (Invitrogen 15040-066) for approximately 6 min at 37° C. and suspended in 10 ml of bath solution containing (in mM): 150 NaCl, 10 KCl, 2.7 $CaCl_2$, 0.5 $MgCl_2$, 5 HEPES, pH 7.4. After centrifugation, the cell pellet was resuspended in approximately 4.0 ml of bath solution and placed in the IonWorks instrument. The intracellular solution consisted of (in mM): 80 K gluconate, 40 KCl, 20 KF, 3.2 $MgCl_2$, 3 EGTA, 5 Hepes, pH 7.4. Electrical access to the cytoplasm was achieved by perforation in 0.13 mg/ml amphotericin B for 4 min. Amphotericin B (Sigma A-4888) was prepared as a 40 mg/ml solution in DMSO. Voltage protocols and current recordings were performed using the IonWorks HT software/hardware system. Currents were sampled at 1 kHz. No correction for liquid junction potentials was used. The test pulse, consisting of a 100 ms step to 0 mV from a holding potential of −70 mV, followed by a 100 ms voltage ramp from −70 mV to +70 mV, was applied before and after a 6 min compound incubation period. Test compounds were prepared by diluting DMSO stock solutions into the bath solution at 3× the final concentration and placed in the instrument in 96-well polypropylene plates. Current amplitudes were measured using the IonWorks software. To assess compound potency, the fractional block during the voltage step to 0 mV was calculated in Microsoft Excel (Microsoft, Redmond, Calif.), and dose-response curves were fitted with Igor Pro 4.0 (WaveMetrics, Lake Oswego, Oreg.). Normally, a control compound is included to support that the assay is giving consistent results compared to previous measurements, although the control is not required to obtain the results for the test compounds. The control can be any compound of Formula I of the present invention, preferably with an $IC_{50}$ potency of less than 1 µM in this assay. Alternatively, the control could be another compound (outside the scope of Formula I) that has an $IC_{50}$ potency in this assay of less than 1 µM.

Representative examples of data collected for compounds of the present invention using the ROMK electrophysiology assay titrations are shown in the Table 4 below.

TABLE 4

| EXAMPLE # | ROMK Electrophysiology Assay $IC_{50}$ (µM) |
|---|---|
| 2A | 0.009 |
| 2B | 0.012 |
| 2C | 0.010 |
| 5 | 0.007 |
| 12 | 0.013 |
| 20 | 0.014 |
| 22 (isomer 2) | 0.015 |
| 52 | 0.036 |
| 55 | 0.023 |

Rat Diuresis Assay

Experimental protocols for evaluating diuretic efficacy of compounds of the present invention in Sprague-Dawley (SD) rats:

1. Adult male SD rats are acclimated to single housing in metabolism cages for at least three (3) days before their use in the diuresis screen. Rats have at lib access to food and water.
2. For most studies the procedure will be to remove food hoppers and water bottles from the metabolic cages 1-2 h before the start of the diuresis screen. Rats will be dosed with compound (see below) and 30 minutes later dosed with water or saline orally at 18 mL/kg to induce voiding and placed in the metabolic cage where urine is collected over the next 4 hours.

For selected studies an overnight fast may be necessary if saline/water loads larger than those described above are required. For these studies a saline or water dose of up to 27 mL/kg will be given.

3. Following the fasting period (usually 1-2 hours but sometimes overnight), animals are removed from the metabolism cages and temporarily housed in shoebox cages for dosing. Compound or vehicle is dosed in 70% PEG200 or Imwitor:Tween (depending on the physical properties of the compound) at 1 mL/Kg PO.
4. The 30 min time period between compound dosing and water/saline loading may be modified depending on the bioavailability of the compound being tested.
5. Urine is collected from each animal for up to 4 hrs at room temperature.
6. The urine volume collected from each animal is measured and recorded. Urine is centrifuged, aliquoted and frozen (−20° C.) until analyzed.
7. Blood (150-200 µL) can be obtained from treated animals by jugular vein bleed for compound plasma exposure levels.

Note: Rats can be re-tested with additional compounds after 1 week of recovery while housed in metabolism cages. Data=Mean/sem. Data analyzed by one way ANOVA and Dunnett's comparison of treatments to vehicle. The known diuretic, hydrochlorothiazide, dosed PO at 10 or 25 mg/kg, can be used as a positive control in this model.

Example No.'s 2A, 2C, 31 (mixture of 4 isomers), 34, 52A, 52B, 57A and 65A were tested using the SD rat diuresis model. The results showed a range from about 2 to about 9-fold change, i.e., increase, in urine volume relative to the vehicle control group based on a PO dose of either 1 mg/kg or 3 mg/kg.

Spontaneously Hypertensive Rat (SHR) Assay

The spontaneously hypertensive rat (SHR) exhibits age-dependent hypertension that does not require administration of exogenous agents to elevate blood pressure nor does it require the use of a high salt diet to elevate blood pressure. Thus it resembles human essential hypertension and provides an opportunity to assess the dose-dependence of novel agents for their ability to lower blood pressure.

Experimental protocols for evaluating blood pressure lowering efficacy of compounds of the present invention in spontaneously hypertensive rats (SHR):

Spontaneously hypertensive rats (SHR, male, 6 months, Charles River) were implanted with DSI TA11PA-C40 telemetry device (Data Sciences, Inc., St. Paul, Minn.) under isoflurane or ketamine/metomidine anesthesia. The telemetry unit catheter was inserted into the descending aorta via the femoral artery and the telemetry device was implanted subcutaneously in the left flank area. Animals were allowed to recover from surgery for 14 days before the start of any studies. Blood pressure, heart rate, and activity signals from conscious, freely moving rats were recorded continuously for 30 seconds every 10 minutes. HCTZ (25 mg/kg/day, PO) was included as a reference diuretic at a dose giving approximately maximal efficacy in SHR. The blood pressure lowering efficacy of compounds of the present invention compared to vehicle control was evaluated following a single oral gavage each day for a typical duration of three to fourteen days. Data were collected as hourly averages, and changes in blood pressure were calculated by subtracting vehicle control baseline data on an hourly basis. Example numbers 2A, 52A, 52B, 57A, 58A, 58B, 60A, 65A, and 65B were evaluated at PO, QD doses of either 3 mg/kg or 10 mg/kg and resulted in typical reductions in daily (24 h) mean systolic blood pressure ranging from 8 mmHg to 32 mmHg by the last day of the studies.

While the invention has been described with reference to certain particular embodiments thereof, numerous alternative embodiments will be apparent to those skilled in the art from the teachings described herein. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:

1. A compound having structural Formula I:

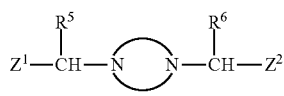

I and the pharmaceutically acceptable salts thereof wherein:

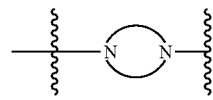

represents

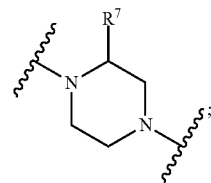

$Z^1$ is

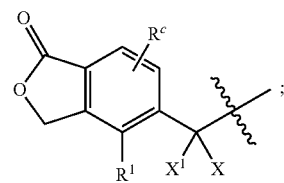

z1-iv $Z^2$ is selected from the group consisting of:

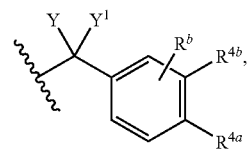

z2-i

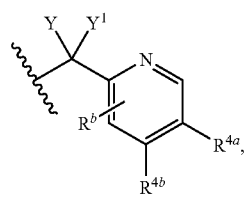

z2-ii

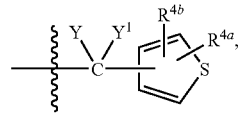

z2-iii

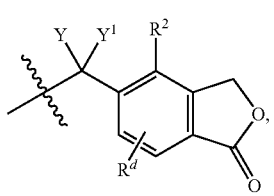

z2-iv

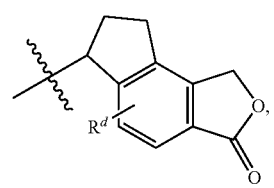

z2-v

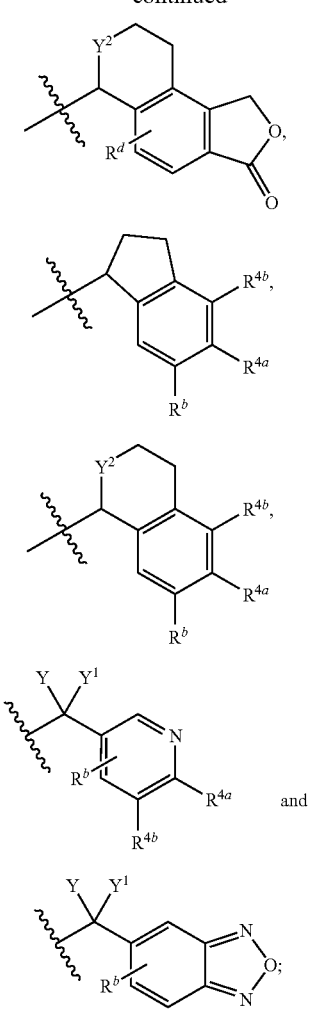

z2-vi z2-vii z2-viii z2-ix z2-x

X is selected from the group consisting of —H, —OH, —OC$_{1-3}$alkyl, —F, oxo, NH$_2$, and —CH$_3$;
Y is selected from the group consisting of —H, —OH, —OC$_{1-3}$alkyl, —F, oxo, NH$_2$, and —CH$_3$;
X$^1$ and Y$^1$ are each independently selected from the group consisting of —H and —CH$_3$;
Y$^2$ is —O—;
provided that when X is oxo then X$^1$ is absent and when Y is oxo then Y$^1$ is absent;
and further provided that when Z$^2$ is z2-i, z2-ii, z2-iii, z2-iv, z2-ix or z2-x, then at least one of X and Y is selected from the group consisting of —OH, —OC$_{1-3}$alkyl, —F and oxo, and when Z$^2$ is z2-v or z2-vii, then X is selected from the group consisting of —OH, —OC$_{1-3}$alkyl, —F and oxo;
R$^1$ and R$^2$ are each independently selected from the group consisting of —H, -halo, —C$_3$-C$_6$cycloalkyl, —OR$^8$, —SR$^8$, —SOR$^8$, —SO$_2$R$^8$, —(CH$_2$)$_n$OR$^8$ and C$_1$-C$_6$alkyl optionally substituted with 1-3 of —F;
one of R$^{4a}$ and R$^{4b}$ is selected from the group consisting of —CN and —NO$_2$ and the other is R$^f$;
R$^5$ and R$^6$ are each independently selected from the group consisting of —H, —C$_{1-6}$ alkyl, —C$_{3-6}$ cycloalkyl, —CF$_3$, —CHF$_2$, —CH$_2$F and —CH$_2$OH;
R$^7$ is selected from the group consisting of —H, —CH$_3$, —CF$_3$, —CHF$_2$, —CH$_2$F and —CH$_2$OH;

R$^b$ is selected from the group consisting of (a) —H, (b) halo, (c) —C$_{1-6}$ alkyl optionally substituted with 1-3 of —F, (d) —C$_{3-6}$ cycloalkyl, (e) —OC$_{1-3}$alkyl optionally substituted with 1-3 of —F, (f) —OR$^8$, (g) —CO$_2$C$_{1-6}$alkyl optionally substituted with 1-3 of —F, (h) —(CH$_2$)$_n$OR$^8$, (i) —SR$^8$, (j) —SOR$^8$, (k) —SO$_2$R$^8$, (l) —NHCOR$^8$ and (m) —NHSO$_2$R$^8$;

R$^c$ and R$^d$ are each independently selected from the group consisting of (a) —H, (b) halo, (c) —C$_{1-6}$ alkyl optionally substituted with 1-3 of —F, (d) —C$_{3-6}$ cycloalkyl, (e) —OC$_{1-3}$alkyl optionally substituted with 1-3 of —F, (f) —OR$^8$, (g) —CO$_2$C$_{1-6}$alkyl optionally substituted with 1-3 of —F, (h) —(CH$_2$)$_n$OR$^8$, (i) —SR$^8$, (j) —SOR$^8$, (k) —SO$_2$R$^8$, (l) —NHCOR$^8$ and (m) —NHSO$_2$R$^8$;

R$^f$ is selected from the group consisting of (a) —H, (b) halo, (c) —C$_{1-6}$ alkyl optionally substituted with 1-3 of —F, (d) —C$_{3-6}$ cycloalkyl, (e) —OC$_{1-3}$alkyl optionally substituted with 1-3 of —F, (f) —OR$^8$, (g) —CO$_2$C$_{1-6}$alkyl optionally substituted with 1-3 of —F, (h) —(CH$_2$)$_n$OR$^8$, (i) —SR$^8$, (j) —SOR$^8$, (k) —SO$_2$R$^8$, (l) —NHCOR$^8$ and (m) —NHSO$_2$R$^8$;

n is an integer selected from 1, 2 and 3; and

R$^8$ is independently selected at each occurrence from the group consisting of —H, —C$_{3-6}$cycloalkyl and —C$_{1-6}$alkyl optionally substituted with 1-3 of —F.

2. The compound of claim 1 wherein Z$^2$ is selected from the group consisting of:

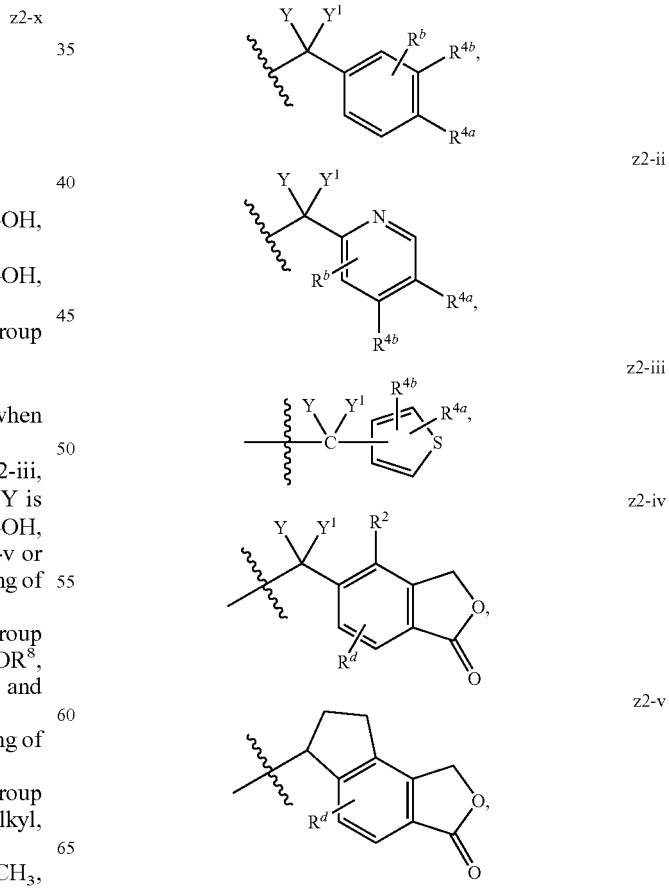

-continued

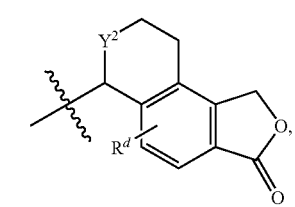
z2-vi

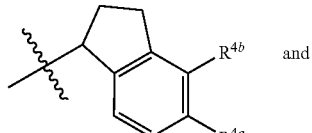
z2-vii and

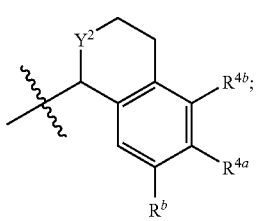
z2-viii and the pharmaceutically acceptable salts thereof.

3. The compound of claim 1 wherein X is selected from —H, —OH, —F and —CH$_3$, and Y, when present, is selected from —H, —OH, —F and —CH$_3$, provided that when Z$^2$ is z2-i, z2-ii, z2-iii, z2-iv, z2-ix or z2-x, then at least one of X and Y is selected from —OH and —F, and when Z$^2$ is z2-v or z2-vii, then X is selected from —OH and —F, and the pharmaceutically acceptable salts thereof.

4. The compound of claim 3 wherein Z$^2$ is selected from the group consisting of z2-i, z2-ii, z2-iv, z2-v and z2-vi, and the pharmaceutically acceptable salts thereof.

5. The compound of claim 4 wherein R$^1$ is selected from the group consisting of (a) —H, (b) —F, (c) —Cl, (d) —Br, (e) —C$_{1-3}$alkyl optionally substituted with 1-3 of —F, (f) cyclopropyl, (g) —OC$_{1-3}$alkyl optionally substituted with 1-3 of —F, and (h) —(CH2)$_{1-3}$—OH, and R$^2$, when present, is selected from the group consisting of (a) —H, (b) —F, (c) —Cl, (d) —Br, (e) —C$_{1-3}$alkyl optionally substituted with 1-3 of —F, (f) cyclopropyl, (g) —OC$_{1-3}$alkyl optionally substituted with 1-3 of —F, and (h) —(CH2)$_{1-3}$—OH; and the pharmaceutically acceptable salts thereof.

6. The compound of claim 5 wherein one of R$^{4a}$ and R$^{4b}$, when present, is —CN and the other is R$^f$, and the pharmaceutically acceptable salts thereof.

7. The compound of claim 6 wherein R$^f$, when present, is selected from the group consisting of —H, —CH$_3$, —OCH$_3$ and —F, and the pharmaceutically acceptable salts thereof.

8. The compound of claim 7 wherein R$^5$ and R$^6$ are each independently selected from the group consisting of —H and —CH$_3$, and the pharmaceutically acceptable salts thereof.

9. The compound of claim 8 wherein R$^c$ is selected from the group consisting of —H, —CH$_3$ and —OCH$_3$; R$^d$, when present, is selected from the group consisting of —H, —CH$_3$ and —OCH$_3$; and R$^b$, when present, is selected from the group consisting of —H, —CH$_3$ and —F; and the pharmaceutically acceptable salts thereof.

10. The compound of claim 1 having a structural Formula VIII:

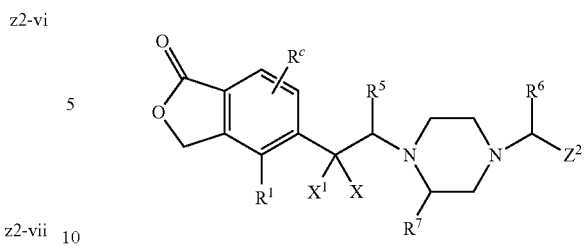
VIII and the pharmaceutically acceptable salts thereof, wherein
Z$^2$ is selected from z2-vi and z2-viii,
X is selected from the group consisting of —H, —OH, —OC$_{1-3}$alkyl, —F, oxo, NH$_2$, and —CH$_3$ and
X$^1$ is selected from the group consisting of —H and —CH$_3$; or
Z$^2$ is selected from z2-ix and z2-x, and
at least one of X and Y is selected from the group consisting of —OH, —OC$_{1-3}$alkyl, —F and oxo and the other is selected from —H, —OH, —OC$_{1-3}$alkyl, —F, oxo, NH$_2$ and —CH$_3$.

11. The compound of claim 2 having structural Formula VIIIa:

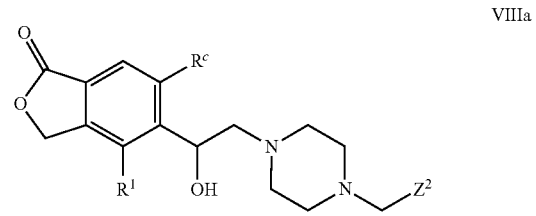
VIIIa and the pharmaceutically acceptable salts thereof wherein:
R$^1$ is selected from the group consisting of —H, —CH$_3$ and —OCH$_3$; R$^c$ is selected from the group consisting of —H and —CH$_3$; Z$^2$ is selected from the group consisting of

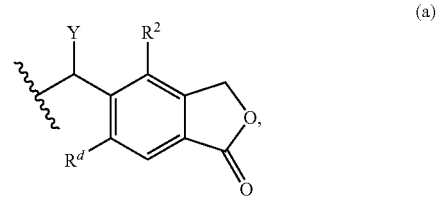
(a)

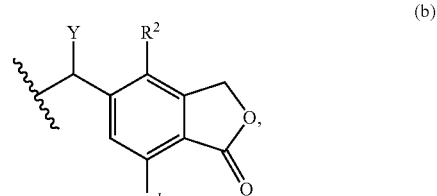
(b)

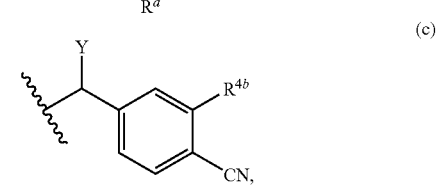
(c)

-continued

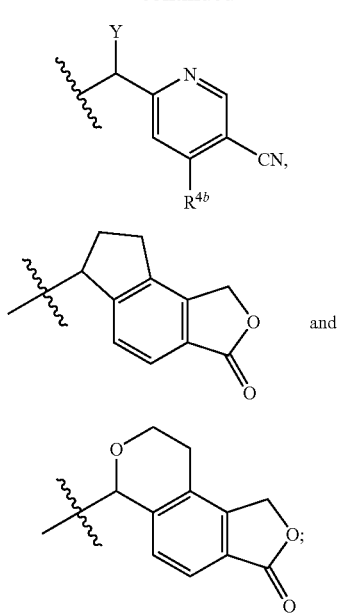

Y is selected from the group consisting of —H, —OH, —F and —CH₃; R² is selected from the group consisting of —H, —CH₃ and —OCH₃; R$^d$ is selected from the group consisting of —H and —CH₃; and R$^{4b}$ is selected from the group consisting of —H, —OCH₃ and —F.

12. The compound of claim 2 having structural Formula X

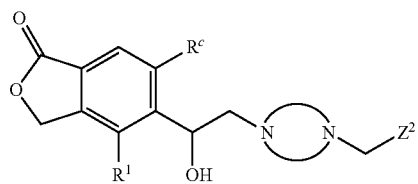

and the pharmaceutically acceptable salts thereof wherein:

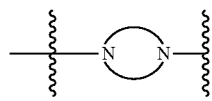

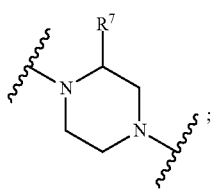

R¹ is selected from —H and —CH₃;
R$^c$ is selected from —H and —CH₃; and
Z² is selected from z2-ii, z2-iv, z2-v and z2-vi.

13. The compound of claim 1 selected from the group consisting of:

6-({4-[2-hydroxy-2-(4-methyl-1-oxo-1,3-dihydro-2-benzofuran-5-yl)ethyl]piperazin-1-yl}methyl)-8,9-dihydro-1H-furo[3,4-f]isochromen-3(6H)-one;
5,5'-[piperazine-1,4-diylbis(1-hydroxyethane-2,1-diyl)]bis(4-methyl-2-benzofuran-1(3H)-one);
5,5'-{piperazine-1,4-diylbis[(1R)-1-hydroxyethane-2,1-diyl]}bis(4-methyl-2-benzofuran-1(3H)-one);
5,5'-{piperazine-1,4-diylbis[(1S)-1-hydroxyethane-2,1-diyl]}bis(4-methyl-2-benzofuran-1(3H)-one);
5-((1R)-1-hydroxy-2-{4-[(2S)-2-hydroxy-2-(4-methyl-1-oxo-1,3-dihydro-2-benzofuran-5-yl)ethyl]piperazin-1-yl}ethyl)-4-methyl-2-benzofuran-1(3H)-one;
5,5'-[piperazine-1,4-diylbis(1-hydroxyethane-2,1-diyl)]bis(6-methyl-2-benzofuran-1(3H)-one);
5,5'-[piperazine-1,4-diylbis(1-hydroxyethane-2,1-diyl)]bis(4-bromo-2-benzofuran-1(3H)-one);
5,5'-[piperazine-1,4-diylbis(1-hydroxyethane-2,1-diyl)]bis(4-chloro-2-benzofuran-1(3H)-one);
5,5'-[piperazine-1,4-diylbis(1-hydroxyethane-2,1-diyl)]bis(2-benzofuran-1(3H)-one);
5,5'-[piperazine-1,4-diylbis(1-hydroxyethane-2,1-diyl)]bis[4-(methyloxy)-2-benzofuran-1(3H)-one];
5,5'-[piperazine-1,4-diylbis(1-hydroxyethane-2,1-diyl)]bis(4,6-dimethyl-2-benzofuran-1(3H)-one);
5,5'-[(2-methylpiperazine-1,4-diyl)bis(1-hydroxyethane-2,1-diyl)]bis(4-methyl-2-benzofuran-1(3H)-one);
5,5'-[Piperazine-1,4-diylbis(1-fluorethane-2,1-diyl)]bis(4-methyl-2-benzofuran-1(3H)-one;)
5-(1-hydroxy-2-{4-[2-(4-methyl-1-oxo-1,3-dihydro-2-benzofuran-5-yl)ethyl]piperazin-1-yl}ethyl)-4-methyl-2-benzofuran-1(3H)-one;
5-(1-hydroxy-2-{4-[2-(1-oxo-1,3-dihydro-2-benzofuran-5-yl)ethyl]piperazin-1-yl}ethyl)-4-methyl-2-benzofuran-1(3H)-one;
5-((1R)-1-hydroxy-2-{4-[2-(4-methyl-1-oxo-1,3-dihydro-2-benzofuran-5-yl)ethyl]piperazin-1-yl}ethyl)-4-methyl-2-benzofuran-1(3H)-one;
5-((1S)-1-hydroxy-2-{4-[2-(4-methyl-1-oxo-1,3-dihydro-2-benzofuran-5-yl)ethyl]piperazin-1-yl}ethyl)-4-methyl-2-benzofuran-1(3H)-one;
5-(2-{4-[2-hydroxy-2-(4-methyl-1-oxo-1,3-dihydro-2-benzofuran-5-yl)ethyl]piperazin-1-yl}-1-methylethyl)-4-methyl-2-benzofuran-1(3H)-one;
5-[2-{4-[2-hydroxy-2-(4-methyl-1-oxo-1,3-dihydro-2-benzofuran-5-yl)ethyl]piperazin-1-yl}-1-(methyloxy)ethyl]-4-methyl-2-benzofuran-1(3H)-one;
5-(1-(ethyloxy)-2-{4-[2-hydroxy-2-(4-methyl-1-oxo-1,3-dihydro-2-benzofuran-5-yl)ethyl]piperazin-1-yl}ethyl)-4-methyl-2-benzofuran-1(3H)-one;
5-(1-fluoro-2-{4-[2-hydroxy-2-(4-methyl-1-oxo-1,3-dihydro-2-benzofuran-5-yl)ethyl]piperazin-1-yl}ethyl)-4-methyl-2-benzofuran-1(3H)-one;
6-({4-[2-hydroxy-2-(4-methyl-1-oxo-1,3-dihydro-2-benzofuran-5-yl)ethyl]piperazin-1-yl}methyl)-1,6,7,8-tetrahydro-3H-indeno[4,5-c]furan-3-one;
4-(1-hydroxy-2-{4-[2-(1-oxo-1,3-dihydro-2-benzofuran-5-yl)ethyl]piperazin-1-yl}ethyl)-2-(methyloxy)benzonitrile;
4-(1-hydroxy-2-{4-[2-(4-methyl-1-oxo-1,3-dihydro-2-benzofuran-5-yl)ethy2-(methyloxy)-4-oxiran-2-ylbenzonitrile;
5-fluoro-4-(1-hydroxy-2-{4-[2-(1-oxo-1,3-dihydro-2-benzofuran-5-yl)ethyl]piperazin-1-yl}ethyl)-2-(methyloxy)benzonitrile;
5-fluoro-4-(1-hydroxy-2-{4-[2-(4-methyl-1-oxo-1,3-dihydro-2-benzofuran-5-yl)ethyl]piperazin-1-yl}ethyl)-2-(methyloxy)benzonitrile;

6-fluoro-3-(1-hydroxy-2-{4-[2-hydroxy-2-(4-methyl-1-oxo-1,3-dihydro-2-benzofuran-5-yl)ethyl]piperazin-1-yl}ethyl)-2-methylbenzonitrile;

5-chloro-4-(1-hydroxy-2-{4-[2-hydroxy-2-(4-methyl-1-oxo-1,3-dihydro-2-benzofuran-5-yl)ethyl]piperazin-1-yl}ethyl)-2-(methyloxy)benzonitrile;

4-(1-hydroxy-2-{4-[2-hydroxy-2-(4-methyl-1-oxo-1,3-dihydro-2-benzofuran-5-yl)ethyl]piperazin-1-yl}ethyl)-5-methyl-2-(methyloxy)benzonitrile;

4-(1-hydroxy-2-{4-[2-hydroxy-2-(4-methyl-1-oxo-1,3-dihydro-2-benzofuran-5-yl)ethyl]piperazin-1-yl}ethyl)-2-(methyloxy)benzonitrile;

5-fluoro-4-(1-hydroxy-2-{4-[2-hydroxy-2-(4-methyl-1-oxo-1,3-dihydro-2-benzofuran-5-yl)ethyl]piperazin-1-yl}ethyl)-2-(methyloxy)benzonitrile;

4-(1-hydroxy-2-{4-[2-hydroxy-2-(4-methyl-1-oxo-1,3-dihydro-2-benzofuran-5-yl)ethyl]piperazin-1-yl}ethyl)-3-methyl-2-(methyloxy)benzonitrile;

2-fluoro-4-(1-hydroxy-2-{4-[2-hydroxy-2-(4-methyl-1-oxo-1,3-dihydro-2-benzofuran-5-yl)ethyl]piperazin-1-yl}ethyl)benzonitrile;

4-(2-{4-[2-fluoro-2-(4-methyl-1-oxo-1,3-dihydro-2-benzofuran-5-yl)ethyl]piperazin-1-yl}ethyl)-2-(methyloxy)benzonitrile;

4-(2-{4-[2-(4-methyl-1-oxo-1,3-dihydro-2-benzofuran-5-yl)-2-(methyloxy)ethyl]piperazin-1-yl}ethyl)-2-(methyloxy)benzonitrile;

4-(2-{4-[2-(ethyloxy)-2-(4-methyl-1-oxo-1,3-dihydro-2-benzofuran-5-yl)ethyl]piperazin-1-yl}ethyl)-2-(methyloxy)benzonitrile;

4-(2-{4-[2-hydroxy-2-(4-methyl-1-oxo-1,3-dihydro-2-benzofuran-5-yl)ethyl]piperazin-1-yl}-1-methylethyl)-2-(methyloxy)benzonitrile;

4-(2-{4-[2-hydroxy-2-(4-methyl-1-oxo-1,3-dihydro-2-benzofuran-5-yl)ethyl]piperazin-1-yl}propyl)-2-(methyloxy)benzonitrile;

5-({4-[(2R)-2-hydroxy-2-(4-methyl-1-oxo-1,3-dihydro-2-benzofuran-5-yl)ethyl]piperazin-1-yl}acetyl)-4,6-dimethyl-2-benzofuran-1(3H)-one;

4-(1-fluoro-2-{4-[2-(1-oxo-1,3-dihydro-2-benzofuran-5-yl)ethyl]piperazin-1-yl}ethyl)-2-(methyloxy)benzonitrile;

1-({4-[2-(1-oxo-1,3-dihydro-2-benzofuran-5-yl)ethyl]piperazin-1-yl}methyl)-3,4-dihydro-1H-isochromene-5-carbonitrile;

1-({4-[2-(4-methyl-1-oxo-1,3-dihydro-2-benzofuran-5-yl)ethyl]piperazin-1-yl}methyl)-5-(methyloxy)-3,4-dihydro-1H-isochromene-6-carbonitrile;

1-({4-[2-(4-methyl-1-oxo-1,3-dihydro-2-benzofuran-5-yl)ethyl]piperazin-1-yl}methyl)-7-(methyloxy)-3,4-dihydro-1H-isochromene-6-carbonitrile;

6-(1-Hydroxy-2-{4-[2-hydroxy-2-(4-methyl-1-oxo-1,3-dihydro-2-benzofuran-5-yl)ethyl]piperazin-1-yl}ethyl)-4-methoxypyridine-3-carbonitrile;

5-({4-[(2S)-2-hydroxy-2-(4-methyl-1-oxo-1,3-dihydro-2-benzofuran-5-yl)ethyl]piperazin-1-yl}acetyl)-4-methyl-2-benzofuran-1(3H)-one;

5-(1-hydroxy-2-{4-[(2S)-2-hydroxy-2-(4-methyl-1-oxo-1,3-dihydro-2-benzofuran-5-yl)ethyl]piperazin-1-yl}-1-methylethyl)-4-methyl-2-benzofuran-1(3H)-one;

5-fluoro-1-({4-[2-hydroxy-2-(4-methyl-1-oxo-1,3-dihydro-2-benzofuran-5-yl)ethyl]piperazin-1-yl}methyl)-2,3-dihydro-1H-indene-4-carbonitrile;

4-(2-{4-[2-hydroxy-2-(4-methyl-1-oxo-1,3-dihydro-2-benzofuran-5-yl)ethyl]piperazin-1-yl}-1-dimethylethyl)-2-(methyloxy)benzonitrile;

6-(1-Hydroxy-2-{4-[(2R)-2-hydroxy-2-(4-methyl-1-oxo-1,3-dihydro-2-benzofuran-5-yl)ethyl]piperazin-1-yl}ethyl)pyridine-3-carbonitrile;

6-(1-Hydroxy-2-{4-[(2R)-2-hydroxy-2-(4-methyl-1-oxo-1,3-dihydro-2-benzofuran-5-yl)ethyl]piperazin-1-yl}ethyl)-4-methylpyridine-3-carbonitrile;

6-(1-Hydroxy-2-{4-[(2R)-2-hydroxy-2-(4-methyl-1-oxo-1,3-dihydro-2-benzofuran-5-yl)ethyl]piperazin-1-yl}ethyl)-5-methylpyridine-3-carbonitrile;

6-[1-Hydroxy-2-[4-[(2R)-2-hydroxy-2-(4-methyl-1-oxo-3H-isobenzofuran-5-yl)ethyl]piperazin-1-yl]ethyl]-2-methyl-pyridine-3-carbonitrile;

5-Chloro-6-[1-hydroxy-2-[4-[(2R)-2-hydroxy-2-(4-methyl-1-oxo-3H-isobenzofuran-5-yl)ethyl]piperazin-1-yl]ethyl]pyridine-3-carbonitrile;

4-[1-Hydroxy-2-[4-[2-hydroxy-2-(4-methyl-1-oxo-3H-isobenzofuran-5-yl)ethyl]piperazin-1-yl]ethyl]benzonitrile;

5,5'-[piperazine-1,4-diylbis(1-hydroxyethane-2,1-diyl)]bis(4-fluoro-2-benzofuran-1(3H)-one);

5,5'-[piperazine-1,4-diylbis(1-hydroxyethane-2,1-diyl)]bis(7-fluoro-4-methyl-2-benzofuran-1(3H)-one);

5-[(1R)-1-hydroxy-2-{4-[2-hydroxy-2-(6-methyl-1-oxo-1,3-dihydro-2-benzofuran-5-yl)ethyl]piperazin-1-yl}ethyl]-4-methyl-2-benzofuran-1(3H)-one;

5-(2-{4-[2-(2,1,3-benzoxadiazol-5-yl)ethyl]piperazin-1-yl}-1-hydroxyethyl)-2-benzofuran-1(3H)-one;

5-[(1R)-2-{4-[2-(2,1,3-benzoxadiazol-5-yl)ethyl]piperazin-1-yl}-1-hydroxyethyl]-4-methyl-2-benzofuran-1(3H)-one;

5-[(1R)-2-{4-[(2S)-2-(2,1,3-benzoxadiazol-5-yl)-2-hydroxyethyl]piperazin-1-yl}-1-hydroxyethyl]-4-methyl-2-benzofuran-1(3H)-one;

5-[(1R)-2-{4-[(2R)-2-(2,1,3-benzoxadiazol-5-yl)-2-hydroxyethyl]piperazin-1-yl}-1-hydroxyethyl]-4-methyl-2-benzofuran-1(3H)-one;

and the pharmaceutically acceptable salts thereof.

14. The compound of claim 1 selected from the group consisting of

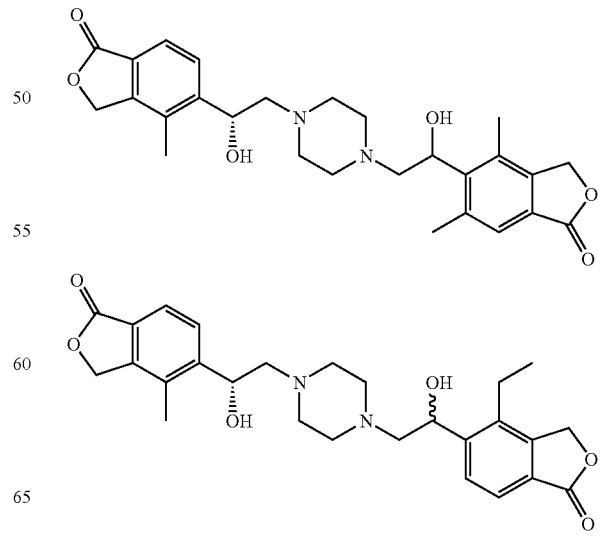

-continued
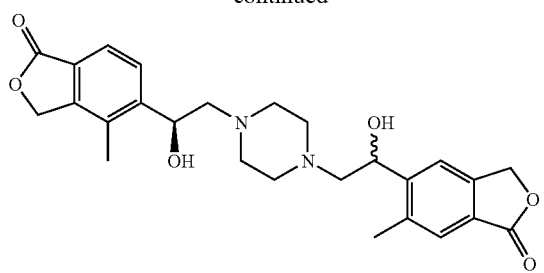
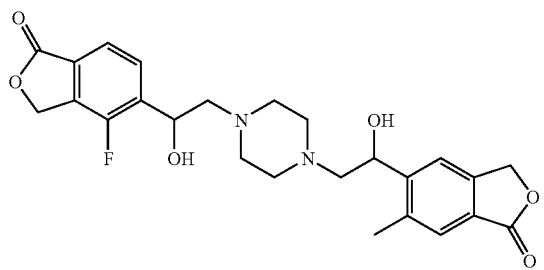
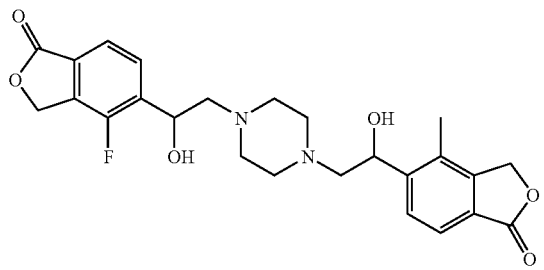
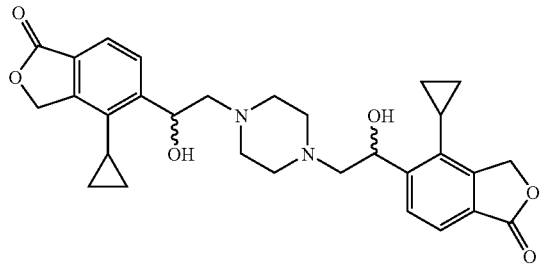
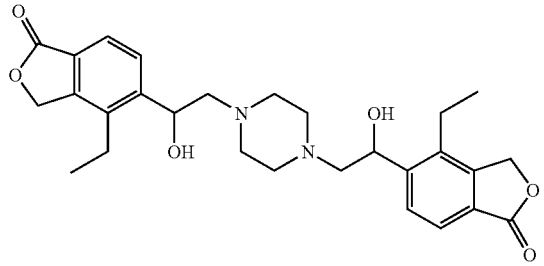
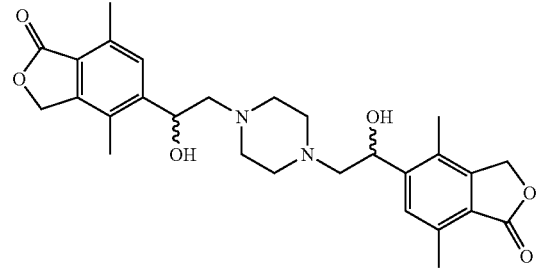
-continued
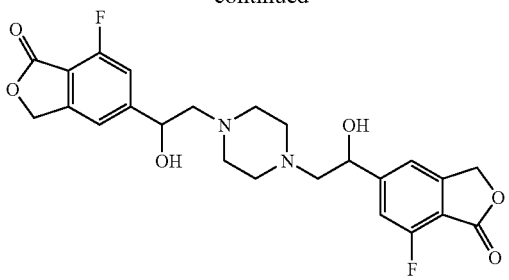
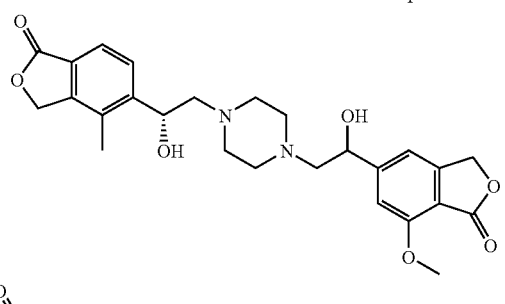
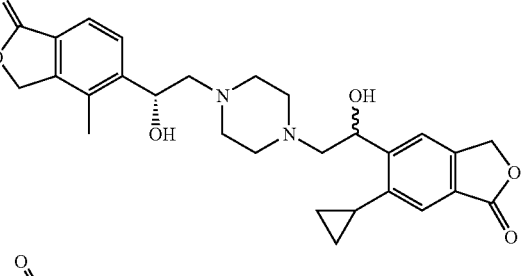
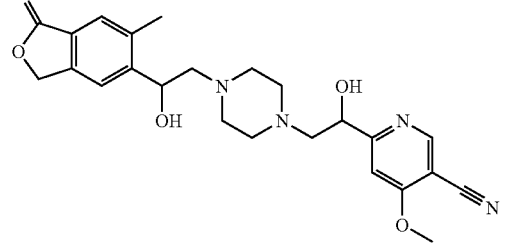
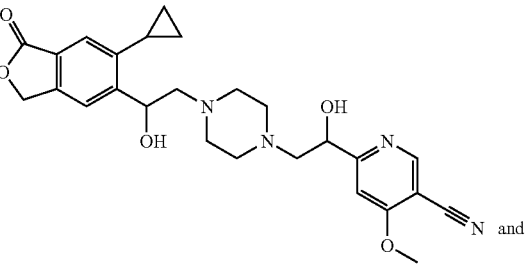
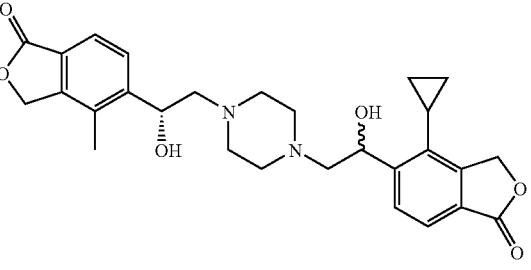
and the pharmaceutically acceptable salts thereof.
15. The compound of claim 1 selected from the group consisting of:

(6S)-6-({4-[(2R)-2-hydroxy-2-(4-methyl-1-oxo-1,3-dihydro-2-benzofuran-5-yl)ethyl]piperazin-1-yl}methyl)-8,9-dihydro-1H-furo[3,4-f]isochromen-3(6H)-one;

(6R)-6-({4-[(2R)-2-hydroxy-2-(4-methyl-1-oxo-1,3-dihydro-2-benzofuran-5-yl)ethyl]piperazin-1-yl}methyl)-8,9-dihydro-1H-furo[3,4-f]isochromen-3(6H)-one;

5,5'-[piperazine-1,4-diylbis(1-hydroxyethane-2,1-diyl)]bis(4-methyl-2-benzofuran-1(3H)-one);

5,5'-{piperazine-1,4-diylbis[(1R)-1-hydroxyethane-2,1-diyl]}bis(4-methyl-2-benzofuran-1(3H)-one);

5,5'-{piperazine-1,4-diylbis[(1S)-1-hydroxyethane-2,1-diyl]}bis(4-methyl-2-benzofuran-1(3H)-one);

5-((1R)-1-hydroxy-2-{4-[(2S)-2-hydroxy-2-(4-methyl-1-oxo-1,3-dihydro-2-benzofuran-5-yl)ethyl]piperazin-1-yl}ethyl)-4-methyl-2-benzofuran-1(3H)-one;

5,5'-[piperazine-1,4-diylbis(1-hydroxyethane-2,1-diyl)]bis(6-methyl-2-benzofuran-1(3H)-one);

5-((1R)-1-hydroxy-2-{4-[2-(4-methyl-1-oxo-1,3-dihydro-2-benzofuran-5-yl)ethyl]piperazin-1-yl}ethyl)-4-methyl-2-benzofuran-1(3H)-one;

5-((1S)-1-hydroxy-2-{4-[2-(4-methyl-1-oxo-1,3-dihydro-2-benzofuran-5-yl)ethyl]piperazin-1-yl}ethyl)-4-methyl-2-benzofuran-1(3H)-one;

6-({4-[2-hydroxy-2-(4-methyl-1-oxo-1,3-dihydro-2-benzofuran-5-yl)ethyl]piperazin-1-yl}methyl)-1,6,7,8-tetrahydro-3H-indeno[4,5-c]furan-3-one;

6-[(1S)-1-hydroxy-2-{4-[(2R)-2-hydroxy-2-(4-methyl-1-oxo-1,3-dihydro-2-benzofuran-5-yl)ethyl]piperazin-1-yl}ethyl]-4-methoxypyridine-3-carbonitrile 6-[(1R)-1-hydroxy-2-{4-[(2R)-2-hydroxy-2-(4-methyl-1-oxo-1,3-dihydro-2-benzofuran-5-yl)ethyl]piperazin-1-yl}ethyl]-4-methoxypyridine-3-carbonitrile;

6-[(1S)-1-hydroxy-2-{4-[(2R)-2-hydroxy-2-(4-methyl-1-oxo-1,3-dihydro-2-benzofuran-5-yl)ethyl]piperazin-1-yl}ethyl]pyridine-3-carbonitrile;

6-[(1R)-1-hydroxy-2-{4-[(2R)-2-hydroxy-2-(4-methyl-1-oxo-1,3-dihydro-2-benzofuran-5-yl)ethyl]piperazin-1-yl}ethyl]pyridine-3-carbonitrile;

6-[(1S)-1-hydroxy-2-{4-[(2R)-2-hydroxy-2-(4-methyl-1-oxo-1,3-dihydro-2-benzofuran-5-yl)ethyl]piperazin-1-yl}ethyl]-4-methylpyridine-3-carbonitrile;

6-[(1R)-1-hydroxy-2-{4-[(2R)-2-hydroxy-2-(4-methyl-1-oxo-1,3-dihydro-2-benzofuran-5-yl)ethyl]piperazin-1-yl}ethyl]-4-methylpyridine-3-carbonitrile;

6-[(1S)-1-hydroxy-2-{4-[(2R)-2-hydroxy-2-(4-methyl-1-oxo-1,3-dihydro-2-benzofuran-5-yl)ethyl]piperazin-1-yl}ethyl]-2-methylpyridine-3-carbonitrile;

6-[(1R)-1-hydroxy-2-{4-[(2R)-2-hydroxy-2-(4-methyl-1-oxo-1,3-dihydro-2-benzofuran-5-yl)ethyl]piperazin-1-yl}ethyl]-2-methylpyridine-3-carbonitrile;

5-[(1R)-1-hydroxy-2-{4-[(2R)-2-hydroxy-2-(6-methyl-1-oxo-1,3-dihydro-2-benzofuran-5-yl)ethyl]piperazin-1-yl}ethyl]-4-methyl-2-benzofuran-1(3H)-one;

5-[(1R)-1-hydroxy-2-{4-[(2S)-2-hydroxy-2-(6-methyl-1-oxo-1,3-dihydro-2-benzofuran-5-yl)ethyl]piperazin-1-yl}ethyl]-4-methyl-2-benzofuran-1(3H)-one; and 5-(1-hydroxy-2-{4-[(2R)-2-hydroxy-2-(4-methyl-1-oxo-1,3-dihydro-2-benzofuran-5-yl)ethyl]piperazin-1-yl}ethyl)-4,6-dimethyl-2-benzofuran-1(3H)-one;

and the pharmaceutically acceptable salts thereof.

16. A pharmaceutical composition comprised of a compound of claim 1 or a pharmaceutically acceptable salt thereof and a pharmaceutically acceptable carrier.

17. A method for causing diuresis, natriuresis or both, comprising administering a compound of claim 1 or a pharmaceutically acceptable salt thereof in a therapeutically effective amount to a patient in need thereof.

18. A method for the treatment of hypertension comprising administering a compound of claim 1 or a pharmaceutically acceptable salt thereof in a therapeutically effective amount to a patient in need thereof.

19. A method for the treatment of one or more disorders selected from the group consisting of hepatic cirrhosis, acute or chronic kidney insufficiency and nephrotic syndrome, comprising administering a compound of claim 1 or a pharmaceutically acceptable salt thereof in a therapeutically effective amount to a patient in need thereof.

20. A method for the treatment of heart failure comprising administering a compound of claim 1 or a pharmaceutically acceptable salt thereof in a therapeutically effective amount to a patient in need thereof.

21. The method of claim 18 which additionally comprises administering a therapeutically effective amount of losartan, valsartan, candesartan, olmesartan or telmisartan, with or without hydrochlorothiazide.

22. The method of claim 20 which additionally comprises administering a therapeutically effective amount of losartan, valsartan, candesartan, olmesartan or telmisartan, with or without hydrochlorothiazide.

23. The pharmaceutical composition of claim 16 further comprising losartan, valsartan, candesartan, olmesartan or telmisartan, and which is optionally additionally comprised of hydrochlorothiazide.

24. The compound of claim 1 that is 5,5'-{piperazine-1,4-diylbis[(1R)-1-hydroxyethane-2,1-diyl]}bis(4-methyl-2-benzofuran-1(3H)-one))

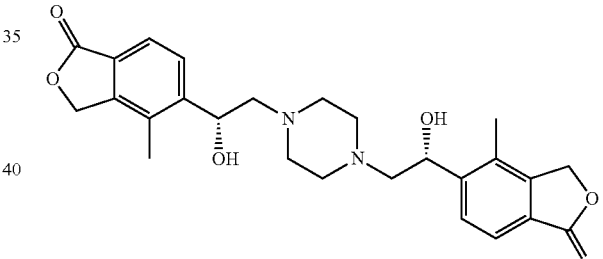

or a pharmaceutically acceptable salt thereof.

25. The compound of claim 1 that is 6-[(1R)-1-hydroxy-2-{4-[(2R)-2-hydroxy-2-(4-methyl-1-oxo-1,3-dihydro-2-benzofuran-5-yl)ethyl]piperazin-1-yl}ethyl]pyridine-3-carbonitrile

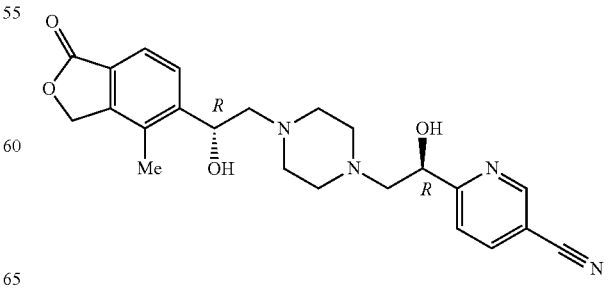

or a pharmaceutically acceptable salt thereof.

26. The compound of claim 1 that is 6-[(1S)-1-hydroxy-2-{4-[(2R)-2-hydroxy-2-(4-methyl-1-oxo-1,3-dihydro-2-benzofuran-5-yl)ethyl]piperazin-1-yl}ethyl]pyridine-3-carbonitrile

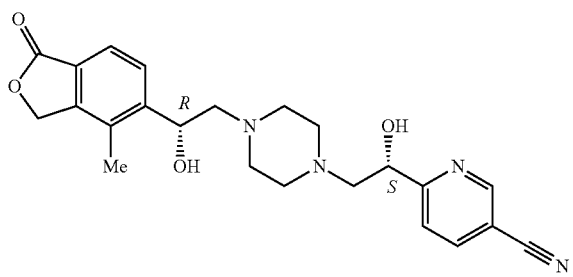

or a pharmaceutically acceptable salt thereof.

27. The compound of claim 1 that is 5-[(1R)-1-hydroxy-2-{4-[(2R)-2-hydroxy-2-(6-methyl-1-oxo-1,3-dihydro-2-benzofuran-5-yl)ethyl]piperazin-1-yl}ethyl]-4-methyl-2-benzofuran-1(3H)-one

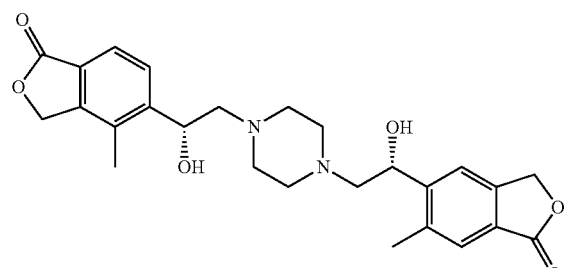

or a pharmaceutically acceptable salt thereof.

28. The compound of claim 1 that is 5-[(1R)-1-hydroxy-2-{4-[(2S)-2-hydroxy-2-(6-methyl-1-oxo-1,3-dihydro-2-benzofuran-5-yl)ethyl]piperazin-1-yl}ethyl]-4-methyl-2-benzofuran-1(3H)-one

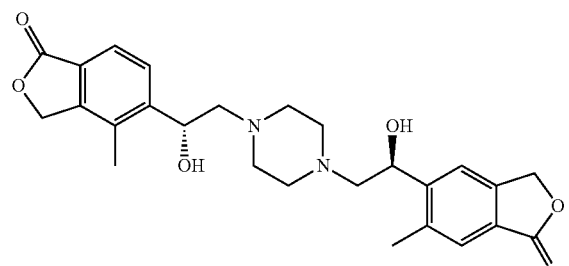

or a pharmaceutically acceptable salt thereof.

29. The compound of claim 1 that is 6-[(1R)-1-hydroxy-2-{4-[(2R)-2-hydroxy-2-(4-methyl-1-oxo-1,3-dihydro-2-benzofuran-5-yl)ethyl]piperazin-1-yl}ethyl]-4-methoxypyridine-3-carbonitrile

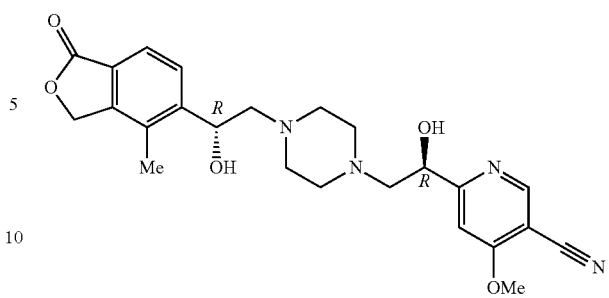

or a pharmaceutically acceptable salt thereof.

30. The compound of claim 1 that is 6-[(1S)-1-hydroxy-2-{4-[(2R)-2-hydroxy-2-(4-methyl-1-oxo-1,3-dihydro-2-benzofuran-5-yl)ethyl]piperazin-1-yl}ethyl]-4-methoxypyridine-3-carbonitrile

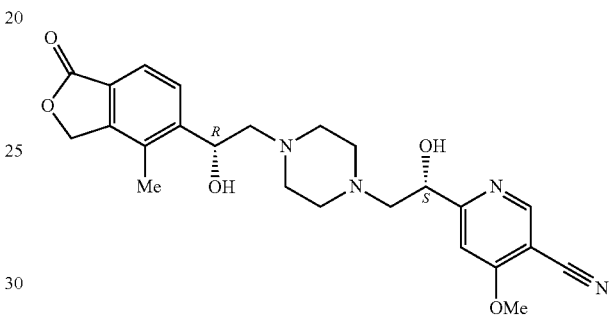

or a pharmaceutically acceptable salt thereof.

31. A pharmaceutical composition comprised of the compound of claim 24 or a pharmaceutically acceptable salt thereof and a pharmaceutically acceptable carrier.

32. The pharmaceutical composition of claim 31 further comprising losartan, valsartan, candesartan, olmesartan or telmisartan, and which is optionally additionally comprised of hydrochlorothiazide.

33. A pharmaceutical composition comprised of the compound of claim 25 or a pharmaceutically acceptable salt thereof and a pharmaceutically acceptable carrier.

34. The pharmaceutical composition of claim 33 further comprising losartan, valsartan, candesartan, olmesartan or telmisartan, and which is optionally additionally comprised of hydrochlorothiazide.

35. A pharmaceutical composition comprised of the compound of claim 26 or a pharmaceutically acceptable salt thereof and a pharmaceutically acceptable carrier.

36. The pharmaceutical composition of claim 35 further comprising losartan, valsartan, candesartan, olmesartan or telmisartan, and which is optionally additionally comprised of hydrochlorothiazide.

37. A pharmaceutical composition comprised of the compound of claim 27 or a pharmaceutically acceptable salt thereof and a pharmaceutically acceptable carrier.

38. The pharmaceutical composition of claim 37 further comprising losartan, valsartan, candesartan, olmesartan or telmisartan, and which is optionally additionally comprised of hydrochlorothiazide.

39. A pharmaceutical composition comprised of the compound of claim 28 or a pharmaceutically acceptable salt thereof and a pharmaceutically acceptable carrier.

40. The pharmaceutical composition of claim 39 further comprising losartan, valsartan, candesartan, olmesartan or telmisartan, and which is optionally additionally comprised of hydrochlorothiazide.

41. A pharmaceutical composition comprised of the compound of claim 29 or a pharmaceutically acceptable salt thereof and a pharmaceutically acceptable carrier.

42. The pharmaceutical composition of claim 41 further comprising losartan, valsartan, candesartan, olmesartan or telmisartan, and which is optionally additionally comprised of hydrochlorothiazide.

43. A pharmaceutical composition comprised of the compound of claim 30 or a pharmaceutically acceptable salt thereof and a pharmaceutically acceptable carrier.

44. The pharmaceutical composition of claim 43 further comprising losartan, valsartan, candesartan, olmesartan or telmisartan, and which is optionally additionally comprised of hydrochlorothiazide.

45. The pharmaceutical composition of claim 16 further comprising an angiotensin converting enzyme inhibitor or an angiotensin receptor blocker, and optionally additionally comprised of a beta-adrenergic blocker.

46. The pharmaceutical composition of claim 45 wherein the angiotensin converting enzyme inhibitor is alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril; the angiotensin receptor blocker is losartan, valsartan, candesartan, olmesartan or telmisartan; and the optional beta-adrenergic blocker is propranolol, atenolol, bisoprolol, carvedilol, metoprolol or metoprolol tartate.

47. The method of claim 17 wherein the patient has one or more of hypertension, heart failure, acute or chronic kidney insufficiency, nephrotic syndrome and hepatic cirrhosis.

48. The method of claim 47 wherein the kidney insufficiency is chronic kidney insufficiency.

49. The compound of claim 24 that is

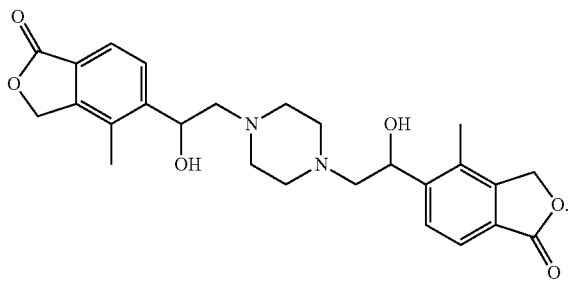 [SMILES: Cc1c(C(O)CN2CCN(CC(O)c3ccc4c(c3C)COC4=O)CC2)ccc2c1COC2=O]

50. The compound of claim 24 that is a pharmaceutically acceptable salt of

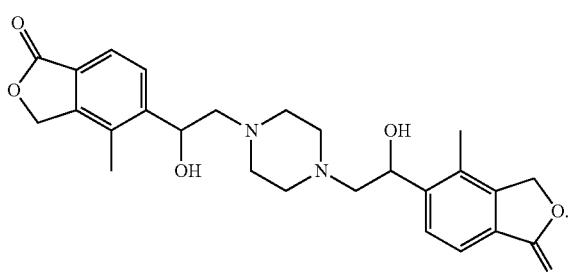

51. The compound of claim 50 which is a mono-HCl salt, di-HCl salt or $H_2SO_4$ salt.

52. The compound of claim 1 that is 5,5'-[piperazine-1,4-diylbis(1-hydroxyethane-2,1-diyl)]bis(4-methyl-2-benzofuran-1(3H)-one)

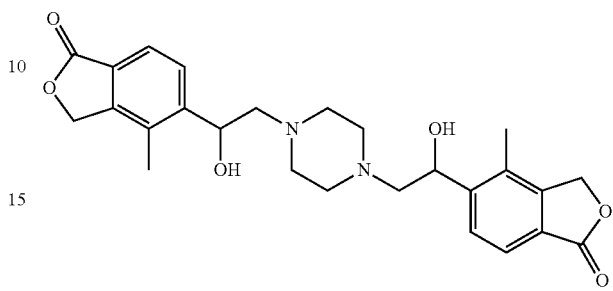

or a pharmaceutically acceptable salt thereof.

53. The compound of claim 1 that is 5,5'-{piperazine-1,4-diylbis[(1S)-1-hydroxyethane-2,1-diyl]}bis(4-methyl-2-benzofuran-1(3H)-one)

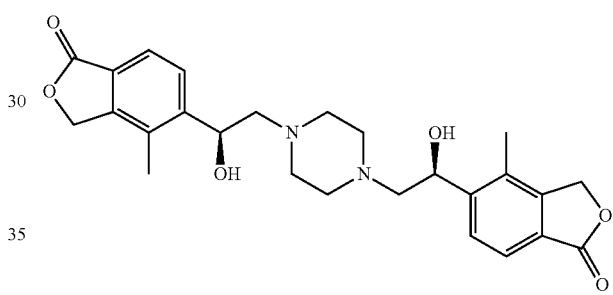

or a pharmaceutically acceptable salt thereof.

54. The compound of claim 1 that is 5-((1R)-1-hydroxy-2-{4-[(2S)-2-hydroxy-2-(4-methyl-1-oxo-1,3-dihydro-2-benzofuran-5-yl)ethyl]piperazin-1-yl}ethyl)-4-methyl-2-benzofuran-1(3H)-one

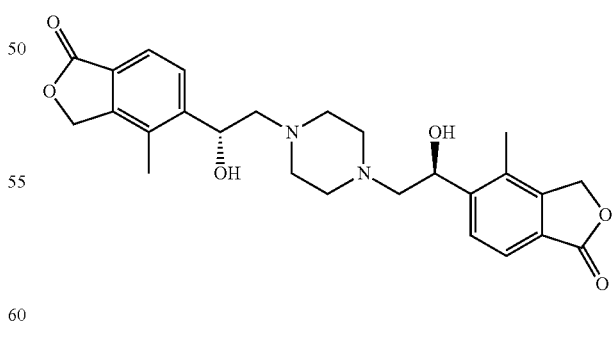

or a pharmaceutically acceptable salt thereof.

\* \* \* \* \*

UNITED STATES PATENT AND TRADEMARK OFFICE
CERTIFICATE OF CORRECTION

| | | |
|---|---|---|
| PATENT NO. | : 8,673,920 B2 | Page 1 of 1 |
| APPLICATION NO. | : 12/768209 | |
| DATED | : March 18, 2014 | |
| INVENTOR(S) | : Pasternak et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 337 days.

Signed and Sealed this
Twenty-first Day of July, 2015

Michelle K. Lee
*Director of the United States Patent and Trademark Office*